US010793580B2

(12) United States Patent
Liang et al.

(10) Patent No.: US 10,793,580 B2
(45) Date of Patent: Oct. 6, 2020

(54) SUBSTITUTED PYRAZOLOAZEPIN-8-ONES AND THEIR USE AS PHOSPHODIESTERASE INHIBITORS

(71) Applicant: LEO Pharma A/S, Ballerup (DK)

(72) Inventors: Xifu Liang, Ballerup (DK); Jens Larsen, Ballerup (DK)

(73) Assignee: LEO Pharma A/S, Ballerup (DK)

( * ) Notice: Subject to any disclaimer, the term of this patent is extended or adjusted under 35 U.S.C. 154(b) by 0 days.

(21) Appl. No.: 16/468,429

(22) PCT Filed: Dec. 12, 2016

(86) PCT No.: PCT/EP2016/080550
§ 371 (c)(1),
(2) Date: Jun. 11, 2019

(87) PCT Pub. No.: WO2018/108231
PCT Pub. Date: Jun. 21, 2018

(65) Prior Publication Data
US 2019/0330223 A1 Oct. 31, 2019

(51) Int. Cl.
*C07D 491/20* (2006.01)

(52) U.S. Cl.
CPC .................. *C07D 491/20* (2013.01)

(58) Field of Classification Search
None
See application file for complete search history.

(56) References Cited

U.S. PATENT DOCUMENTS

2010/0099688 A1* 4/2010 Felding ............... C07D 491/10
514/255.05

FOREIGN PATENT DOCUMENTS

| WO | WO 01/49689 A2 | 7/2001 |
| WO | WO 2004/098520 A2 | 11/2004 |
| WO | WO 2005/056554 A2 | 6/2005 |
| WO | WO 2007/040435 A1 | 4/2007 |
| WO | WO 2008/060597 A2 | 5/2008 |
| WO | WO 2008/104175 A2 | 9/2008 |

OTHER PUBLICATIONS

Holden, Colin A, B.Sc., et al., "Monocyte Localization of Elevated cAMP Phosphodiesterase Activity in Atopic Dermatitis," The Society for Investigative Dermatology, vol. 87, No. 3, pp. 372-376 (1986).
Houslay, Miles D. et al., "Phosphodiesterase-4 as a therapeutic target," Drug Discovery Today, vol. 1, No. 22, pp. 1503-1519 (2005).
Kroegel, Claus et al., "Phosphodiesterase-4 inhibitors as a novel approach for the treatment of respiratory disease: cilomilast," Exp. Opinion Investig. Drugs, vol. 16, No. 1, pp. 109-124 (2007).
Lipworth, Brian J, "Phosphodiesterase-4 inhibitors for asthma and chronic obstructive pulmonary disease," Lancet, vol. 265, pp. 167-175 (2005).
Smith, Victoria Boswell et la., "Selective phosphodiesterase 4 inhibitors in the treatment of allergy and inflammation," Curr. Opinion Investig. Drugs, vol. 6, No. 11, pp. 1136-1142 (2006).
International Search Report for International Application No. PCT/EP2016/080550, dated Jun. 2, 2017. (2 pages).
Written Opinion of the International Searching Authority for International Application No. PCT/EP2016/080550. (5 pages).
Translation of Search Report in Russian Application No. 2019121681, filed Dec. 12, 2016. (2 pages).
Translation of Official Action in Russian Application No. 2019121681, filed Dec. 12, 2016. (6 pages).

* cited by examiner

*Primary Examiner* — Kamal A Saeed
(74) *Attorney, Agent, or Firm* — Finnegan, Henderson, Farabow, Garrett & Dunner, LLP

(57) ABSTRACT

The present invention relates to novel pyrazoloazepin-8-ones with phosphodiesterase inhibitory activity, as well as to their use as therapeutic agents in the treatment of inflammatory diseases and conditions.

13 Claims, No Drawings

SUBSTITUTED PYRAZOLOAZEPIN-8-ONES AND THEIR USE AS PHOSPHODIESTERASE INHIBITORS

This application is a national stage filing under 35 U.S.C. § 371 of International Application No. PCT/EP2016/080550, filed on Dec. 12, 2016. The contents of this application is incorporated herein by reference.

FIELD OF THE INVENTION

The present invention relates to novel substituted pyrazoloazepin-8-ones with phosphodiesterase inhibitory activity, and to their use as therapeutic agents in the treatment of inflammatory diseases and conditions.

BACKGROUND OF THE INVENTION

Phosphodiesterases are enzymes that catalyse the hydrolysis of cyclic AMP and/or cyclic GMP in cells to 5-AMP and 5-GMP, respectively, and as such they are critical to cellular regulation of cAMP or cGMP levels. Of the 11 phosphodiesterases identified so far, phosphodiesterase (PDE) 4, PDE7 and PDE8 are selective for cAMP. PDE4 is the most important modulator of cAMP expressed in immune and inflammatory cells such as neutrophils, macrophages and T-lymphocytes. As cAMP is a key second messenger in the modulation of inflammatory responses, PDE4 has been found to regulate inflammatory responses of inflammatory cells by modulating proinflammatory cytokines such as TNF-α, IL-2, IFN-γ, GM-CSF and LTB4. Inhibition of PDE4 has therefore become an attractive target for the therapy of inflammatory diseases such as asthma, chronic obstructive pulmonary disease (COPD), rheumatoid arthritis, atopic dermatitis, psoriasis, inflammatory bowel disease such as Crohn's disease etc. (M. D. Houslay et al., Drug Discovery Today 10 (22), 2005, pp. 1503-1519). As atopic dermatitis (AD) patients have increased PDE-activity, PDE4-inhibition would also appear to be a viable treatment of AD (Journal of Investigative Dermatology (1986), 87(3), 372-6).

The PDE4 gene family consists at least of four genes, A, B, C and D, which have a high degree of homology (V. Boswell Smith and D. Spina, Curr. Opinion Investig. Drugs 6(11), 2006, pp. 1136-1141). The four PDE4 isoforms are differentially expressed in different tissues and cell types. Thus, PDE4B is predominantly expressed in monocytes and neutrophils, but not in cortex and epithelial cells, while PDE4D is expressed in lung, cortex, cerebellum and T-cells (C. Kroegel and M. Foerster, Exp. Opinion Investig. Drugs 16(1), 2007, pp. 109-124). It has been speculated that inhibition of PDE4D in the brain is associated with the adverse effects found when administering PDE4 inhibitors clinically, primarily nausea and emesis, whereas inhibition of PDE4B is associated with anti-inflammatory effects (B. Lipworth, Lancet 365, 2005, pp. 167-175).

Numerous PDE4 inhibitors have been studied for their therapeutic effect on inflammatory diseases, primarily asthma and COPD.

WO 2007/040435 (Astrazeneca AB) discloses 5,6-dihydropyrazolo[3,4-e][1,4]diazepin-4(1H)-one derivatives for the treatment of asthma and chronic obstructive pulmonary disease. The Compounds are stated to be selective inhibitors of PDE4 over other PDEs.

WO 2001/049689 (Warner-Lambert Company) discloses pyrazolo[3,4-e]diazepines. The Compounds are stated to inhibit the PDE4 enzyme.

WO2008/060597 (Vertex Pharmaceuticals Inc) relates to Compounds as protein kinase inhibitors.

WO2004/098520 (IRM LLC) relates to Compounds as protein kinase inhibitors.

There is a continuous need for developing novel PDE4 inhibitors which have a more favourable therapeutic window, i.e. fewer adverse effects, while retaining their therapeutic effect.

SUMMARY OF THE INVENTION

It is an object of the present invention to provide novel Compounds. In one aspect the present invention relates to PDE4 inhibitors that could have a stability profile in biological tissue that implies that a low systemic exposure of the Compounds to be observed upon e.g. topical administration, indicating that the Compounds of the present invention could have high clearance in human liver microsomes, that they could hydrolyse in human whole blood and could display stability towards enzymatic hydrolyses in human keratinocytes.

In one aspect the invention provides a Compound of Formula (I)

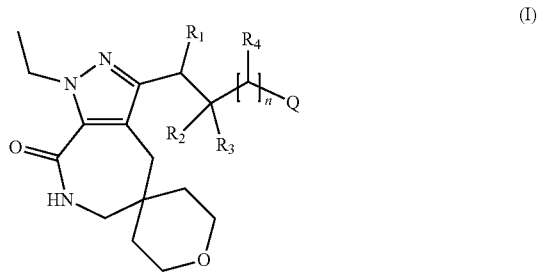

wherein $R_1$ and $R_4$ are independently selected from the group consisting of hydrogen and $(C_1-C_4)$alkyl;

$R_2$ and $R_3$ are independently selected from the group consisting of hydrogen and $(C_1-C_4)$alkyl; or $R_2$ and $R_3$ may together with the carbon atom to which they are attached form a cyclopropyl, cyclobutyl, cyclopentyl, oxetanyl, tetrahydrofuranyl or tetrahydropyranyl ring;

n=0, 1 or 2;

Q is selected from the group consisting of —O—C(O)—$R_5$;

$R_5$ is selected from the group consisting of $(C_1-C_6)$alkyl, $(C_3-C_7)$cycloalkyl, (4-7)-membered heterocycloalkyl, heteroaryl and aryl, wherein said heteroaryl and aryl are optionally substituted with one or more substituents selected from $R_6$, and wherein said $(C_1-C_6)$alkyl, $(C_3-C_7)$cycloalkyl and (4-7)-membered heterocycloalkyl are optionally substituted with one or more substituents selected from $R_7$;

$R_6$ consists of halogen, cyano, hydroxyl, $(C_1-C_4)$alkyl, halo$(C_1-C_4)$alkyl, —S(O)$_2$R$_x$, —S(O)$_2$NR$_a$R$_b$, C(O)NR$_a$R$_b$, —C(O)OR$_a$, —C(O)R$_x$ and —OR$_x$;

$R_7$ consists of halogen, hydroxyl, $(C_1-C_4)$alkyl, cyano, oxo, —C(O)NR$_a$R$_b$, —C(O)OR$_a$, —C(O)R$_x$, —S(O)$_2$R$_x$, —OR$_x$, —SR$_x$, aryl and heteroaryl;

$R_x$ consist of $(C_1-C_6)$alkyl, $(C_3-C_6)$cycloalkyl;

$R_a$ and $R_b$ are independently selected from the group consisting of hydrogen, $(C_1-C_4)$alkyl, halo$(C_1-C_4)$alkyl and phenyl$(C_1-C_4)$alkyl, or $R_a$ and $R_b$ may together with the nitrogen atom to which they are attached form a 4-6 membered heterocycloalkyl, wherein said heterocycloalkyl is optionally substituted with one or more $(C_1-C_4)$alkyl or —C(O)$R_x$; or pharmaceutically acceptable salts, hydrates or solvates thereof.

In another aspect, the invention provides pharmaceutical compositions comprising a Compound of general formula (I) as defined above together with a pharmaceutically acceptable vehicle or excipient or pharmaceutically acceptable carrier(s), optionally together with one or more other therapeutically active Compound(s).

In another aspect, the invention provides the use of a Compound of the invention, for the manufacture of pharmaceutical compositions for the prophylaxis, treatment, prevention or amelioration of a disease, disorder or condition responsive to PDE4 inhibitory activity.

In yet another aspect the invention provides a method for treatment, prevention or alleviation of diseases, disorders or conditions responsive to PDE4 inhibitory activity, and which method comprises the step of administering to a living animal body a therapeutically effective amount of the Compound of formula (I) of the invention.

Other objects of the invention will be apparent to the person skilled in the art from the following detailed description and examples.

DETAILED DESCRIPTION OF THE INVENTION

In one aspect the invention provides a Compound of Formula (I)

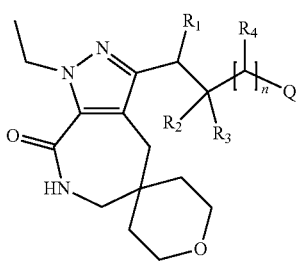

(I)

wherein $R_1$ and $R_4$ are independently selected from the group consisting of hydrogen and $(C_1-C_4)$alkyl;

$R_2$ and $R_3$ are independently selected from the group consisting of hydrogen and $(C_1-C_4)$alkyl; or $R_2$ and $R_3$ may together with the carbon atom to which they are attached form a cyclopropyl, cyclobutyl, cyclopentyl, oxetanyl, tetrahydrofuranyl or tetrahydropyranyl ring;

n=0, 1 or 2;

Q is selected from the group consisting of —O—C(O)—$R_5$;

$R_5$ is selected from the group consisting of $(C_1-C_6)$alkyl, $(C_3-C_7)$cycloalkyl, (4-7)-membered heterocycloalkyl, heteroaryl and aryl, wherein said heteroaryl and aryl are optionally substituted with one or more substituents selected from $R_6$, and wherein said $(C_1-C_6)$alkyl, $(C_3-C_7)$cycloalkyl and (4-7)-membered heterocycloalkyl are optionally substituted with one or more substituents selected from $R_7$;

$R_6$ consists of halogen, cyano, hydroxyl, $(C_1-C_4)$alkyl, halo$(C_1-C_4)$alkyl, —S(O)$_2R_x$, —S(O)$_2NR_aR_b$, C(O)$NR_aR_b$, —C(O)OR$_a$, —C(O)R$_x$ and —OR$_x$;

$R_7$ consists of halogen, hydroxyl, $(C_1-C_4)$alkyl, cyano, oxo, —C(O)$NR_aR_b$, —C(O)OR$_a$, —C(O)R$_x$, —S(O)$_2R_x$, —OR$_x$, —SR$_x$, aryl and heteroaryl;

$R_x$ consist of $(C_1-C_6)$alkyl, $(C_3-C_6)$cycloalkyl;

$R_a$ and $R_b$ are independently selected from the group consisting of hydrogen, $(C_1-C_4)$alkyl, halo$(C_1-C_4)$alkyl and phenyl$(C_1-C_4)$alkyl, or $R_a$ and $R_b$ may together with the nitrogen atom to which they are attached form a 4-6 membered heterocycloalkyl, wherein said heterocycloalkyl is optionally substituted with one or more $(C_1-C_4)$alkyl or —C(O)$R_x$; and pharmaceutically acceptable salts, hydrates or solvates thereof.

In another aspect the invention provides a Compound of Formula (I) wherein $R_1$ and $R_4$ are independently selected from the group consisting of hydrogen and $(C_1-C_4)$alkyl;

$R_2$ and $R_3$ are independently selected from the group consisting of hydrogen and $(C_1-C_4)$alkyl;

n=0, 1 or 2;

Q is selected from the group consisting of —O—C(O)—$R_5$;

$R_5$ is selected from the group consisting of $(C_1-C_6)$alkyl, $(C_3-C_7)$cycloalkyl, (4-7)-membered heterocycloalkyl, heteroaryl and aryl, wherein said heteroaryl and aryl are optionally substituted with one or more substituents selected from $R_6$, and wherein said $(C_1-C_6)$alkyl, $(C_3-C_7)$cycloalkyl and (4-7)-membered heterocycloalkyl are optionally substituted with one or more substituents selected from $R_7$;

$R_6$ consists of halogen, cyano, hydroxyl, $(C_1-C_4)$alkyl, halo$(C_1-C_4)$alkyl, —S(O)$_2R_x$, —S(O)$_2NR_aR_b$, C(O)$NR_aR_b$, —C(O)OR$_a$, —C(O)R$_x$ and —OR$_x$;

$R_7$ consists of halogen, hydroxyl, $(C_1-C_4)$alkyl, cyano, oxo, —C(O)$NR_aR_b$, —C(O)OR$_a$, —C(O)R$_x$, —S(O)$_2R_x$, —OR$_x$, —SR$_x$, aryl and heteroaryl;

$R_x$ consist of $(C_1-C_6)$alkyl, $(C_3-C_6)$cycloalkyl;

$R_a$ and $R_b$ are independently selected from the group consisting of hydrogen, $(C_1-C_4)$alkyl, halo$(C_1-C_4)$alkyl and phenyl$(C_1-C_4)$alkyl, or $R_a$ and $R_b$ may together with the nitrogen atom to which they are attached form a 4-6 membered heterocycloalkyl, wherein said heterocycloalkyl is optionally substituted with one or more $(C_1-C_4)$alkyl or —C(O)$R_x$; and pharmaceutically acceptable salts, hydrates or solvates thereof.

In another aspect the invention provides a Compound of Formula (I) wherein $R_1$ and $R_4$ are independently selected from the group consisting of hydrogen and $(C_1-C_4)$alkyl;

$R_2$ and $R_3$ are independently selected from the group consisting of hydrogen and $(C_1-C_4)$alkyl;

n=0, 1 or 2;

Q is selected from the group consisting of —O—C(O)—$R_5$;

$R_5$ is selected from the group consisting of $(C_1-C_6)$alkyl, $(C_3-C_7)$cycloalkyl, a (4-6)-membered heterocycloalkyl, a (5-6)-membered heteroaryl and phenyl, wherein said (5-6)-membered heteroaryl and phenyl are optionally substituted with one or more substituents selected from $R_6$, and wherein said $(C_1-C_6)$alkyl, $(C_3-C_7)$cycloalkyl and (4-6)-membered heterocycloalkyl are optionally substituted with one or more substituents selected from $R_7$;

$R_6$ consists of halogen, cyano, hydroxyl, $(C_1-C_4)$alkyl, halo$(C_1-C_4)$alkyl, —S(O)$_2R_x$, —S(O)$_2NR_aR_b$, C(O)$NR_aR_b$, —C(O)R$_x$ and —OR$_x$;

$R_7$ consists of halogen, hydroxyl, $(C_1-C_4)$alkyl, cyano, oxo, —C(O)$NR_aR_b$, —C(O)OR$_a$, —C(O)R$_x$, —S(O)$_2R_x$, —OR$_x$, and —SR$_x$;

$R_x$ consist of $(C_1-C_6)$alkyl, $(C_3-C_6)$cycloalkyl;

$R_a$ and $R_b$ are independently selected from the group consisting of hydrogen, $(C_1$-$C_4)$alkyl, halo$(C_1$-$C_4)$alkyl and phenyl$(C_1$-$C_4)$alkyl, or $R_a$ and $R_b$ may together with the nitrogen atom to which they are attached form a 4-6 membered heterocycloalkyl, wherein said heterocycloalkyl is optionally substituted with one or more $(C_1$-$C_4)$alkyl or —C(O)$R_x$; and pharmaceutically acceptable salts, hydrates or solvates thereof.

In another aspect the invention provides a Compound of Formula (I) wherein $R_1$ and $R_4$ are independently selected from the group consisting of hydrogen and $(C_1$-$C_4)$alkyl;

$R_2$ and $R_3$ are independently selected from the group consisting of hydrogen and $(C_1$-$C_4)$alkyl; or $R_2$ and $R_3$ may together with the carbon atom to which they are attached form a cyclopropyl, cyclobutyl, cyclopentyl, oxetanyl, tetrahydrofuranyl or tetrahydropyranyl ring;

n=0, 1 or 2;

Q is selected from the group consisting of —O—C(O)—$R_5$;

$R_5$ is selected from the group consisting of $(C_1$-$C_6)$alkyl, $(C_3$-$C_7)$cycloalkyl, (4-7)-membered heterocycloalkyl and aryl, wherein said aryl is optionally substituted with one or more substituents selected from $R_6$, and wherein said $(C_1$-$C_6)$alkyl, $(C_3$-$C_7)$cycloalkyl and (4-7)-membered heterocycloalkyl are optionally substituted with one or more substituents selected from $R_7$;

$R_6$ consists of halogen, cyano, hydroxyl, $(C_1$-$C_4)$alkyl, halo$(C_1$-$C_4)$alkyl, —S(O)$_2R_x$, —S(O)$_2$NR$_a$R$_b$, and —OR$_x$;

$R_7$ consists of halogen, hydroxyl, cyano, —C(O)NR$_a$R$_b$, —C(O)OR$_x$, aryl and heteroaryl; $R_x$ is $(C_1$-$C_6)$alkyl;

$R_a$ and $R_b$ are independently selected from the group consisting of hydrogen, $(C_1$-$C_4)$alkyl, halo$(C_1$-$C_4)$alkyl and phenyl$(C_1$-$C_4)$alkyl, or $R_a$ and $R_b$ may together with the nitrogen atom to which they are attached form a 4-6 membered heterocycloalkyl, wherein said heterocycloalkyl is optionally substituted with one or more $(C_1$-$C_4)$alkyl; or pharmaceutically acceptable salts, hydrates or solvates thereof.

In one embodiment of the present invention, $R_1$ and $R_4$ are both hydrogen.

In another embodiment of the present invention, one of $R_2$ and $R_3$ is hydrogen and the other one of $R_2$ and $R_3$ is $(C_1$-$C_4)$alkyl.

In another embodiment of the present invention, $R_2$ and $R_3$ are both hydrogen.

In another embodiment of the present invention, $R_2$ and $R_3$ are both $(C_1$-$C_4)$alkyl, e.g. both methyl.

In another embodiment of the present invention, $R_2$ and $R_3$ together with the carbon atom to which they are attached form a cyclopropyl, cyclobutyl, cyclopentyl, oxetanyl, tetrahydrofuranyl, or tetrahydropyranyl ring.

In another embodiment of the present invention, n is 1.

In another embodiment of the present invention, $R_5$ is $(C_1$-$C_6)$alkyl.

In another embodiment of the present invention, $R_5$ is $(C_3$-$C_6)$cycloalkyl, e.g. cyclopentyl.

In another embodiment of the present invention, $R_5$ is (4-7)-membered heterocycloalkyl.

In another embodiment of the present invention, $R_5$ is (4-6)-membered heterocycloalkyl.

In another embodiment of the present invention, $R_5$ is selected from the group consisting of piperidinyl, tetrahydrofuranyl, azetidinyl, tetrahydropyranyl, tetrahydrothiopyranyl, and dioxothianyl, all of which are optionally substituted with one or more substituents independently selected from $R_6$.

In another embodiment of the present invention, $R_5$ is tetrahydrofuranyl.

In another embodiment of the present invention, $R_5$ is tetrahydropyranyl.

In another embodiment of the present invention, $R_5$ is heteroaryl.

In another embodiment of the present invention, $R_5$ is a (5-6) membered heteroaryl.

In another embodiment of the present invention, $R_5$ is heteroaryl, optionally substituted with one or more substituents independently selected from $R_6$.

In another embodiment of the present invention, $R_5$ is selected from the group consisting of imidazolyl, pyrazolyl, oxazolyl, pyrimidinyl, pyridyl, isothiazolyl, and thiazolyl, all of which are optionally substituted with one or more substituents independently selected from $R_6$.

In another embodiment of the present invention, $R_5$ is aryl, optionally substituted with one or more substituents independently selected from $R_6$.

In another embodiment of the present invention, $R_5$ is phenyl, optionally substituted with one or more substituents independently selected from $R_6$.

In another embodiment of the present invention, $R_5$ is phenyl, substituted with one substituent selected from $R_6$.

In another embodiment of the present invention, when $R_5$ is substituted with one of $R_6$ consisting of —S(O)$_2R_x$ and —S(O)$_2$NR$_a$R$_b$, then the subsistent is in the para position.

In another embodiment of the present invention, $R_5$ is phenyl, substituted with two substituents independently selected from $R_6$.

In another embodiment of the present invention, $R_6$ consists of halogen, cyano, hydroxyl, $(C_1$-$C_4)$alkyl, halo$(C_1$-$C_4)$alkyl and $(C_1$-$C_4)$alkyloxy.

In another embodiment of the present invention, $R_6$ consists of $(C_1$-$C_4)$alkyl, —C(O)NR$_a$R$_b$, and —C(O)OR$_a$, wherein all of $R_a$, $R_b$ are independently selected from hydrogen and $(C_1$-$C_4)$alkyl.

In another embodiment of the present invention, $R_6$ is —S(O)$_2R_x$.

In another embodiment of the present invention, $R_6$ is —C(O)$R_x$.

In another embodiment of the present invention, $R_6$ is C(O)NR$_a$R$_b$.

In another embodiment of the present invention $R_7$ consists of halogen, hydroxyl, $(C_1$-$C_4)$alkyl, cyano, oxo, —C(O)NR$_a$R$_b$, —C(O)OR$_a$, —C(O)$R_x$, —S(O)$_2R_x$, —OR$_x$, and —SR$_x$.

In another embodiment of the present invention, $R_x$ is $(C_1$-$C_4)$alkyl.

In another embodiment of the present invention, $R_x$ is methyl.

In another embodiment of the present invention, $R_x$ is $(C_3$-$C_6)$cycloalkyl.

In another embodiment of the present invention, $R_6$ is —S(O)$_2$NR$_a$R$_b$.

In another embodiment of the present invention, $R_a$ and $R_b$ are independently selected from the group consisting of hydrogen and $(C_1$-$C_4)$alkyl, e.g independently selected from the group consisting of hydrogen and methyl.

In another embodiment of the present invention, $R_a$ and $R_b$ are both $(C_1$-$C_4)$alkyl, e.g. both methyl.

In another embodiment of the present invention, one of $R_a$ and $R_b$ is hydrogen and the other one of $R_a$ and $R_b$ is methyl.

In another embodiment of the present invention, all of $R_1$, $R_2$, $R_3$, $R_4$ are hydrogen, n is 1, $R_5$ is phenyl, optionally substituted with one or two of $R_6$ selected from the group consisting of halogen, cyano, hydroxyl, $(C_1$-$C_4)$alkyl, halo $(C_1$-$C_4)$alkyl and $(C_1$-$C_4)$alkyloxy.

In another embodiment of the present invention, all of $R_1$, $R_2$, $R_3$, $R_4$ are hydrogen, n is 1, $R_5$ is phenyl, $R_6$ is —$S(O)_2R_x$ and $R_x$ is $(C_1$-$C_4)$alkyl.

In another embodiment of the present invention, all of $R_1$, $R_2$, $R_3$, $R_4$ are hydrogen, n is 1, $R_5$ is phenyl, $R_6$ is —$S(O)_2NR_aR_b$, and $R_a$ and $R_b$ are independently selected from the group consisting of hydrogen and $(C_1$-$C_4)$alkyl.

In another embodiment of the present invention, all of $R_1$, $R_2$, $R_3$, $R_4$ are hydrogen, n is 1, $R_5$ is selected from the group consisting of $(C_1$-$C_6)$alkyl, $(C_3$-$C_7)$cycloalkyl, and aryl, wherein said aryl is optionally substituted with one or more substituents selected from $R_6$; $R_6$ consists of halogen, cyano, $(C_1$-$C_4)$alkyl, halo$(C_1$-$C_4)$alkyl, —$S(O)_2R_x$, —$S(O)_2NR_aR_b$, —$C(O)R_x$ and —$OR_x$; $R_x$ consist of $(C_1$-$C_6)$alkyl, $(C_3$-$C_6)$cycloalkyl; $R_a$ and $R_b$ are independently selected from the group consisting of hydrogen, and $(C_1$-$C_4)$alkyl, or $R_a$ and $R_b$ may together with the nitrogen atom to which they are attached form a 4-6 membered heterocycloalkyl, wherein said heterocycloalkyl is optionally substituted with one or more $(C_1$-$C_4)$alkyl or —$C(O)R_x$.

In another embodiment of the present invention, all of $R_1$, $R_2$, $R_3$, $R_4$ are hydrogen, n is 1, $R_5$ is phenyl, optionally substituted with one or more substituents selected from $R_6$; $R_6$ consists of halogen, cyano, $(C_1$-$C_4)$alkyl, halo$(C_1$-$C_4)$alkyl, —$S(O)_2R_x$, —$S(O)_2NR_aR_b$, —$C(O)R_x$ and —$OR_x$; $R_x$ consist of $(C_1$-$C_6)$alkyl, $(C_3$-$C_6)$cycloalkyl; $R_a$ and $R_b$ are independently selected from the group consisting of hydrogen, and $(C_1$-$C_4)$alkyl, or $R_a$ and $R_b$ may together with the nitrogen atom to which they are attached form a 4-6 membered heterocycloalkyl, wherein said heterocycloalkyl is optionally substituted with one or more $(C_1$-$C_4)$alkyl or —$C(O)R_x$.

In another embodiment of the present invention, all of $R_1$, $R_2$, $R_3$, $R_4$ are hydrogen, n is 1, $R_5$ is phenyl substituted with $C(O)NR_aR_b$; $R_a$ and $R_b$ are independently selected from the group consisting of hydrogen and $(C_1$-$C_4)$alkyl, or $R_a$ and $R_b$ may together with the nitrogen atom to which they are attached form a 4-6 membered heterocycloalkyl, wherein said heterocycloalkyl is optionally substituted with one or more $(C_1$-$C_4)$alkyl or —$C(O)R_x$; $R_x$ is $(C_1$-$C_6)$alkyl.

In another embodiment of the present invention, all of $R_1$, $R_2$, $R_3$, $R_4$ are hydrogen, n is 2, $R_5$ is selected from the group consisting of $(C_1$-$C_6)$alkyl, $(C_3$-$C_7)$cycloalkyl, and aryl, wherein said aryl is optionally substituted with one or more substituents selected from $R_6$; $R_6$ consists of halogen, $(C_1$-$C_4)$alkyl, —$S(O)_2R_x$, —$S(O)_2NR_aR_b$, $C(O)NR_aR_b$, —$C(O)R_x$ and —$OR_x$; $R_x$ consist is $(C_1$-$C_6)$alkyl; $R_a$ and $R_b$ are independently selected from the group consisting of hydrogen, $(C_1$-$C_4)$alkyl, or $R_a$ and $R_b$ may together with the nitrogen atom to which they are attached form a 4-6 membered heterocycloalkyl.

In another embodiment of the present invention, $R_1$, $R_2$, $R_3$ hydrogen, n is 0, $R_5$ is selected from the group consisting of $(C_3$-$C_7)$cycloalkyl, and phenyl, wherein said phenyl is optionally substituted with one or more substituents selected from $R_6$; $R_6$ consists of $(C_1$-$C_4)$alkyl, —$S(O)_2R_x$; $R_x$ is $(C_1$-$C_6)$alkyl.

In one embodiment of the present invention, $R_1$ and $R_4$ are both hydrogen, one of $R_2$ and $R_3$ is hydrogen and the other one of $R_2$ and $R_3$ is $(C_1$-$C_4)$alkyl, n is 1; $R_5$ is selected from the group consisting of $(C_1$-$C_6)$alkyl, $(C_3$-$C_7)$cycloalkyl, and aryl, wherein said aryl is optionally substituted with one or more substituents selected from $R_6$, and wherein said $(C_1$-$C_6)$alkyl, and $(C_3$-$C_7)$ are optionally substituted with one or more substituents selected from $R_7$; $R_6$ consists of halogen, $(C_1$-$C_4)$alkyl, —$S(O)_2R_x$, —$S(O)_2NR_aR_b$, —$C(O)R_x$ and —$OR_x$; $R_7$ consists of hydroxyl, —$OR_x$, —$SR_x$, —$S(O)_2R_x$; $R_x$ consist of $(C_1$-$C_6)$alkyl, $(C_3$-$C_6)$cycloalkyl; $R_a$ and $R_b$ are independently selected from the group consisting of hydrogen, $(C_1$-$C_4)$alkyl, or $R_a$ and $R_b$ may together with the nitrogen atom to which they are attached form a 4-6 membered heterocycloalkyl, wherein said heterocycloalkyl is optionally substituted with one or more $(C_1$-$C_4)$alkyl or —$C(O)R_x$.

In one embodiment of the present invention, $R_1$ and $R_4$ are both hydrogen, one of $R_2$ and $R_3$ is hydrogen and the other one of $R_2$ and $R_3$ is $(C_1$-$C_4)$alkyl, n is 1; $R_5$ is phenyl which is optionally substituted with one or more substituents selected from halogen, $(C_1$-$C_4)$alkyl, —$S(O)_2R_x$, —$S(O)_2NR_aR_b$, —$C(O)R_x$ and —$OR_x$; $R_x$ consist of $(C_1$-$C_6)$alkyl, $(C_3$-$C_6)$cycloalkyl; $R_a$ and $R_b$ are independently selected from the group consisting of hydrogen, $(C_1$-$C_4)$alkyl, or $R_a$ and $R_b$ may together with the nitrogen atom to which they are attached form a 4-6 membered heterocycloalkyl, wherein said heterocycloalkyl is optionally substituted with one or more $(C_1$-$C_4)$alkyl or —$C(O)R_x$.

In another embodiment of the present invention, $R_1$ and $R_4$ are both hydrogen, one of $R_2$ and $R_3$ is hydrogen and the other one of $R_2$ and $R_3$ is $(C_1$-$C_4)$alkyl, n is 1; $R_5$ is phenyl substituted with $C(O)NR_aR_b$; $R_a$ and $R_b$ are independently selected from the group consisting of hydrogen and $(C_1$-$C_4)$ alkyl, or $R_a$ and $R_b$ may together with the nitrogen atom to which they are attached form a 4-6 membered heterocycloalkyl, wherein said heterocycloalkyl is optionally substituted with one or more $(C_1$-$C_4)$alkyl or —$C(O)R_x$; $R_x$ is $(C_1$-$C_6)$alkyl.

In another embodiment of the present invention, $R_1$ and $R_4$ are both hydrogen, $R_2$ and $R_3$ are both $(C_1$-$C_4)$alkyl, n is 1; $R_5$ is selected from the group consisting of $(C_1$-$C_6)$alkyl, $(C_3$-$C_7)$cycloalkyl, and aryl, wherein said aryl is optionally substituted with one or more substituents selected from $R_x$, and wherein said $(C_1$-$C_6)$alkyl, and $(C_3$-$C_7)$ are optionally substituted with one or more substituents selected from $R_7$; $R_6$ consists of halogen, $(C_1$-$C_4)$alkyl, —$S(O)_2R_x$, —$S(O)_2NR_aR_b$, —$C(O)R_x$ and —$OR_x$; $R_7$ consists of hydroxyl, —$OR_x$, —$SR_x$, —$S(O)_2R_x$; $R_x$ consist of $(C_1$-$C_6)$ alkyl, $(C_3$-$C_6)$cycloalkyl; $R_a$ and $R_b$ are independently selected from the group consisting of hydrogen, $(C_1$-$C_4)$ alkyl and phenyl$(C_1$-$C_4)$alkyl, or $R_a$ and $R_b$ may together with the nitrogen atom to which they are attached form a 4-6 membered heterocycloalkyl, wherein said heterocycloalkyl is optionally substituted with one or more $(C_1$-$C_4)$alkyl or —$C(O)R_x$.

In another embodiment of the present invention, $R_1$ and $R_4$ are both hydrogen, $R_2$ and $R_3$ are both $(C_1$-$C_4)$alkyl, n is 1; $R_5$ is phenyl which is optionally substituted with one or more of halogen, $(C_1$-$C_4)$alkyl, —$S(O)_2R_x$, —$S(O)_2NR_aR_b$, —$C(O)R_x$ and —$OR_x$; $R_7$ consist of $(C_1$-$C_6)$alkyl, $(C_3$-$C_6)$ cycloalkyl; $R_a$ and $R_b$ are independently selected from the group consisting of hydrogen, $(C_1$-$C_4)$alkyl and phenyl$(C_1$-$C_4)$alkyl, or $R_a$ and $R_b$ may together with the nitrogen atom to which they are attached form a 4-6 membered heterocycloalkyl, wherein said heterocycloalkyl is optionally substituted with one or more $(C_1$-$C_4)$alkyl or —$C(O)R_x$.

In another embodiment of the present invention, $R_1$ and $R_4$ are both hydrogen, $R_2$ and $R_3$ are both $(C_1$-$C_4)$alkyl, n is 1; $R_5$ is phenyl substituted with $C(O)NR_aR_b$; $R_a$ and $R_b$ are independently selected from the group consisting of hydrogen and $(C_1$-$C_4)$alkyl, or $R_a$ and $R_b$ may together with the nitrogen atom to which they are attached form a 4-6 membered heterocycloalkyl, wherein said heterocycloalkyl is optionally substituted with one or more $(C_1-C_4)$alkyl or —C(O)R$_x$; R$_x$ is $(C_1-C_6)$alkyl.

In another embodiment of the present invention, all of R$_1$, R$_2$, R$_3$, R$_4$ are hydrogen, n is 1, Q is —O—C(O)—R$_5$; wherein R$_5$ is selected from the group consisting of a (5-6) membered heteroaryl, and a (4-6) membered heterocycloalkyl, wherein said heteroaryl is optionally substituted with one or more substituents independently selected from R$_6$, and wherein said heterocycloalkyl is optionally substituted with one or more substituents independently selected from R$_7$; R$_6$ consists of cyano, $(C_1-C_4)$alkyl, —C(O)NR$_a$R$_b$, —C(O)OR$_a$, —C(O)R$_x$; R$_7$ consists of $(C_1-C_4)$alkyl, —C(O)NR$_a$R$_b$, —C(O)OR$_a$, —C(O)R$_x$; R$_a$, R$_b$ are independently selected from hydrogen and $(C_1-C_4)$alkyl. In another embodiment of the present invention, all of R$_1$, R$_2$, R$_3$, R$_4$ are hydrogen, n is 2, Q is —O—C(O)—R$_5$; wherein R$_5$ is selected from the group consisting of a (5-6) membered heteroaryl, and a (4-6) membered heterocycloalkyl, wherein said heteroaryl is optionally substituted with one or more substituents independently selected from R$_6$, and wherein said heterocycloalkyl is optionally substituted with one or more substituents independently selected from R$_7$; R$_6$ consists of $(C_1-C_4)$alkyl, —C(O)R$_a$, R$_7$ consists of $(C_1-C_4)$alkyl, —C(O)R$_a$; R$_a$ is $(C_1-C_4)$alkyl.

In another embodiment of the present invention, all of R$_1$, R$_2$, R$_3$ are hydrogen, n is 0, Q is selected from the group consisting of —O—C(O)—R$_5$, wherein R$_5$ is selected from the group consisting of a (5-6) membered heteroaryl and a (4-6) membered heterocycloalkyl.

In another embodiment of the present invention, R$_1$ and R$_4$ are both hydrogen, one of R$_2$ and R$_3$ is hydrogen and the other one of R$_2$ and R$_3$ is $(C_1-C_4)$alkyl; n is 1, Q is —O—C(O)—R$_5$, wherein R$_5$ is selected from the group consisting of a (5-6) membered heteroaryl and a (4-6) membered heterocycloalkyl, wherein said heteroaryl is optionally substituted with one or more substituents independently selected from R$_6$, and wherein said heterocycloalkyl is optionally substituted with one or more substituents independently selected from R$_7$; R$_6$ consists of $(C_1-C_4)$alkyl, —C(O)NR$_a$R$_b$, —C(O)OR$_a$, —C(O)R$_x$; R$_7$ consists of $(C_1-C_4)$alkyl, —C(O)NR$_a$R$_b$, —C(O)OR$_a$, —C(O)R$_x$; R$_a$, R$_b$ are independently selected from hydrogen and $(C_1-C_4)$alkyl.

In another embodiment of the present invention, R$_1$ and R$_4$ are both hydrogen, R$_2$ and R$_3$ are both $(C_1-C_4)$alkyl; n is 1, Q is —O—C(O)—R$_5$, wherein R$_5$ is selected from the group consisting of a (5-6) membered heteroaryl and a (4-6) membered heterocycloalkyl, wherein said heteroaryl is optionally substituted with one or more substituents independently selected from R$_6$, and wherein said heterocycloalkyl is optionally substituted with one or more substituents independently selected from R$_7$; R$_6$ consists of $(C_1-C_4)$alkyl, —C(O)NR$_a$R$_b$, —C(O)OR$_a$, —C(O)R$_x$; R$_7$ consists of $(C_1-C_4)$alkyl, —C(O)NR$_a$R$_b$, —C(O)OR$_a$, —C(O)R$_x$; R$_a$, R$_b$ are independently selected from hydrogen and $(C_1-C_4)$alkyl.

Specific examples of Compounds of formula (I) may be selected from the group consisting of:

3-(1-Ethyl-8-oxo-spiro[6,7-dihydro-4H-pyrazolo[3,4-c]azepine-5,4'-tetrahydropyran]-3-yl)propyl 4-(methylsulfamoyl)benzoate (Compound 101), 3-(1-Ethyl-8-oxo-spiro[6,7-dihydro-4H-pyrazolo[3,4-c]azepine-5,4'-tetrahydropyran]-3-yl)propyl 4-(dimethylsulfamoyl)benzoate (Compound 102), 3-(1-Ethyl-8-oxo-spiro[6,7-dihydro-4H-pyrazolo[3,4-c]azepine-5,4'-tetrahydropyran]-3-yl)propyl 4-methylsulfonylbenzoate (Compound 103).

Definitions

As used throughout the present specification and appended claims, the following terms have the indicated meaning:

The term "alkyl" is intended to indicate a radical obtained when one hydrogen atom is removed from a branched or linear hydrocarbon. Said alkyl comprises 1-6, such as 1-4, such as 1-3, such as 2-3 or such as 1-2 carbon atoms. The term includes the subclasses normal alkyl (n-alkyl), secondary and tertiary alkyl, such as methyl, ethyl, n-propyl, isopropyl, n-butyl, isobutyl, sec.-butyl, tert.-butyl, n-pentyl, isopentyl, neopentyl, n-hexyl and isohexyl.

The terms "alkyloxy" and "alkoxy" are intended to indicate a radical of the formula —OR', wherein R' is alkyl as indicated herein, wherein the alkyl group is appended to the parent molecular moiety through an oxygen atom, e.g. methoxy (—OCH$_3$), ethoxy (—OCH$_2$CH$_3$), n-propoxy, isopropoxy, butoxy, tert-butoxy, and the like.

The term alkoxyalkyl is intended to indicate an alkyl group as defined above substituted with one or more alkoxy groups as defined above, e.g. methoxymethyl, ethoxymethyl, 2-methoxyethyl, 2-ethoxyethyl, 3-methoxyprop-1-yl, and the like.

The term "haloalkyl" is intended to indicate an alkyl group as defined herein substituted with one or more halogen atoms as defined herein, e.g. fluoro or chloro, such as fluoromethyl, difluoromethyl or trifluoromethyl.

The terms "haloalkyloxy" and "haloalkoxy" are intended to indicate a haloalkyl group as defined herein which is appended to the parent molecular moiety through an oxygen atom, such as difluoromethoxy or trifluoromethoxy.

The term "halogen" is intended to indicate a substituent from the 7$^{th}$ main group of the periodic table, such as fluoro, chloro and bromo.

The term "alkylthio" is intended to indicate a radical of the formula —S—R', wherein R' is alkyl as indicated herein, wherein the alkyl group is appended to the parent molecular moiety through a sulphur atom, e.g. —S—CH$_3$ (methylthio) or —S—CH$_2$CH$_3$ (ethylthio).

The term "cyano" is intended to indicate a —CN group attached to the parent molecular moiety through the carbon atom.

The term "cycloalkyl" is intended to indicate a saturated cycloalkane hydrocarbon radical, comprising 3-7 carbon atoms, 3-6 carbon atoms, 3-5 carbon atoms, 3-4 carbon atoms, e.g. cyclopropyl, cyclobutyl, cyclopentyl and cyclohexyl.

The term "aryl" is intended to indicate a radical of aromatic carbocyclic rings comprising 6-13 carbon atoms, 6-9 carbon atoms, such as 6 carbon atoms, in particular 5- or 6-membered rings, including fused carbocyclic rings with at least one aromatic ring. If the aryl group is a fused carbocyclic ring, the point of attachment of the aryl group to the parent molecular moiety may be through an aromatic or through an alifatic carbon atom within the aryl group. Representative examples of aryl include, but are not limited to phenyl, naphthyl, indenyl, indanyl, dihydronaphtyl, tetrahydro-naphtyl and fluorenyl.

The term "heteroaryl" is intended to indicate radicals of monocyclic heteroaromatic rings comprising 5- or 6-membered ring which contains from 1-5 carbon atoms and from 1-4 heteroatoms selected from oxygen, sulphur and nitrogen. The heteroaryl radical may be connected to the parent molecular moiety through a carbon atom or a nitrogen atom contained anywhere within the heteroaryl group. Representative examples of heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, tetrazolyl, thiadiazolyl, thiazolyl, thienyl, triazolyl.

The term "heterocycloalkyl" is intended to indicate a cycloalkane radical as described herein, wherein one or more carbon atoms are replaced by heteroatoms, comprising 1-6 carbon atoms, e.g. 2-5 or 2-4 carbon atoms, further comprising 1-3 heteroatoms, preferably 1 to 2 heteroatoms, selected from O, N, or S, $S(=O)$ or $S(=O)_2$. The heterocycloalkyl radical may be connected to the parent molecular moiety through a carbon atom or a nitrogen atom contained anywhere within the heterocycloalkyl group. Representative examples of heterocycloalkyl groups include, but are not limited to azepanyl, azetidinyl, aziridinyl, dioxolanyl, dioxolyl, imidazolidinyl, morpholinyl, oxetanyl, piperazinyl, piperidinyl, pyrrolidinyl, tetrahydrofuranyl, tetrahydropyranyl, tetrahydrothiophenyl, tetrahydrothiopyranyl.

The term "(4-6) membered heterocycloalkyl" is intended to indicate a heterocyloalkyl as defined herein, comprising 4-6 ring-atoms, and comprising 1-5 carbon atoms, e.g. 2-5 or 2-4 carbon atoms, further comprising 1-3 heteroatoms, preferably 1 to 2 heteroatoms, selected from O, N, S, $S(=O)$ or $S(=O)_2$. Representative examples of (4-6) membered heterocycloalkyl groups include azetidinyl, dioxanyl, dioxolanyl, imidazolidinyl, morpholinyl, thiomorpholinyl, thiomorpholinyl-1-oxide, thiomorpholinyl-1,1-dioxide, oxetanyl, piperazinyl, piperidinyl, pyrrolidinyl, tetrahydrofuranyl, tetrahydropyranyl, tetrahydrothiopyranyl, tetrahydrothiophenyl, thietanyl.

The term "hydrocarbon radical" is intended to indicate a radical containing only hydrogen and carbon atoms, it may contain one or more double and/or triple carbon-carbon bonds, and it may comprise cyclic moieties in combination with branched or linear moieties. Said hydrocarbon comprises 1-6 carbon atoms, and preferably comprises 1-5, e.g. 1-4, e.g. 1-3, e.g. 1-2 carbon atoms. The term includes alkyl, cycloalkyl and aryl, as indicated herein.

In some instances, the number of carbon atoms in a hydrocarbon radical (e.g. alkyl, cycloalkyl and aryl) is indicated by the prefix "(Ca-Cb)", wherein a is the minimum number and b is the maximum number of carbons in the hydrocarbon radical. Thus, for example $(C_1-C_4)$alkyl is intended to indicate an alkyl radical comprising from 1 to 4 carbon atoms, and $(C_3-C_6)$cycloalkyl is intended to indicate a cycloalkyl radical comprising from 3 to 5 carbon ring atoms.

The term "hydroxyalkyl" is intended to indicate an alkyl group as defined above substituted with one or more hydroxy, e.g. hydroxymethyl, hydroxyethyl, hydroxypropyl.

The term "hydroxyl" is intended to indicate an —OH group.

The term "oxo" is intended to indicate an oxygen atom which is connected to the parent molecular moiety via a double bond (=O).

The term "thioxo" is intended to indicate a sulfur atom which is connected to the parent molecular moiety via a double bond (=S).

The group C(O) is intended to represent a carbonyl group (C=O).

The term "pharmaceutically acceptable salt" is intended to indicate salts prepared by reacting a Compound of formula I, which comprise a basic moiety, with a suitable inorganic or organic acid, such as hydrochloric, hydrobromic, hydroiodic, sulfuric, nitric, phosphoric, formic, acetic, 2,2-dichloroaetic, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic or fumaric acid. Further examples of pharmaceutical acceptable salts are listed in Berge, S. M.; J. Pharm. Sci.; (1977), 66(1), 1-19, which is incorporated herein by reference.

The term "solvate" is intended to indicate a species formed by interaction between a Compound, e.g. a Compound of formula I, and a solvent, e.g. alcohol, glycerol or water, wherein said species are in a crystalline form. When water is the solvent, said species is referred to as a hydrate.

The term "treatment" as used herein means the management and care of a patient for the purpose of combating a disease, disorder or condition. The term is intended to include the delaying of the progression of the disease, disorder or condition, the amelioration, alleviation or relief of symptoms and complications, and/or the cure or elimination of the disease, disorder or condition. The term may also include prevention of the condition, wherein prevention is to be understood as the management and care of a patient for the purpose of combating the disease, condition or disorder and includes the administration of the active Compounds to prevent the onset of the symptoms or complications. Nonetheless, prophylactic (preventive) and therapeutic (curative) treatments are two separate aspects.

The terms "disease", "condition" and "disorder" as used herein are used interchangeably to specify a state of a patient which is not the normal physiological state of man.

The term "medicament" as used herein means a pharmaceutical composition suitable for administration of the pharmaceutically active Compound to a patient.

The term "pharmaceutically acceptable" as used herein means suited for normal pharmaceutical applications, i.e. giving rise to no adverse events in patients etc.

The Compounds of the invention may be obtained in crystalline form either directly by concentration from an organic solvent or by crystallisation or recrystallisation from an organic solvent or mixture of said solvent and a cosolvent that may be organic or inorganic, such as water. The crystals may be isolated in essentially solvent-free form or as a solvate, such as a hydrate. The invention covers all crystalline modifications and forms and also mixtures thereof.

Compounds of formula (I) may or may not comprise asymmetrically substituted (chiral) carbon atoms which give rise to the existence of isomeric forms, e.g. enantiomers and possibly diastereomers. The present invention relates to all such isomers, either in optically pure form or as mixtures thereof (e.g. racemic mixtures or partially purified optical mixtures). Pure stereoisomeric forms of the Compounds and the intermediates of this invention may be obtained by the application of procedures known in the art. The various isomeric forms may be separated by physical separation methods such as selective crystallization and chromatographic techniques, e.g. high pressure liquid chromatography using chiral stationary phases. Enantiomers may be separated from each other by selective crystallization of their diastereomeric salts which may be formed with optically active amines, such as l-ephedrine, or with optically active acids. Optically purified Compounds may subsequently be liberated from said purified diastereomeric salts. Enantiomers may also be resolved by the formation of diastereomeric derivatives. Alternatively, enantiomers may be separated by chromatographic techniques using chiral stationary phases. Pure stereoisomeric forms may also be derived from the corresponding pure stereoisomeric forms of the appropriate starting materials, provided that the reaction occur stereoselectively or stereospecifically. If a specific stereoisomer is desired, said Compound will be synthesized by stereoselective or stereospecific methods of preparation. These methods will advantageously employ chiral pure starting materials.

Furthermore, when a double bond or a fully or partially saturated ring system is present in the molecule geometric isomers may be formed. It is intended that any geometric isomer, as separated, pure or partially purified geometric isomers or mixtures thereof are included within the scope of the invention.

Deuterated analogues. Any formula given herein is also intended to represent unlabelled forms as well as isotopically labeled forms of the compounds. For example, any hydrogen represented by "H" in any of the formulae herein is intended to represent all isotopic forms of hydrogen, e.g. $^1H$, $^2H$ or D, $^3H$. Enrichment with heavier isotopes, particularly deuterium (i.e. $^2H$ or D) may afford certain therapeutic advantages due to for example an increased metabolic skin stability or an increased, systemic, in vivo clearance. Changes that would result in reduced dosage requirements or an improvement in therapeutic index. It is understood that deuterium in this context is regarded as a substituent of a compound of the formula (I).

Isotopically-enriched compounds of formula (I) can generally be prepared by conventional techniques known to those skilled in the art or by processes analogous to those described in the accompanying Preparations and Examples using any appropriate isotopically enriched reagent in place of the non-enriched reagent previously employed.

Medical Use

As the Compounds of the invention could exhibit PDE4 inhibitory activity, the Compounds could be useful as therapeutic agents for inflammatory allergic diseases such as bronchial asthma, COPD, allergic rhinitis, and nephritis; autoimmune diseases such as rheumatoid arthritis, multiple sclerosis, Crohn's disease, and systemic lupus erythematosus; acute or chronic cutaneous wound disorders; diseases of the central nervous system such as depression, amnesia, and dementia; organopathy associated with ischemic reflux caused by cardiac failure, shock, and cerebrovascular diseases, and the like; insulin-resistant diabetes; wounds; AIDS, and the like.

In one embodiment, the Compounds of the present invention are considered useful for the treatment, prevention or alleviation of dermal diseases or conditions.

In another embodiment, the Compounds of the present invention are considered useful for the treatment, prevention or alleviation of dermal diseases or conditions selected from the group consisting of proliferative and inflammatory skin disorders, dermatitis, atopic dermatitis, seborrheic dermatitis, contact dermatitis, psoriasis, cancer, epidermal inflammation, alopecia, alopecia areata, skin atrophy, steroid induced skin atrophy, skin ageing, photo skin ageing, acne, urticaria, pruritus, and eczema.

In another embodiment, the Compounds of the present invention are considered useful for the treatment or alleviation of atopic dermatitis.

In another embodiment, the Compounds of the present invention are considered useful for the treatment or alleviation of psoriasis.

In another embodiment, the Compounds of the present invention are considered useful for the treatment or alleviation of alopecia areata.

In another embodiment, the Compounds of the present invention are considered useful for the treatment or alleviation of acne.

In another embodiment, the Compounds of the present invention are considered useful for the treatment or alleviation of pruritus.

In another embodiment, the Compounds of the present invention are considered useful for the treatment or alleviation of eczema.

Compounds of the invention, optionally in combination with other active Compounds, may be useful for the treatment of dermal diseases or conditions, in particular for the treatment of proliferative and inflammatory skin disorders, dermatitis, atopic dermatitis, seborrheic dermatitis, contact dermatitis, psoriasis, cancer, epidermal inflammation, alopecia, alopecia areata, skin atrophy, steroid induced skin atrophy, skin ageing, photo skin ageing, acne, urticaria, pruritus, and eczema.

Besides being useful for human treatment, the Compounds of the present invention may also be useful for veterinary treatment of animals including mammals such as horses, cattle, sheep, pigs, dogs, and cats.

For use in therapy, Compounds of the present invention are typically in the form of a pharmaceutical composition. The invention therefore relates to a pharmaceutical composition comprising a Compound of formula (I), optionally together with one or more other therapeutically active Compound(s), together with a pharmaceutically acceptable excipient or vehicle. The excipient must be "acceptable" in the sense of being compatible with the other ingredients of the composition and not deleterious to the recipient thereof.

In the form of a dosage unit, the Compound may be administered one or more times a day at appropriate intervals, always depending, however, on the condition of the patient, and in accordance with the prescription made by the medical practitioner. Conveniently, a dosage unit of a topical formulation contain between 0.001 mg and 1000 mg, preferably between 0.01 mg and 100 mg, such as 0.1-50 mg of a Compound of formula (I). Also, conveniently, a dosage unit of a topical formulation contain between 0.01 mg and 10 g mg, preferably between 0.1 mg and 1000 mg, such as 1-500 mg of a compound of formula (I).

A suitable dosage of the Compound of the invention will depend, inter alia, on the age and condition of the patient, the severity of the disease to be treated and other factors well known to the practising physician. The Compound may be administered either orally, parenterally or topically according to different dosing schedules, e.g. daily or with weekly intervals. In general a single dose will be in the range from 0.0001 to 10 mg/kg body weight, e.g. in the range from 0.001 to 5 mg/kg body weight. Also, in general a single dose will be in the range from 0.001 to 100 mg/kg body weight, e.g. in the range from 0.01 to 10 mg/kg body weight. The Compound may be administered as a bolus (i.e. the entire daily dosage is administered at once) or in divided doses two or more times a day.

In the context of topical treatment it may be more appropriate to refer to a "usage unit", which denotes unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers. A "usage unit" is capable of being administered topically to a patient in an application per square centimetre of the skin of from 0.1 mg to 50 mg and preferably from 0.2 mg to 5 mg of the final formulation in question.

It is also envisaged that in certain treatment regimes, administration with longer intervals, e.g. every other day, every week, or even with longer intervals may be beneficial.

If the treatment involves administration of another therapeutically active Compound it is recommended to consult Goodman & Gilman's The Pharmacological Basis of Therapeutics, 9$^{th}$ Ed., J. G. Hardman and L. E. Limbird (Eds.), McGraw-Hill 1995, for useful dosages of said Compounds.

The administration of a Compound of the present invention with one or more other active Compounds may be either concomitantly or sequentially.

The formulations include e.g. those in a form suitable for oral (including sustained or timed release), rectal, parenteral (including subcutaneous, intraperitoneal, intramus-cular, intraarticular and intravenous), transdermal, ophthalmic, topical, dermal, nasal or buccal administration. Topical administration of the claimed formulation is particularly suitable.

The formulations may conveniently be presented in dosage unit form and may be prepared by but not restricted to any of the methods well known in the art of pharmacy, e.g. as disclosed in Remington, The Science and Practice of Pharmacy, 21ed ed., 2005. All methods include the step of bringing the active ingredient into association with the carrier, which constitutes one or more accessory ingredients. In general, the formulations are prepared by uniformly and intimately bringing the active ingredient into association with a liquid carrier, semisolid carrier or a finely divided solid carrier or combinations of these, and then, if necessary, shaping the product into the desired formulation.

Formulations of the present invention suitable for oral and buccal administration may be in the form of discrete units as capsules, sachets, tablets, chewing gum or lozenges, each containing a predetermined amount of the active ingredient; in the form of a powder, granules or pellets; in the form of a solution or a suspension in an aqueous liquid or non-aqueous liquid, such as ethanol or glycerol; or in the form of a gel, a nano- or microemulsion, an oil-in-water emulsion, a water-in-oil emulsion or other dispensing systems. The oils may be edible oils, such as but not restricted to e.g. cotton-seed oil, sesame oil, coconut oil or peanut oil. Suitable dispersing or suspending agents for aqueous suspensions include synthetic or natural surfactants and viscosifyring agents such as but not restricted to tragacanth, alginate, acacia, dextran, sodium carboxymethylcellulose, gelatin, methylcellulose, hydroxypropylmethylcellulose, hydroxypropylcellulose, carbomers, polyvinylpyrrolidone, polysorbates, sorbitan fatty acid esters. The active ingredients may also be administered in the form of a bolus, electuary or paste.

A tablet may be made by compressing, moulding or freeze drying the active ingredient optionally with one or more accessory ingredients. Compressed tablets may be prepared by compressing, in a suitable machine, the active ingredient(s) in a free-flowing form such as a powder or granules, optionally mixed by a binder and/or filler, such as e.g. lactose, glucose, mannitol starch, gelatine, acacia gum, tragacanth gum, sodium alginate, calcium phosphates, microcrystalline cellulose, carboxymethylcellulose, methylcellulose, hydroxypropylcellulose, hydroxypropylmethylcellulose, ethylcellulose, hydroxyethylcellulose, polyethylene glycol, waxes or the like; a lubricant such as e.g. sodium oleate, sodium stearate, magnesium stearate, sodium benzoate, sodium acetate, sodium chloride or the like; a disintegrating agent such as e.g. starch, methylcellulose, agar, bentonite, croscarmellose sodium, sodium starch glycollate, crospovidone or the like or a dispersing agent, such as polysorbate 80. Moulded tablets may be made by moulding, in a suitable machine, a mixture of the powdered active ingredient and suitable carrier moistened with an inert liquid diluent. Freeze dryed tablets may be formed in a freeze-dryer from a solution of the drug substance. A suitable filler can be included.

Formulations for rectal administration may be in the form of suppositories in which the Compound of the present invention is admixed with low melting point, water soluble or insoluble solids such as cocoa butter, hydrogenated vegetable oils, polyethylene glycol or fatty acids esters of polyethylene glycols, while elixirs may be prepared using myristyl palmitate.

Formulations suitable for parenteral administration conveniently comprise a sterile oily or aqueous preparation of the active ingredients, which is preferably isotonic with the blood of the recipient, e.g. isotonic saline, isotonic glucose solution or buffer solution. Furthermore, the formulation may containe cosolvent, solubilising agent and/or complexation agents. The formulation may be conveniently sterilised by for instance filtration through a bacteria retaining filter, addition of sterilising agent to the formulation, irradiation of the formulation or heating of the formulation. Liposomal formulations as disclosed in e.g. Encyclopedia of Pharmaceutical Technology, vol. 9, 1994, are also suitable for parenteral administration.

Alternatively, the Compounds of formula (I) may be presented as a sterile, solid preparation, e.g. a freeze-dried powder, which is readily dissolved in a sterile solvent immediately prior to use.

Transdermal formulations may be in the form of a plaster, patch, microneedles, liposomal or nanoparticulate delivery systems or other cutaneous formulations applied to the skin.

Formulations suitable for ophthalmic administration may be in the form of a sterile aqueous preparation of the active ingredients, which may be in microcrystalline form, for example, in the form of an aqueous microcrystalline suspension. Liposomal formulations or biodegradable polymer systems e.g. as disclosed in Encyclopedia of Pharmaceutical Technology, vol. 2, 1989, may also be used to present the active ingredient for ophthalmic administration.

Formulations suitable for topical, such as dermal, intradermal or ophthalmic administration include liquid or semi-solid preparations such as liniments, lotions, gels, applicants, sprays, foams, filmforming systems, microneedles, micro- or nano-emulsions, oil-in-water or water-in-oil emulsions such as creams, ointments or pastes; or solutions or suspensions such as drops. Compositions for ophthalmic treatment may additionally contain cyclodextrin.

For topical administration, the Compound of formula (I) may typically be present in an amount of from 0.001 to 20% by weight of the composition, such as 0.01% to about 10%, but may also be present in an amount of up to about 100% of the composition.

Formulations suitable for nasal or buccal administration include powder, self-propelling and spray formulations, such as aerosols and atomisers. Such formulations are disclosed in greater detail in e.g. Modern Pharmaceutics, 2$^{nd}$ ed., G. S. Banker and C. T. Rhodes (Eds.), page 427-432, Marcel Dekker, New York; Modern Pharmaceutics, 3th ed., G. S. Banker and C. T. Rhodes (Eds.), page 618-619 and 718-721, Marcel Dekker, New York and_Encyclopedia of Pharmaceutical Technology, vol. 10, J. Swarbrick and J. C. Boylan (Eds), page 191-221, Marcel Dekker, New York.

In addition to the aforementioned ingredients, the formulations of a Compound of formula (I) may include one or more additional ingredients such as diluents, buffers, flavouring agents, colourant, surface active agents, thickeners, penetration enhancing agents, solubility enhancing agents preservatives, e.g. methyl hydroxybenzoate (including antioxidants), emulsifying agents and the like.

When the active ingredient is administered in the form of salts with pharmaceutically acceptable non-toxic acids or bases, preferred salts are for instance easily water-soluble or slightly soluble in water, in order to obtain a particular and appropriate rate of absorption.

The pharmaceutical composition may additionally comprise one or more other active components conventionally used in the treatment of dermal disease or conditions, e.g. selected from the group consisting of glucocorticoids, vitamin D and vitamin D analogues, antihistamines, platelet activating factor (PAF) antagonists, anticholinergic agents, methylxanthines, β-adrenergic agents, COX-2 inhibitors, JAK inhibitors, other PDEs, salicylates, indomethacin, flufenamate, naproxen, timegadine, gold salts, penicillamine, serum cholesterol lowering agents, retinoids, zinc salts, salicylazosulfapyridine and calcineurin inhibitors.

Methods of Preparation

The Compounds of the present invention can be prepared in a number of ways well known to those skilled in the art of synthesis. The Compounds of formula (I) may for example be prepared using the reactions and techniques outlined below together with methods known in the art of synthetic organic chemistry, or variations thereof as appreciated by those skilled in the art. Preferred methods include, but are not limited to, those described below. The reactions are carried out in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognized by one skilled in the art. Not all Compounds falling into a given class may be compatible with some of the reaction conditions required in some of the methods described. Such restrictions to the substituents which are compatible with the reaction conditions will be readily apparent to one skilled in the art and alternative methods can be used.

The Compounds of the present invention or any intermediate may be purified if required using standard methods well known to a synthetic organist chemist, e.g. methods described in "Purification of Laboratory Chemicals", 6$^{th}$ ed. 2009, W. Amarego and C. Chai, Butterworth-Heinemann.

Starting materials are either known or commercially available Compounds or can be prepared by routine synthetic methods well known to a person skilled in the art.

$^1$H nuclear magnetic resonance (NMR) spectra were recorded at 400 or 600 MHz unless otherwise specified. Chemical shift values (δ, in ppm) are quoted relative to internal tetramethylsilane (δ=0.00) standards. The value of a multiplet, either defined doublet (d), triplet (t), quartet (q) or (m) at the approximate midpoint is given unless a range is quoted. (br) indicates a broad peak, whilst (s) indicates a singlet. The organic solvents used were usually anhydrous. Chromatography was performed on Merck silica gel 60 (0.040-0-063 mm). The solvent ratios indicated refer to v:v unless otherwise noted. All NMR spectra are recorded in DMSO-$d_6$ unless another solvent is stated.

Analytical SFC Conditions
Column/dimensions: Chiralpak AD-H (250×4.6) mm, 5 u
$CO_2$: 70.0%
% Co solvent: 30.0% (IPA)
Total Flow: 3.0 g/min
Back Pressure: 100 bar
Temperature: 30° C.
UV: 211 nm Preparative SFC Conditions
Column/dimensions: Chiralpak-AD-H (250×30) mm
% $CO_2$: 70.0%
% Co solvent: 30.0% (100% IPA)
Total Flow: 90.0 g/min
Back Pressure: 100.0 bar
UV: 211 nm
Stack time: 4.5 min
Load/inj: 120.0 mg
Solubility: MeOH
Total No of injections: 133
Instrument details: Make/Model: Thar SFC-200 (NEW-2)

Analytical UPLC/MS

Analytical UPLC/MS is performed on a Waters Acquity UPLC-system and SQD-MS. Column: Waters Acquity HSS T3 1.8 μm, 2.1×50 mm; solvent system: A=10 mM Ammonium acetate in water+0.1% HCOOH and B=acetonitrile+ 0.1% HCOOH; flow rate=1.2 mL/min; method (1.4 min): Linear gradient method from 5% B to 95% B over 0.9 minutes then 95% B for 0.3 minutes. Column temperature is 60° C.

Preparative Purification HPLC/MS:

Preparative HPLC/MS was performed on a Waters AutoPurification system with a Waters SQD2 mass spectrometer. This includes three steps, pre-analysis, preparative purification and re-analysis on the purified Compound.

Solvent: A=0.1% formic acid and solvent B=acetonitrile with 0.1% formic acid

Analytical Pre-Analysis Using the Following Method:
Column: Waters SUNFIRE C-18, 100 mm×4.6 mm, 5 μm
Flow rate=1.2 mL/min. (method 10 min)
Method: Linear gradient method going from 10% B to 95% B in 6.5 minutes and staying at 95% B for another 1.5 minutes to obtain the retention time of the Compounds provides the following four different preparative gradient methods:

Preparative Methods:
Column: Waters SUNFIRE C-18, 100 mm×19 mm, 5 μm
Flow rate=20 mL/min. (method 8 min)
0-3 min: 5% B for 2 minutes followed by a linear gradient method going from 5% B to 35% B in 3 minutes and going to 100% B and staying at 100% B for another 1.4 minutes.
3.01-5 min: 15% B for 1 minutes followed by a linear gradient method going from 15% B to 55% B in 4 minutes and going to 100% B and staying at 100% B for another 1.4 minutes.
5.01-7.5 min: 30% B for 1 minutes followed by a linear gradient method going from 30% B to 70% B in 4 minutes and going to 100% B and staying at 100% B for another 1.4 minutes.
7.51-10 min: 50% B for 1 minutes followed by a linear gradient method going from 50% B to 100% B in 4 minutes and staying at 100% B for another 1.5 minutes.

The fractions were collected based on ion traces of relevant ions and PDA signal (240-400 nm).

Re-analysis method for fractions:
Column: Waters Xselect C18; 50×3.0 mm 5 μm
Flow rate=1.2 mL/min. (method 5 min)
Method: Linear gradient method going from 10% B to 95% B in 3 minutes and staying at 95% B for another 0.5 min.

Instruments:
Waters 2767 Sample Manager
Waters 2545 Binary Gradient Module
Waters SFO System Fluidics Organizer Waters 515 HPLC Pump
Waters 2998 Photodiode Array Detector
Waters SQDetector 2
LCMS Method "XE Metode 7 CM"

A quality check was performed on a Waters LCT Premier MS instrument and a Waters Aquity UPLC.

Column: Waters Aquity UPLC HSS T3 1.8 μm, 2.1×50 mm, at 40° C.

Solvents: A=10 mM ammonium acetate+0.1% HCOOH, B=MeCN+0.1% HCOOH.

Flow: 0.7 ml/min. Injection volume 2 μl. UV detection range 240-400 nm.

|  | Time | % A | % B |
|---|---|---|---|
| Gradient: | 0.00 min | 99 | 1 |
|  | 0.50 min | 94 | 6 |
|  | 1.00 min | 94 | 6 |
|  | 2.60 min | 5 | 95 |
|  | 3.80 min | 5 | 95 |
|  | 3.81 min | 99 | 1 |
|  | 4.80 min | 99 | 1 |

The MW confirmation and purity was extracted and checked with OpenLynx.

The following abbreviations have been used throughout:
Cpd Compound
DCE 1,2-dichloroethane
DCM dichloromethane
DMAP N,N-dimethylpyridin-4-amine
DMF N,N-dimethylformamide
DMSO dimethylsulfoxide
EDCI (3-dimethylamino-propyl)-ethyl-carbodiimide
EtOH ethanol
MeOH methanol
EtOAc ethyl acetate
LDA lithium diisopropylamide
Me methyl
NMR nuclear magnetic resonance
RT room temperature
THF tetrahydrofuran General Methods Compounds of general formula (I) of the invention may for example be prepared according to the following non-limiting general methods and examples. $R_1$, $R_2$, $R_3$, $R_4$, Q, and n are as previously defined for the Compounds of general formula (I):

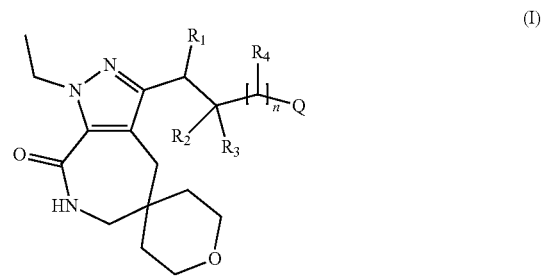

a) Synthesis of General Formula (V) is Outlined in Scheme 1

A Compound of general formula (III) may be prepared by treatment of 9-oxaspiro-[5.5]undec-4-en-3-one with a suitable base such as LDA (lithium diisopropylamide), followed by reaction with a suitable protected aldehyde (general formula II) in a suitable solvent such as THF at low temperature (preferably at −78 to −50° C.). Protecting group may be benzyl, 2,4-dimethoxybenzyl, or 4-methoxybenzyl. A Compound of general formula (V) may be prepared by Swern oxidation (Cl(O=C)—(C=O)Cl, DMSO, $Et_3N$ or modified Swern oxidation (($CF_3CO)_2O$, DMSO, $Et_3N$) of a Compound of general formula III in a suitable solvent such as DCM at low temperature (preferably at −78 to −50° C.).

Alternatively, a Compound of general formula (V) can be prepared by treatment of 9-oxaspiro[5.5]undec-4-en-3-one with a suitable base such as LDA (lithium diisopropylamide), sodium hydride, alkali metal alcoxide, alkali metal hexamethyldisilazide followed by reaction with a Compound of general formula (IV) (L represents a leaving group such as chloride, alkoxy, acyloxy, and cyano in a suitable solvent such as THF, diethylether, glycol ether at a suitable temperature, which depends on the base used.

Scheme 1

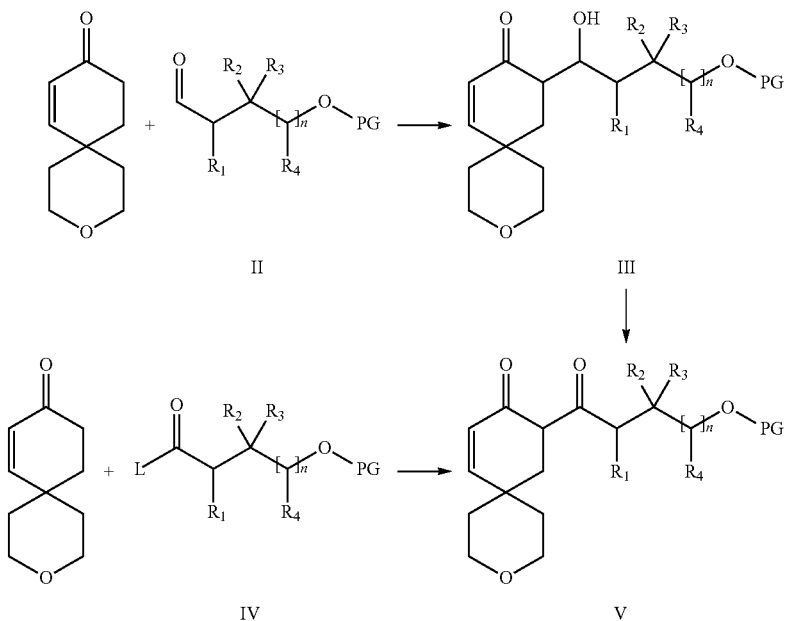

b) Synthesis of a Compound of General Formula (VI) is Outlined in Scheme 2

A Compound of general formula (VI) may be prepared by treatment of a Compound of general formula V with ethylhydrazine in the presence of a suitable acid such as acetic acid and 4-toluenesulphonic acid or in the absence of an acid in a suitable solvent such as methanol, ethanol, propanol, isopropanol, butanol, and THF at suitable temperature between rt and 150° C. (preferably 50° C. to 120° C.).

A Compound of general formula (VI) may also be prepared by treatment of a Compound of general formula (V) with ethylhydrazine in the presence of a suitable base such as triethylamine, $K_2CO_3$, $Bu_4NOH$, KOH in a suitable solvent such as methanol, ethanol, propanol, isopropanol, butanol, and THF at suitable temperature between rt and 150° C. (preferably 50° C. to 120° C.), especially when a Compound of general formula (II) is in a salt form such as hydrochloride and oxalate.

Scheme 2

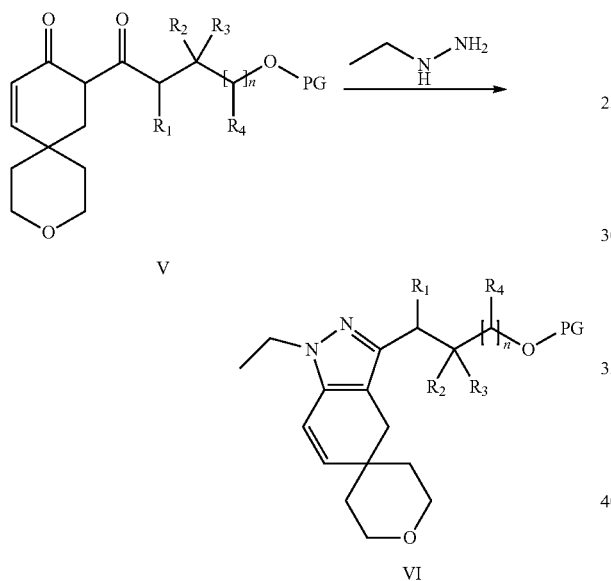

Synthesis of a Compound of General Formula (X) is Outlined in Scheme 3

A Compound of general formula (VII) may be prepared by ozonolysis of a Compound of general formula (VI) (for ozonolysis, see: Collett, Christopher, J. et al. Angew. Chem. Int. Ed. (2015), 54 (23), 6887-6892). Alternatively, a Compound of general formula (VII) may be prepared by a modified Lemieux-Johnson reaction (cat. osmium tetraoxide, 2,6-lutidine, sodium periodate) in a suitable mixture of solvents such as water/1,4-dioxane.

A Compound of general formula (VIII) may be prepared by reductive amination of a Compound of general formula (VII) with a suitable amine such as 4-methoxybenzylamine and 2,4-dimethoxybenzylamine in the presence of a suitable reducing agent such as sodium cyanoborohydride, sodium triacetoxyborohydride in a suitable solvent such as methanol, DCM, chloroform, 1,2-dichloroethane and acetonitrile. A suitable acid such as acetic acid may be used to accelerate the reaction.

A Compound of general formula (IX) may be prepared by treatment of a Compound of general formula (VIII) with $KMnO_4$, $KMnO_4/Me(CH_2)_{13}NMe_3.Br$ and sodium chlorite in a suitable solvent such as acetone, DCM, water, and 1,1,1-trichloroethane or a mixture of two or more.

Finally, an alcohol of general formula (X) may be prepared by removal of the protecting groups such as benzyl, 4-methoxybenzyl and 2,4-dimethoxybenzyl with a strong acid such as methanesulphonic acid and trifluromethanesulphonic acid in a suitable solvent such as toluene, DCM, and chloroform.

Scheme 3

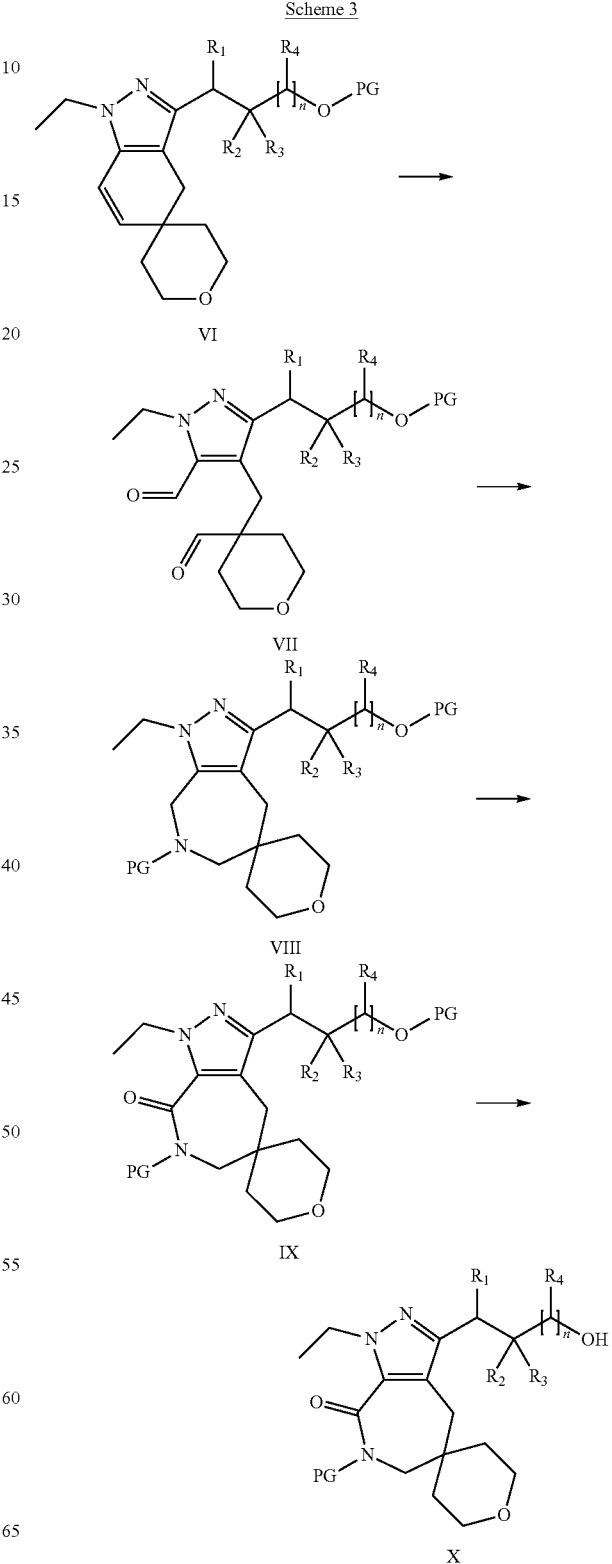

c) Synthesis of a Compound of General Formula (I) where Q Represents —O—C(O)—$R_5$ ($R_5$ is as Previous Defined) is Outlined in Scheme 4

A Compound of general formula (I) where Q represents —O—C(O)—$R_5$ may be prepared from a Compound of formula (x) according to standard procedures known to a chemist skilled in the art of organic synthesis (for ester formation, see: Junzo Otera, Esterification: Methods, Reactions, and Applications, Wiley-VCH, Weinheim (2004)). For example, a Compound of general formula (I) may be prepared by reaction of a Compound of general formula (X) with HO—(CO)—$R_5$ in the presence of a suitable coupling reagent such as DCC, EDAC and a suitable catalyst such as DMAP in a suitable solvent such dichloromethane, dichloroethane, acetonitrile and ethyl acetate.

Scheme 4

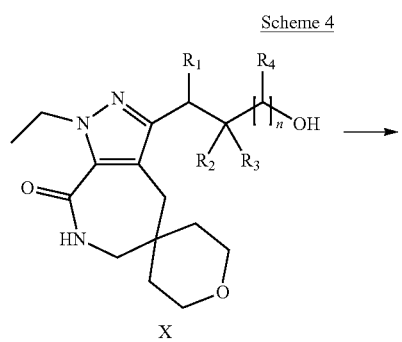

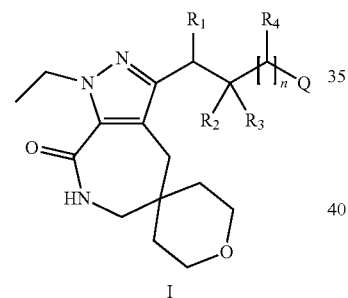

PREPARATIONS AND EXAMPLES

Preparation 1 (Compound 001)

(R/S)-8-(4-Benzyloxy-1-hydroxy-butyl)-3-oxaspiro[5.5]undec-10-en-9-one

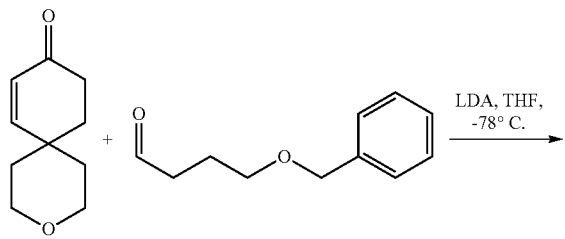

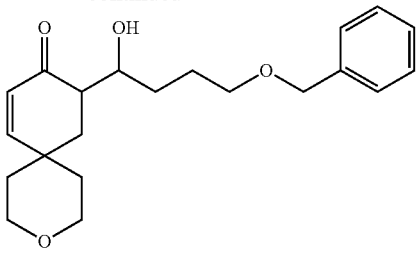

001

To a solution of 9-oxaspiro[5.5]undec-4-en-3-one (50 g, 301 mmol) in THF (600 mL), LDA (180 mL, 361 mmol, 2M in THF) was added slowly at −78° C. and it was stirred for 2 h. To the reaction mixture a solution of 4-benzyloxybutanal (70 g, 391 mmol) in THF (200 mL) was added at −78° C. and it was stirred for another 2 h. On completion, the reaction mixture was quenched with sat.NH$_4$Cl and extracted twice with EtOAc (250 mL×2). The combined organic layers were washed with brine (200 mL), dried over Na$_2$SO$_4$, concentrated in vacuo and the resulting residue was purified by silica gel column chromatography (50% EtOAc in PE as eluent) to afford the title compound as brown liquid.

$^1$H NMR (400 MHz, CDCl$_3$): δ=7.38-7.27 (m, 5H), 6.92 (m, 1H), 5.94 (d, J=9.8 Hz, 1H), 4.52 (s, 2H), 3.96-3.88 (m, 1H), 3.85-3.64 (m, 4H), 3.58-3.49 (m, 2H), 2.52 (m, 1H), 2.17 (m, 1H), 1.88-1.65 (m, 5H), 1.64-1.50 (m, 5H).

Preparation 2 (Compound 002)

8-(4-Benzyloxybutanoyl)-3-oxaspiro[5.5]undec-10-en-9-one

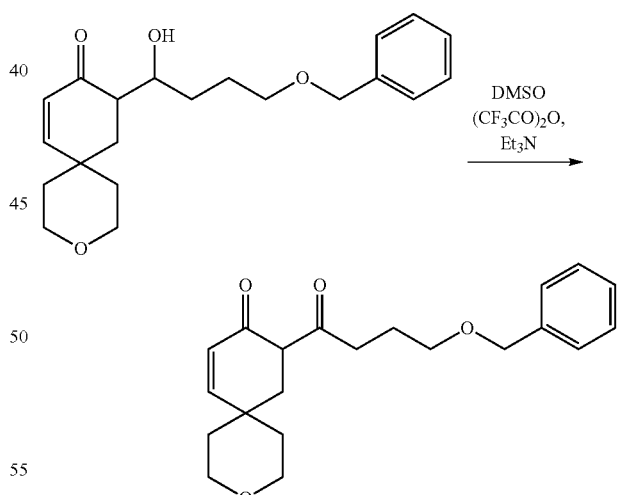

002

To a solution of DMSO (54.4 g, 697 mmol) in DCM (1.6 L) at −78° C., trifluoroacetic anhydride (73.2 mL, 523 mmol) was added and stirred for 30 min, then a solution of (R/S)-8-(4-benzyloxy-1-hydroxy-butyl)-3-oxaspiro[5.5]undec-10-en-9-one (120 g, 344.8 mmol) in DCM (400 mL) was added slowly at −78° C. and stirred for 1 h. On completion, the reaction mixture was treated with Et$_3$N (241 mL, 1740 mmol) followed by aq.NaHCO$_3$ solution and then extracted twice with DCM (500 mL×2). The combined organic layers were washed with brine (700 mL), dried over Na$_2$SO$_4$, concentrated in vacuo and the resulting residue was purified by silica gel column chromatography (30% EtOAc in petroleum ether) to afford the title compound as brown liquid.

$^1$H NMR (300 MHz, CDCl$_3$): δ 15.85 (s, 1H), 7.40-7.27 (m, 5H), 6.62 (d, J=9.9 Hz, 1H), 6.03 (d, J=9.9 Hz, 1H), 4.51 (s, 2H), 3.73-3.65 (m, 4H), 3.54 (t, J=6.0 Hz, 2H), 2.59-2.45 (m, 4H), 2.01-1.90 (m, 2H), 1.70-1.53 (m, 4H).

Preparation 3 (Compounds 003 and 004)

3-(3-Benzyloxypropyl)-1-ethyl-spiro[4H-indazole-5,4'-tetrahydropyran] and 3-(3-benzyloxypropyl)-2-ethyl-spiro[4H-indazole-5,4'-tetrahydropyran]

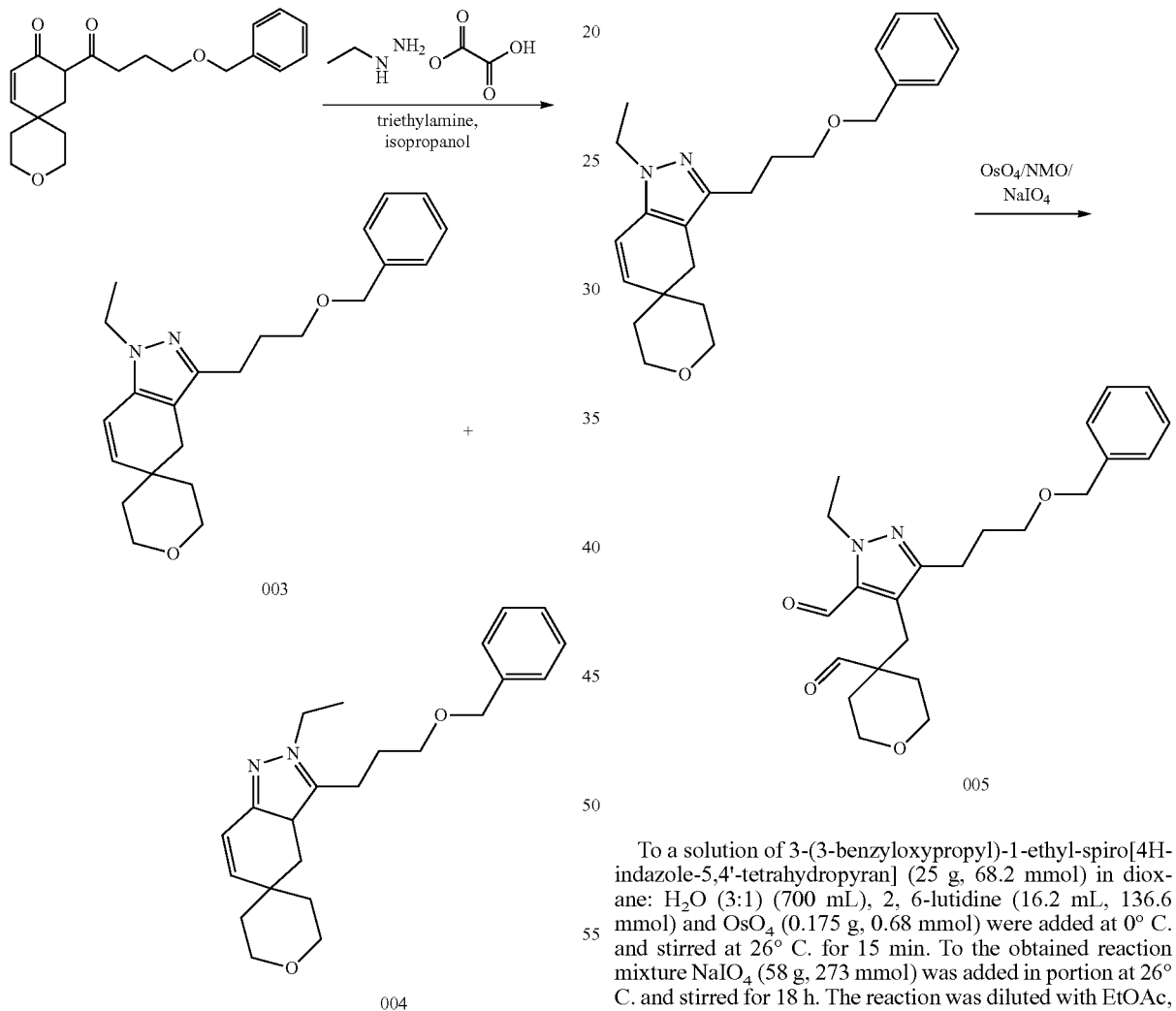

003

004

To a solution of 8-(4-benzyloxybutanoyl)-3-oxaspiro[5.5]undec-10-en-9-one (100 g, 292 mmol) in isopropanol (1.5 Liter), ethyl hydrazine oxalate (87.7 g, 584 mmol) and Et$_3$N (121 mL, 877 mmol) were added and stirred at reflux for 4 h. On completion, excess solvent was evaporated under vacuum and the resulting residue was purified by silica gel column chromatography (30% EtOAc in Pet ether) to afford 3-(3-benzyl-oxypropyl)-1-ethyl-spiro[4H-indazole-5,4'-tet-rahydropyran] and 3-(3-benzyloxy-propyl)-2-ethyl-spiro[4H-indazole-5,4'-tetrahydropyran], which was separated by Chiral SFC to afford 3-(3-benzyloxypropyl)-1-ethyl-spiro[4H-indazole-5,4'-tetrahydropyran] (Compound 003) as brown liquid.

NMR data for Compound 003:
$^1$H NMR (300 MHz, DMSO-d$_6$): δ 7.38-7.24 (m, 5H), 6.52 (d, J=10.1 Hz, 1H), 5.94 (d, J=10.1 Hz, 1H), 4.45 (s, 2H), 4.00 (q, J=7.1 Hz, 2H), 3.63-3.53 (m, 4H), 3.43 (t, J=6.5 Hz, 2H), 2.57-2.50 (m, 4H), 1.80 (m, 2H), 1.58-1.32 (m, 4H), 1.23 (t, J=7.2 Hz, 3H).

Preparation 4 (Compound 005)

5-(3-Benzyloxypropyl)-2-ethyl-4-[(4-formyltetrahydropyran-4-yl)methyl]pyrazole-3-carbaldehyde

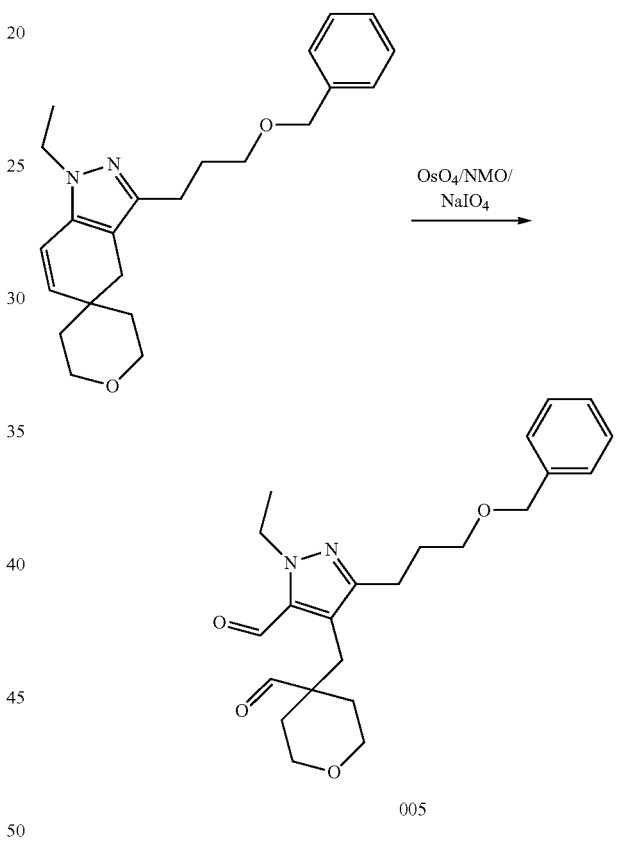

005

To a solution of 3-(3-benzyloxypropyl)-1-ethyl-spiro[4H-indazole-5,4'-tetrahydropyran] (25 g, 68.2 mmol) in dioxane: H$_2$O (3:1) (700 mL), 2, 6-lutidine (16.2 mL, 136.6 mmol) and OsO$_4$ (0.175 g, 0.68 mmol) were added at 0° C. and stirred at 26° C. for 15 min. To the obtained reaction mixture NaIO$_4$ (58 g, 273 mmol) was added in portion at 26° C. and stirred for 18 h. The reaction was diluted with EtOAc, the organic layer was washed with brine (250 mL), dried over Na$_2$SO$_4$, concentrated and the resulting residue was purified by silica gel column chromatography (30% EtOAc in petroleum ether) to afford the title compound as pale yellow liquid.

$^1$H NMR (400 MHz, CDCl$_3$): δ 9.82 (s, 1H), 9.55 (s, 1H), 7.37-7.27 (m, 5H), 4.50 (s, 2H), 4.48-4.42 (m, 2H), 3.82 (m, 2H), 3.50 (t, J=6.1 Hz, 2H), 3.34-3.26 (m, 2H), 2.80 (s, 2H), 2.66-2.60 (m, 2H), 2.05-1.89 (m, 4H), 1.64 (m, 2H), 1.40 (t, J=7.2 Hz, 3H).

Preparation 5 (Compound 006)

3-(3-Benzyloxypropyl)-1-ethyl-7-[(4-methoxyphenyl)methyl]spiro[6,8-dihydro-4H-pyrazolo[3,4-c]azepine-5,4'-tetrahydropyran]

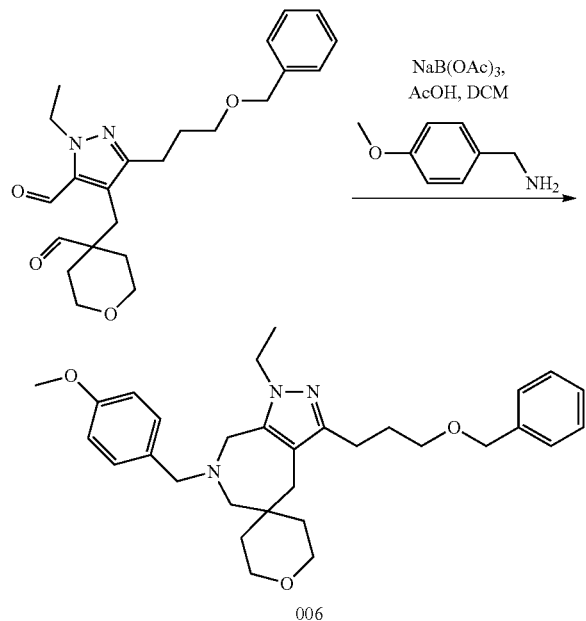

006

To a solution of 5-(3-benzyloxypropyl)-2-ethyl-4-[(4-formyltetrahydropyran-4-yl)methyl]pyrazole-3-carbaldehyde (23 g, 57.7 mmol) in DCM (1 L), 4-methoxy benzylamine (9.5 g, 69.2 mmol), and NaBH(OAc)$_3$ (36.7 g, 173 mmol) were added slowly at 0° C. and stirred at 26° C. for 16 h. On completion, the reaction mixture was diluted with DCM and washed with aq.NaHCO$_3$ (200 mL), dried over Na$_2$SO$_4$, concentrated in vacuo and the resulting residue was purified by silica gel column chromatography (30% EtOAc in petroleum ether) to afford the title compound as brown liquid.

$^1$H NMR (300 MHz, CDCl$_3$): δ 7.34 (d, J=4.4 Hz, 4H), 7.26-7.20 (m, 3H), 6.85 (d, J=8.4 Hz, 2H), 4.51 (s, 2H), 3.88-3.77 (m, 5H), 3.65-3.48 (m, 8H), 3.48-3.38 (m, 2H), 2.68-2.56 (m, 4H), 2.48 (s, 2H), 1.97-1.85 (m, 2H), 1.36 (t, J=5.3 Hz, 4H), 1.18 (t, J=7.2 Hz, 3H).

Preparation 6 (Compound 007)

3-(3-Benzyloxypropyl)-1-ethyl-7-[(4-methoxyphenyl)methyl]spiro[4,6-dihydro-pyrazolo[3,4-c]azepine-5,4'-tetrahydropyran]-8-one

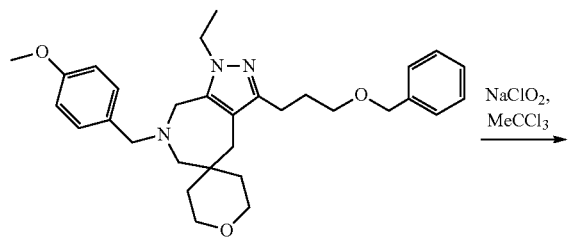

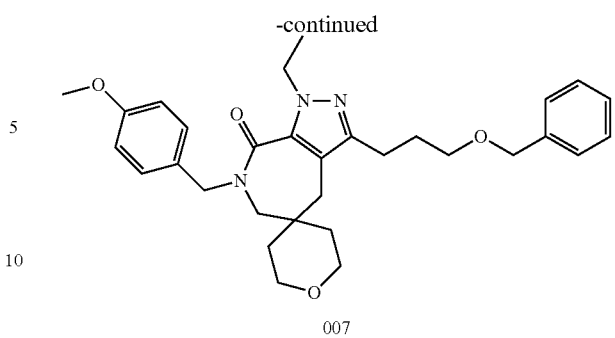

007

To a solution of 3-(3-benzyloxypropyl)-1-ethyl-7-[(4-methoxyphenyl)methyl]spiro-[6,8-dihydro-4H-pyrazolo[3,4-c]azepine-5,4'-tetrahydropyran] (5 g, 9.94 mmol) in CH$_3$CCl$_3$ (50 mL), NaClO$_2$ (1.78 g, 19.8 mmol) in H$_2$O (25 mL) was added and stirred at 60° C. for 1 h. On completion, the reaction mixture was diluted with DCM, and the organic layer was washed with H$_2$O (50 mL), dried over Na$_2$SO$_4$, concentrated in vacuo and the resulting residue was purified by silica gel column chromatography (30% EtOAc in petroleum ether) to afford title compound as pale brown liquid.

$^1$H NMR (300 MHz, CDCl$_3$): δ 7.37-7.28 (m, 4H), 7.27-7.22 (m, 3H), 6.92-6.84 (m, 2H), 4.67 (s, 2H), 4.52-4.37 (m, 4H), 3.80 (s, 3H), 3.69-3.56 (m, 4H), 3.50 (t, 3=6.3 Hz, 2H), 2.95 (s, 2H), 2.70-2.60 (m, 2H), 2.52 (s, 2H), 1.99-1.87 (m, 2H), 1.48-1.34 (m, 7H).

Preparation 7 (Compound 008)

1-Ethyl-3-(3-hydroxypropyl)spiro[6,7-dihydro-4H-pyrazolo[3,4-c]azepine-5,4'-tetrahydropyran]-8-one

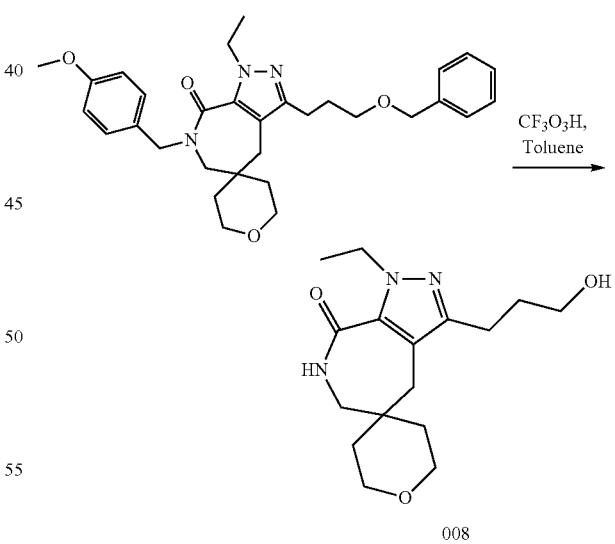

008

To a solution of 3-(3-benzyloxypropyl)-1-ethyl-7-[(4-methoxyphenyl)methyl]-spiro[4,6-dihydropyrazolo[3,4-c]azepine-5,4'-tetrahydropyran]-8-one (20 g, 38.6 mmol) in toluene (100 mL), CF$_3$SO$_3$H (20 mL, 232 mmol) was added at 0° C. and stirred at 26° C. for 3 h. On completion, the reaction mixture was neutralized with aq.NaHCO$_3$ solution, and extracted twice with EtOAc (200 mL×2). The combined organic layers were washed with brine (100 mL), dried over Na₂SO₄, concentrated and the resulting residue was purified by silica gel column chromatography (10% MeOH in DCM) to afford the title compound as white solid.

¹H NMR (400 MHz, DMSO-d₆) δ 8.01 (t, J=5.6 Hz, 1H), 4.43 (t, J=5.2 Hz, 1H), 4.29 (q, J=7.1 Hz, 2H), 3.68-3.50 (m, 4H), 3.48-3.37 (m, 2H), 2.89 (d, J=6.1 Hz, 2H), 2.52-2.44 (m, 3H), 1.74-1.64 (m, 2H), 1.44-1.34 (m, 4H), 1.27 (t, J=7.2 Hz, 3H).

HPLC-Retention time (XE Metode 7 CM): 1.66 minutes.

Detected "M+H"-mass: 308.19.

Preparation 8 (Compound 009)

3-(1-Ethyl-8-oxo-spiro[6,7-dihydro-4H-pyrazolo[3,4-c]azepine-5,4'-tetrahydropyran]-3-yl)propyl methanesulfonate

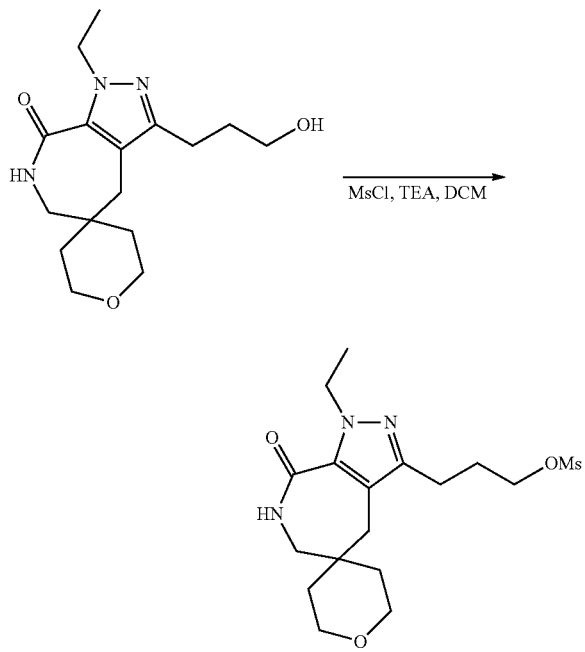

To a stirred solution of 1-ethyl-3-(3-hydroxypropyl)spiro[6,7-dihydro-4H-pyrazolo-[3,4-c]azepine-5,4'-tetrahydropyran]-8-one (1 g, 3.25 mmol) in DCM (20 mL), TEA (986 mg, 9.77 mmol) and mesyl chloride (556 mg, 4.88 mmol) were added at 0° C. The resulting reaction mixture was stirred for 2 h at RT. On completion, the reaction mixture was diluted with water (50 mL) and extracted twice with DCM (2×50 mL). The combined organic layers were washed with water (50 mL) and brine (50 mL), dried over anhydrous sodium sulfate and evaporated under vacuum to afford the title compound as pale yellow liquid (crude), which was used in the next step without further purification.

¹H NMR (300 MHz, CDCl₃) δ=5.96 (br t, J=5.7 Hz, 1H), 4.44 (q, J=7.1 Hz, 2H), 4.31 (t, J=6.2 Hz, 2H), 3.83-3.67 (m, 4H), 3.07-3.01 (m, 5H), 2.69 (t, J=7.3 Hz, 2H), 2.57 (s, 2H), 2.12 (quin, J=6.9 Hz, 2H), 1.54 (td, J=3.0, 5.7 Hz, 4H), 1.41 (t, J=7.3 Hz, 3H).

LCMS: 98% (M+H) 386.

Preparation 9 (Compound 010)

4-(1-Ethyl-8-oxo-spiro[6,7-dihydro-4H-pyrazolo[3,4-c]azepine-5,4'-tetrahydropyran]-3-yl)butanenitrile

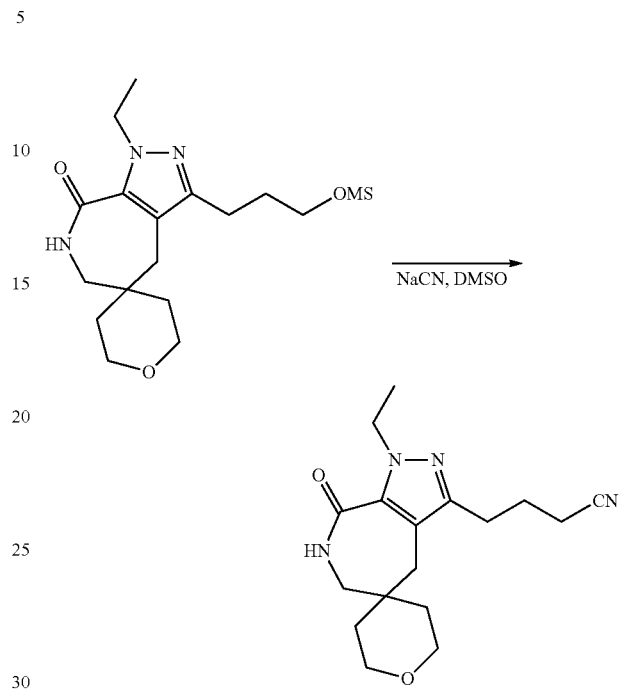

To a stirred solution of 3-(1-ethyl-8-oxo-spiro[6,7-dihydro-4H-pyrazolo[3,4-c]azepine-5,4'-tetrahydropyran]-3-yl)propyl methanesulfonate (1.2 g, 3.116 mmol) in DMSO (20 mL), NaCN (458 mg, 9.35 mmol) was added and it was stirred at 100° C. for 16 h. On completion, the reaction mixture was diluted with H₂O (50 mL) and extracted twice with EtOAc (2×50 mL). The combined organic layers were dried over anhydrous sodium sulfate and evaporated under vacuum afforded the title compound as pale yellow liquid (crude), which was used in the next step without further purification. 1H NMR (300 MHz, CDCl₃) δ=6.06 (br s, 1H), 4.44 (q, J=6.9 Hz, 2H), 3.82-3.63 (m, 4H), 3.05 (d, J=6.2 Hz, 2H), 2.72 (t, J=7.3 Hz, 2H), 2.62 (s, 2H), 2.58 (s, 2H), 2.45 (t, J=6.9 Hz, 2H), 2.04 (quin, J=7.1 Hz, 2H), 1.61-1.51 (m, 4H), 1.41 (t, J=7.1 Hz, 3H).

LCMS: 98% (M+H) 317.

Preparation 10 (Compound 011)

4-(1-Ethyl-8-oxo-spiro[6,7-dihydro-4H-pyrazolo[3,4-c]azepine-5,4'-tetrahydropyran]-3-yl)butanal

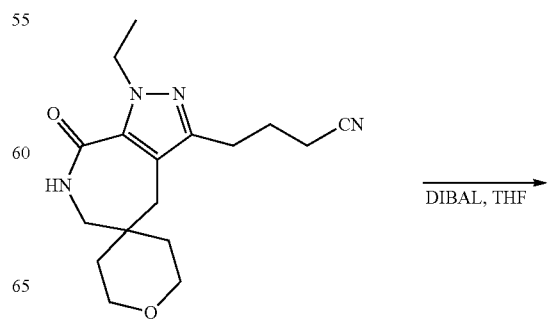

-continued

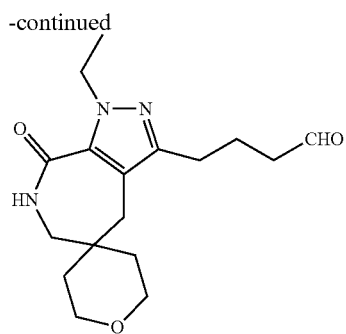

To a stirred solution of 4-(1-ethyl-8-oxo-spiro[6,7-dihydro-4H-pyrazolo[3,4-c]azepine-5,4'-tetrahydropyran]-3-yl)butanenitrile (1 g, 3.16 mmol) in THF (20 mL), diisobutyl-aluminum hydride (12.6 mL, 12.65 mmol, 1M in toluene) was added slowly at 0° C.

The mixture was stirred for 2 h at RT. On completion, the reaction mixture was quenched with saturated NH$_4$Cl and extracted twice with EtOAc (2×50 mL). The combined organic layers were washed with brine (50 mL), dried over anhydrous sodium sulfate and concentrated to afford the title compound as pale yellow liquid. The crude was used in the next step without further purification.

$^1$H NMR (300 MHz, CDCl$_3$) δ=9.77 (s, 1H), 5.89 (br s, 1H), 4.59-4.30 (m, 2H), 3.72 (br s, 4H), 3.11-2.95 (m, 2H), 2.67-2.51 (m, 4H), 2.36 (s, 2H), 2.08-1.88 (m, 2H), 1.48-1.19 (m, 7H).

Preparation 11 (Compound 012)

1-Ethyl-3-(4-hydroxybutyl)spiro[6,7-dihydro-4H-pyrazolo[3,4-c]azepine-5,4'-tetrahydropyran]-8-one

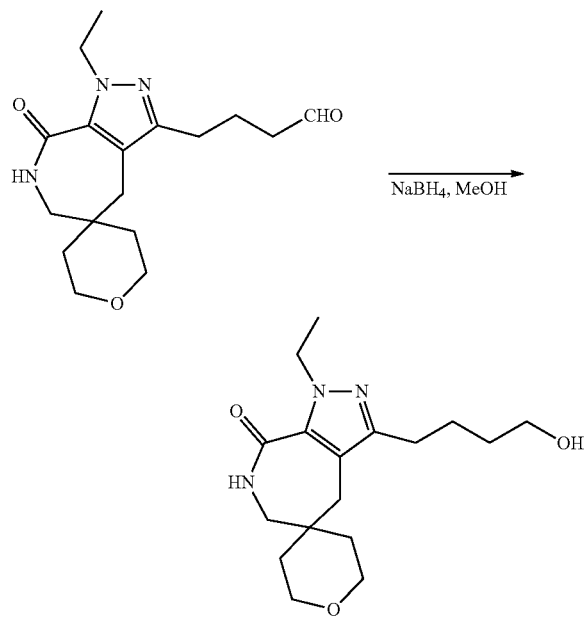

To a stirred solution of 4-(1-ethyl-8-oxo-spiro[6,7-dihydro-4H-pyrazolo[3,4-c]azepine-5,4'-tetrahydropyran]-3-yl)butanal (500 mg, 1.56 mol) in MeOH (10 mL), sodium borohydride (178 mg, 4.702 mmol) was added portion wise at 0° C. The mixture was stirred for 2 h at RT. On completion, the reaction mixture was diluted with H$_2$O (50 mL) and extracted twice with EtOAc (2×50 mL). The combined organic layers were dried over anhydrous sodium sulfate, concentrated and the resulting residue was purified by silica gel column chromatography (5% MeOH in DCM as eluent) to afford the title compound as off-white solid.

$^1$H NMR (300 MHz, DMSO-d$_6$) δ=8.01 (br t, J=5.7 Hz, 1H), 4.39-4.21 (m, 3H), 3.59 (qt, J=5.7, 11.6 Hz, 4H), 3.40 (q, J=6.2 Hz, 2H), 2.89 (d, J=5.9 Hz, 2H), 2.49-2.43 (m, 4H), 1.63-1.35 (m, 8H), 1.26 (t, J=7.2 Hz, 3H).

LCMS: 98% (M+H) 322.

HPLC-Retention time (XE Metode 7 CM): 1.70 minutes.

Detected "M+1"-mass: 322.21.

Preparation 12 (Compound 013)

3-(1-Ethyl-8-oxo-spiro[6,7-dihydro-4H-pyrazolo[3,4-c]azepine-5,4'-tetrahydropyran]-3-yl)propanoic acid

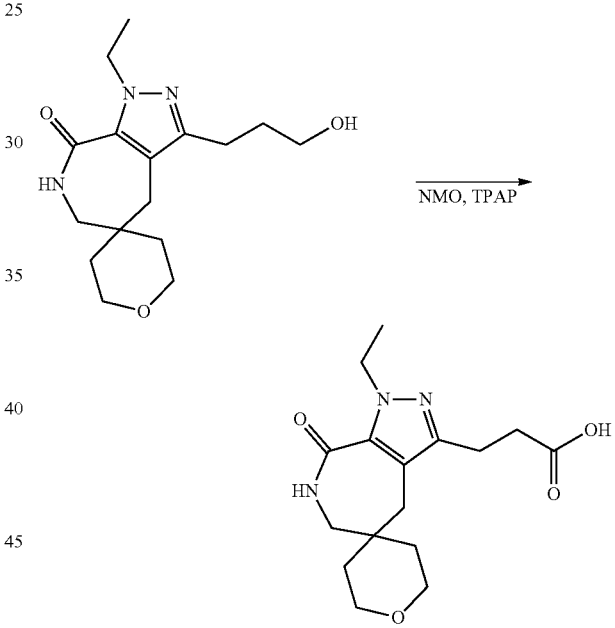

To a solution of 1-ethyl-3-(3-hydroxypropyl)spiro[6,7-dihydro-4H-pyrazolo[3,4-c]azepine-5,4'-tetrahydropyran]-8-one (1.0 g, 3.25 mmol) in acetonitrile (40 mL), 4-methylmorpholine N-oxide solution 50 wt. % in H$_2$O (3.07 g, 22.8 mmol) and tetrapropylammonium perruthenate (0.115 g, 0.325 mmol) were added slowly at 0° C. The mixture was stirred for 3 h at 26° C. On completion, the reaction mass was quenched with 2-propanol (1 mL) and then stirred at RT for 30 min. Volatiles were evaporated under vacuum and silica gel (100-200 mesh) column chromatography (0-10% MeOH in DCM as eluent) afforded the title compound as off-white solid.

$^1$H NMR (300 MHz, DMSO-d$_6$) δ=8.08-7.97 (m, 1H), 4.29 (q, J=7.0 Hz, 2H), 3.67-3.50 (m, 4H), 2.95-2.83 (m, 2H), 2.76-2.66 (m, 2H), 2.59-2.48 (m, 2H), 2.37 (br s, 2H), 1.47-1.32 (m, 4H), 1.31-1.17 (m, 3H).

LCMS: 96% (M+H) 322.

Preparation 13 (Compound 014)

1-Ethyl-3-(2-iodoethyl)spiro[6,7-dihydro-4H-pyrazolo[3,4-c]azepine-5,4'-tetrahydropyran]-8-one

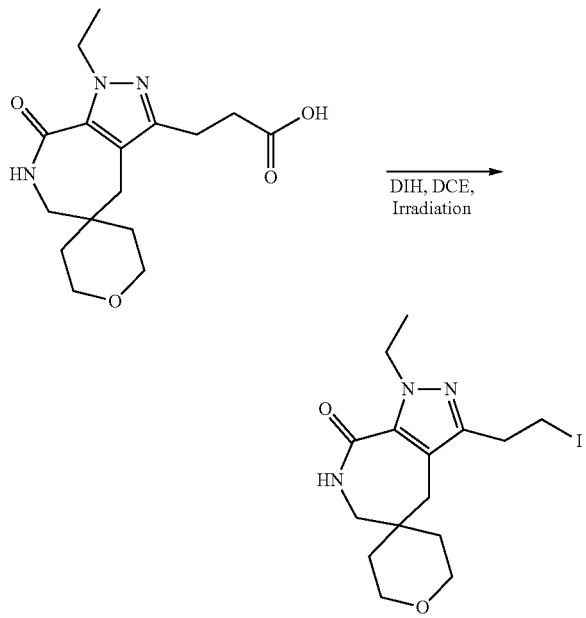

To a solution of 3-(1-ethyl-8-oxo-spiro[6,7-dihydro-4H-pyrazolo[3,4-c]azepine-5,4'-tetrahydropyran]-3-yl)propanoic acid (800 mg, 2.492 mmol) in 1,2-dichloroethene (30 mL), 1,3-diiodo-5,5-dimethylhydantoin (3.78 g, 9.968 mmol) was added slowly at 0° C. The mixture was irradiated under a 200 W tungsten filament lamp for 16 h. On completion, the reaction mass was quenched with aq. saturated NaHSO$_4$ (30 mL), then stirred at RT for 30 min. and finally extracted twice with DCM (2×50 mL). The combined organic phases were dried over anhydrous sodium sulfate, concentrated under reduced pressure and purified by silica gel (100-200 mesh) column chromatography (EtOAc as eluent) to afford the title compound as pale brown gummy.

$^1$H NMR (400 MHz, CDCl$_3$) δ=4.46 (q, J=7.0 Hz, 2H), 3.75-3.61 (m, 4H), 3.45-3.32 (m, 2H), 3.20-3.09 (m, 2H), 3.06 (d, J=6.4 Hz, 2H), 2.58 (s, 2H), 1.60-1.54 (m, 4H), 1.42 (t, J=7.1 Hz, 3H).
LCMS: 68% (M+H) 404.

Preparation 14 (Compound 015)

2-(1-Ethyl-8-oxo-spiro[6,7-dihydro-4H-pyrazolo[3,4-c]azepine-5,4'-tetrahydropyran]-3-yl)ethyl acetate

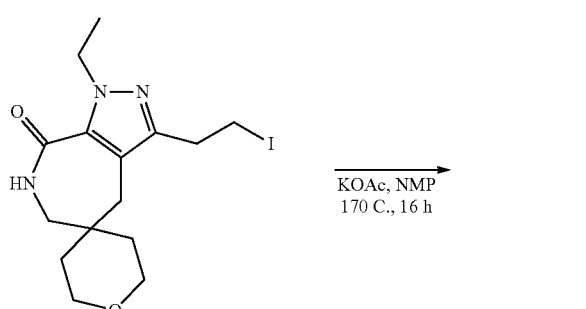

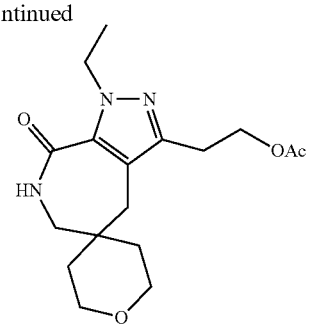

To a solution of 1-ethyl-3-(2-iodoethyl)spiro[6,7-dihydro-4H-pyrazolo[3,4-c]azepine-5,4'-tetrahydropyran]-8-one (350 mg, 0.868 mmol) in 1-methyl-2-pyrrolidone (10 mL), potassium acetate (340 mg, 3.473 mmol) was added slowly and stirred at 140° C. for 16 h. On completion, the reaction mass was diluted with ice cold water (30 mL), and then extracted three times with EtOAc (3×30 mL). The combined organic phases were dried over anhydrous sodium sulfate, concentrated under reduced pressure and purified by silica gel (100-200 mesh) column chromatography (EtOAc as eluent) to afford the title compound as light brown gummy.

$^1$H NMR (400 MHz, CDCl$_3$) δ=6.17-6.00 (m, 1H), 4.53-4.38 (m, 2H), 4.29 (t, J=7.3 Hz, 2H), 3.79-3.64 (m, 4H), 3.04 (d, J=5.9 Hz, 2H), 2.94-2.83 (m, 2H), 2.61 (s, 2H), 2.07-1.98 (m, 3H), 1.59-1.49 (m, 4H), 1.46-1.37 (m, 3H).
LCMS: 56% (M+H) 336.

Preparation 15 (Compound 016)

1-Ethyl-3-(2-hydroxyethyl)spiro[6,7-dihydro-4H-pyrazolo[3,4-c]azepine-5,4'-tetrahydropyran]-8-one

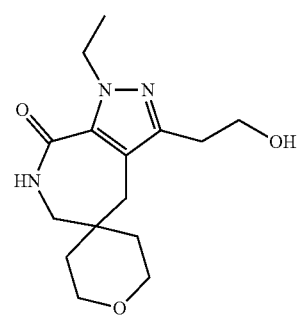

To a solution of 2-(1-ethyl-8-oxo-spiro[6,7-dihydro-4H-pyrazolo[3,4-c]azepine-5,4'-tetrahydropyran]-3-yl)ethyl acetate (110 mg, 0.328 mmol) in THF:H$_2$O (3:1, 4 mL), lithium hydroxide monohydrate (27 mg, 0.656 mmol) was added at 0° C. The mixture was stirred at 26° C. for 16 h. On completion, the reaction mass was diluted with water (30 mL) and extracted three times with EtOAc (3×30 mL). The combined organic phases were dried over anhydrous sodium sulfate, concentrated under reduced pressure and purified by Prep-HPLC to afford the title compound as off-white solid.

$^1$H NMR (400 MHz, DMSO-d$_6$) δ=8.02 (br t, J=5.6 Hz, 1H), 4.61 (br t, J=5.4 Hz, 1H), 4.29 (q, J=7.2 Hz, 2H), 3.68-3.51 (m, 6H), 2.88 (d, J=5.9 Hz, 2H), 2.66-2.64 (t, 2H), 2.47 (s, 2H), 1.46-1.32 (m, 4H), 1.27 (t, J=7.1 Hz, 3H).

LCMS: 99.8% (M+H) 294.

HPLC-Retention time (XE Metode 7 CM): 1.61 minutes. Detected "M+1"-mass: 294.18

Preparation 16 (Compound 017)

(4S)-4-Benzyl-3-[(2R)-2-methylpent-4-enoyl]oxazolidin-2-one

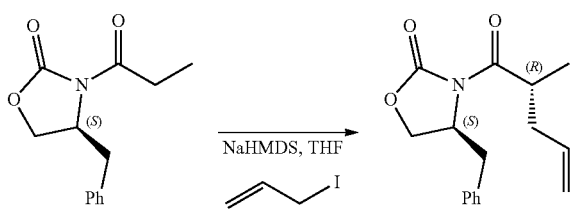

To a stirred solution of (S)-4-benzyl-3-propionyl oxazolidin-2-one (30 g, 128.755 mmol) in THF (50 mL), sodium bis(trimethylsilyl)amide (128.7 mL, 128.755 mmol, 1M in THF) was added slowly at −78° C. and the mixture was stirred at that temperature for 2 h. A solution of 3-iodo-1-propane (64.89 g, 386.265 mmol) was added to the reaction mixture at −78° C. and it was stirred for additionally 2 h. On completion, the reaction mixture was quenched with saturated NH$_4$Cl and extracted twice with EtOAc (2×200 mL). The combined organic layers were washed with brine (200 mL), dried over anhydrous sodium sulfate, concentrated and the resulting residue was purified by silica gel column chromatography (0-10% EtOAc in pet ether as elute) to afford the title compound as colorless liquid.

$^1$H NMR (400 MHz, CDCl$_3$) δ=7.36-7.30 (m, 2H), 7.30-7.27 (m, 1H), 7.24-7.19 (m, 2H), 5.83 (tdd, J=7.2, 10.0, 17.1 Hz, 1H), 5.17-5.00 (m, 2H), 4.75-4.61 (m, 1H), 4.28-4.07 (m, 2H), 3.94-3.80 (m, 1H), 3.29 (dd, J=3.4, 13.2 Hz, 1H), 2.70 (dd, J=10.0, 13.5 Hz, 1H), 2.53 (td, J=6.7, 13.9 Hz, 1H), 2.24 (td, J=7.0, 13.8 Hz, 1H), 1.19 (d, J=6.8 Hz, 3H).

LCMS: 84% (M+H) 274.

Preparation 17 (Compound 018)

(2R)-2-Methylpent-4-en-1-ol

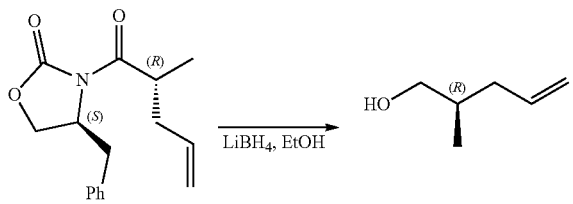

To a stirred solution of (4S)-4-benzyl-3-[(2R)-2-methylpent-4-enoyl]oxazolidin-2-one (30 g, 109.890 mmol) in diehtyl ether (600 mL), EtOH (6 g, 131.868 mmol) and lithium hydroborate (66 mL, 131.868 mmol, 2M in THF) was added slowly at 0° C. The mixture was stirred for 6 h at RT. On completion, the reaction mixture was quenched with saturated NH$_4$Cl (600 mL) and extracted twice with diethyl ether (2×300 mL). The combined organic layers were washed with brine (200 mL), dried over anhydrous sodium sulfate, concentrated and the resulting residue was purified by silica gel column chromatography (0-20% EtOAc in pet ether as elute) to afford the title compound as colorless liquid.

$^1$H NMR (400 MHz, CDCl$_3$) δ=5.82 (tdd, J=7.3, 10.0, 17.1 Hz, 1H), 5.13-4.94 (m, 2H), 3.55-3.42 (m, 2H), 2.24-2.11 (m, 1H), 1.95 (td, J=7.1, 14.2 Hz, 1H), 1.74 (qd, J=6.7, 13.1 Hz, 1H), 1.35 (br s, 1H), 0.93 (d, J=6.8 Hz, 3H).

Preparation 18 (Compound 019)

[(2R)-2-Methylpent-4-enoxy]methylbenzene

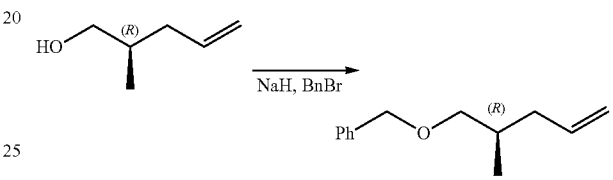

To a suspension of NaH (3.8 g, 160.0 mmol) in DMF (50 mL), (2R)-2-methylpent-4-en-1-ol (8 g, 80.0 mmol) and benzyl bromide (16.41 g, 96.0 mmol) was added slowly at 0° C. The mixture was stirred for 16 h at RT. On completion, the reaction mixture was quenched with cold water (100 mL) and extracted twice with diethyl ether (2×100 mL). The combined organic layers were washed with brine (100 mL), dried over anhydrous sodium sulfate, concentrated and the resulting residue was purified by silica gel column chromatography (0-10% DCM in pet ether as elute) to afford the title compound as colorless liquid.

$^1$H NMR (400 MHz, CDCl$_3$) δ=7.44-7.26 (m, 4H), 5.88-5.67 (m, 1H), 5.09-4.92 (m, 2H), 4.50 (s, 2H), 3.30 (dq, J=6.2, 9.1 Hz, 2H), 2.29-2.15 (m, 1H), 1.99-1.79 (m, 2H), 0.93 (d, J=6.6 Hz, 3H).

Preparation 19 (Compound 020)

(3R)-4-Benzyloxy-3-methyl-butanal

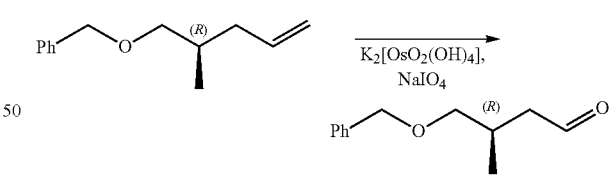

To a stirred solution of [(2R)-2-methylpent-4-enoxy]methylbenzene (10 g, 52.63 mmol) in acetone:H$_2$O (5:1, 1.3 L), potassium osmate (193 mg, 5.263 mmol 4M in H$_2$O) and sodium periodate (115.7 mmol) were added lot wise at 0° C. The mixture was stirred for 5 h at RT. On completion, the reaction mixture was filtered through a pad of celite and washed with diethyl ether. The combined organic phases were concentrated and the resulting residue was purified by silica gel column chromatography (0-10% EtOAc in Pet ether as elute) to afford the title compound as colorless liquid.

$^1$H NMR (400 MHz, CDCl$_3$) δ=9.76 (s, 1H), 7.43-7.22 (m, 5H), 4.49 (s, 2H), 3.42 (dd, J=5.1, 8.8 Hz, 1H), 3.33-3.18 (m, 1H), 2.64-2.49 (m, 1H), 2.42 (qd, J=6.3, 12.8 Hz, 1H), 2.34-2.21 (m, 1H), 0.99 (d, J=6.6 Hz, 3H).

Preparation 20 (Compound 021)

8-[(3R)-4-Benzyloxy-1-hydroxy-3-methyl-butyl]-3-oxaspiro[5.5]undec-10-en-9-one

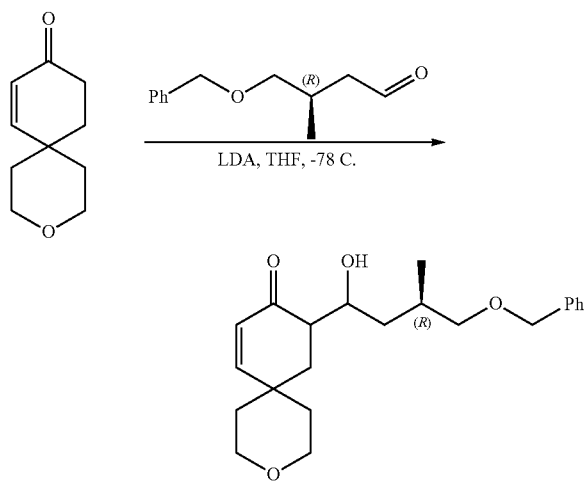

To a stirred solution of 9-oxaspiro[5.5]undec-4-en-3-one (5 g, 30.12 mmol) in THF (50 mL), lithium diisopropylamide (36 mL, 36.14 mmol, 1M in THF) was added slowly at −78° C. The mixture was stirred at that temperature for 1 h, after which (3R)-4-benzyloxy-3-methyl-butanal (6.9 g, 36.14 mmol) in THF (50 mL) were added at −78° C. The mixture was stirred for an additional 2 hours. On completion, the reaction mixture was quenched with saturated NH₄Cl and extracted twice with EtOAc (2×100 mL). The combined organic layers were washed with brine (100 mL), dried over anhydrous sodium sulfate, concentrated and the resulting residue was purified by silica gel column chromatography (0-30% EtOAc in Pet ether as elute) to afford the title compound as brown liquid.

¹H NMR (400 MHz, CDCl₃) showed a ~1:1 diastereomeric mixture; δ=7.42-7.27 (m, 5H), 6.91 (br d, J=9.9 Hz, 1H), 5.93 (d, J=9.9 Hz, 1H), 4.57-4.49 (m, 2H), 4.10-4.01 (m, 1H), 3.86-3.61 (m, 4H), 3.46-3.29 (m, 2H), 2.61-2.45 (m, 1H), 2.26-2.06 (m, 2H), 1.84-1.59 (m, 5H), 1.49-1.29 (m, 2H), 1.03 (d, J=6.9 Hz, 3/2H), 0.96 (d, J=6.6 Hz, 3/2H).

Preparation 21 (Compound 022)

8-[(3R)-4-Benzyloxy-3-methyl-butanoyl]-3-oxaspiro[5.5]undec-10-en-9-one

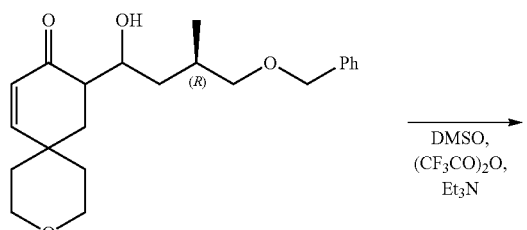

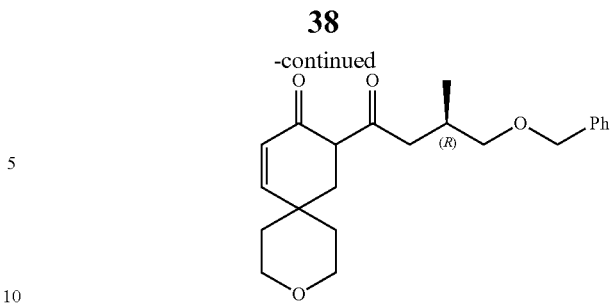

To a stirred solution of DMSO (2.73 mL, 39.10 mmol) in DCM (100 mL) at −78° C., trifluoroacetic anhydride (6 g, 29.32 mmol) was added. The mixture was stirred for 30 min, followed by addition of 8-[(3R)-4-benzyloxy-1-hydroxy-3-methyl-butyl]-3-oxaspiro[5.5]undec-10-en-9-one (7 g, 19.55 mmol) in DCM (50 mL) at −78° C. The mixture was stirred for 1 h. On completion, the reaction mixture was treated with Et₃N (11.8 g, 117.318 mmol) and allowed to reach RT followed by treatment with aq. NaHCO₃ solution. The mixture was extracted twice with DCM (2×200 mL). The combined organic layers were washed with brine (200 mL), dried over anhydrous sodium sulfate, concentrated and the resulting residue was purified by silica gel column chromatography (0-20% EtOAc in Pet ether) to afford the title compound as pale yellow liquid.

¹H NMR (400 MHz, CDCl₃) δ=15.90 (s, 1H), 7.41-7.27 (m, 5H), 6.64 (d, J=10.3 Hz, 1H), 6.03 (d, J=10.3 Hz, 1H), 4.51 (d, J=1.5 Hz, 2H), 3.72-3.63 (m, 4H), 3.46-3.38 (m, 1H), 3.37-3.32 (m, 1H), 2.65 (dd, J=5.4, 14.2 Hz, 1H), 2.50 (s, 2H), 2.38-2.26 (m, 1H), 2.23-2.15 (m, 1H), 1.68-1.59 (m, 2H), 1.57-1.49 (m, 2H), 1.01 (d, J=6.8 Hz, 3H).

LCMS: 92% (M+H) 357.

Preparation 22 (Compound 023)

3-[(2R)-3-Benzyloxy-2-methyl-propyl]spiro[1,4-dihydroindazole-5,4'-tetrahydropyran]

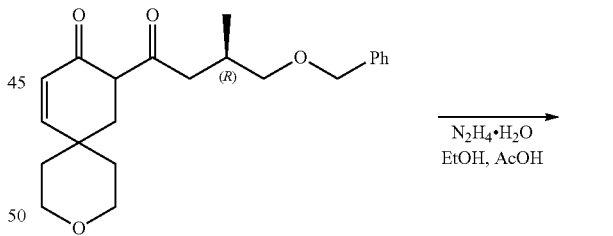

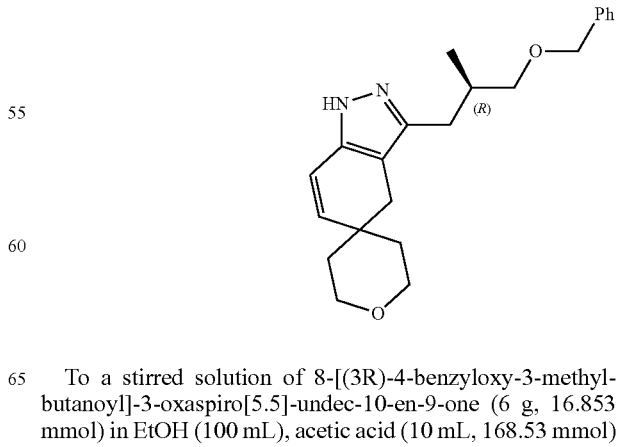

To a stirred solution of 8-[(3R)-4-benzyloxy-3-methyl-butanoyl]-3-oxaspiro[5.5]-undec-10-en-9-one (6 g, 16.853 mmol) in EtOH (100 mL), acetic acid (10 mL, 168.53 mmol)

and hydrazine monohydrate (1 mL, 20.22 mmol) were added. The mixture was stirred at RT for 16 h. On completion, excess solvent was evaporated under vacuum and the resulting residue was treatment with aq. NaHCO$_3$ solution. The mixture was extracted twice with EtOAc (2×100 mL). The combined organic layers were washed with brine (100 mL), dried over anhydrous sodium sulfate, concentrated and the resulting residue was purified by silica gel column chromatography (0-40% EtOAc in Pet ether as elute) to afford the title compound as pale yellow liquid.

$^1$H NMR (300 MHz, CDCl$_3$) δ=7.43-7.24 (m, 5H), 6.53 (d, J=9.9 Hz, 1H), 6.02 (d, J=10.3 Hz, 1H), 4.59-4.46 (m, 2H), 3.76-3.65 (m, 4H), 3.37 (dd, J=5.1, 9.2 Hz, 1H), 3.29-3.20 (m, 1H), 2.77-2.66 (m, 1H), 2.58 (br d, J=6.6 Hz, 1H), 2.52 (s, 2H), 2.19-2.06 (m, 1H), 1.71-1.60 (m, 2H), 1.58-1.46 (m, 2H), 0.91 (d, J=7.0 Hz, 3H).

LCMS: 95% (M+H) 353.

Preparation 23 (Compound 024)

3-[(2R)-3-Benzyloxy-2-methyl-propyl]-1-ethyl-spiro[4H-indazole-5,4'-tetrahydropyran]

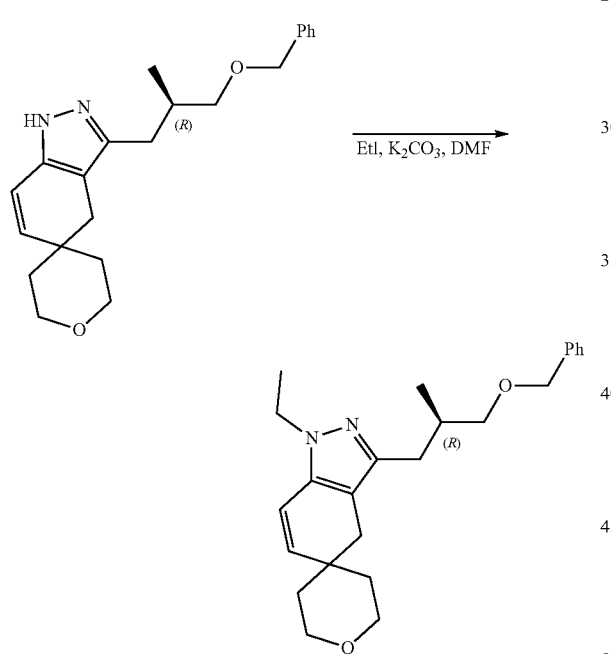

To a stirred solution of 3-[(2R)-3-benzyloxy-2-methyl-propyl]spiro[1,4-dihydro-indazole-5,4'-tetrahydropyran] (5.5 g, 15.62 mmol) in DMF (50 mL), K$_2$CO$_3$ (4.3 g, 31.25 mmol) and ethyl iodide (12 g, 78.125 mmol) were added. The mixture was stirred at 75° C. for 16 h. On completion, reaction was allowed reach to room temperature and diluted with H$_2$O (100 mL). The reaction mixture was extracted twice with EtOAc (2×150 mL). The combined organic layers were washed with H$_2$O (3×100 mL) and brine (100 mL), dried over anhydrous sodium sulfate and evaporated under vacuum to afford the title compound as brown liquid (crude), which was used in the next step without further purification.

$^1$H NMR (300 MHz, CDCl$_3$) δ=7.39-7.26 (m, 5H), 6.34 (d, J=9.9 Hz, 1H), 5.91 (d, J=9.9 Hz, 1H), 4.51 (s, 2H), 4.05 (q, J=7.3 Hz, 2H), 3.75-3.62 (m, 4H), 3.44-3.37 (m, 1H), 3.35-3.26 (m, 1H), 2.69 (dd, J=6.2, 13.9 Hz, 1H), 2.55 (d, J=1.5 Hz, 2H), 2.40 (dd, J=8.3, 14.1 Hz, 1H), 2.13 (td, J=6.8, 13.6 Hz, 1H), 1.69-1.60 (m, 2H), 1.58-1.47 (m, 2H), 1.36 (t, J=7.2 Hz, 3H), 0.96 (d, J=6.6 Hz, 3H).

LCMS: 92% (M+H) 353 (mixture of isomers).

Preparation 24 (Compound 025)

5-[(2R)-3-Benzyloxy-2-methyl-propyl]-2-ethyl-4-[(4-formyltetrahydropyran-4-yl)-methyl]pyrazole-3-carbaldehyde

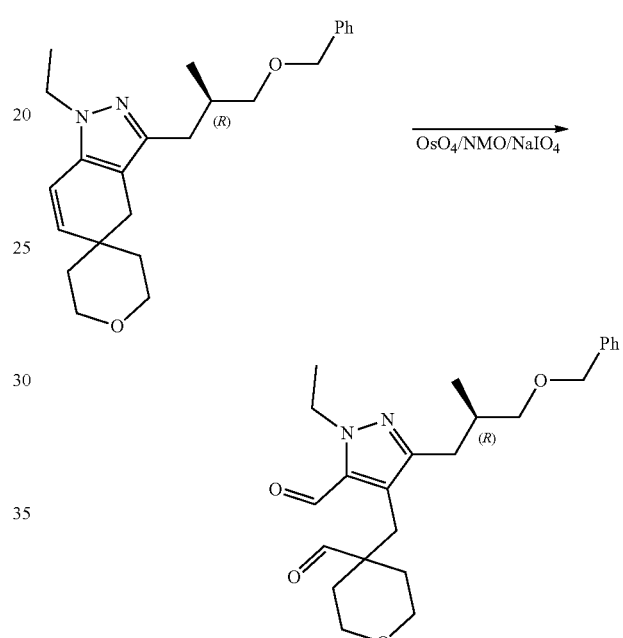

To a stirred solution of 3-[(2R)-3-benzyloxy-2-methyl-propyl]-1-ethyl-spiro[4H-indazole-5,4'-tetrahydropyran] (4.5 g, 12.784 mmol) in dioxane:H$_2$O (2:1, 60 mL), 2,6-lutidine (2.7 g, 25.56 mmol), N-methylmorpholine N-oxide (2.7 g, 23.56 mmol) and osmium tetraoxide (0.5 mL, 0.127 mmol) were added at 0° C. The mixture was stirred at RT for 1 h, followed by addition of sodium periodate (10.98 g, 51.136 mmol) at 25° C. The mixture was stirred for additionally 3 h. On completion, the reaction was quenched with saturated citric acid solution. The reaction mixture was extracted with EtOAc (200 mL) and the organic layer was washed with brine (100 mL), dried over anhydrous sodium sulfate and concentrated. The resulting residue was purified by silica gel column chromatography (0-30% EtOAc in Pet ether) to afford the title compound as pale yellow liquid.

$^1$H NMR (400 MHz, CDCl$_3$) δ=9.82 (s, 1H), 9.52 (s, 1H), 7.41-7.26 (m, 5H), 4.54-4.40 (m, 4H), 3.81 (br dd, J=3.4, 11.7 Hz, 2H), 3.36-3.23 (m, 4H), 2.86-2.75 (m, 2H), 2.75-2.69 (m, 1H), 2.38 (dd, J=7.8, 14.2 Hz, 1H), 2.20 (qd, J=6.5, 13.3 Hz, 1H), 1.89 (br dd, J=2.0, 13.7 Hz, 2H), 1.62 (tdd, J=4.2, 8.7, 17.2 Hz, 2H), 1.39 (t, 3=7.1 Hz, 3H), 0.97 (d, J=6.8 Hz, 3H).

LCMS: 79% (M+H) 413 (mixture of isomers).

Preparation 25 (Compound 026)

3-[(2R)-3-Benzyloxy-2-methyl-propyl]-1-ethyl-7-[(4-methoxyphenyl)methyl]-spiro[6,8-dihydro-4H-pyrazolo[3,4-c]azepine-5,4'-tetrahydropyran]

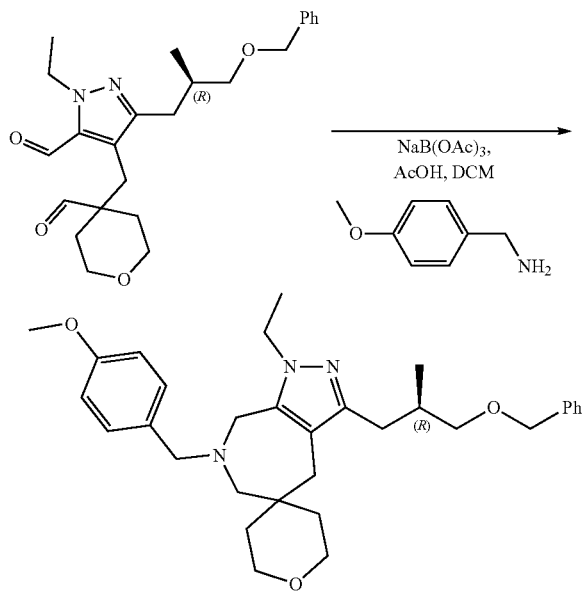

To a stirred solution of 5-[(2R)-3-benzyloxy-2-methyl-propyl]-2-ethyl-4-[(4-formyl-tetrahydropyran-4-yl)methyl]pyrazole-3-carbaldehyde (4 g, 9.7 mmol) in DCM (60 mL), 4-methoxy benzylamine (1.4 mL, 10.6 mmol), acetic acid (0.3 mL) and sodium triacetoxyhydroborate (6.1 g, 29.12 mmol) were added slowly at 0° C. The mixture was stirred at 26° C. for 16 h. On completion, the reaction mixture was diluted with DCM. The organic phase was washed with aq. NaHCO₃ (100 mL), dried over anhydrous sodium sulfate, concentrated and the resulting residue was purified by silica gel column chromatography (0-30% EtOAc in pet ether) to afford the title compound as colorless liquid.

¹H NMR (400 MHz, CDCl₃) δ=7.35-7.27 (m, 5H), 7.23 (d, J=8.8 Hz, 2H), 6.86 (d, J=8.8 Hz, 2H), 4.51 (s, 2H), 3.88-3.78 (m, 5H), 3.61 (s, 2H), 3.58 (br d, J=7.8 Hz, 1H), 3.55 (s, 2H), 3.46-3.41 (m, 1H), 3.38 (dd, J=5.9, 8.8 Hz, 1H), 3.33-3.28 (m, 1H), 2.70-2.62 (m, 3H), 2.53-2.41 (m, 2H), 2.31 (dd, J=8.1, 13.9 Hz, 1H), 2.11-2.05 (m, 1H), 1.40-1.32 (m, 4H), 1.17 (t, J=7.1 Hz, 3H), 0.95 (d, J=6.4 Hz, 3H).

LCMS: 95% (M+H) δ18 (mixture of isomers).

Preparation 26 (Compound 027)

3-[(2R)-3-Benzyloxy-2-methyl-propyl]-1-ethyl-7-[(4-methoxyphenyl)methyl]-spiro[4,6-dihydropyrazolo[3,4-c]azepine-5,4'-tetrahydropyran]-8-one

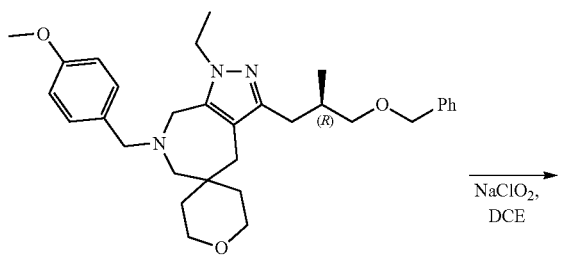

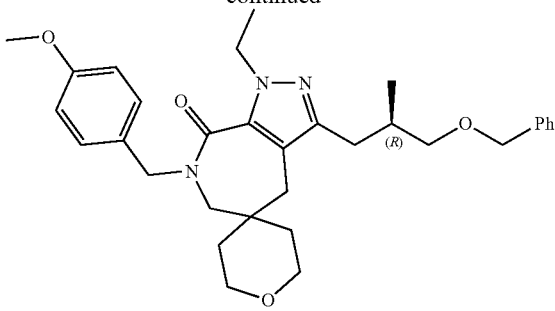

To a stirred solution of 3-[(2R)-3-benzyloxy-2-methyl-propyl]-1-ethyl-7-[(4-methoxyphenyl)methyl]spiro[6,8-dihydro-4H-pyrazolo[3,4-c]azepine-5,4'-tetrahydropyran] (4 g, 7.73 mmol) in 1,2-dichloroethene (40 mL), sodium chlorite (1 g, 11.60 mmol) in H₂O (20 mL) was added. The mixture was stirred at 27° C. for 2 h. On completion, the reaction mixture was diluted with DCM, and the organic layer was washed with H₂O (2×100 mL), dried over anhydrous sodium sulfate, concentrated and the resulting residue was purified by silica gel column chromatography (0-40% EtOAc in pet ether) to afford the title compound as colorless liquid.

¹H NMR (400 MHz, DMSO-d₆) δ=7.37-7.22 (m, 7H), 6.91 (d, J=8.8 Hz, 2H), 4.60 (s, 2H), 4.45 (s, 2H), 4.29 (q, J=7.0 Hz, 2H), 3.74 (s, 3H), 3.56-3.46 (m, 4H), 3.35-3.22 (m, 4H), 2.62 (dd, J=6.4, 14.2 Hz, 1H), 2.44 (s, 2H), 2.31 (dd, J=7.8, 14.2 Hz, 1H), 2.06-1.97 (m, 1H), 1.35-1.22 (m, 7H), 0.89 (d, J=6.8 Hz, 3H).

LCMS: 77% (M+H) δ32.

Preparation 27 (Compound 028)

1-Ethyl-3-[(2R)-3-hydroxy-2-methyl-propyl]spiro[6,7-dihydro-4H-pyrazolo[3,4-c]azepine-5,4'-tetrahydropyran]-8-one

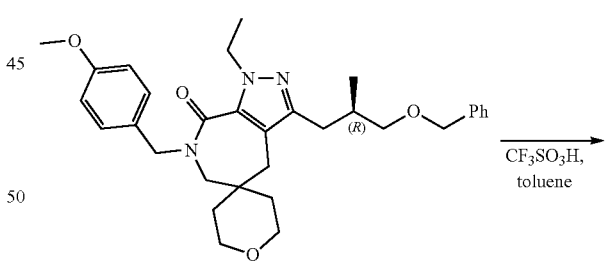

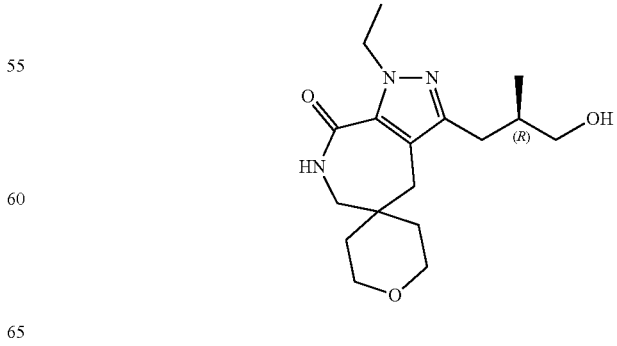

To a stirred solution of 3-[(2R)-3-benzyloxy-2-methyl-propyl]-1-ethyl-7-[(4-methoxyphenyl)methyl]spiro[4,6-dihydropyrazolo[3,4-c]azepine-5,4'-tetrahydropyran]-8-one (2 g, 3.76 mmol) in toluene (20 mL), trifluoromethanesulfonic acid (5.6 g, 37.6 mmol) was added at 0° C. The mixture was stirred at 26° C. for 3 h. On completion, the reaction mixture was neutralized with aq. NaHCO₃ solution, and extracted ten times with EtOAc (10×50 mL). The combined organic layers were dried over anhydrous sodium sulfate, concentrated and the resulting residue was purified by silica gel column chromatography (0-5% MeOH in DCM) to afford the title compound as off-white solid.

¹H NMR (400 MHz, DMSO-d₆) δ=8.01 (br t, J=5.4 Hz, 1H), 4.48 (t, J=5.1 Hz, 1H), 4.29 (q, J=7.3 Hz, 2H), 3.67-3.48 (m, 4H), 3.29-3.21 (m, 2H), 2.88 (br d, J=5.9 Hz, 2H), 2.60 (dd, J=5.4, 14.2 Hz, 1H), 2.45 (s, 2H), 2.19 (dd, J=8.6, 13.9 Hz, 1H), 1.80 (dt, J=6.6, 13.3 Hz, 1H), 1.45-1.32 (m, 4H), 1.26 (t, J=7.1 Hz, 3H), 0.81 (d, J=6.4 Hz, 3H).

LCMS: 99% (M+H) 322.

HPLC-Retention time (XE Metode 7 CM): 1.72 minutes. Detected "M+1"-mass: 322.21

Preparation 28 (Compound 029)

3-Benzyloxy-2,2-dimethyl-propan-1-ol

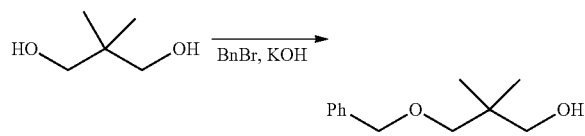

To a stirred solution of 2,2-dimethyl propane-1,3-diol (100 g, 961.153 mmol) in toluene (1000 mL), potassium hydroxide (53.84 g, 961.5 mmol) and benzyl bromide (34 mL, 288.4 mmol) were added at 0° C. The resulting reaction mixture was stirred for 12 h at RT. On completion, the reaction mixture was diluted with H₂O (1000 mL) and extracted twice with EtOAc (2×1000 mL). The combined organic layers were washed with H₂O (500 mL) and brine (500 mL), dried over anhydrous sodium sulfate and evaporated under vacuum. The resulting residue was purified by silica gel column chromatography (0-7% EtOAc in Pet ether as elute) to afford the title compound as colorless liquid.

¹H NMR (400 MHz, CDCl₃) δ=7.40-7.23 (m, 5H), 4.51 (s, 2H), 3.46 (s, 2H), 3.32 (s, 2H), 2.60 (br s, 1H), 0.93 (s, 6H).

LCMS: 86% (M+H) 234.

Preparation 29 (Compound 030)

(3-Benzyloxy-2,2-dimethyl-propyl) methanesulfonate

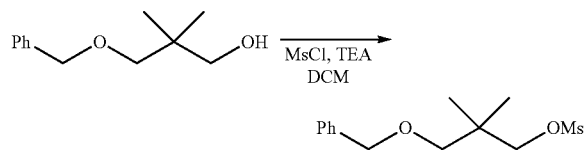

To a stirred solution of 3-benzyloxy-2,2-dimethyl-propan-1-ol (55 g, 283.5 mmol) in DCM (1000 mL), TEA (119 mL, 850 mmol) and mesyl chloride (32.7 mL, 425.0) were added at 0° C. The mixture was stirred for 3 h at RT. On completion, the reaction mixture was diluted with H₂O (500 mL) and extracted twice with EtOAc (2×1000 mL). The combined organic layers were washed with H₂O (500 mL) and brine (500 mL), dried over anhydrous sodium sulfate and evaporated under vacuum to afford the title compound as pale yellow liquid (crude), which was used in the next step without further purification.

¹H NMR (400 MHz, CDCl₃) δ=7.44-7.26 (m, 5H), 4.50 (s, 2H), 4.05 (s, 2H), 3.25 (s, 2H), 2.94 (s, 3H), 0.99 (s, 6H).

LCMS: 89% (M+Na) 295.

Preparation 30 (Compound 031)

4-Benzyloxy-3,3-dimethyl-butanenitrile

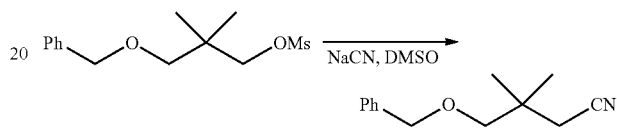

To a stirred solution of (3-benzyloxy-2,2-dimethyl-propyl) methanesulfonate (70 g, 257.35 mmol) in DMSO (500 mL), sodium cyanide (37.83 g, 772.05 mmol) was added at RT. The mixture was stirred for 90 h at 110° c. On completion, the reaction mixture was diluted with H₂O (1 L) and extracted twice with EtOAc (2×1.5 L). The combined organic layers were washed with H₂O (500 mL) and brine (500 mL), dried over anhydrous sodium sulfate, concentrated and the resulting residue was purified by silica gel column chromatography (0-10% EtOAc in Pet ether as elute) to afford the title compound as colorless liquid.

¹H NMR (400 MHz, CDCl₃) δ=7.41-7.25 (m, 5H), 4.52 (s, 2H), 3.24 (s, 2H), 2.37 (s, 2H), 1.08 (s, 6H).

LCMS: 71% (M+H) 204.

Preparation 31 (Compound 032)

4-Benzyloxy-3,3-dimethyl-butanal

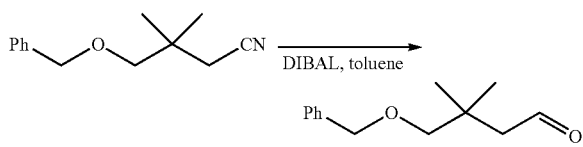

To a stirred solution of 4-benzyloxy-3,3-dimethyl-butanenitrile (30 g, 147.78 mol) in toluene (500 mL), diisobutylaluminum hydride (221.6 mL, 221.67 mmol, 1M in toluene) were added at −8° C. The mixture was stirred for 4 h at RT. On completion, the reaction mixture was quenched with saturated NH₄Cl, filtered through a pad of celite, washed with EtOAc and concentrated. The resulting residue was purified by silica gel column chromatography (0-5% EtOAc in Pet ether as elute) to afford the title compound as colorless liquid.

¹H NMR (300 MHz, CDCl₃) δ=9.82 (t, J=2.9 Hz, 1H), 7.43-7.25 (m, 5H), 4.50 (s, 2H), 3.24 (s, 2H), 2.34 (d, J=2.9 Hz, 2H), 1.08 (s, 6H).

LCMS: 83% (M+H) 208.

Preparation 32 (Compound 033)

8-(4-Benzyloxy-1-hydroxy-3,3-dimethyl-butyl)-3-oxaspiro[5.5]undec-10-en-9-one

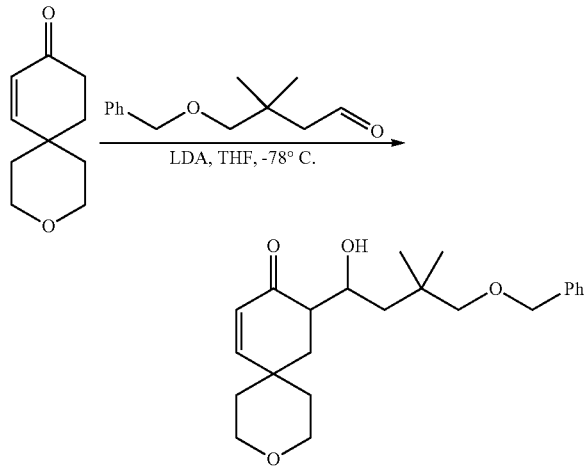

To a stirred solution of 9-oxaspiro[5.5]undec-4-en-3-one (7 g, 42.168 mmol) in THF (120 mL), lithium diisopropylamide (25.3 mL, 50.602 mmol, 1M in THF) was added slowly at −78° C. The mixture was stirred at that temperature for 1 h after which 4-benzyloxy-3,3-dimethyl-butanal (10.4 g, 50.602 mmol) in THF (50 mL) was added at −78° C. and the mixture was stirred for another 2 h. On completion, the reaction mixture was quenched with saturated NH₄Cl and extracted twice with EtOAc (2×200 mL). The combined organic layers were washed with brine (100 mL), dried over anhydrous sodium sulfate, concentrated and the resulting residue was purified by silica gel column chromatography (30% EtOAc in Pet ether as elute) to afford the title compound as brown liquid.

¹H NMR showed as a diastereomeric mixture ~1.5:1 ratio.

¹H NMR (400 MHz, CDCl₃) δ=7.40-7.26 (m, 5H), 6.91-6.81 (m, 1H), 5.99-5.85 (m, 1H), 4.56-4.50 (m, 2H), 4.47-4.29 (m, 1H), 3.85-3.63 (m, 4H), 3.30-3.25 (m, 2H), 2.68 (td, J=4.4, 14.2 Hz, 1H), 2.43-2.26 (m, 1H), 1.78-1.50 (m, 6H), 1.08-1.01 (m, 3H), 0.99-0.91 (m, 3H).

LCMS: 72% (M+H) 373.

Preparation 33 (Compound 034)

8-(4-Benzyloxy-3,3-dimethyl-butanoyl)-3-oxaspiro[5.5]undec-10-en-9-one

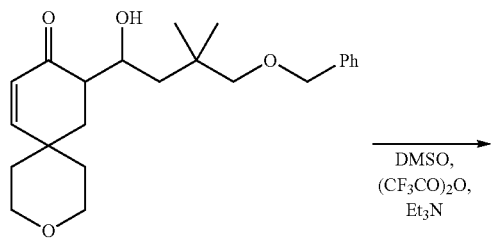

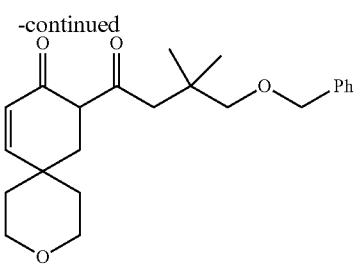

To a stirred solution of DMSO (3.4 mL, 48.38 mmol) in DCM (120 mL) at −78° C., trifluoroacetic anhydride (5.1 g, 36.48 mmol) was added. The mixture was stirred for 30 min, followed by addition of 8-(4-benzyloxy-1-hydroxy-3,3-dimethyl-butyl)-3-oxaspiro[5.5]undec-10-en-9-one (9 g, 24.193 mmol) in DCM (50 mL) at −78° C. The mixture was subsequently stirred for another hour. On completion, the reaction mixture was treated with Et₃N (16.9 mL, 120.96 mmol) and allowed to reach RT followed by treatment with aq. NaHCO₃ solution. The mixture was extracted twice with DCM (2×200 mL). The combined organic layers were washed with brine (200 mL), dried over anhydrous sodium sulfate, concentrated and the resulting residue was purified by silica gel column chromatography (0-20% EtOAc in Pet ether) to afford the title compound as pale yellow liquid.

¹H NMR (300 MHz, CDCl₃) δ=16.04 (s, 1H), 7.40-7.27 (m, 5H), 6.69 (d, J=10.2 Hz, 1H), 6.04 (d, J=10.2 Hz, 1H), 4.53 (s, 2H), 3.73-3.65 (m, 4H), 3.26 (s, 2H), 2.42 (s, 2H), 1.66-1.55 (m, 4H), 1.06 (s, 6H).

LCMS: 90% (M+H) 371.

Preparation 34 (Compound 035)

3-(3-Benzyloxy-2,2-dimethyl-propyl)spiro[1,4-dihydroindazole-5,4'-tetrahydropyran]

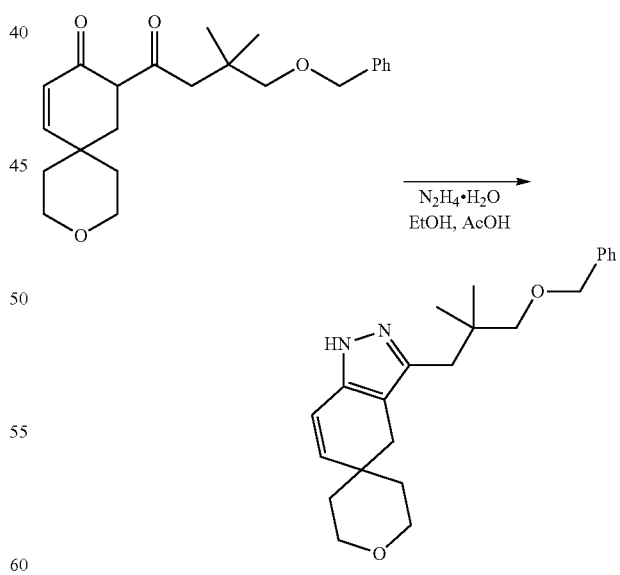

To a stirred solution of 8-(4-benzyloxy-3,3-dimethyl-butanoyl)-3-oxaspiro[5.5]undec-10-en-9-one (6 g, 16.21 mmol) in EtOH (120 mL), AcOH (9.7 mL, 162.16 mmol) and hydrazine monohydrate (0.9 mL, 162.16 mmol) were added. The mixture was stirred at RT for 16 h. On completion, excess solvent was evaporated under vacuum and the resulting residue was treatment with aq. NaHCO₃ solution. The mixture was extracted twice with EtOAc (2×200 mL). The combined organic layers were washed with brine (100 mL), dried over anhydrous sodium sulfate, concentrated and the resulting residue was purified by silica gel column chromatography (0-40% EtOAc in Pet ether as elute) to afford the title compound as pale yellow liquid.

¹H NMR (300 MHz, CDCl₃) δ=7.44-7.26 (m, 5H), 6.54 (d, J=9.9 Hz, 1H), 6.02 (d, J=9.9 Hz, 1H), 4.56 (s, 2H), 3.78-3.64 (m, 4H), 3.10 (s, 2H), 2.57 (s, 2H), 2.52 (s, 2H), 1.71-1.45 (m, 4H), 0.94 (s, 6H).

LCMS: 94% (M+H) 367.

Preparation 35 (Compound 036)

3-(3-Benzyloxy-2,2-dimethyl-propyl)-1-ethyl-spiro[4H-indazole-5,4'-tetrahydropyran]

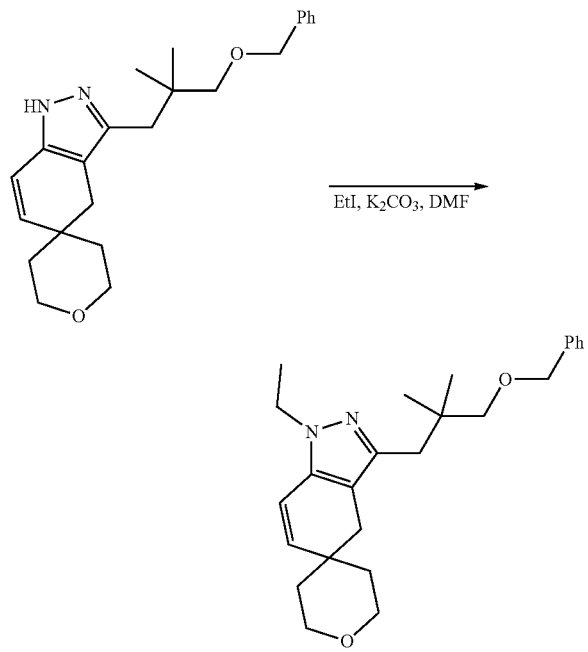

To a stirred solution of 3-(3-benzyloxy-2,2-dimethyl-propyl)spiro[1,4-dihydroindazole-5,4'-tetrahydropyran] (4 g, 10.92 mmol) in DMF (20 mL), K₂CO₃ (3 g, 21.85 mmol) and ethyl iodide (2.6 mL, 32.78 mmol) were added. The mixture was stirred at 75° C. for 16 h. On completion, the reaction mixture was allowed to reach room temperature before it was diluted with H₂O (100 mL) and extracted twice with EtOAc (2×200 mL). The combined organic layers were washed with H₂O (3×100 mL) and brine (100 mL), dried over anhydrous sodium sulfate and evaporated under vacuum to afford the title compound as brown liquid (crude), which was used in the next step without further purification.

¹H NMR (300 MHz, CDCl₃) δ=7.41-7.26 (m, 5H), 6.34 (d, J=9.9 Hz, 1H), 5.91 (d, J=9.9 Hz, 1H), 4.54 (s, 2H), 4.06 (q, J=7.2 Hz, 2H), 3.73-3.64 (m, 4H), 3.20 (s, 2H), 2.54 (s, 4H), 1.69-1.50 (m, 4H), 1.36 (t, J=7.3 Hz, 3H), 0.95 (s, 6H).

LCMS: 91% (M+H) 395 (mixture of isomers).

Preparation 36 (Compound 037)

5-(3-benzyloxy-2,2-dimethyl-propyl)-2-ethyl-4-[(4-formyltetrahydropyran-4-yl)methyl]pyrazole-3-carbaldehyde

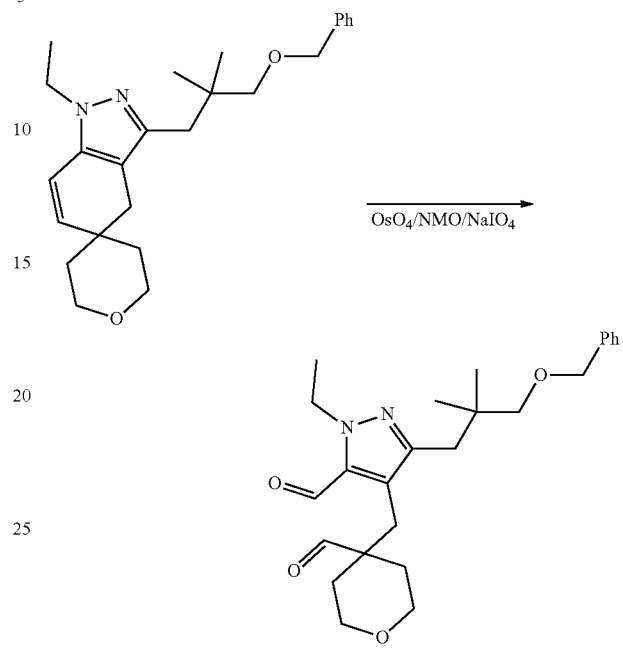

To a stirred solution of 3-(3-benzyloxy-2,2-dimethyl-propyl)-1-ethyl-spiro[4H-indazole-5,4'-tetrahydropyran] (3 g, 7.614 mmol) in dioxane:H₂O (2:1, 60 mL), 2,6-lutidine (1.8 mL, 15.228 mmol), N-methylmorpholine N-oxide (1.6 g, 13.7 mmol) and osmium tetraoxide (0.5 mL, 0.152 mmol) were added at 0° C. The mixture was stirred at RT for 1 h, followed by addition of NaIO₄ (6.4 g, 30.45 mmol) at 25° C. The mixture was then stirred for additionally 3 hours. On completion, the reaction was quenched with saturated citric acid solution and later diluted with EtOAc (200 mL). The organic layer was washed with brine (100 mL), dried over anhydrous sodium sulfate, concentrated and the resulting residue was purified by silica gel column chromatography (0-30% EtOAc in Pet ether) to afford the title compound as pale yellow liquid.

¹H NMR (400 MHz, CDCl₃) δ=9.81 (s, 1H), 9.46 (s, 1H), 7.39-7.27 (m, 5H), 4.55-4.44 (m, 4H), 3.78 (br dd, J=2.9, 11.7 Hz, 2H), 3.26 (dt, J=2.0, 12.0 Hz, 2H), 3.07 (s, 2H), 2.83 (s, 2H), 2.58 (s, 2H), 1.83 (dd, J=1.5, 13.2 Hz, 2H), 1.61-1.53 (m, 2H), 1.39 (t, J=7.3 Hz, 3H), 0.96 (s, 6H).

LCMS: 95% (M+H) 427 (mixture of isomers).

Preparation 37 (Compound 038)

3-(3-Benzyloxy-2,2-dimethyl-propyl)-1-ethyl-7-[(4-methoxyphenyl)methyl]spiro[6,8-dihydro-4H-pyrazolo[3,4-c]azepine-5,4'-tetrahydropyran]

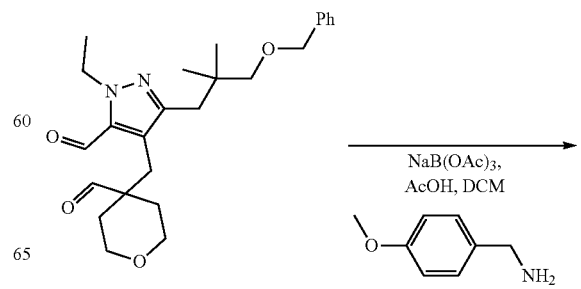

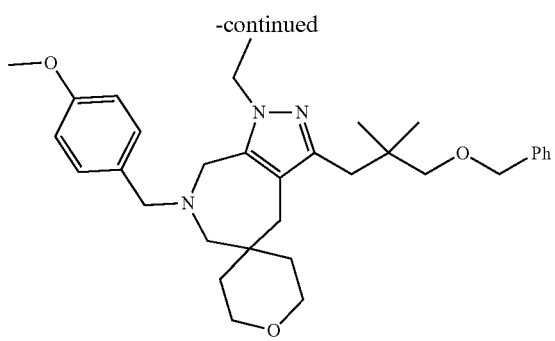

To a stirred solution of 5-(3-benzyloxy-2,2-dimethyl-propyl)-2-ethyl-4-[(4-formyl-tetrahydropyran-4-yl)methyl]pyrazole-3-carbaldehyde (3 g, 7.04 mmol) in DCM (60 mL), 4-methoxy benzylamine (1.2 mL, 9.15 mmol), acetic acid (0.5 mL) and sodium triacetoxyhydroborate (4.4 g, 21.12 mmol) were added slowly at 0° C. The mixture was stirred at 26° C. for 16 h. On completion, the reaction mixture was diluted with DCM. The organic phase was washed with aq. NaHCO$_3$ (100 mL), dried over anhydrous sodium sulfate, concentrated and the resulting residue was purified by silica gel column chromatography (0-30% EtOAc in Pet ether) to afford the title compound as colorless liquid.

$^1$H NMR (400 MHz, CDCl$_3$) δ=7.38-7.29 (m, 4H), 7.28-7.22 (m, 3H), 6.85 (d, J=8.8 Hz, 2H), 4.52 (s, 2H), 3.84 (q, J=7.2 Hz, 2H), 3.80 (s, 3H), 3.60 (s, 2H), 3.57-3.50 (m, 4H), 3.45-3.37 (m, 2H), 3.17 (s, 2H), 2.63 (s, 2H), 2.51 (s, 2H), 2.48 (s, 2H), 1.31 (br t, J=5.4 Hz, 4H), 1.16 (t, J=7.1 Hz, 3H), 0.93 (s, 6H).

LCMS: 97.5% (M+H) δ32 (mixture of isomers).

Preparation 38 (Compound 039)

3-(3-benzyloxy-2,2-dimethyl-propyl)-1-ethyl-7-[(4-methoxyphenyl)methyl]spiro[4,6-dihydropyrazolo[3,4-c]azepine-5,4'-tetrahydropyran]-8-one

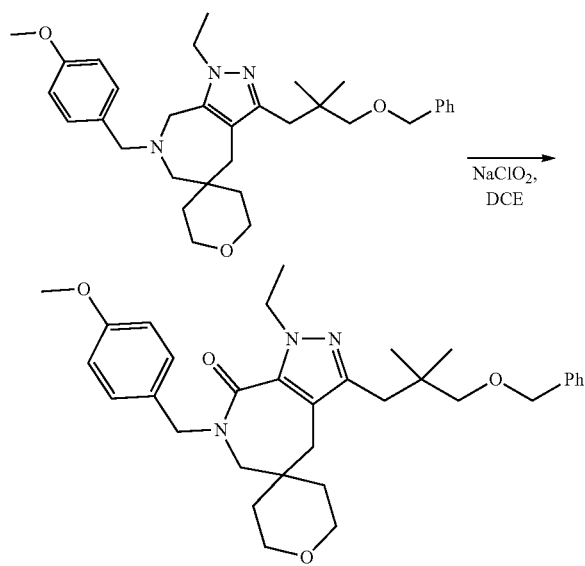

To a stirred solution of 3-(3-benzyloxy-2,2-dimethyl-propyl)-1-ethyl-7-[(4-methoxy-phenyl)methyl]spiro[6,8-dihydro-4H-pyrazolo[3,4-c]azepine-5,4'-tetrahydropyran] (2.5 g, 4.708 mmol) in 1,2-dichloroethene (40 mL), sodium chlorite (635 mg, 7.06 mmol) in H$_2$O (10 mL) was added. The mixture was stirred at 27° C. for 2 h. On completion, the reaction mixture was diluted with DCM, and the organic layer was washed with H$_2$O (2×100 mL), dried over anhydrous sodium sulfate and concentrated. The resulting residue was purified by silica gel column chromatography (0-30% EtOAc in Pet ether) to afford the title compound as colorless liquid.

$^1$H NMR (300 MHz, DMSO-d$_6$) δ=7.39-7.31 (m, 4H), 7.30-7.22 (m, 3H), 6.91 (d, J=8.8 Hz, 2H), 4.60 (s, 2H), 4.48 (s, 2H), 4.30 (q, J=7.1 Hz, 2H), 3.74 (s, 3H), 3.56-3.39 (m, 4H), 3.15 (s, 2H), 2.95 (s, 2H), 2.46 (br d, J=3.3 Hz, 4H), 1.36-1.17 (m, 7H), 0.90 (s, 6H).

LCMS: 96.2% (M+H) δ46.

Preparation 39 (Compound 040)

1-Ethyl-3-(3-hydroxy-2,2-dimethyl-propyl)spiro[6,7-dihydro-4H-pyrazolo[3,4-c]azepine-5,4'-tetrahydropyran]-8-one

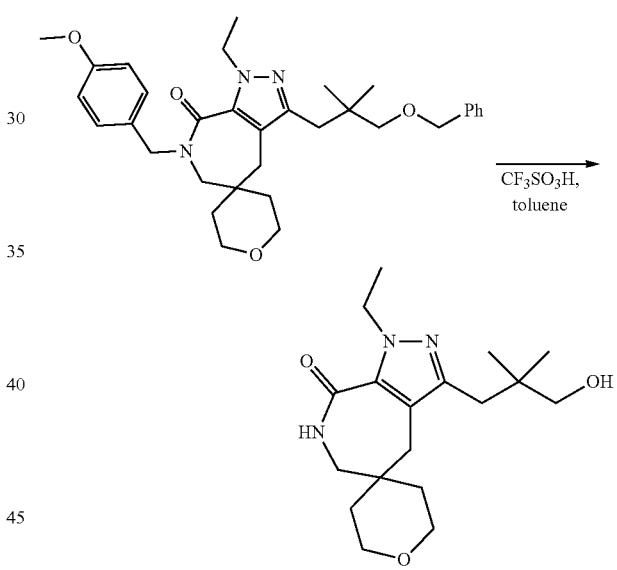

To a stirred solution of 3-(3-benzyloxy-2,2-dimethyl-propyl)-1-ethyl-7-[(4-methoxy-phenyl)methyl]spiro[4,6-dihydropyrazolo[3,4-c]azepine-5,4'-tetrahydropyran]-8-one (1.3 g, 2.38 mmol) in toluene (20 mL), trifluoromethanesulfonic acid (2.8 g, 19.08 mmol) was added at 0° C. The mixture was stirred at 26° C. for 3 h. On completion, the reaction mixture was neutralized with aq. NaHCO$_3$ solution, and extracted five times with EtOAc (5×200 mL). The combined organic layers were dried over anhydrous sodium sulfate, concentrated and the resulting residue was purified by silica gel column chromatography (0-5% MeOH in DCM) to afford the title compound as off-white solid.

$^1$H NMR (300 MHz, DMSO-d$_6$) δ=8.01 (br t, J=5.5 Hz, 1H), 4.50 (t, J=5.3 Hz, 1H), 4.28 (q, J=6.9 Hz, 2H), 3.66-3.48 (m, 4H), 3.11 (d, J=5.5 Hz, 2H), 2.85 (d, J=5.8 Hz, 2H), 2.46 (s, 2H), 2.37 (s, 2H), 1.37 (br d, J=4.4 Hz, 4H), 1.25 (t, J=7.1 Hz, 3H), 0.79 (s, 6H).

LCMS: 99% (M+H) 336.

HPLC-Retention time (XE Metode 7 CM): 1.82 minutes.

Detected "M+1"-mass: 336.22

General Procedure 1: Esterification

An alcohol (0.013 mmol) was dissolved in DCE (0.15 mL). A solution of an acid (2 equiv) in DCE (0.2 mL) and a solution of DMAP (1 equiv) in DCE (0.1 mL) were added. To the resulting mixture was added EDAC (2 equiv). The mixture was then shaken at 50° C. overnight and concentrated in vacuo. The residue was redissolved in DMF (0.3 mL) and subjected to subject to preparative LCMS purification, giving an ester.

General Procedure 2: Amide Formation

DMF (0.2 mL) solutions of the acid (0.022 mmol), DIPEA (3 equiv.) and HATU (1.2 equiv.) were added to a vial containing an amine (2 equiv.) and the mixture was shaken at room temperature overnight. The crude was subjected to preparative LCMS purification, giving an amide.

Example 1 (Compound 101)

3-(1-Ethyl-8-oxo-spiro[6,7-dihydro-4H-pyrazolo[3,4-c]azepine-5,4'-tetrahydropyran]-3-yl)propyl 4-(methylsulfamoyl)benzoate

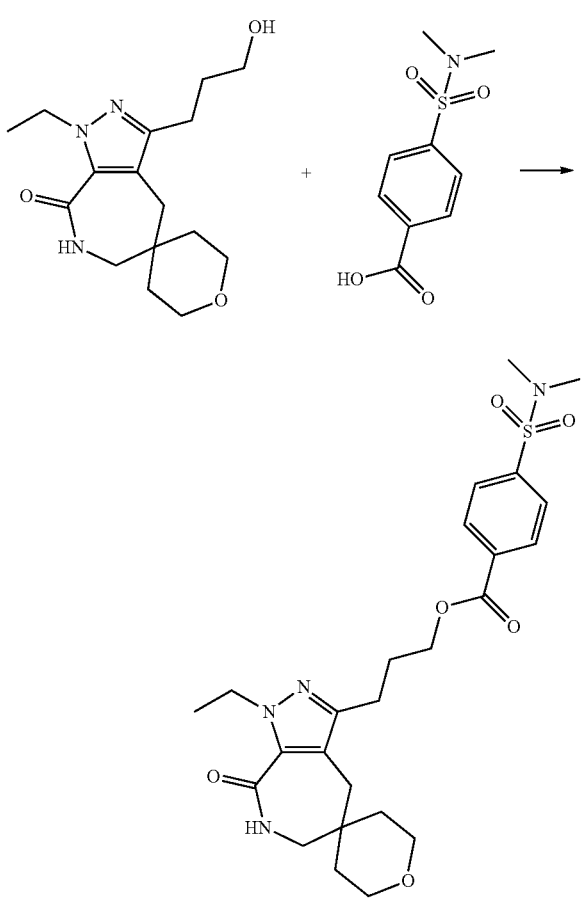

1-Ethyl-3-(3-hydroxypropyl)spiro[6,7-dihydro-4H-pyrazolo[3,4-c]azepine-5,4'-tetrahydropyran]-8-one and 4-(methylsulfamoyl)benzoic acid were treated as described in the General Procedure 1: Esterification, giving the title compound.

$^1$H NMR (300 MHz, DMSO-$d_6$) δ 8.18-8.08 (m, 2H), 8.01 (t, J=5.8 Hz, 1H), 7.94-7.87 (m, 2H), 7.65 (s, 1H), 4.46-4.18 (m, 4H), 3.53 (q, J=4.9 Hz, 4H), 2.88 (d, J=5.9 Hz, 2H), 2.67 (t, J=7.4 Hz, 2H), 2.45 (s, 2H), 2.44 (s, 3H), 2.11-1.99 (m, 2H), 1.36 (t, J=5.4 Hz, 4H), 1.26 (t, J=7.1 Hz, 3H).

HPLC-Retention time (XE Metode 7 CM): 2.03 minutes.

Detected "M+1"-mass: 505.18.

Example 2 (Compound 102)

3-(1-Ethyl-8-oxo-spiro[6,7-dihydro-4H-pyrazolo[3,4-c]azepine-5,4'-tetrahydropyran]-3-yl)propyl 4-(dimethylsulfamoyl)benzoate

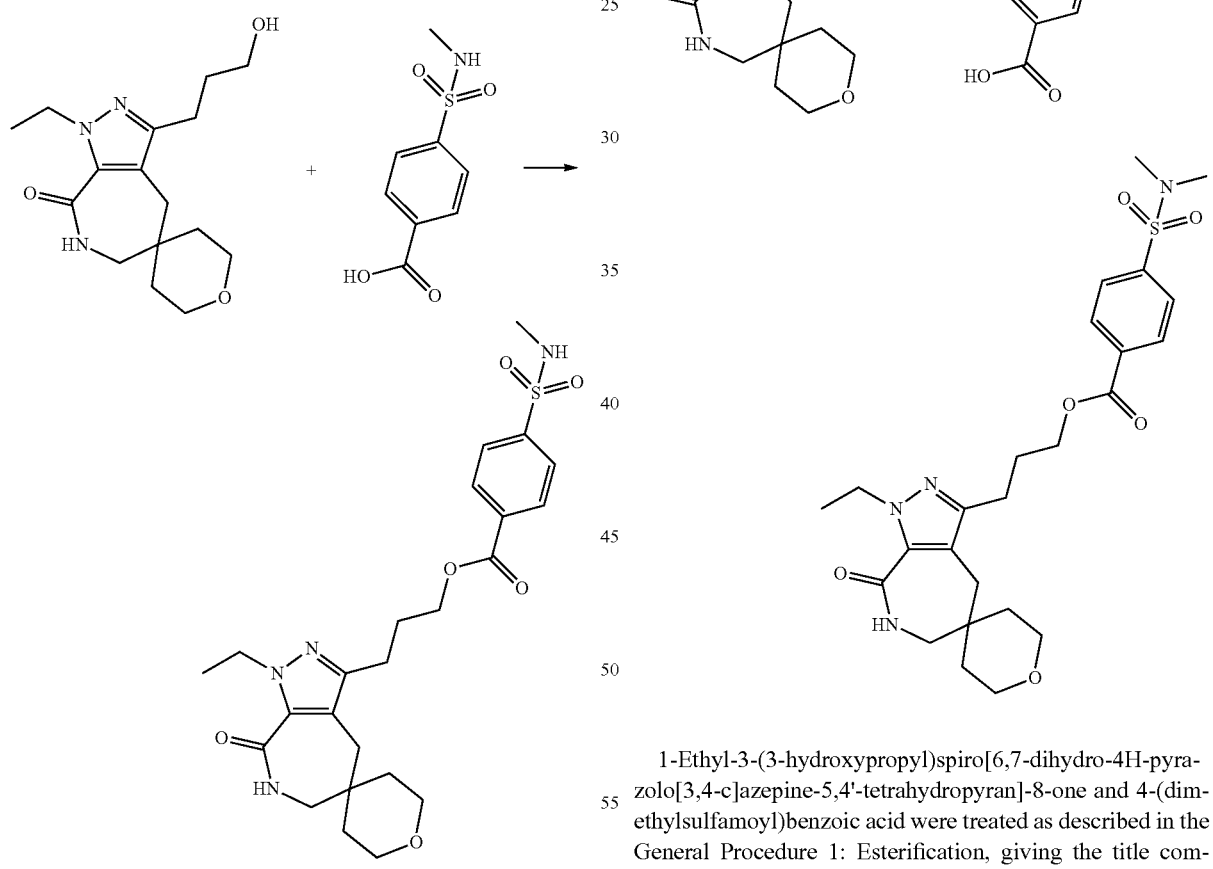

1-Ethyl-3-(3-hydroxypropyl)spiro[6,7-dihydro-4H-pyrazolo[3,4-c]azepine-5,4'-tetrahydropyran]-8-one and 4-(dimethylsulfamoyl)benzoic acid were treated as described in the General Procedure 1: Esterification, giving the title compound.

$^1$H NMR (300 MHz, DMSO-$d_6$) δ 8.21-8.07 (m, 2H), 8.01 (t, J=5.8 Hz, 1H), 7.95-7.79 (m, 2H), 4.45-4.18 (m, 4H), 3.53 (d, J=6.4 Hz, 4H), 2.87 (d, J=5.8 Hz, 2H), 2.64 (s, 8H), 2.45 (s, 2H), 2.12-1.97 (m, 2H), 1.35 (t, J=5.4 Hz, 4H), 1.25 (t, J=7.1 Hz, 3H).

HPLC-Retention time (XE Metode 7 CM): 2.15 minutes.

Detected "M+1"-mass: 519.20.

Example 3 (Compound 103)

3-(1-Ethyl-8-oxo-spiro[6,7-dihydro-4H-pyrazolo[3,4-c]azepine-5,4'-tetrahydropyran]-3-yl)propyl 4-methylsulfonylbenzoate

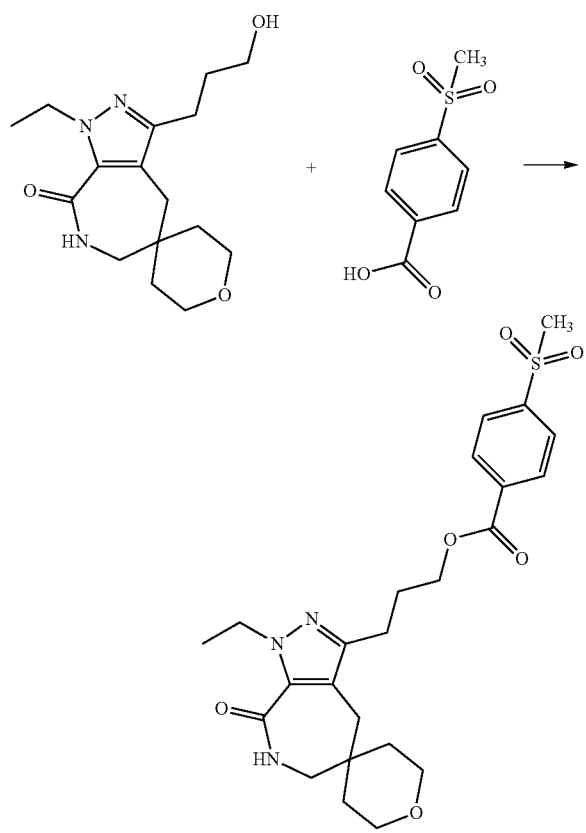

1-Ethyl-3-(3-hydroxypropyl)spiro[6,7-dihydro-4H-pyrazolo[3,4-c]azepine-5,4'-tetra-hydropyran]-8-one and 4-methylsulfonylbenzoic acid were treated as described in the General Procedure 1: Esterification, giving the title compound.

$^1$H NMR (300 MHz, DMSO-d$_6$) δ 8.21-8.12 (m, 2H), 8.10-8.04 (m, 2H), 8.01 (t, 3=5.8 Hz, 1H), 4.37 (t, J=6.2 Hz, 2H), 4.28 (q, J=7.1 Hz, 2H), 3.64-3.44 (m, 4H), 3.27 (s, 3H), 2.88 (d, J=5.8 Hz, 2H), 2.67 (t, J=7.3 Hz, 2H), 2.45 (s, 2H), 2.05 (p, 3=6.8 Hz, 2H), 1.35 (t, J=5.4 Hz, 4H), 1.25 (t, J=7.1 Hz, 3H).

HPLC-Retention time (XE Metode 7 CM): 2.02 minutes.
Detected "M+1"-mass: 490.17.

PDE4 Assay

The human PDE4D catalytic domain (UniProt no. Q08499 [S380-L740]) was incubated with a mixture of non-labelled cAMP (cyclic adenosine monophosphate) and fluorescein amidite (FAM) conjugated cAMP and titrated test or reference Compound. Following brief incubation the enzymatic reaction was stopped by addition of binding buffer containing nanoparticles with immobilized trivalent metal ions capable of binding 1) AMP phospho groups and 2) terbium (Tb) donor fluorophores. Subsequent excitation of the Tb donor triggers time-resolved FRET to adjacent FAM acceptor molecules resulting in light emission. In the presence of a PDE4 inhibitor, AMP generation was reduced resulting in a lower fluorescence signal. The cAMP phosphodiester is not bound by the detection system.

The results were calculated as the molar concentrations resulting in 50% inhibition of the substrate cleavage compared to controls samples, and are expressed as a range of IC$_{50}$ (nM).

The results are shown in Table 1 below.

PDE4 IC$_{50}$ ranges
* indicates that IC$_{50}$ values are >500 nM
** indicates that IC$_{50}$ values are >100 and <500 nM
*** indicates that IC$_5$O values are <100 nM

| Example (Compound No) | PDE4 IC$_{50}$ range |
|---|---|
| 1 (101) | *** |
| 2 (102) | *** |
| 3 (103) | *** |

The Examples 4-102 shown in Table 2 were prepared by reacting Compound 008 as described in General Procedure 1 with the appropriate acid:

| Ex. | Cpd | Structure | IUPAC Name | HPLC Rt (min) | PDE4 IC$_{50}$ range |
|---|---|---|---|---|---|
| 4 | 104 | 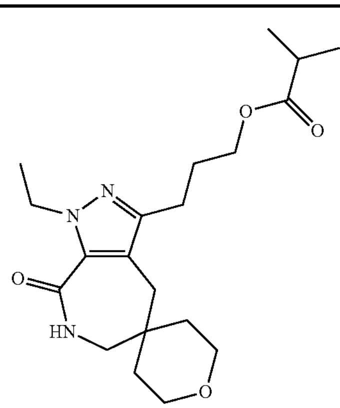 | 3-(1-ethyl-8-oxo-spiro[6,7-dihydro-4H-pyrazolo[3,4-c]azepine-5,4'-tetrahydropyran]-3-yl)propyl 2-methylpropanoate | 2.08 | *** |

-continued

| Ex. | Cpd | Structure | IUPAC Name | HPLC Rt (min) | PDE4 IC$_{50}$ range |
|---|---|---|---|---|---|
| 5 | 105 | 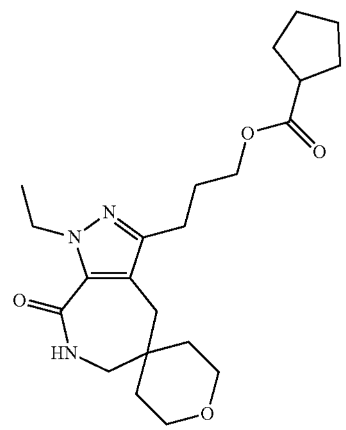 [SMILES: CCn1nc(CCCOC(=O)C2CCCC2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl cyclopentanecarboxylate | 2.22 | *** |
| 6 | 106 | 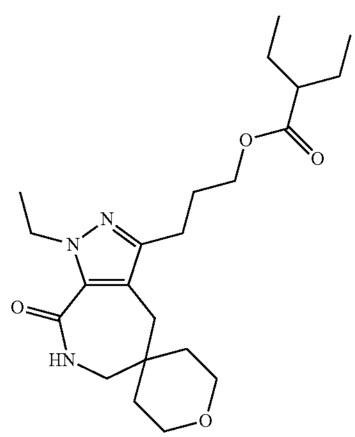 [SMILES: CCC(CC)C(=O)OCCCc1nn(CC)c2c1CC1(CCOCC1)CNC2=O] | 3-(1-ethyl-8-oxo-spiro[6,7-dihydro-4H-pyrazolo[3,4-c]azepine-5,4'-tetrahydropyran]-3-yl)propyl 2-ethylbutanoate | 2.28 | *** |
| 7 | 107 | 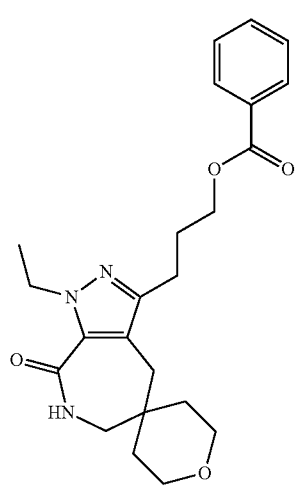 [SMILES: CCn1nc(CCCOC(=O)c2ccccc2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl benzoate | 2.17 | *** |

-continued

| Ex. | Cpd | Structure | IUPAC Name | HPLC Rt (min) | PDE4 IC$_{50}$ range |
|---|---|---|---|---|---|
| 8 | 108 | 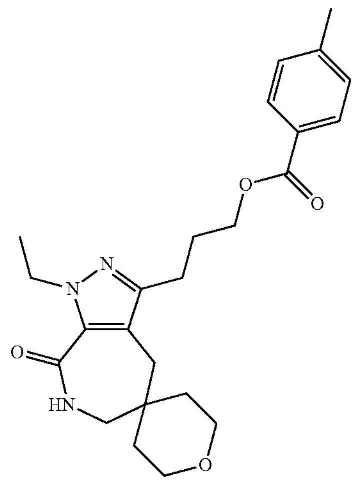 [SMILES: CCn1nc(CCCOC(=O)c2ccc(C)cc2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 4-methylbenzoate | 2.27 | *** |
| 9 | 109 | 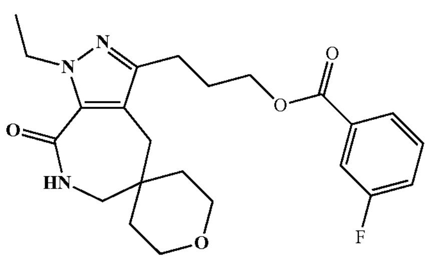 [SMILES: CCn1nc(CCCOC(=O)c2cccc(F)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3-fluorobenzoate | 2.22 | *** |
| 10 | 110 | 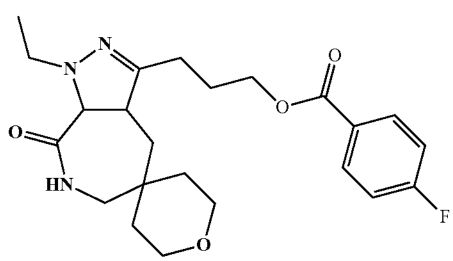 [SMILES: CCN1N=C(CCCOC(=O)c2ccc(F)cc2)C2CC3(CCOCC3)CNC(=O)C21] | 3-(1-ethyl-8-oxo-spiro[6,7-dihydro-4H-pyrazolo[3,4-c]azepine-5,4'-tetrahydropyran]-3-yl)propyl 4-fluorobenzoate | 2.21 | *** |
| 11 | 111 | 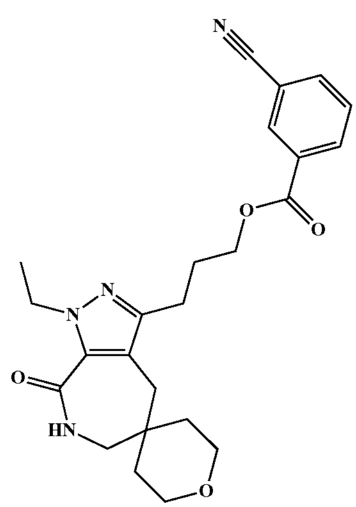 [SMILES: CCn1nc(CCCOC(=O)c2cccc(C#N)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl) propyl 3-cyanobenzoate | 2.12 | *** |

| Ex. | Cpd | Structure | IUPAC Name | HPLC Rt (min) | PDE4 IC$_{50}$ range |
|---|---|---|---|---|---|
| 12 | 112 | 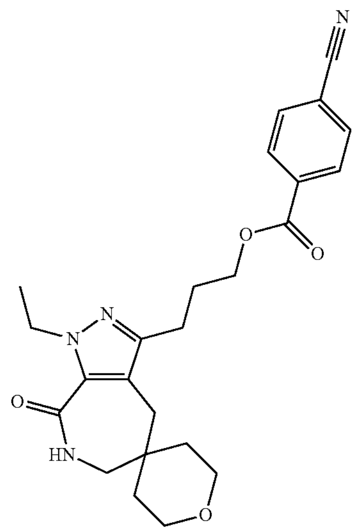 [SMILES: CCn1nc(CCCOC(=O)c2ccc(C#N)cc2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl) propyl 4-cyanobenzoate | 2.14 | *** |
| 13 | 113 | 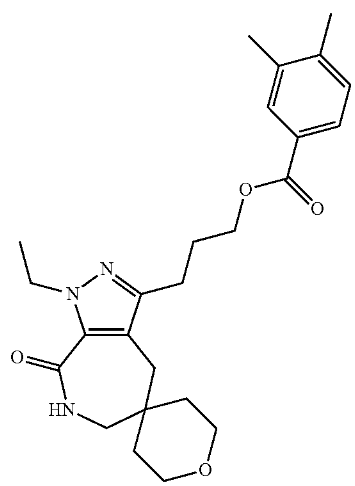 [SMILES: CCn1nc(CCCOC(=O)c2ccc(C)c(C)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl) propyl 3,4-dimethylbenzoate | 2.34 | *** |
| 14 | 114 | 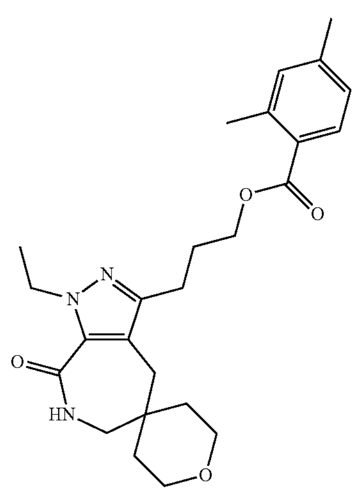 [SMILES: CCn1nc(CCCOC(=O)c2ccc(C)cc2C)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 2,4-dimethylbenzoate | 2.37 | *** |

-continued

| Ex. | Cpd | Structure | IUPAC Name | HPLC Rt (min) | PDE4 IC$_{50}$ range |
|---|---|---|---|---|---|
| 15 | 115 | 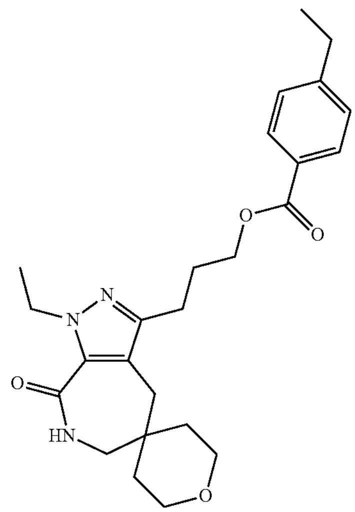 | 3-(1-ethyl-8-oxo-spiro[6,7-dihydro-4H-pyrazolo[3,4-c]azepine-5,4'-tetrahydropyran]-3-yl)propyl 4-ethylbenzoate | 2.36 | *** |
| 16 | 116 | 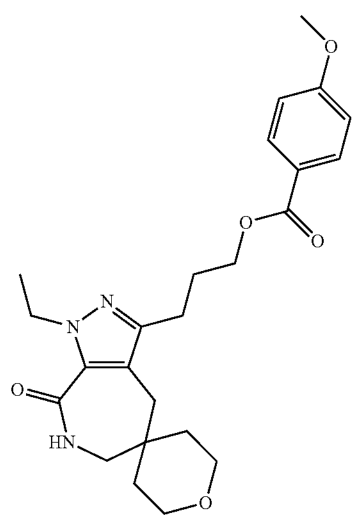 [SMILES: CCn1nc(CCCOC(=O)c2ccc(OC)cc2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 4-methoxybenzoate | 2.17 | *** |
| 17 | 117 | 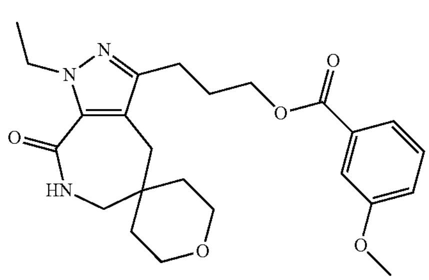 [SMILES: CCn1nc(CCCOC(=O)c2cccc(OC)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3-methoxybenzoate | 2.19 | *** |

-continued

| Ex. | Cpd | Structure | IUPAC Name | HPLC Rt (min) | PDE4 IC$_{50}$ range |
|---|---|---|---|---|---|
| 18 | 118 | 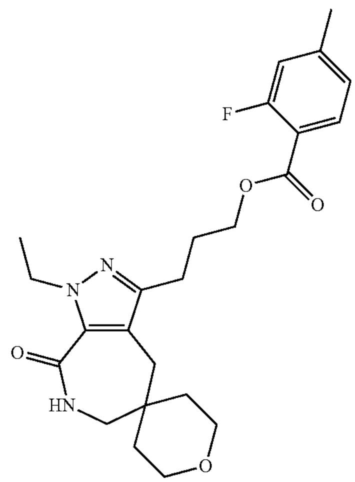 | 3-(1-ethyl-8-oxo-spiro[6,7-dihydro-4H-pyrazolo[3,4-c]azepine-5,4'-tetrahydropyran]-3-yl)propyl 2-fluoro-4-methyl-benzoate | 2.25 | *** |
| 19 | 119 | 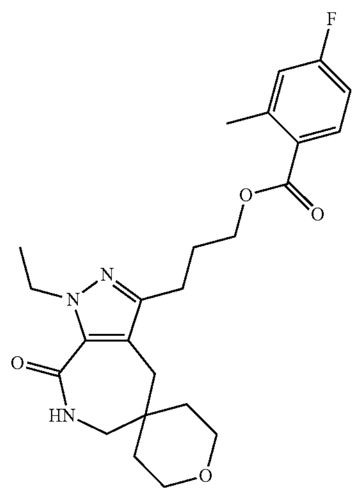 [SMILES: CCn1nc(CCCOC(=O)c2ccc(F)cc2C)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 4-fluoro-2-methyl-benzoate | 2.31 | *** |
| 20 | 120 | 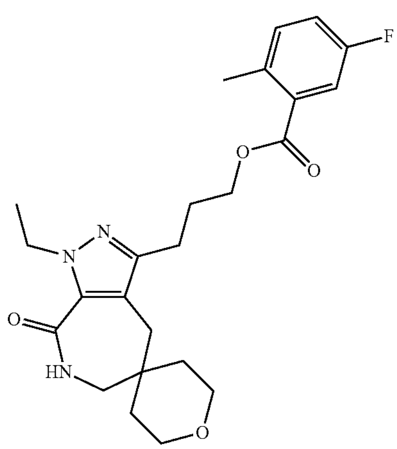 [SMILES: CCn1nc(CCCOC(=O)c2cc(F)ccc2C)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 5-fluoro-2-methyl-benzoate | 2.31 | *** |

-continued

| Ex. | Cpd | Structure | IUPAC Name | HPLC Rt (min) | PDE4 IC$_{50}$ range |
|---|---|---|---|---|---|
| 21 | 121 | 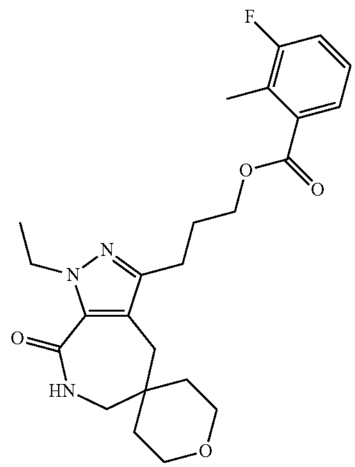 [SMILES: CCn1nc(CCCOC(=O)c2cccc(F)c2C)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3-fluoro-2-methyl-benzoate | 2.31 | *** |
| 22 | 122 | 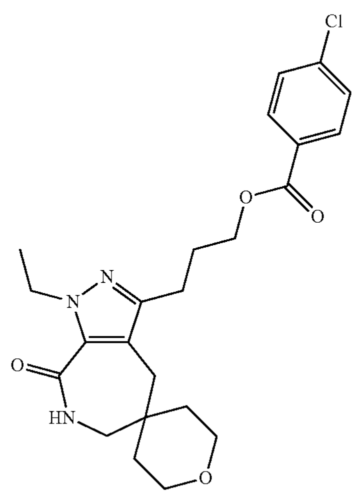 [SMILES: CCn1nc(CCCOC(=O)c2ccc(Cl)cc2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 4-chlorobenzoate | 2.32 | *** |
| 23 | 123 | 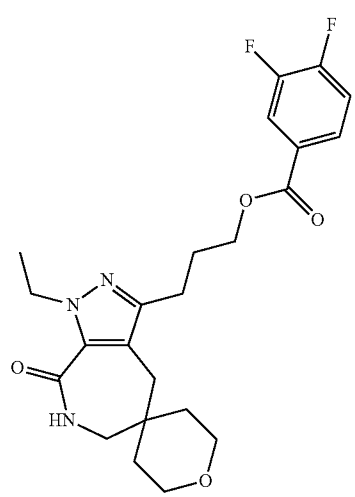 [SMILES: CCn1nc(CCCOC(=O)c2ccc(F)c(F)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3,4-difluorobenzoate | 2.26 | *** |

-continued

| Ex. | Cpd | Structure | IUPAC Name | HPLC Rt (min) | PDE4 IC$_{50}$ range |
|---|---|---|---|---|---|
| 24 | 124 | 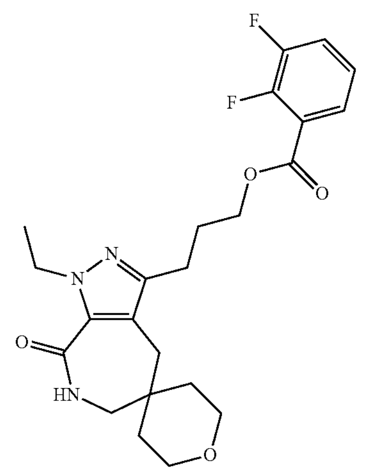 [SMILES: CCn1nc(CCCOC(=O)c2cccc(F)c2F)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 2,3-difluorobenzoate | 2.21 | *** |
| 25 | 125 | 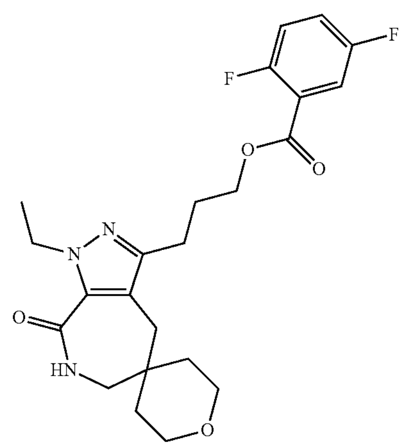 [SMILES: CCn1nc(CCCOC(=O)c2cc(F)ccc2F)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 2,5-difluorobenzoate | 2.20 | *** |
| 26 | 126 | 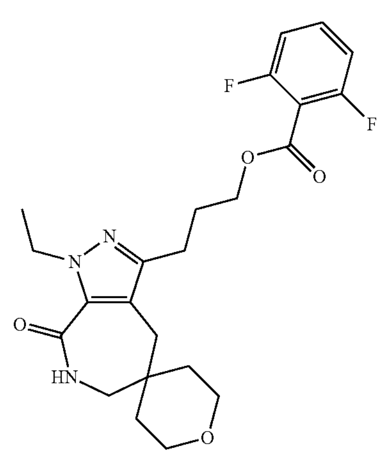 [SMILES: CCn1nc(CCCOC(=O)c2c(F)cccc2F)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 2,6-difluorobenzoate | 2.17 | *** |

-continued

| Ex. | Cpd | Structure | IUPAC Name | HPLC Rt (min) | PDE4 IC$_{50}$ range |
|---|---|---|---|---|---|
| 27 | 127 | 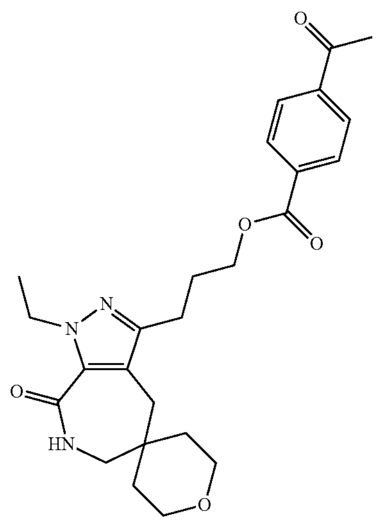 [SMILES: CCn1nc(CCCOC(=O)c2ccc(C(C)=O)cc2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 4-acetylbenzoate | 2.13 | *** |
| 28 | 128 | 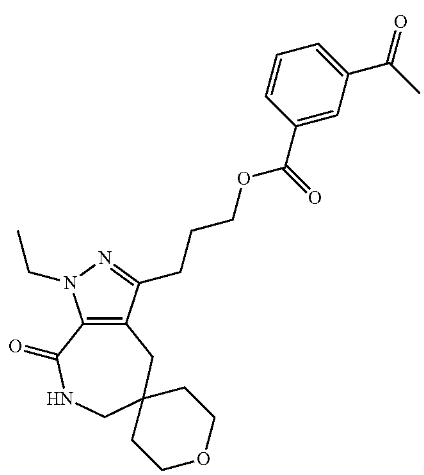 [SMILES: CCn1nc(CCCOC(=O)c2cccc(C(C)=O)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3-acetylbenzoate | 2.11 | *** |
| 29 | 129 | 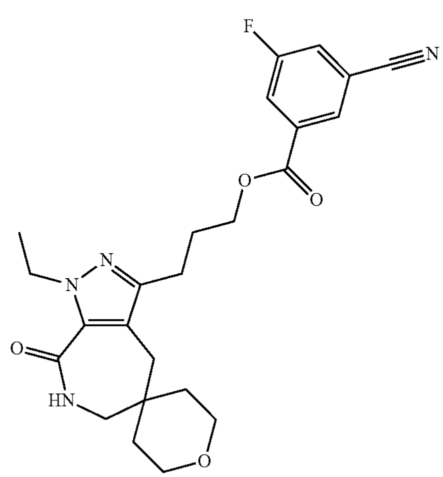 [SMILES: CCn1nc(CCCOC(=O)c2cc(F)cc(C#N)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3-cyano-5-fluoro-benzoate | 2.19 | *** |

-continued

| Ex. | Cpd | Structure | IUPAC Name | HPLC Rt (min) | PDE4 IC$_{50}$ range |
|---|---|---|---|---|---|
| 30 | 130 | 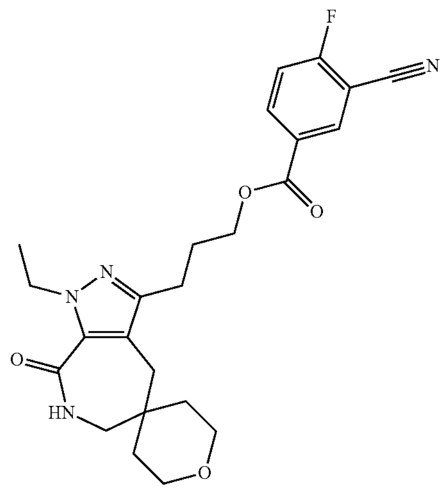 [SMILES: CCn1nc(CCCOC(=O)c2ccc(F)c(C#N)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3-cyano-4-fluoro-benzoate | 2.18 | *** |
| 31 | 131 | 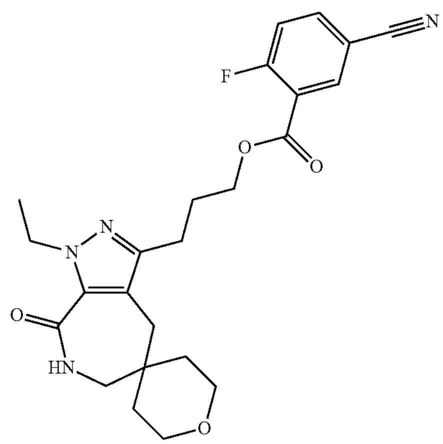 [SMILES: CCn1nc(CCCOC(=O)c2cc(C#N)ccc2F)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 5-cyano-2-fluoro-benzoate | 2.12 | *** |
| 32 | 132 | 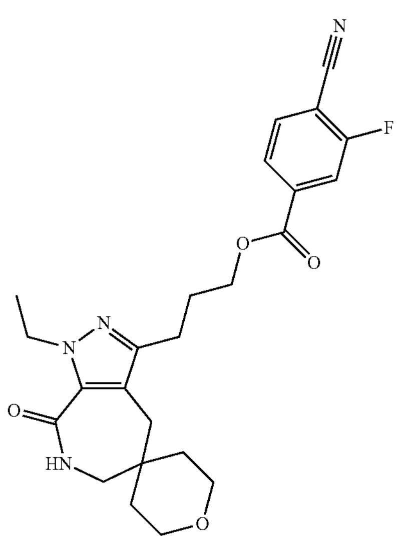 [SMILES: CCn1nc(CCCOC(=O)c2ccc(C#N)c(F)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 4-cyano-3-fluoro-benzoate | 2.20 | *** |

| Ex. | Cpd | Structure | IUPAC Name | HPLC Rt (min) | PDE4 IC$_{50}$ range |
|---|---|---|---|---|---|
| 33 | 133 | 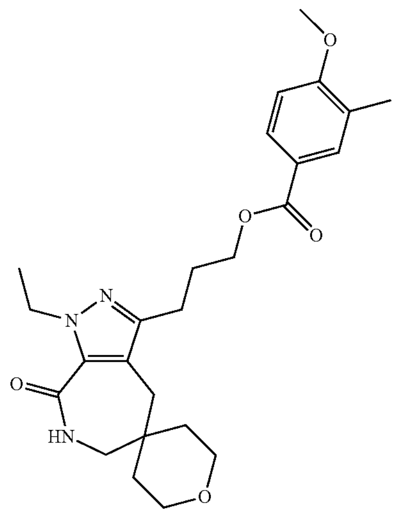 [SMILES: CCn1nc(CCCOC(=O)c2ccc(OC)c(C)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 4-methoxy-3-methyl-benzoate | 2.28 | *** |
| 34 | 134 | 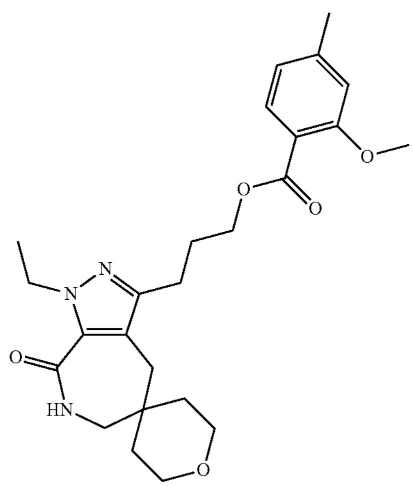 [SMILES: CCn1nc(CCCOC(=O)c2ccc(C)cc2OC)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 2-methoxy-4-methyl-benzoate | 2.16 | *** |
| 35 | 135 | 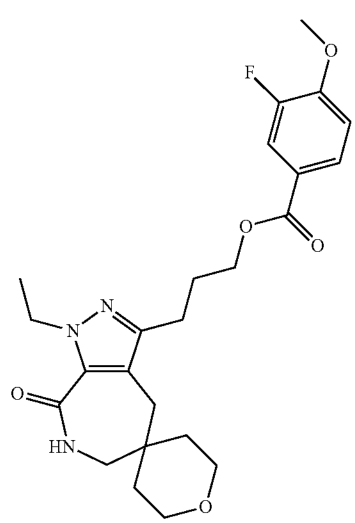 [SMILES: CCn1nc(CCCOC(=O)c2ccc(OC)c(F)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3-fluoro-4-methoxy-benzoate | 2.20 | *** |

-continued

| Ex. | Cpd | Structure | IUPAC Name | HPLC Rt (min) | PDE4 IC$_{50}$ range |
|---|---|---|---|---|---|
| 36 | 136 | 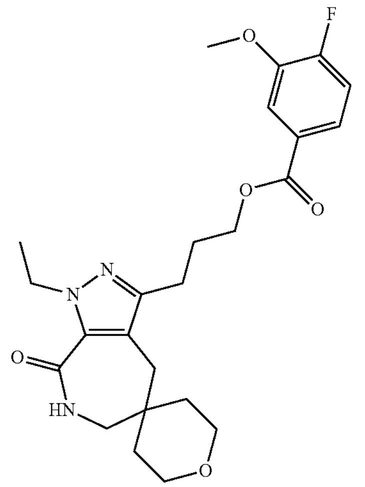 [SMILES: CCn1nc(CCCOC(=O)c2ccc(F)c(OC)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 4-fluoro-3-methoxy-benzoate | 2.22 | *** |
| 37 | 137 | 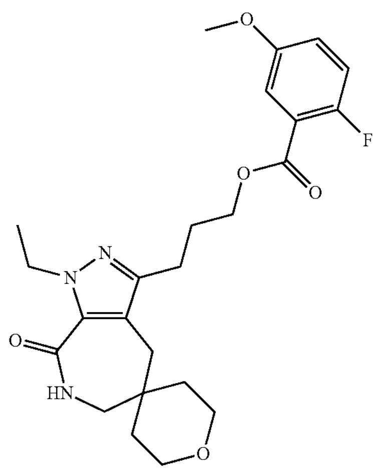 [SMILES: CCn1nc(CCCOC(=O)c2cc(OC)ccc2F)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 2-fluoro-5-methoxy-benzoate | 2.19 | *** |
| 38 | 138 | 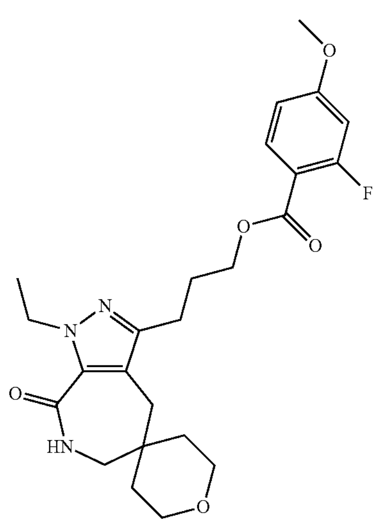 [SMILES: CCn1nc(CCCOC(=O)c2ccc(OC)cc2F)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 2-fluoro-4-methoxy-benzoate | 2.19 | *** |

-continued

| Ex. | Cpd | Structure | IUPAC Name | HPLC Rt (min) | PDE4 IC$_{50}$ range |
|---|---|---|---|---|---|
| 39 | 139 | 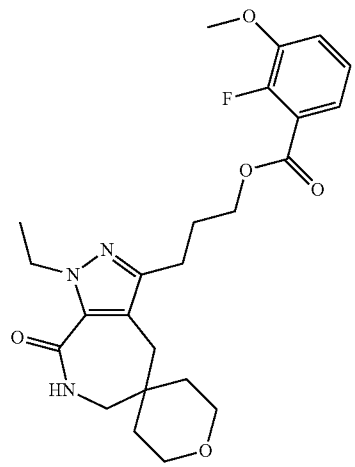 [SMILES: CCn1nc(CCCOC(=O)c2cccc(OC)c2F)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 2-fluoro-3-methoxy-benzoate | 2.15 | *** |
| 40 | 140 | 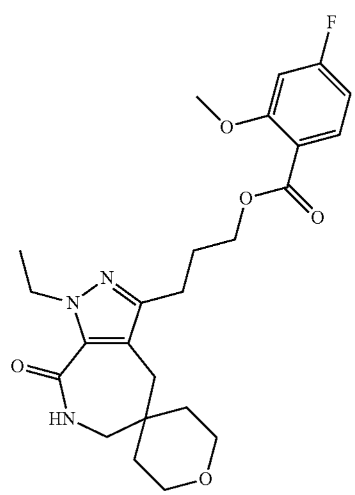 [SMILES: CCn1nc(CCCOC(=O)c2ccc(F)cc2OC)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 4-fluoro-2-methoxy-benzoate | 2.14 | *** |
| 41 | 141 | 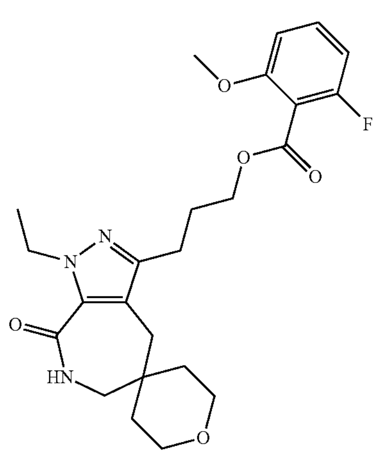 [SMILES: CCn1nc(CCCOC(=O)c2c(F)cccc2OC)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 2-fluoro-6-methoxy-benzoate | 2.14 | *** |

-continued

| Ex. | Cpd | Structure | IUPAC Name | HPLC Rt (min) | PDE4 IC$_{50}$ range |
|---|---|---|---|---|---|
| 42 | 142 | 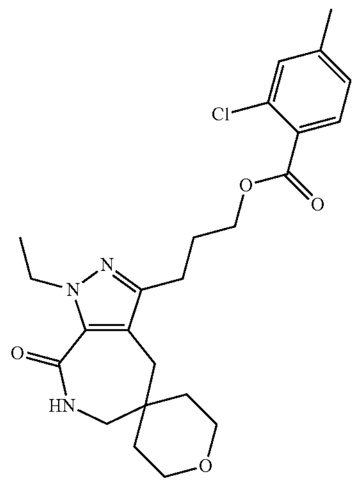 | 3-(1-ethyl-8-oxo-spiro[6,7-dihydro-4H-pyrazolo[3,4-c]azepine-5,4'-tetrahydropyran]-3-yl)propyl 2-chloro-4-methyl-benzoate | 2.33 | *** |
| 43 | 143 | 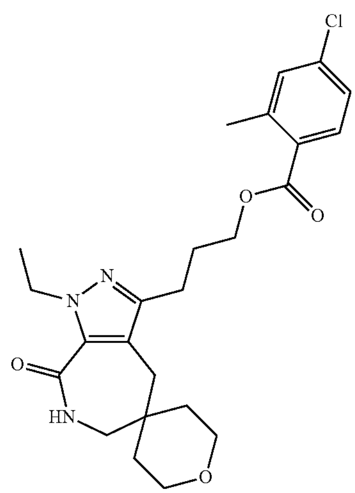 [SMILES: CCn1nc(CCCOC(=O)c2ccc(Cl)cc2C)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 4-chloro-2-methyl-benzoate | 2.43 | *** |
| 44 | 144 | 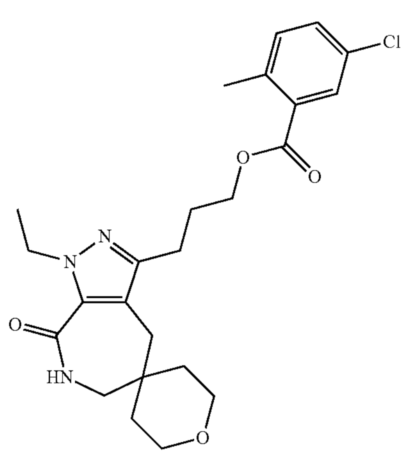 [SMILES: CCn1nc(CCCOC(=O)c2cc(Cl)ccc2C)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 5-chloro-2-methyl-benzoate | 2.41 | *** |

-continued

| Ex. | Cpd | Structure | IUPAC Name | HPLC Rt (min) | PDE4 IC$_{50}$ range |
|---|---|---|---|---|---|
| 45 | 145 | 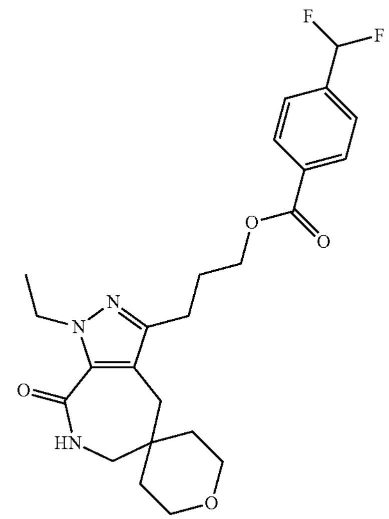 [SMILES: CCn1nc(CCCOC(=O)c2ccc(C(F)F)cc2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 4-(difluoromethyl)benzoate | 2.24 | *** |
| 46 | 146 | 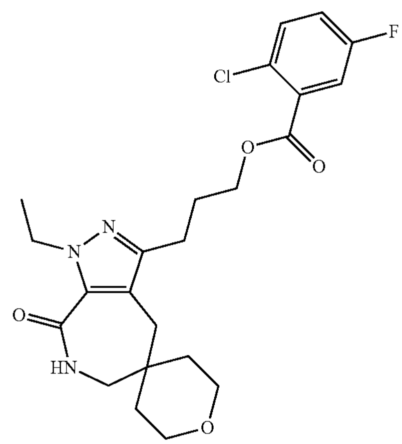 [SMILES: CCn1nc(CCCOC(=O)c2cc(F)ccc2Cl)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 2-chloro-5-fluoro-benzoate | 2.27 | *** |
| 47 | 147 | 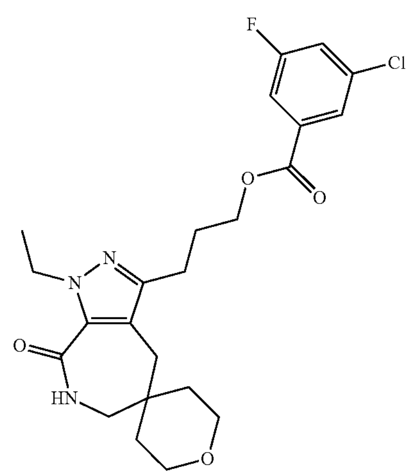 [SMILES: CCn1nc(CCCOC(=O)c2cc(F)cc(Cl)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3-chloro-5-fluoro-benzoate | 2.37 | *** |

-continued

| Ex. | Cpd | Structure | IUPAC Name | HPLC Rt (min) | PDE4 IC$_{50}$ range |
|---|---|---|---|---|---|
| 48 | 148 | 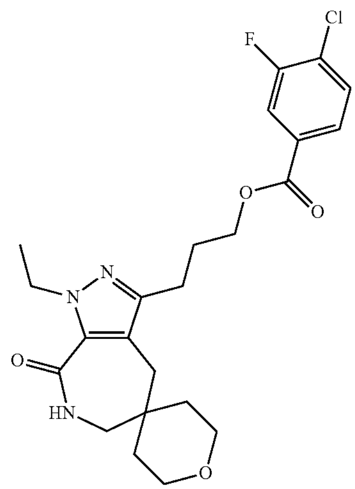 [SMILES: CCn1nc(CCCOC(=O)c2ccc(Cl)c(F)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 4-chloro-3-fluoro-benzoate | 2.36 | *** |
| 49 | 149 | 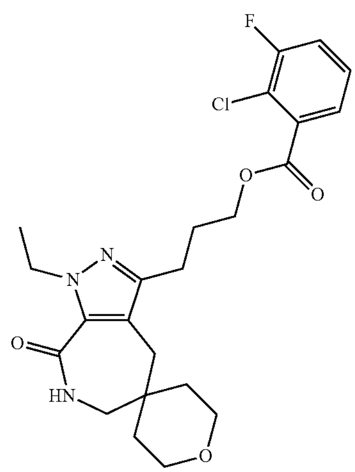 [SMILES: CCn1nc(CCCOC(=O)c2cccc(F)c2Cl)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 2-chloro-3-fluoro-benzoate | 2.26 | *** |
| 50 | 150 | 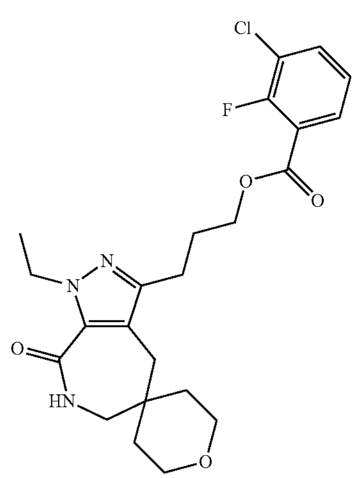 [SMILES: CCn1nc(CCCOC(=O)c2cccc(Cl)c2F)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3-chloro-2-fluoro-benzoate | 2.29 | *** |

-continued

| Ex. | Cpd | Structure | IUPAC Name | HPLC Rt (min) | PDE4 IC$_{50}$ range |
|---|---|---|---|---|---|
| 51 | 151 | 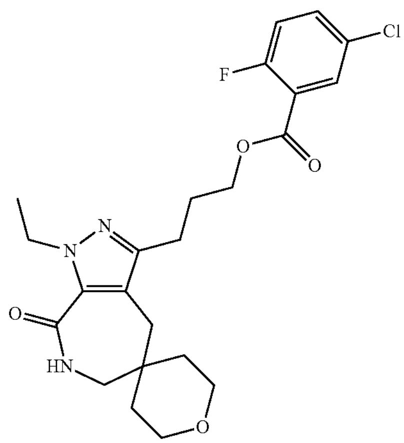 [SMILES: CCn1nc(CCCOC(=O)c2cc(Cl)ccc2F)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 5-chloro-2-fluoro-benzoate | 2.29 | *** |
| 52 | 152 | 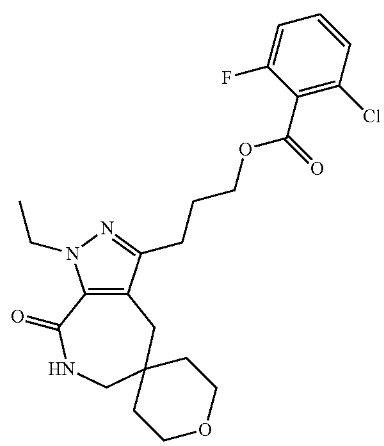 [SMILES: CCn1nc(CCCOC(=O)c2c(F)cccc2Cl)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 2-chloro-6-fluoro-benzoate | 2.25 | *** |
| 53 | 153 | 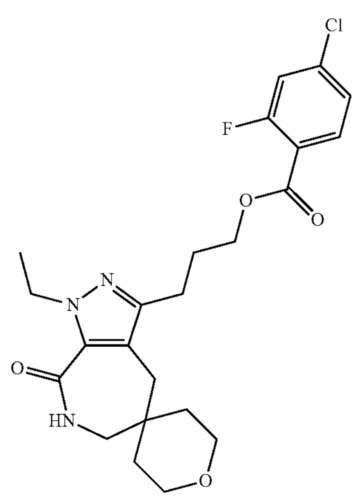 [SMILES: CCn1nc(CCCOC(=O)c2ccc(Cl)cc2F)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 4-chloro-2-fluoro-benzoate | 2.31 | *** |

| Ex. | Cpd | Structure | IUPAC Name | HPLC Rt (min) | PDE4 IC$_{50}$ range |
|---|---|---|---|---|---|
| 54 | 154 | 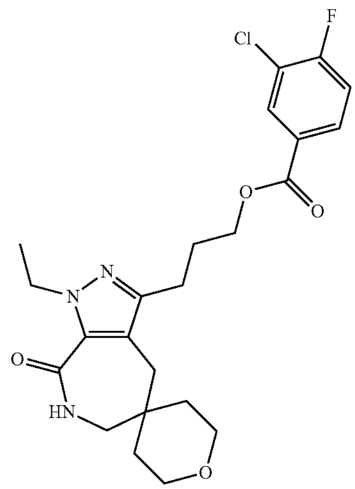 [SMILES: CCn1nc(CCCOC(=O)c2ccc(F)c(Cl)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3-chloro-4-fluoro-benzoate | 2.34 | *** |
| 55 | 155 | 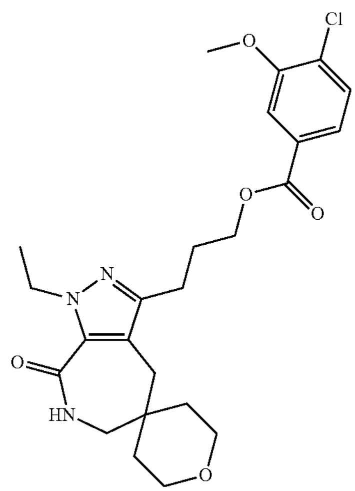 [SMILES: CCn1nc(CCCOC(=O)c2ccc(Cl)c(OC)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 4-chloro-3-methoxy-benzoate | 2.32 | *** |
| 56 | 156 | 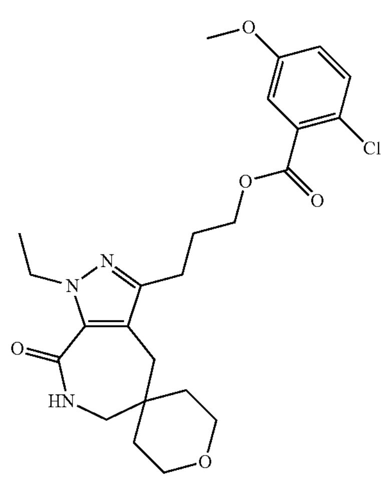 [SMILES: CCn1nc(CCCOC(=O)c2cc(OC)ccc2Cl)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 2-chloro-5-methoxy-benzoate | 2.26 | *** |

| Ex. | Cpd | Structure | IUPAC Name | HPLC Rt (min) | PDE4 IC$_{50}$ range |
|---|---|---|---|---|---|
| 57 | 157 | 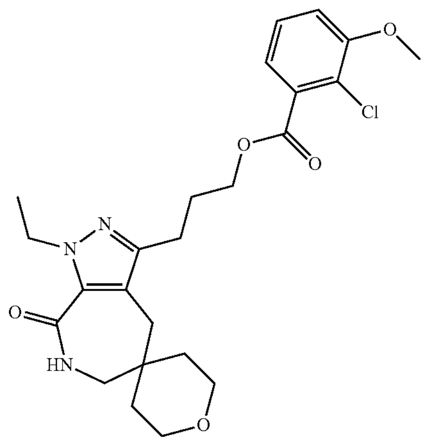 [SMILES: CCn1nc(CCCOC(=O)c2cccc(OC)c2Cl)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 2-chloro-3-methoxy-benzoate | 2.19 | *** |
| 58 | 158 | 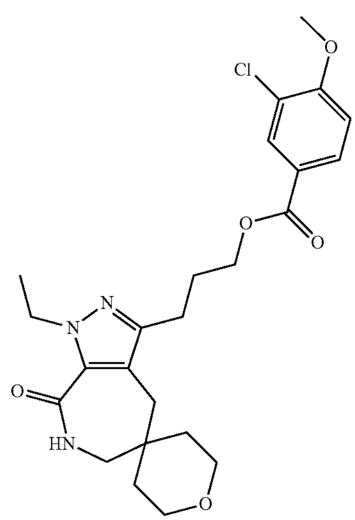 [SMILES: CCn1nc(CCCOC(=O)c2ccc(OC)c(Cl)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3-chloro-4-methoxy-benzoate | 2.27 | *** |
| 59 | 159 | 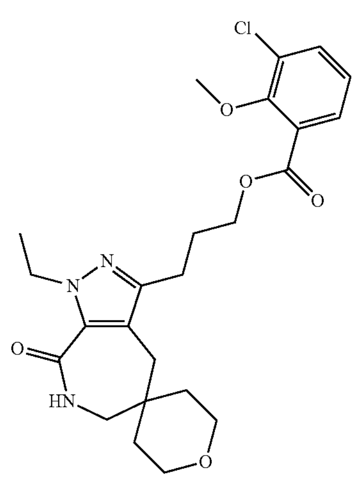 [SMILES: CCn1nc(CCCOC(=O)c2cccc(Cl)c2OC)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3-chloro-2-methoxy-benzoate | 2.28 | *** |

| Ex. | Cpd | Structure | IUPAC Name | HPLC Rt (min) | PDE4 IC$_{50}$ range |
|---|---|---|---|---|---|
| 60 | 160 | 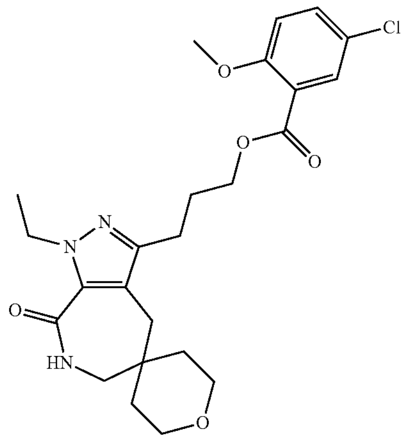 [SMILES: CCn1nc(CCCOC(=O)c2cc(Cl)ccc2OC)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 5-chloro-2-methoxy-benzoate | 2.22 | *** |
| 61 | 161 | 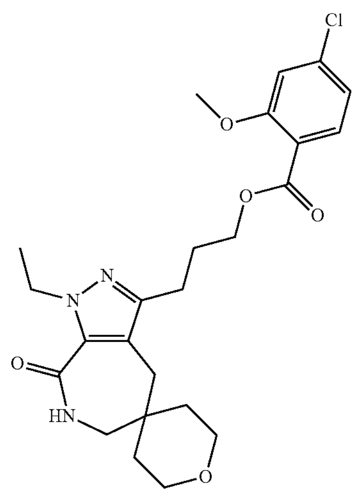 [SMILES: CCn1nc(CCCOC(=O)c2ccc(Cl)cc2OC)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 4-chloro-2-methoxy-benzoate | 2.24 | *** |
| 62 | 162 | 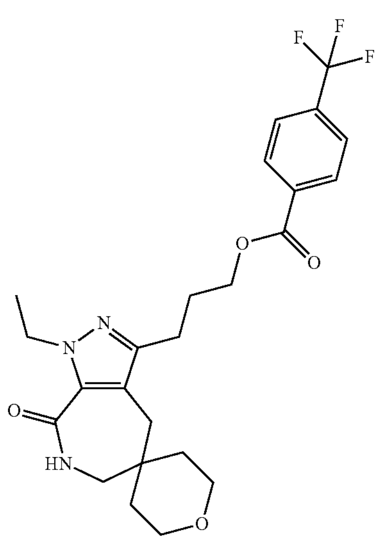 [SMILES: CCn1nc(CCCOC(=O)c2ccc(C(F)(F)F)cc2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 4-(trifluoromethyl)benzoate | 2.37 | *** |

| Ex. | Cpd | Structure | IUPAC Name | HPLC Rt (min) | PDE4 IC$_{50}$ range |
|---|---|---|---|---|---|
| 63 | 163 | 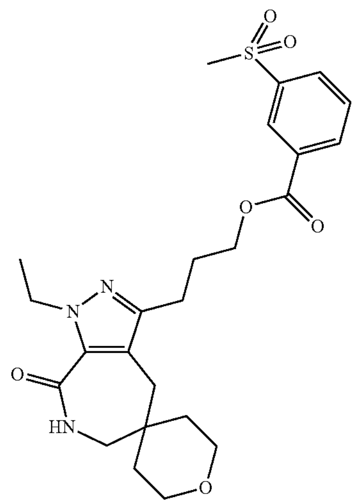 [SMILES: CCn1nc(CCCOC(=O)c2cccc(S(C)(=O)=O)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3-methylsulfonylbenzoate | 2.00 | *** |
| 64 | 164 | 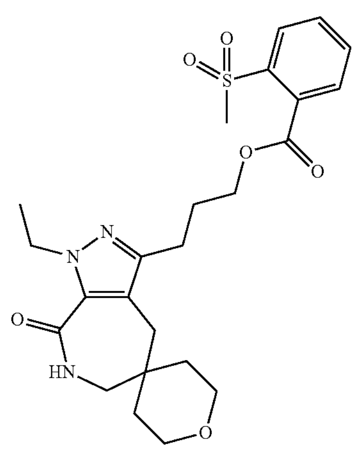 [SMILES: CCn1nc(CCCOC(=O)c2ccccc2S(C)(=O)=O)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 2-methylsulfonylbenzoate | 2.00 | *** |
| 65 | 165 | 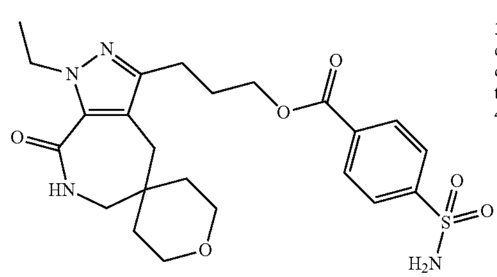 [SMILES: CCn1nc(CCCOC(=O)c2ccc(S(N)(=O)=O)cc2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 4-sulfamoylbenzoate | 1.93 | *** |

| Ex. | Cpd | Structure | IUPAC Name | HPLC Rt (min) | PDE4 IC$_{50}$ range |
|---|---|---|---|---|---|
| 66 | 166 | 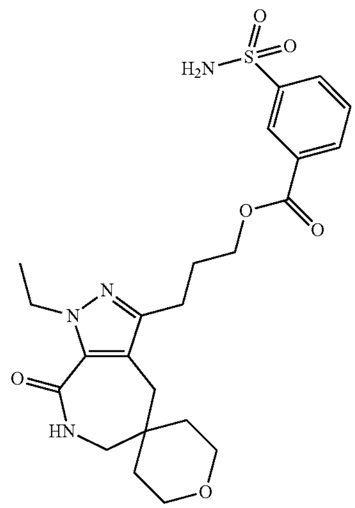 [SMILES: CCn1nc(CCCOC(=O)c2cccc(S(N)(=O)=O)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3-sulfamoylbenzoate | 1.93 | *** |
| 67 | 167 | 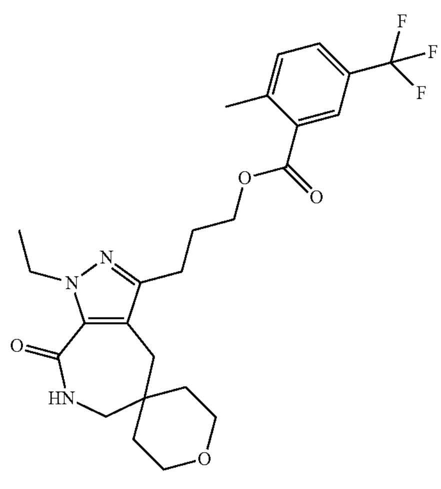 [SMILES: CCn1nc(CCCOC(=O)c2cc(C(F)(F)F)ccc2C)c2c1C(=O)NCC1(CCOCC1)C2] | 3-(1-ethyl-8-oxo-spiro[6,7-dihydro-4H-pyrazolo[3,4-c]azepine-5,4'-tetrahydro-pyran]-3-yl)propyl 2-methyl-5-(trifluoromethyl)benzoate | 2.44 | *** |
| 68 | 168 | 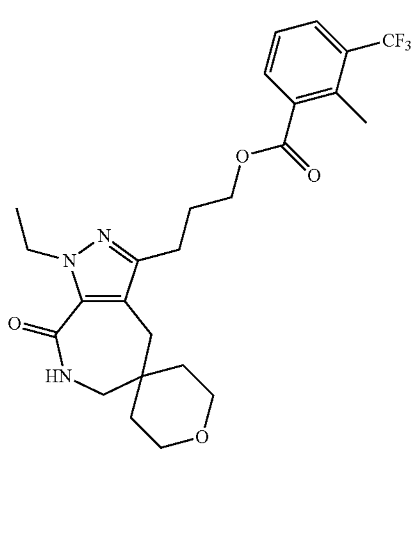 [SMILES: CCn1nc(CCCOC(=O)c2cccc(C(F)(F)F)c2C)c2c1C(=O)NCC1(CCOCC1)C2] | 3-(1-ethyl-8-oxo-spiro[6,7-dihydro-4H-pyrazolo[3,4-c]azepine-5,4'-tetrahydro-pyran]-3-yl)propyl 2-methyl-3-(trifluoromethyl)benzoate | 2.43 | *** |

-continued

| Ex. | Cpd | Structure | IUPAC Name | HPLC Rt (min) | PDE4 IC$_{50}$ range |
|---|---|---|---|---|---|
| 69 | 169 | 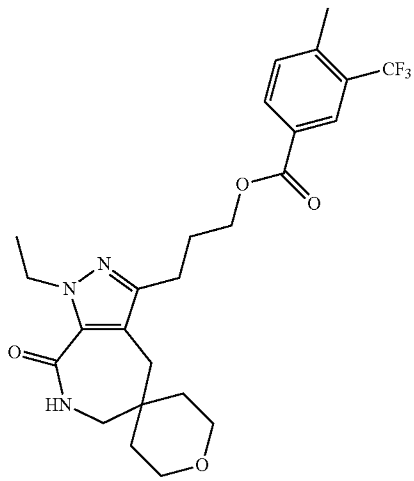 [SMILES: CCn1nc(CCCOC(=O)c2ccc(C)c(C(F)(F)F)c2)c2c1C(=O)NCC1(CCOCC1)C2] | 3-(1-ethyl-8-oxo-spiro[6,7-dihydro-4H-pyrazolo[3,4-c]azepine-5,4'-tetrahydro-pyran]-3-yl)propyl 4-fluoro-3-(trifluoromethyl)benzoate | 2.39 | *** |
| 70 | 170 | 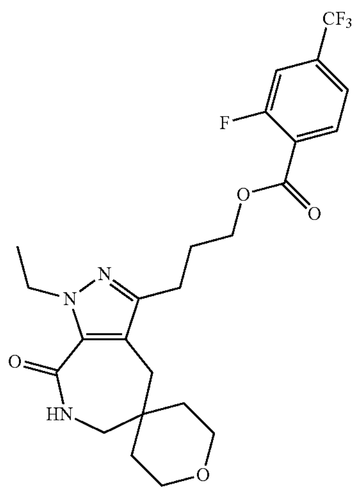 [SMILES: CCn1nc(CCCOC(=O)c2ccc(C(F)(F)F)cc2F)c2c1C(=O)NCC1(CCOCC1)C2] | 3-(1-ethyl-8-oxo-spiro[6,7-dihydro-4H-pyrazolo[3,4-c]azepine-5,4'-tetrahydro-pyran]-3-yl)propyl 2-fluoro-4-(trifluoromethyl)benzoate | 2.37 | *** |
| 71 | 171 | 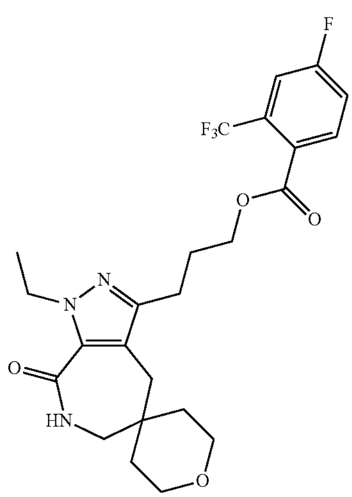 [SMILES: CCn1nc(CCCOC(=O)c2ccc(F)cc2C(F)(F)F)c2c1C(=O)NCC1(CCOCC1)C2] | 3-(1-ethyl-8-oxo-spiro[6,7-dihydro-4H-pyrazolo[3,4-c]azepine-5,4'-tetrahydro-pyran]-3-yl)propyl 4-fluoro-2-(trifluoromethyl)benzoate | 2.32 | *** |

| Ex. | Cpd | Structure | IUPAC Name | HPLC Rt (min) | PDE4 IC$_{50}$ range |
|---|---|---|---|---|---|
| 72 | 172 | 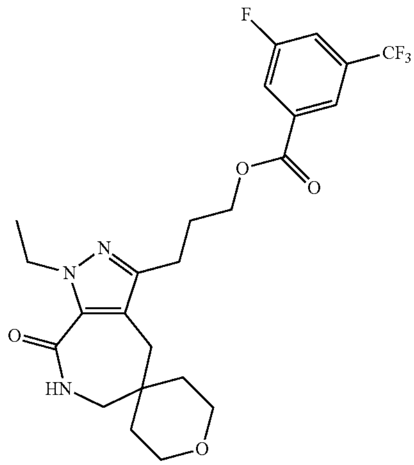 [SMILES: CCn1nc(CCCOC(=O)c2cc(F)cc(C(F)(F)F)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3-fluoro-5-(trifluoromethyl)benzoate | 2.41 | *** |
| 73 | 173 | 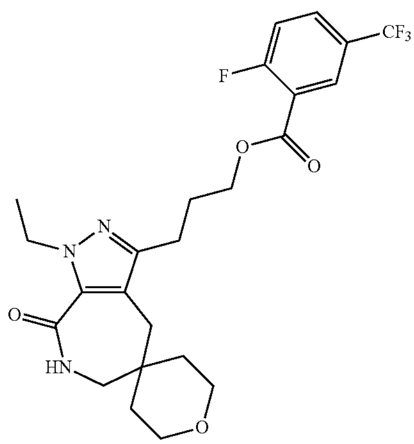 [SMILES: CCn1nc(CCCOC(=O)c2cc(C(F)(F)F)ccc2F)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 2-fluoro-5-(trifluoromethyl)benzoate | 2.34 | *** |
| 74 | 174 | 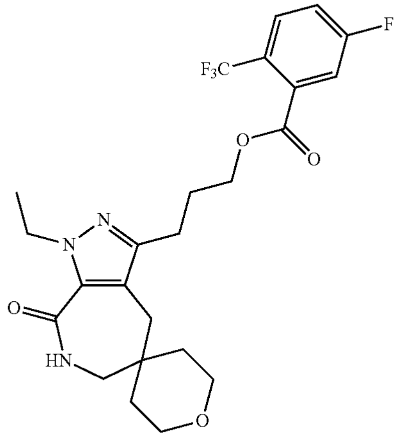 [SMILES: CCn1nc(CCCOC(=O)c2cc(F)ccc2C(F)(F)F)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 5-fluoro-2-(trifluoromethyl)benzoate | 2.32 | *** |

-continued

| Ex. | Cpd | Structure | IUPAC Name | HPLC Rt (min) | PDE4 IC$_{50}$ range |
|---|---|---|---|---|---|
| 75 | 175 | 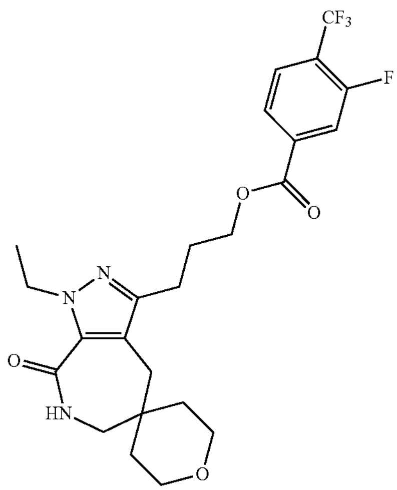 [SMILES: CCn1nc(CCCOC(=O)c2ccc(C(F)(F)F)c(F)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3-fluoro-4-(trifluoromethyl)benzoate | 2.41 | *** |
| 76 | 176 | 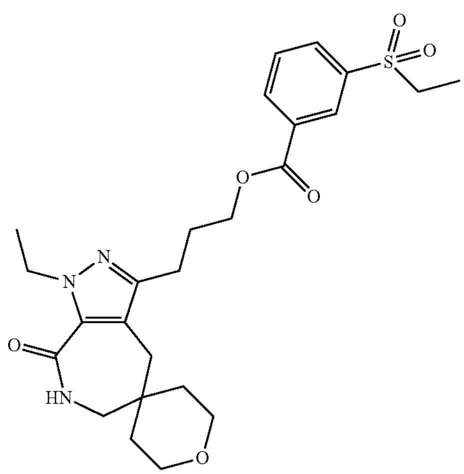 [SMILES: CCn1nc(CCCOC(=O)c2cccc(S(=O)(=O)CC)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3-ethylsulfonylbenzoate | 2.07 | *** |
| 77 | 177 | 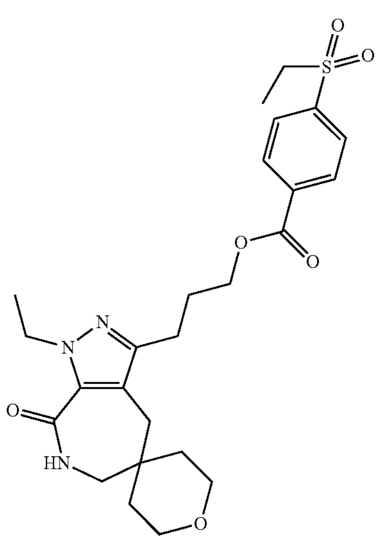 [SMILES: CCn1nc(CCCOC(=O)c2ccc(S(=O)(=O)CC)cc2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 4-ethylsulfonylbenzoate | 2.08 | *** |

| Ex. | Cpd | Structure | IUPAC Name | HPLC Rt (min) | PDE4 IC$_{50}$ range |
|---|---|---|---|---|---|
| 78 | 178 | 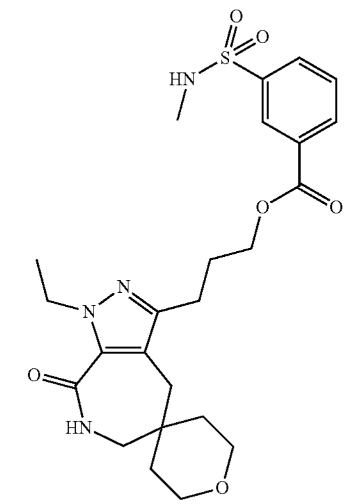 [SMILES: CCn1nc(CCCOC(=O)c2cccc(S(=O)(=O)NC)c2)c2c1C(=O)NCC1(CCOCC1)C2] | 3-(1-ethyl-8-oxo-spiro[6,7-dihydro-4H-pyrazolo[3,4-c]azepine-5,4'-tetrahydro-pyran]-3-yl)propyl 3-(methylsulfamoyl)benzoate | 2.02 | *** |
| 79 | 179 | 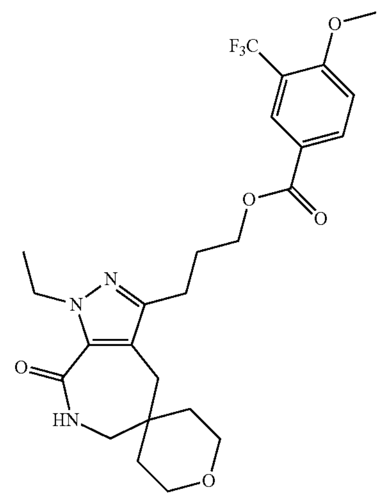 [SMILES: CCn1nc(CCCOC(=O)c2ccc(OC)c(C(F)(F)F)c2)c2c1C(=O)NCC1(CCOCC1)C2] | 3-(1-ethyl-8-oxo-spiro[6,7-dihydro-4H-pyrazolo[3,4-c]azepine-5,4'-tetrahydro-pyran]-3-yl)propyl 4-methoxy-3-(trifluoromethyl)benzoate | 2.34 | *** |
| 80 | 180 | 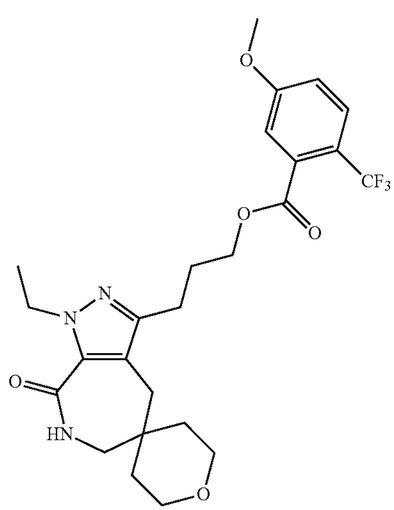 [SMILES: CCn1nc(CCCOC(=O)c2cc(OC)ccc2C(F)(F)F)c2c1C(=O)NCC1(CCOCC1)C2] | 3-(1-ethyl-8-oxo-spiro[6,7-dihydro-4H-pyrazolo[3,4-c]azepine-5,4'-tetrahydro-pyran]-3-yl)propyl 5-methoxy-2-(trifluoromethyl)benzoate | 2.31 | *** |

-continued

| Ex. | Cpd | Structure | IUPAC Name | HPLC Rt (min) | PDE4 IC$_{50}$ range |
|---|---|---|---|---|---|
| 81 | 181 | 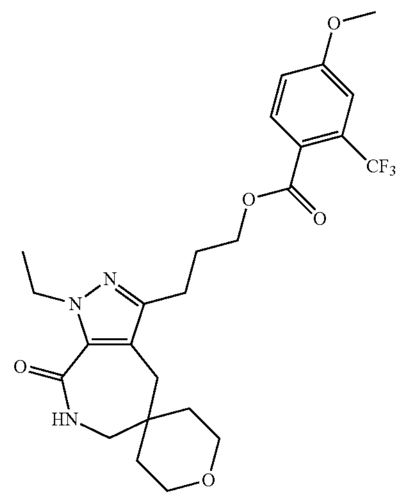 [SMILES: CCn1nc(CCCOC(=O)c2ccc(OC)cc2C(F)(F)F)c2c1C(=O)NCC1(CCOCC1)C2] | 3-(1-ethyl-8-oxo-spiro[6,7-dihydro-4H-pyrazolo[3,4-c]azepine-5,4'-tetrahydro-pyran]-3-yl)propyl 4-methoxy-2-(trifluoromethyl)benzoate | 2.32 | *** |
| 82 | 182 | 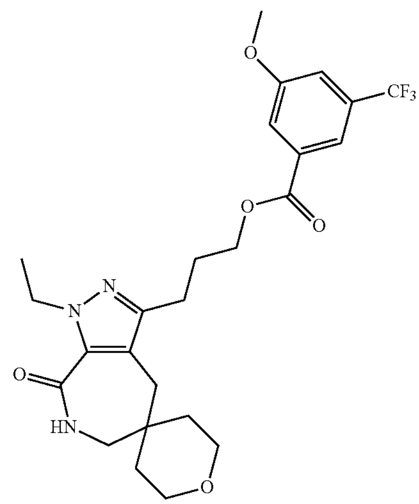 [SMILES: CCn1nc(CCCOC(=O)c2cc(OC)cc(C(F)(F)F)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3-methoxy-5-(trifluoromethyl)benzoate | 2.41 | *** |
| 83 | 183 | 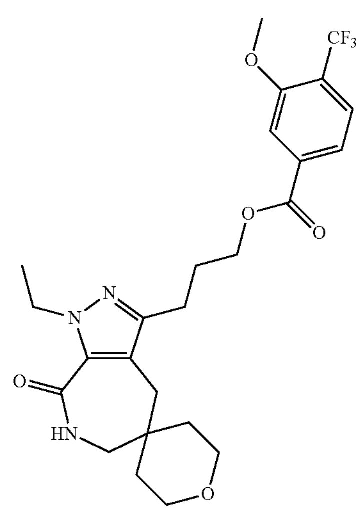 [SMILES: CCn1nc(CCCOC(=O)c2ccc(C(F)(F)F)c(OC)c2)c2c1C(=O)NCC1(CCOCC1)C2] | 3-(1-ethyl-8-oxo-spiro[6,7-dihydro-4H-pyrazolo[3,4-c]azepine-5,4'-tetrahydro-pyran]-3-yl)propyl 3-methoxy-4-(trifluoromethyl)benzoate | 2.39 | *** |

| Ex. | Cpd | Structure | IUPAC Name | HPLC Rt (min) | PDE4 IC$_{50}$ range |
|---|---|---|---|---|---|
| 84 | 184 | 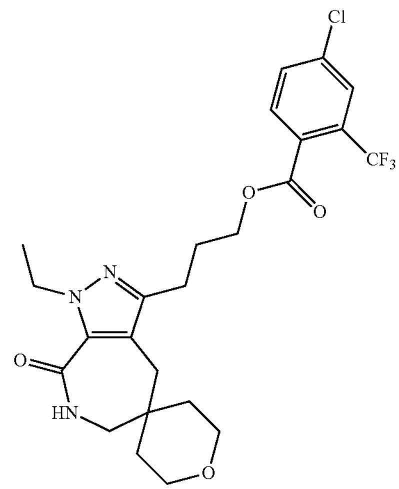 [SMILES: CCn1nc(CCCOC(=O)c2ccc(Cl)cc2C(F)(F)F)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 4-chloro-2-(trifluoromethyl)benzoate | 2.43 | *** |
| 85 | 185 | 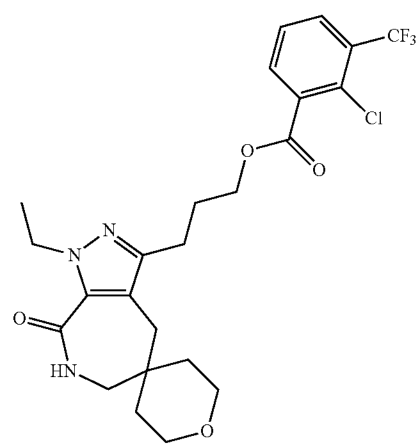 [SMILES: CCn1nc(CCCOC(=O)c2cccc(C(F)(F)F)c2Cl)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 2-chloro-3-(trifluoromethyl)benzoate | 2.38 | *** |
| 86 | 186 | 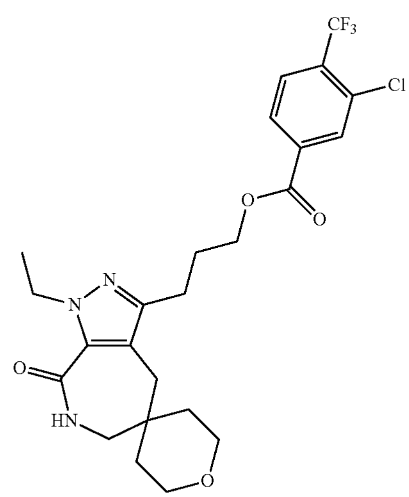 [SMILES: CCn1nc(CCCOC(=O)c2ccc(C(F)(F)F)c(Cl)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3-chloro-4-(trifluoromethyl)benzoate | 2.48 | *** |

| Ex. | Cpd | Structure | IUPAC Name | HPLC Rt (min) | PDE4 IC$_{50}$ range |
|---|---|---|---|---|---|
| 87 | 187 | 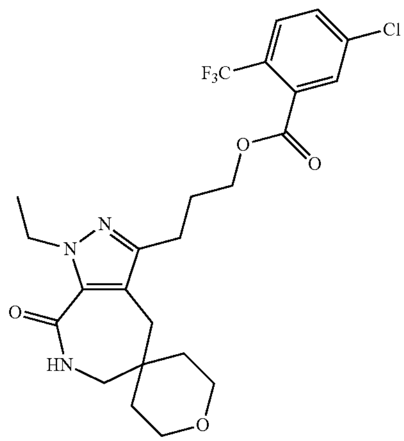 [SMILES: CCn1nc(CCCOC(=O)c2cc(Cl)ccc2C(F)(F)F)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 5-chloro-2-(trifluoromethyl)benzoate | 2.41 | *** |
| 88 | 188 | 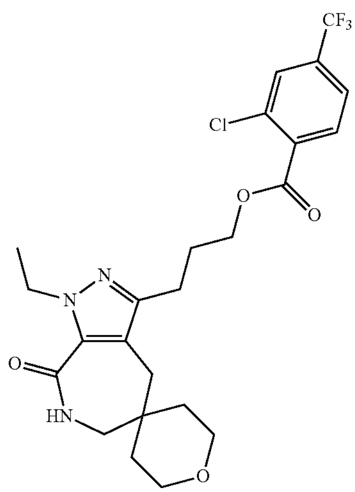 [SMILES: CCn1nc(CCCOC(=O)c2ccc(C(F)(F)F)cc2Cl)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 2-chloro-4-(trifluoromethyl)benzoate | 2.43 | *** |
| 89 | 189 | 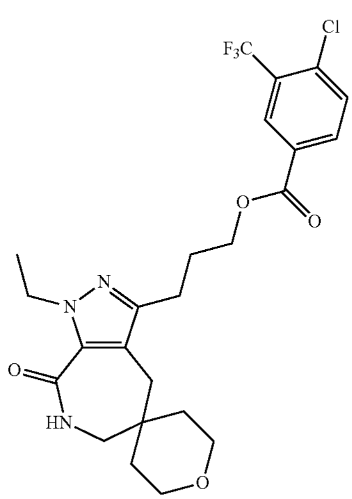 [SMILES: CCn1nc(CCCOC(=O)c2ccc(Cl)c(C(F)(F)F)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 4-chloro-3-(trifluoromethyl)benzoate | 2.47 | *** |

-continued

| Ex. | Cpd | Structure | IUPAC Name | HPLC Rt (min) | PDE4 IC$_{50}$ range |
|---|---|---|---|---|---|
| 90 | 190 | 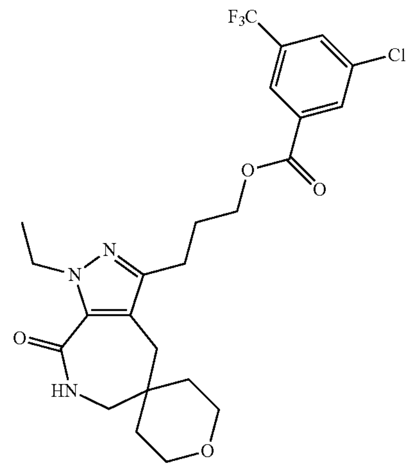 [SMILES: CCn1nc(CCCOC(=O)c2cc(Cl)cc(C(F)(F)F)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3-chloro-5-(trifluoromethyl)benzoate | 2.50 | *** |
| 91 | 191 | 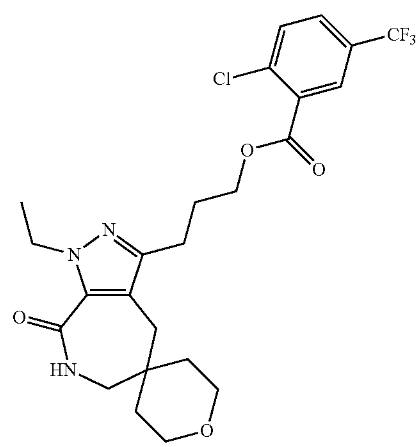 [SMILES: CCn1nc(CCCOC(=O)c2cc(C(F)(F)F)ccc2Cl)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 2-chloro-5-(trifluoromethyl)benzoate | 2.41 | *** |
| 92 | 192 | 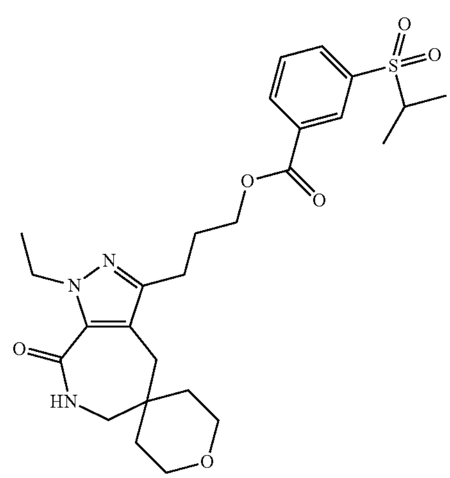 [SMILES: CCn1nc(CCCOC(=O)c2cccc(S(=O)(=O)C(C)C)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3-isopropylsulfonylbenzoate | 2.13 | *** |

-continued

| Ex. | Cpd | Structure | IUPAC Name | HPLC Rt (min) | PDE4 IC$_{50}$ range |
|---|---|---|---|---|---|
| 93 | 193 | 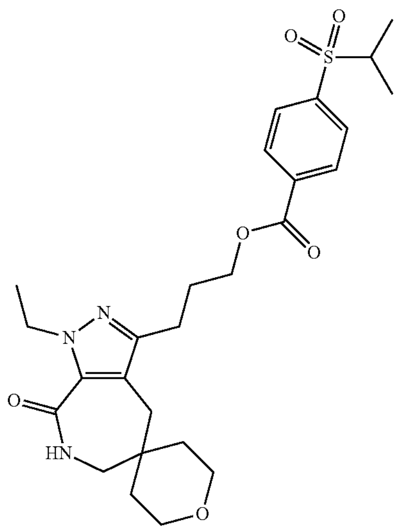 [SMILES: CCn1nc(CCCOC(=O)c2ccc(S(=O)(=O)C(C)C)cc2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 4-isopropylsulfonylbenzoate | 2.14 | *** |
| 94 | 194 | 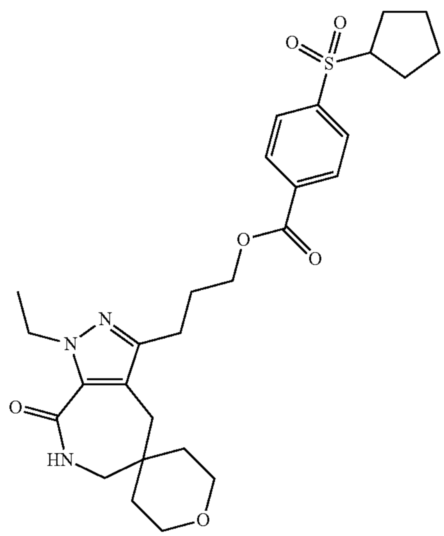 [SMILES: CCn1nc(CCCOC(=O)c2ccc(S(=O)(=O)C3CCCC3)cc2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 4-cyclopentylsulfonylbenzoate | 2.25 | *** |
| 95 | 195 | 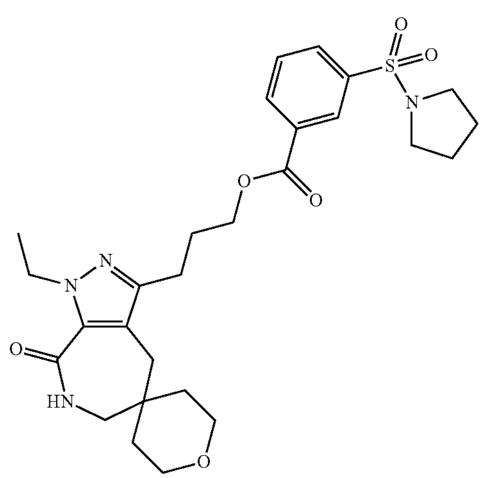 [SMILES: CCn1nc(CCCOC(=O)c2cccc(S(=O)(=O)N3CCCC3)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3-pyrrolidin-1-ylsulfonylbenzoate | 2.21 | *** |

-continued

| Ex. | Cpd | Structure | IUPAC Name | HPLC Rt (min) | PDE4 IC$_{50}$ range |
|---|---|---|---|---|---|
| 96 | 196 | 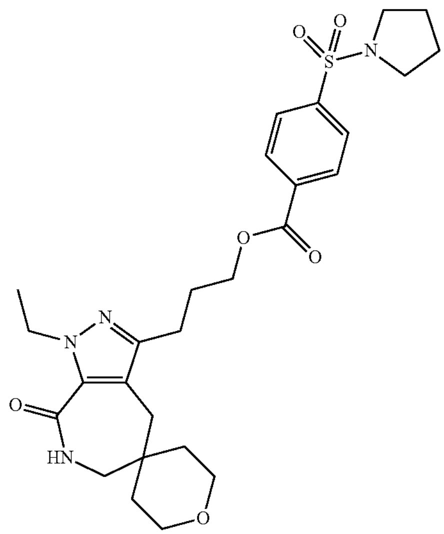 [SMILES: CCn1nc(CCCOC(=O)c2ccc(S(=O)(=O)N3CCCC3)cc2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 4-pyrrolidin-1-ylsulfonylbenzoate | 2.22 | *** |
| 97 | 197 | 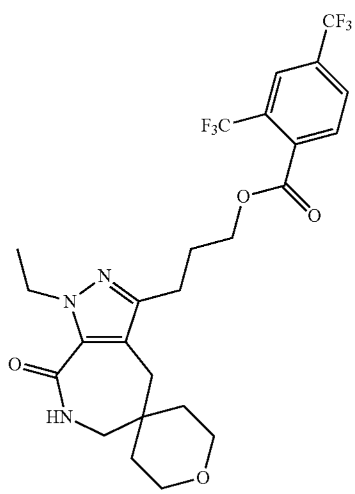 [SMILES: CCn1nc(CCCOC(=O)c2ccc(C(F)(F)F)cc2C(F)(F)F)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 2,4-bis(trifluoromethyl)benzoate | 2.46 | *** |
| 98 | 198 | 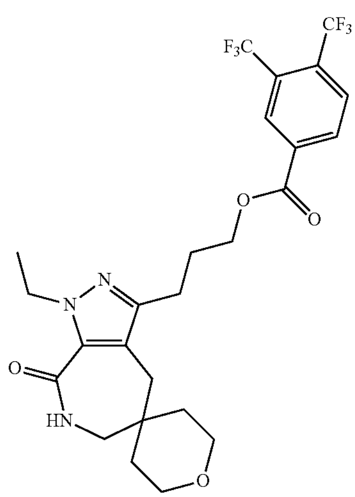 [SMILES: CCn1nc(CCCOC(=O)c2ccc(C(F)(F)F)c(C(F)(F)F)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3,4-bis(trifluoromethyl)benzoate | 2.50 | *** |

| Ex. | Cpd | Structure | IUPAC Name | HPLC Rt (min) | PDE4 IC$_{50}$ range |
|---|---|---|---|---|---|
| 99 | 199 | 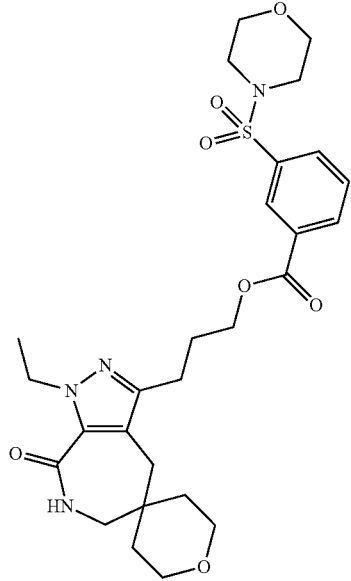 [SMILES: CCn1nc(CCCOC(=O)c2cccc(S(=O)(=O)N3CCOCC3)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3-morpholinosulfonylbenzoate | 2.12 | *** |
| 100 | 200 | 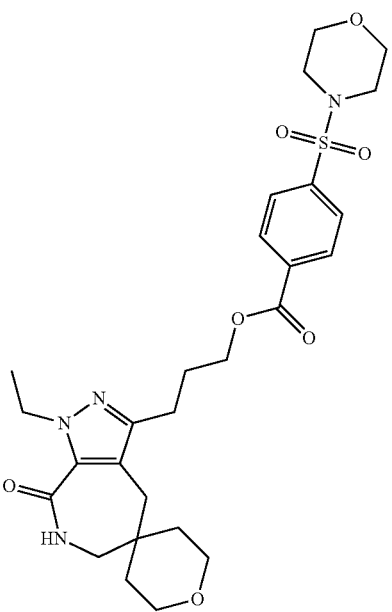 [SMILES: CCn1nc(CCCOC(=O)c2ccc(S(=O)(=O)N3CCOCC3)cc2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 4-morpholinosulfonylbenzoate | 2.14 | *** |

| Ex. | Cpd | Structure | IUPAC Name | HPLC Rt (min) | PDE4 IC$_{50}$ range |
|---|---|---|---|---|---|
| 101 | 201 | 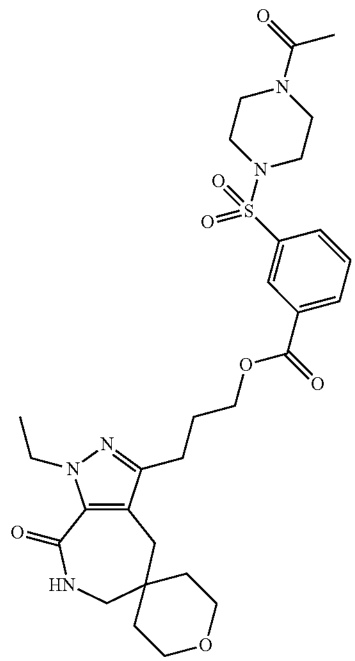 [SMILES: CCn1nc(CCCOC(=O)c2cccc(S(=O)(=O)N3CCN(C(C)=O)CC3)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3-(4-acetylpiperazin-1-yl)sulfonylbenzoate | 2.02 | *** |
| 102 | 202 | 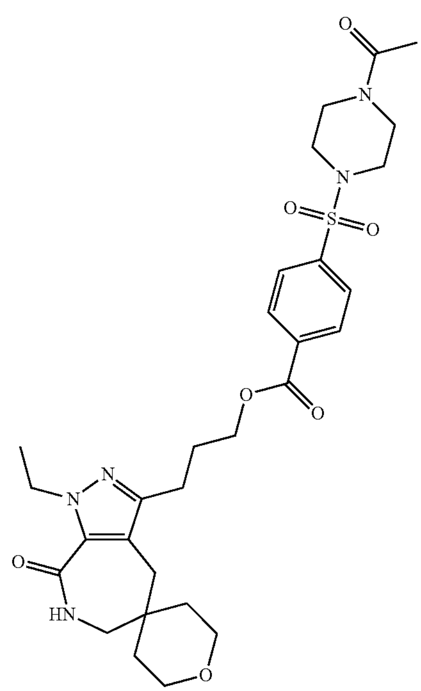 [SMILES: CCn1nc(CCCOC(=O)c2ccc(S(=O)(=O)N3CCN(C(C)=O)CC3)cc2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 4-(4-acetylpiperazin-1-yl)sulfonylbenzoate | 2.04 | *** |

121

Preparation 40 (Compound 203)

3-(1-Ethyl-8-oxo-spiro[6,7-dihydro-4H-pyrazolo[3,4-c]azepine-5,4'-tetrahydropyran]-3-yl)propyl 4-formylbenzoate

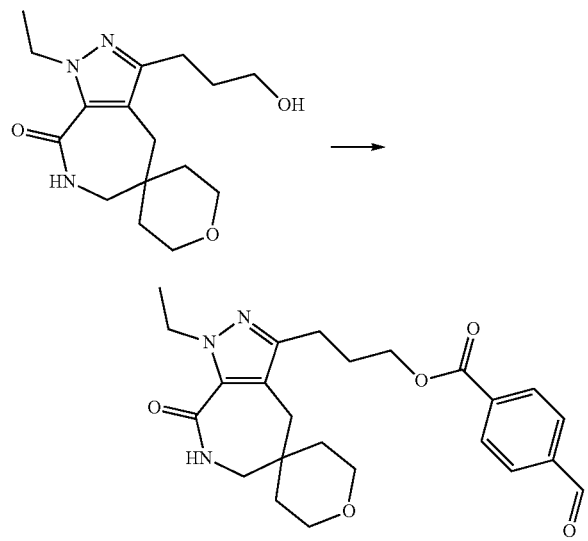

To a solution of 1-ethyl-3-(3-hydroxypropyl)spiro[6,7-dihydro-4H-pyrazolo[3,4-c]azepine-5,4'-tetrahydropyran]-8-one (200 mg, 0.651 mmol) in MeCN (1.0 mL) was added 4-formylbenzoic acid (117 mg, 0.781 mmol), EDAC (150 mg, 0.781 mmol) and DMAP (24 mg, 0.195 mmol). The mixture was stirred for 90 minutes at RT before it was evaporated to dryness under vacuum. Basic prep-HPLC purification afforded the title compound.

122

Example 103 (Compound 204)

4-[3-(1-Ethyl-8-oxo-spiro[6,7-dihydro-4H-pyrazolo[3,4-c]azepine-5,4'-tetrahydropyran]-3-yl)propoxycarbonyl]benzoic acid

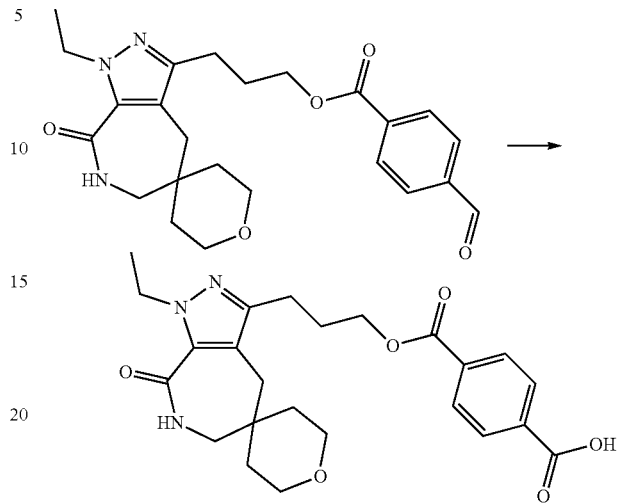

Jones Reagent (2.5 mL) was at 0° C. added to a stirred solution of 3-(1-ethyl-8-oxo-spiro[6,7-dihydro-4H-pyrazolo[3,4-c]azepine-5,4'-tetrahydropyran]-3-yl)propyl 4-formylbenzoate (130 mg, 0.296 mmol) in acetone:water (2:1, 30 mL). The solution was allowed to reach at room temperature over night before isopropanol (2.5 mL) was added. The obtained mixture was stirred for another 30 min, diluted with water (10 mL) and extracted three times with DCM (3×50 mL). The combined organic phases were washed with brine (50 mL) and concentrated in vacuo. Basic prep-HPLC purification afforded the title compound as colorless solid.

$^1$H NMR (DMSO-$d_6$) δ: 8.03 (t, J=5.9 Hz, 1H), 7.92 (d, 2H), 7.85 (d, 2H), 4.32-4.26 (m, 4H), 3.58-3.49 (m, 4H), 2.88 (d, J=5.9 Hz, 2H), 2.66 (t, J=7.4 Hz, 2H), 2.46 (s, 2H), 2.03 (p, J=6.7 Hz, 2H), 1.36 (t, J=5.5 Hz, 4H), 1.26 (t, J=7.1 Hz, 3H).

Retention time (XE Metode 7 CM): 2.00 minutes.
Detected "M+1"-mass: 456.21.

The Examples 104-111 in Table 3 were prepared by reacting Compound 204 as described in General Procedure 2 with the appropriate amine:

| Ex. | Cpd | Structure | IUPAC Name | HPLC Rt (min) | PDE4 IC$_{50}$ range |
|---|---|---|---|---|---|
| 104 | 205 | (structure shown) | 3-(1-ethyl-8-oxo-spiro[6,7-dihydro-4H-pyrazolo[3,4-c]azepine-5,4'-tetrahydropyran]-3-yl)propyl 4-carbamoylbenzoate | 1.86 | *** |

-continued

| Ex. | Cpd | Structure | IUPAC Name | HPLC Rt (min) | PDE4 IC$_{50}$ range |
|---|---|---|---|---|---|
| 105 | 206 | 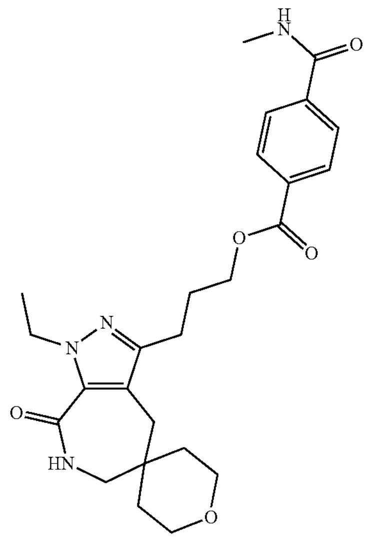 [SMILES: CCn1nc(CCCOC(=O)c2ccc(C(=O)NC)cc2)c2c1C(=O)NCC1(CCOCC1)C2] | 3-(1-ethyl-8-oxo-spiro[6,7-dihydro-4H-pyrazolo[3,4-c]azepine-5,4'-tetrahydro-pyran]-3-yl)propyl 4-(methylcarbamoyl)benzoate | 1.90 | *** |
| 106 | 207 | 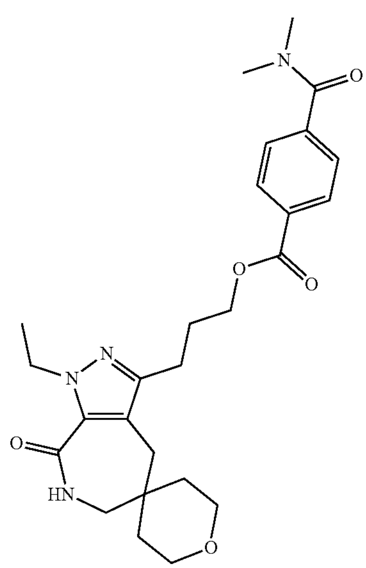 [SMILES: CCn1nc(CCCOC(=O)c2ccc(C(=O)N(C)C)cc2)c2c1C(=O)NCC1(CCOCC1)C2] | 3-(1-ethyl-8-oxo-spiro[6,7-dihydro-4H-pyrazolo[3,4-c]azepine-5,4'-tetrahydro-pyran]-3-yl)propyl 4-(dimethylcarbamoyl)benzoate | 1.95 | *** |

| Ex. | Cpd | Structure | IUPAC Name | HPLC Rt (min) | PDE4 IC$_{50}$ range |
|---|---|---|---|---|---|
| 107 | 208 | 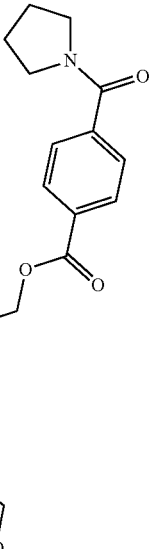 | 3-(1-ethyl-8-oxo-spiro[6,7-dihydro-4H-pyrazolo[3,4-c]azepine-5,4'-tetrahydro-pyran]-3-yl)propyl 4-(pyrrolidine-1-carbonyl)benzoate | 2.02 | *** |
| 108 | 209 | 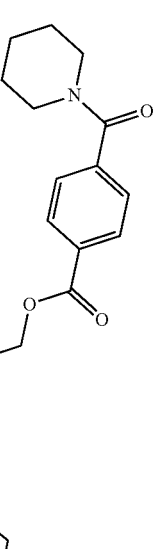 | 3-(1-ethyl-8-oxo-spiro[6,7-dihydro-4H-pyrazolo[3,4-c]azepine-5,4'-tetrahydro-pyran]-3-yl)propyl 4-(piperidine-1-carbonyl)benzoate | 2.13 | *** |

| Ex. | Cpd | Structure | IUPAC Name | HPLC Rt (min) | PDE4 IC$_{50}$ range |
|---|---|---|---|---|---|
| 109 | 210 | 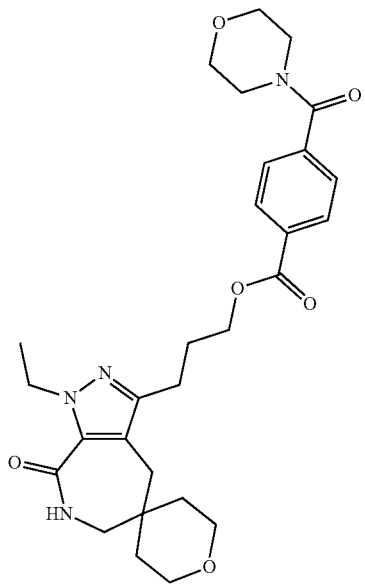 [SMILES: CCn1nc(CCCOC(=O)c2ccc(C(=O)N3CCOCC3)cc2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 4-(morpholine-4-carbonyl)benzoate | 1.94 | *** |
| 110 | 211 | 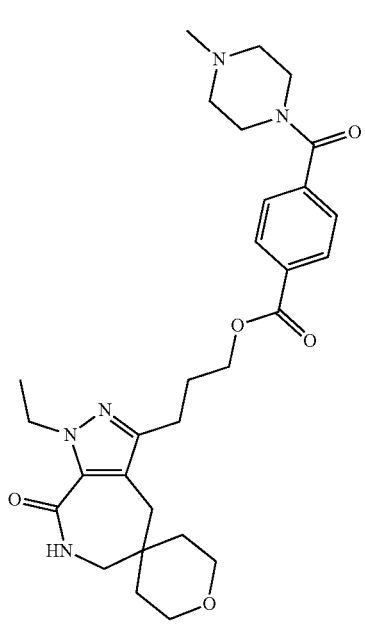 [SMILES: CCn1nc(CCCOC(=O)c2ccc(C(=O)N3CCN(C)CC3)cc2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 4-(4-methylpiperazine-1-carbonyl)benzoate | 1.73 | *** |

| Ex. | Cpd | Structure | IUPAC Name | HPLC Rt (min) | PDE4 IC$_{50}$ range |
|---|---|---|---|---|---|
| 111 | 212 | 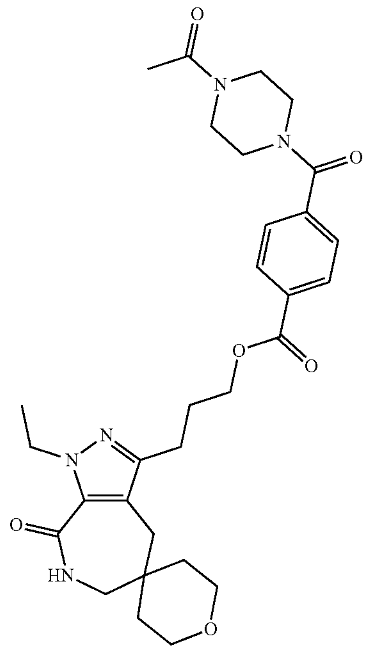 [SMILES: CCn1nc(CCCOC(=O)c2ccc(C(=O)N3CCN(C(C)=O)CC3)cc2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 4-(4-acetylpiperazine-1-carbonyl)benzoate | 1.87 | *** |

Preparation 41 (Compound 213)

3-(1-Ethyl-8-oxo-spiro[6,7-dihydro-4H-pyrazolo[3,4-c]azepine-5,4'-tetrahydropyran]-3-yl)propyl 3-formylbenzoate

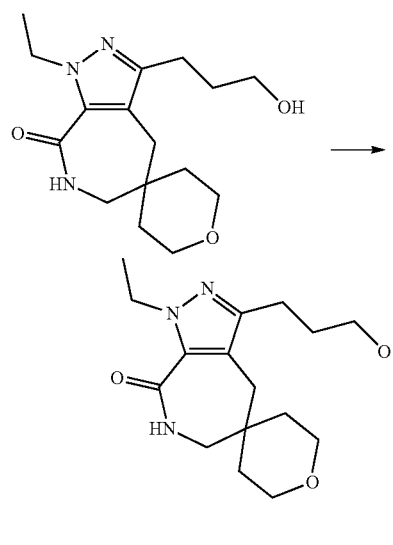

To a solution of 1-ethyl-3-(3-hydroxypropyl)spiro[6,7-dihydro-4H-pyrazolo[3,4-c]azepine-5,4'-tetrahydropyran]-8-one (200 mg, 0.651 mmol) in MeCN (5.0 mL) was added 3-formylbenzoic acid (117 mg, 0.781 mmol), EDAC (150 mg, 0.781 mmol) and DMAP (24 mg, 0.195 mmol). The mixture was stirred for 90 minutes at RT before it was evaporated to dryness under vacuum. Basic prep-HPLC purification afforded the title compound as colorless oil.

Example 112 (Compound 214)

3-[3-(1-Ethyl-8-oxo-spiro[6,7-dihydro-4H-pyrazolo[3,4-c]azepine-5,4'-tetrahydropyran]-3-yl)propoxy-carbonyl]benzoic acid

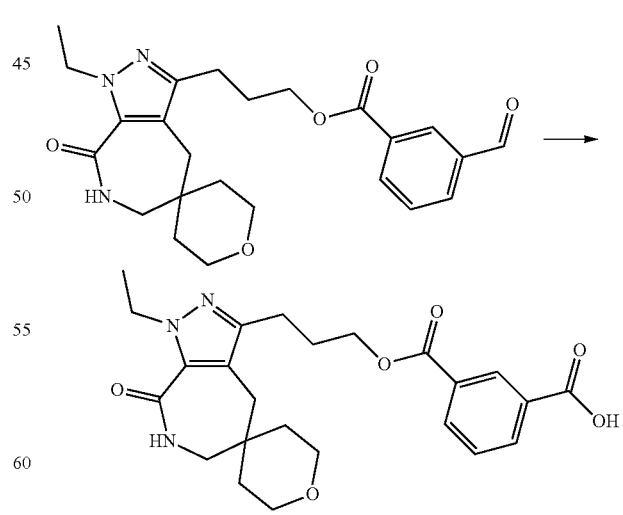

Jones Reagent (3.0 mL) was at 0° C. added to a stirred solution of 3-(1-ethyl-8-oxo-spiro[6,7-dihydro-4H-pyrazolo[3,4-c]azepine-5,4'-tetrahydropyran]-3-yl)propyl 3-formyl-benzoate (154 mg, 0.350 mmol) in acetone:water (2:1, 37.5 mL). The solution was allowed to reach at room temperature over night before isopropanol (3.0 mL) was added. The obtained mixture was stirred for another 30 min, diluted with water (50 mL) and extracted three times with DCM (3×50 mL). The combined organic phases were washed with brine (50 mL), dried over Na$_2$SO$_4$ and concentrated in vacuo. Basic prep-HPLC purification afforded the title compound as colorless solid.

$^1$H NMR (DMSO-d$_6$) δ: 8.47 (t, J=1.7 Hz, 1H), 8.10 (dt, J=7.6, 1.5 Hz, 1H), 8.03 (t, J=5.9 Hz, 1H), 7.89 (dt, J=7.7, 1.6 Hz, 1H), 7.44 (t, J=7.6 Hz, 1H), 4.34-4.26 (m, 4H), 3.58-3.48 (m, 4H), 2.88 (d, J=5.9 Hz, 2H), 2.66 (t, J=7.5 Hz, 2H), 2.45 (s, 2H), 2.07-2.00 (m, 2H), 1.40-1.31 (m, 4H), 1.27 (t, J=7.1 Hz, 3H).

Retention time (XE Metode 7 CM): 2.00 minutes.

Detected "M+1"-mass: 456.21.

The Examples 113-120 in Table 4 were prepared by reacting Compound 214 as described in General Procedure 2 with the appropriate amine:

| Ex. | Cpd | Structure | IUPAC Name | HPLC Rt (min) | PDE4 IC$_{50}$ range |
|---|---|---|---|---|---|
| 113 | 215 | 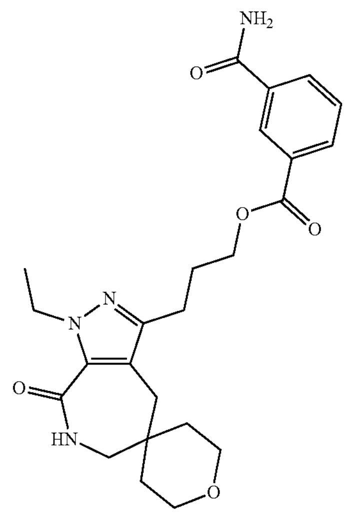 [SMILES: CCn1nc(CCCOC(=O)c2cccc(C(N)=O)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3-carbamoylbenzoate | 1.86 | *** |
| 114 | 216 | 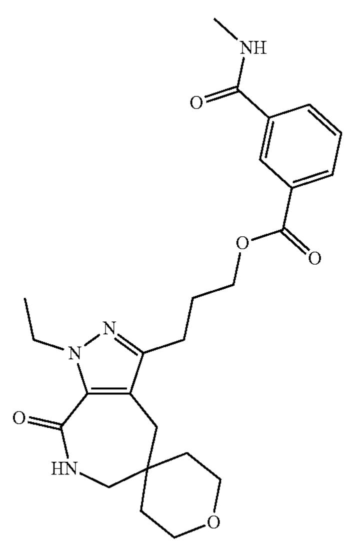 [SMILES: CCn1nc(CCCOC(=O)c2cccc(C(=O)NC)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3-(methyl-carbamoyl)benzoate | 1.91 | *** |

-continued

| Ex. | Cpd | Structure | IUPAC Name | HPLC Rt (min) | PDE4 IC$_{50}$ range |
|---|---|---|---|---|---|
| 115 | 217 | 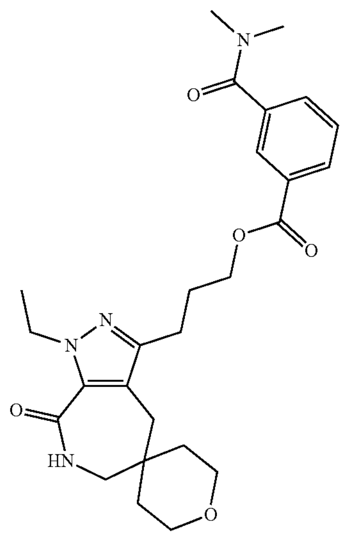 [SMILES: CCn1nc(CCCOC(=O)c2cccc(C(=O)N(C)C)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3-(dimethylcarbamoyl)benzoate | 1.95 | *** |
| 116 | 218 | 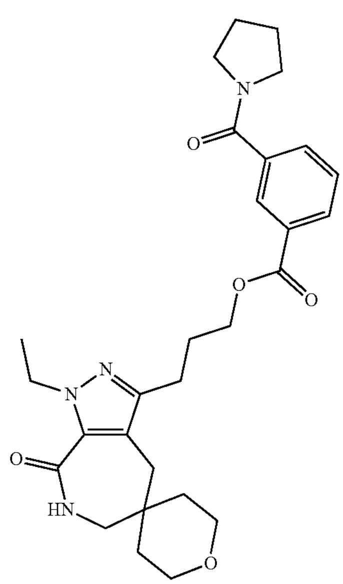 [SMILES: CCn1nc(CCCOC(=O)c2cccc(C(=O)N3CCCC3)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3-(pyrrolidine-1-carbonyl)benzoate | 2.02 | *** |

-continued
| Ex. | Cpd | Structure | IUPAC Name | HPLC Rt (min) | PDE4 IC$_{50}$ range |
|---|---|---|---|---|---|
| 117 | 219 | 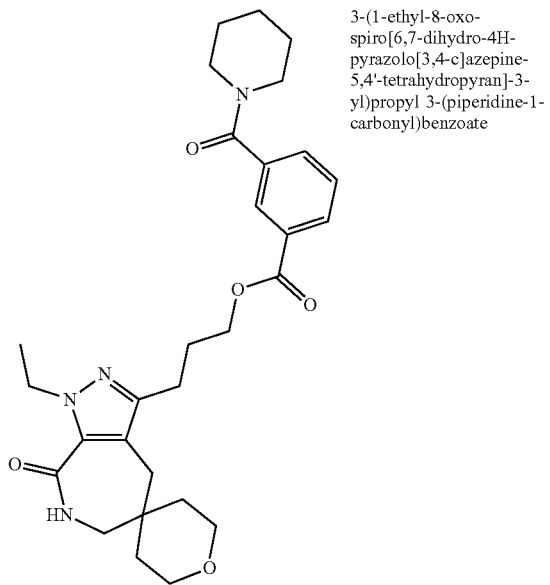 | 3-(1-ethyl-8-oxo-spiro[6,7-dihydro-4H-pyrazolo[3,4-c]azepine-5,4'-tetrahydropyran]-3-yl)propyl 3-(piperidine-1-carbonyl)benzoate | 2.13 | *** |
| 118 | 220 | 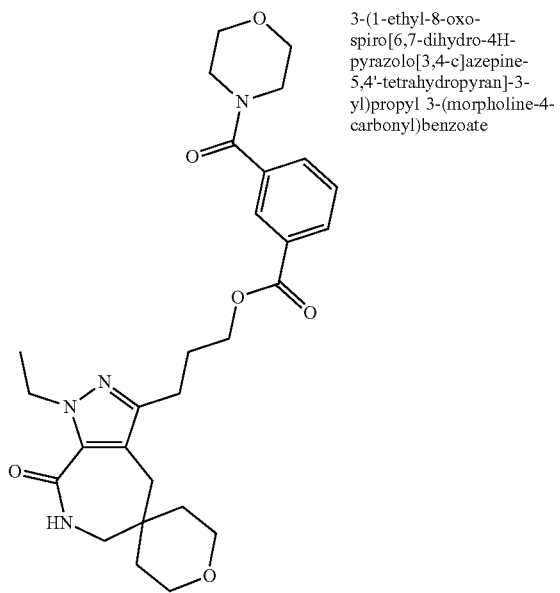 | 3-(1-ethyl-8-oxo-spiro[6,7-dihydro-4H-pyrazolo[3,4-c]azepine-5,4'-tetrahydropyran]-3-yl)propyl 3-(morpholine-4-carbonyl)benzoate | 1.94 | *** |

| Ex. | Cpd | Structure | IUPAC Name | HPLC Rt (min) | PDE4 IC$_{50}$ range |
|---|---|---|---|---|---|
| 119 | 221 | 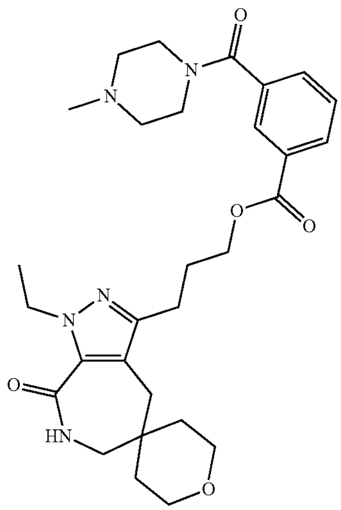 [SMILES: CCn1nc(CCCOC(=O)c2cccc(C(=O)N3CCN(C)CC3)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3-(4-methylpiperazine-1-carbonyl)benzoate | 1.73 | *** |
| 120 | 222 | 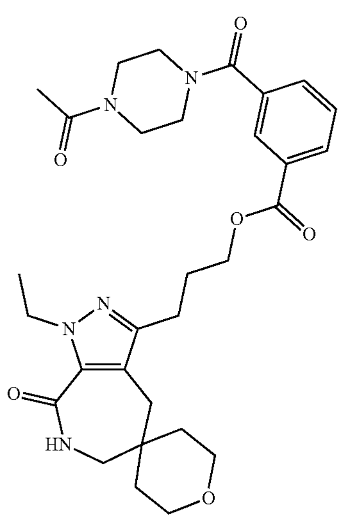 [SMILES: CCn1nc(CCCOC(=O)c2cccc(C(=O)N3CCN(C(C)=O)CC3)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3-(4-acetylpiperazine-1-carbonyl)benzoate | 1.87 | *** |

The Examples 121-133 shown in Table 5 were prepared by reacting Compound 012 as described in General Procedure 1 with the appropriate acid:

| Ex. | Cpd | Structure | IUPAC Name | HPLC Rt (min) | PDE4 IC$_{50}$ range |
|---|---|---|---|---|---|
| 121 | 223 | 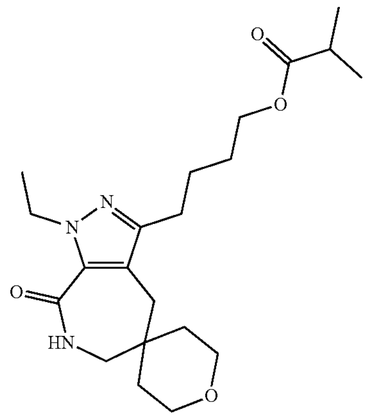 [SMILES: CCn1nc(CCCCOC(=O)C(C)C)c2c1C(=O)NCC1(CCOCC1)C2] | 4-(1-ethyl-8-oxo-spiro[6,7-dihydro-4H-pyrazolo[3,4-c]azepine-5,4'-tetrahydropyran]-3-yl)butyl 2-methyl-propanoate | 2.15 | *** |
| 122 | 224 | 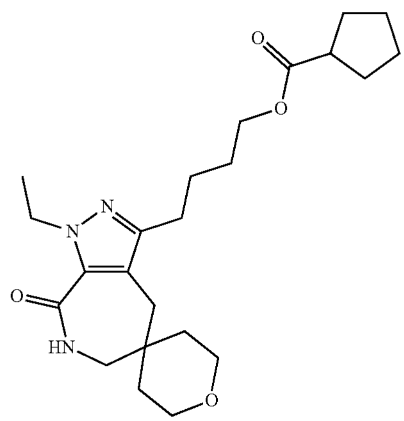 [SMILES: CCn1nc(CCCCOC(=O)C2CCCC2)c2c1C(=O)NCC1(CCOCC1)C2] | 4-(1-ethyl-8-oxo-spiro[6,7-dihydro-4H-pyrazolo[3,4-c]azepine-5,4'-tetrahydropyran]-3-yl)butyl cyclopentane-carboxylate | 2.29 | *** |
| 123 | 225 | 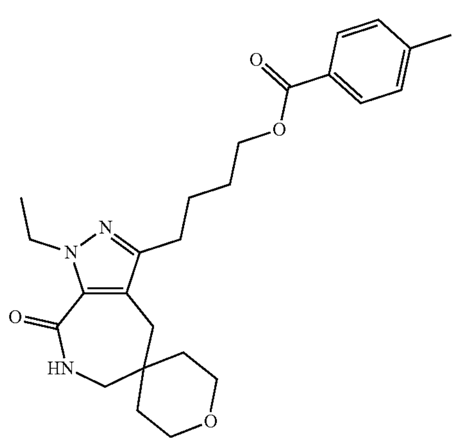 [SMILES: CCn1nc(CCCCOC(=O)c2ccc(C)cc2)c2c1C(=O)NCC1(CCOCC1)C2] | 4-(1-ethyl-8-oxo-spiro[6,7-dihydro-4H-pyrazolo[3,4-c]azepine-5,4'-tetrahydropyran]-3-yl)butyl 4-methylbenzoate | 2.34 | *** |

-continued

| Ex. | Cpd | Structure | IUPAC Name | HPLC Rt (min) | PDE4 IC$_{50}$ range |
|---|---|---|---|---|---|
| 124 | 226 | 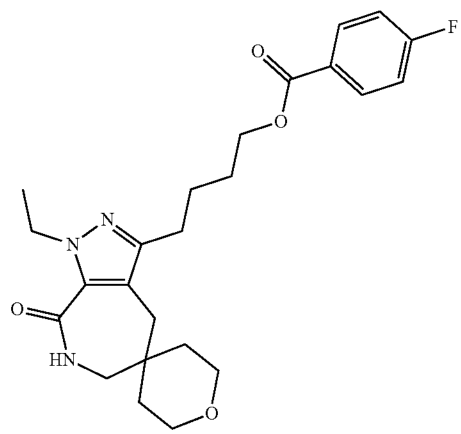 [SMILES: CCn1nc(CCCCOC(=O)c2ccc(F)cc2)c2c1C(=O)NCC1(CCOCC1)C2] | 4-(1-ethyl-8-oxo-spiro[6,7-dihydro-4H-pyrazolo[3,4-c]azepine-5,4'-tetrahydropyran]-3-yl)butyl 4-fluorobenzoate | 2.28 | *** |
| 125 | 227 | 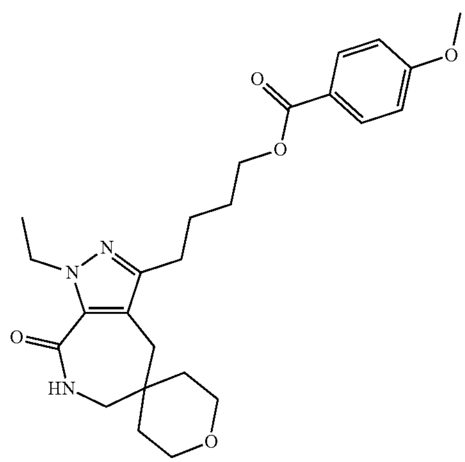 [SMILES: CCn1nc(CCCCOC(=O)c2ccc(OC)cc2)c2c1C(=O)NCC1(CCOCC1)C2] | 4-(1-ethyl-8-oxo-spiro[6,7-dihydro-4H-pyrazolo[3,4-c]azepine-5,4'-tetrahydropyran]-3-yl)butyl 4-methoxybenzoate | 2.25 | *** |
| 126 | 228 | 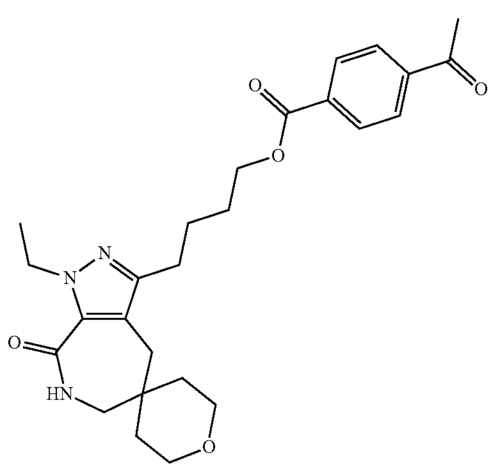 [SMILES: CCn1nc(CCCCOC(=O)c2ccc(C(C)=O)cc2)c2c1C(=O)NCC1(CCOCC1)C2] | 4-(1-ethyl-8-oxo-spiro[6,7-dihydro-4H-pyrazolo[3,4-c]azepine-5,4'-tetrahydropyran]-3-yl)butyl 4-acetylbenzoate | 2.18 | *** |

-continued

| Ex. | Cpd | Structure | IUPAC Name | HPLC Rt (min) | PDE4 IC$_{50}$ range |
|---|---|---|---|---|---|
| 127 | 229 | 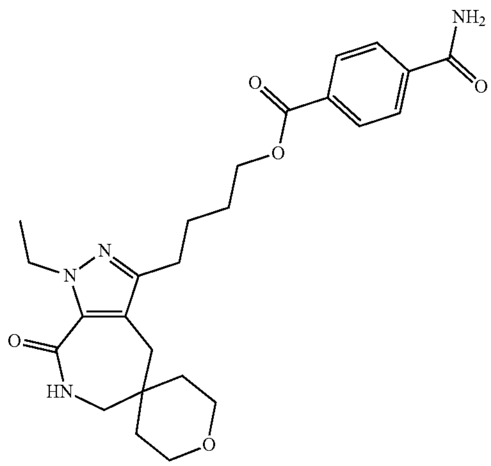 [SMILES: CCn1nc(CCCCOC(=O)c2ccc(C(N)=O)cc2)c2c1C(=O)NCC1(CCOCC1)C2] | 4-(1-ethyl-8-oxo-spiro[6,7-dihydro-4H-pyrazolo[3,4-c]azepine-5,4'-tetrahydropyran]-3-yl)butyl 4-carbamoylbenzoate | 1.91 | *** |
| 128 | 230 | 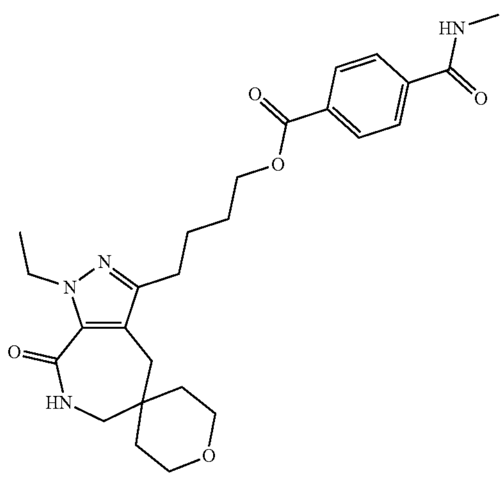 [SMILES: CCn1nc(CCCCOC(=O)c2ccc(C(=O)NC)cc2)c2c1C(=O)NCC1(CCOCC1)C2] | 4-(1-ethyl-8-oxo-spiro[6,7-dihydro-4H-pyrazolo[3,4-c]azepine-5,4'-tetrahydropyran]-3-yl)butyl 4-(methylcarbamoyl)benzoate | 1.96 | *** |
| 129 | 231 | 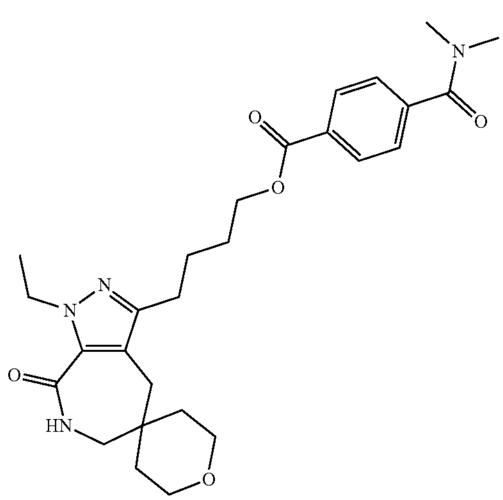 [SMILES: CCn1nc(CCCCOC(=O)c2ccc(C(=O)N(C)C)cc2)c2c1C(=O)NCC1(CCOCC1)C2] | 4-(1-ethyl-8-oxo-spiro[6,7-dihydro-4H-pyrazolo[3,4-c]azepine-5,4'-tetrahydropyran]-3-yl)butyl 4-(dimethylcarbamoyl)benzoate | 2.01 | *** |

| Ex. | Cpd | Structure | IUPAC Name | HPLC Rt (min) | PDE4 IC$_{50}$ range |
|---|---|---|---|---|---|
| 130 | 232 | 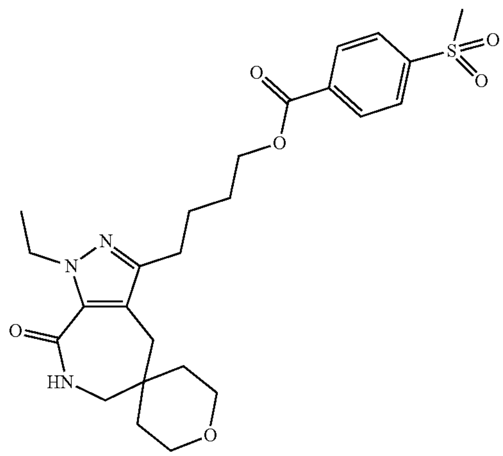 [SMILES: CCn1nc(CCCCOC(=O)c2ccc(S(C)(=O)=O)cc2)c2c1C(=O)NCC1(CCOCC1)C2] | 4-(1-ethyl-8-oxo-spiro[6,7-dihydro-4H-pyrazolo[3,4-c]azepine-5,4'-tetrahydropyran]-3-yl)butyl 4-methylsulfonylbenzoate | 2.07 | *** |
| 131 | 233 | 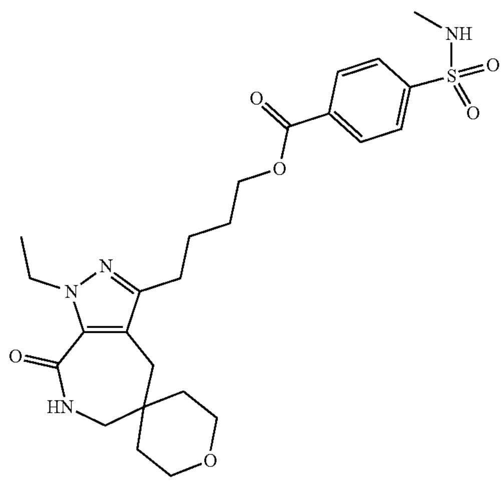 [SMILES: CCn1nc(CCCCOC(=O)c2ccc(S(=O)(=O)NC)cc2)c2c1C(=O)NCC1(CCOCC1)C2] | 4-(1-ethyl-8-oxo-spiro[6,7-dihydro-4H-pyrazolo[3,4-c]azepine-5,4'-tetrahydropyran]-3-yl)butyl 4-(methylsulfamoyl)benzoate | 2.09 | *** |
| 132 | 234 | 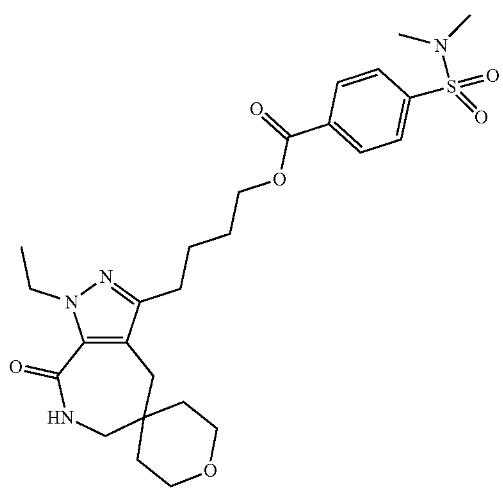 [SMILES: CCn1nc(CCCCOC(=O)c2ccc(S(=O)(=O)N(C)C)cc2)c2c1C(=O)NCC1(CCOCC1)C2] | 4-(1-ethyl-8-oxo-spiro[6,7-dihydro-4H-pyrazolo[3,4-c]azepine-5,4'-tetrahydropyran]-3-yl)butyl 4-(dimethylsulfamoyl)benzoate | 2.21 | *** |

| Ex. | Cpd | Structure | IUPAC Name | HPLC Rt (min) | PDE4 IC$_{50}$ range |
|---|---|---|---|---|---|
| 133 | 235 | 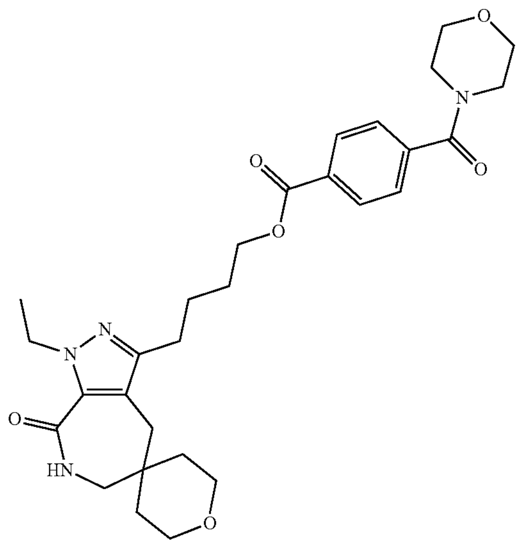 [SMILES: CCn1nc(CCCCOC(=O)c2ccc(C(=O)N3CCOCC3)cc2)c2c1C(=O)NCC1(CCOCC1)C2] | 4-(1-ethyl-8-oxo-spiro[6,7-dihydro-4H-pyrazolo[3,4-c]azepine-5,4'-tetrahydropyran]-3-yl)butyl 4-(morpholine-4-carbonyl)benzoate | 2.00 | *** |

The Examples 134-136 shown in Table 6 were prepared by reacting Compound 016 as described in General Procedure 1 with the appropriate acid:

| Ex. | Cpd | Structure | IUPAC Name | HPLC Rt (min) | PDE4 IC$_{50}$ range |
|---|---|---|---|---|---|
| 134 | 236 | 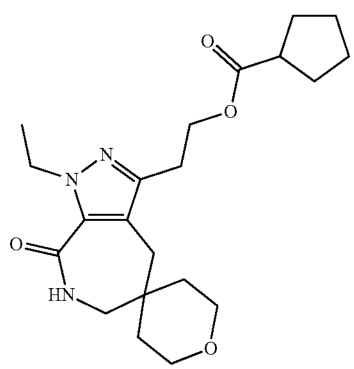 [SMILES: CCn1nc(CCOC(=O)C2CCCC2)c2c1C(=O)NCC1(CCOCC1)C2] | 2-(1-ethyl-8-oxo-spiro-[6,7-dihydro-4H-pyrazolo-[3,4-c]azepine-5,4'-tetrahydropyran]-3-yl)ethyl cyclopentanecarboxylate | 2.15 | *** |
| 135 | 237 | 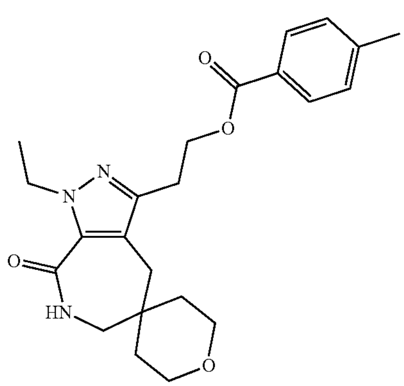 [SMILES: CCn1nc(CCOC(=O)c2ccc(C)cc2)c2c1C(=O)NCC1(CCOCC1)C2] | 2-(1-ethyl-8-oxo-spiro[6,7-dihydro-4H-pyrazolo[3,4-c]azepine-5,4'-tetrahydropyran]-3-yl)ethyl 4-methylbenzoate | 2.22 | *** |

-continued

| Ex. | Cpd | Structure | IUPAC Name | HPLC Rt (min) | PDE4 IC$_{50}$ range |
|---|---|---|---|---|---|
| 136 | 238 | 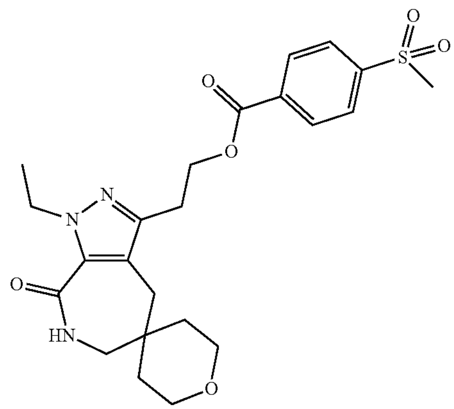 [SMILES: CCn1nc(CCOC(=O)c2ccc(S(C)(=O)=O)cc2)c2c1C(=O)NCC1(CCOCC1)C2] | 2-(1-ethyl-8-oxo-spiro-[6,7-dihydro-4H-pyrazolo-[3,4-c]azepine-5,4'-tetra-hydropyran]-3-yl)ethyl 4-methylsulfonylbenzoate | 1.96 | *** |

The Examples 137-167 shown in Table 7 were prepared by reacting Compound 028 as described in General Procedure 1 with the appropriate acid:

| Ex. | Cpd | Structure | IUPAC Name | HPLC Rt (min) | PDE4 IC$_{50}$ range |
|---|---|---|---|---|---|
| 137 | 239 | 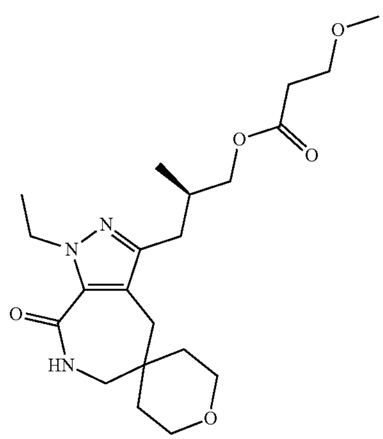 [SMILES: CCn1nc(C[C@@H](C)COC(=O)CCOC)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 3-methoxypropanoate | 1.97 | *** |
| 138 | 240 | 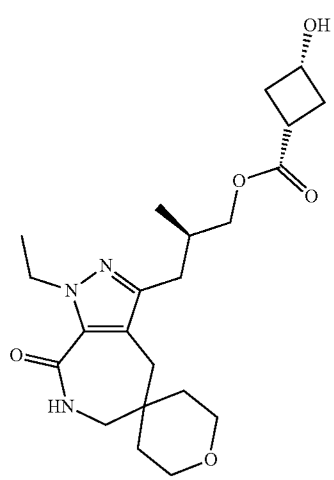 | [(2R)-3-(1-ethyl-8-oxo-spiro[6,7-dihydro-4H-pyrazolo[3,4-c]azepine-5,4'-tetrahydropyran]-3-yl)-2-methyl-propyl] 3-hydroxy-cyclobutanecarboxylate | 1.86 | *** |

| Ex. | Cpd | Structure | IUPAC Name | HPLC Rt (min) | PDE4 IC$_{50}$ range |
|---|---|---|---|---|---|
| 139 | 241 | 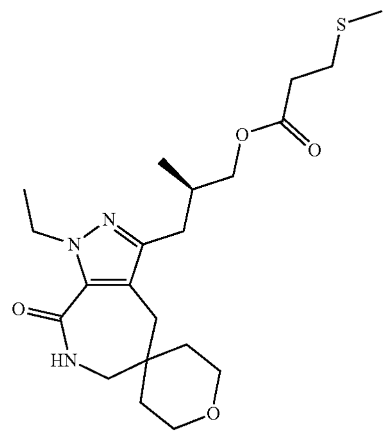 [SMILES: CCn1nc(C[C@@H](C)COC(=O)CCSC)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 3-methylsulfanylpropanoate | 2.13 | *** |
| 140 | 242 | 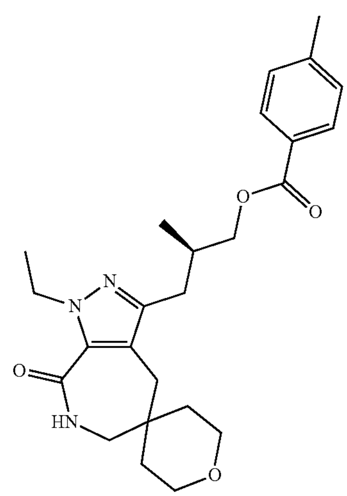 [SMILES: CCn1nc(C[C@@H](C)COC(=O)c2ccc(C)cc2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 4-methylbenzoate | 2.35 | *** |
| 141 | 243 | 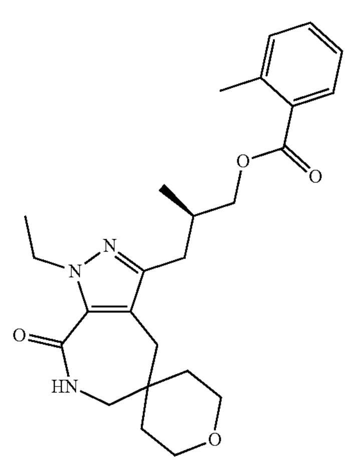 [SMILES: CCn1nc(C[C@@H](C)COC(=O)c2ccccc2C)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 2-methylbenzoate | 2.36 | *** |

-continued

| Ex. | Cpd | Structure | IUPAC Name | HPLC Rt (min) | PDE4 IC$_{50}$ range |
|---|---|---|---|---|---|
| 142 | 244 | 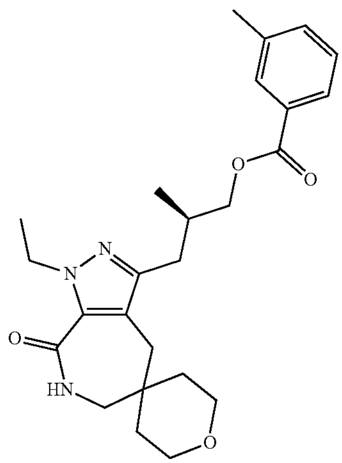 [SMILES: CCn1nc(C[C@@H](C)COC(=O)c2cccc(C)c2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 3-methylbenzoate | 2.35 | *** |
| 143 | 245 | 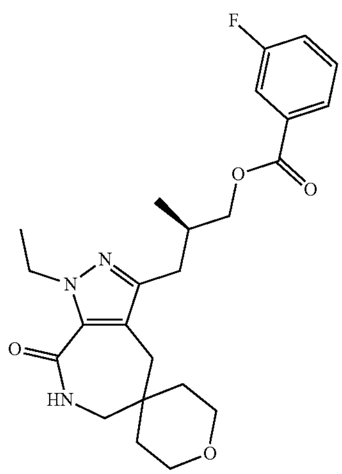 [SMILES: CCn1nc(C[C@@H](C)COC(=O)c2cccc(F)c2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 3-fluorobenzoate | 2.3 | *** |
| 144 | 246 | 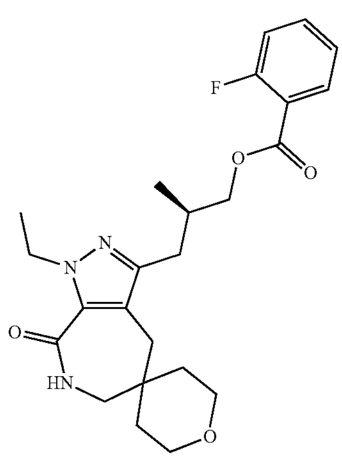 [SMILES: CCn1nc(C[C@@H](C)COC(=O)c2ccccc2F)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 2-fluorobenzoate | 2.24 | *** |

-continued

| Ex. | Cpd | Structure | IUPAC Name | HPLC Rt (min) | PDE4 IC$_{50}$ range |
|---|---|---|---|---|---|
| 145 | 247 | 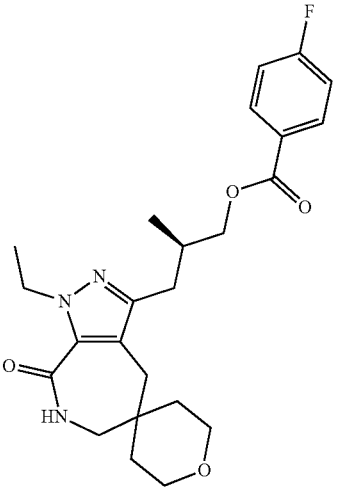 [SMILES: CCn1nc(C[C@@H](C)COC(=O)c2ccc(F)cc2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 4-fluorobenzoate | 2.29 | *** |
| 146 | 248 | 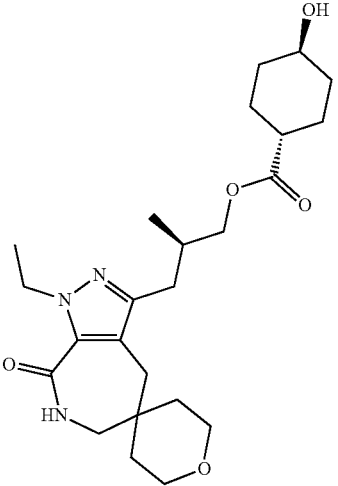 [SMILES: CCn1nc(C[C@@H](C)COC(=O)[C@H]2CC[C@H](O)CC2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 4-hydroxy-cyclohexanecarboxylate | 1.91 | *** |
| 147 | 249 | 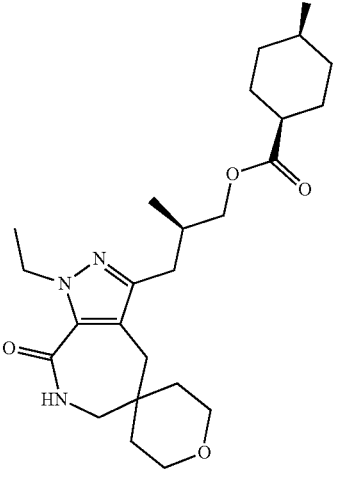 | [(2R)-3-(1-ethyl-8-oxo-spiro[6,7-dihydro-4H-pyrazolo[3,4-c]azepine-5,4'-tetrahydropyran]-3-yl)-2-methyl-propyl] 4-hydroxy-cyclohexanecarboxylate | 1.95 | *** |

-continued

| Ex. | Cpd | Structure | IUPAC Name | HPLC Rt (min) | PDE4 IC$_{50}$ range |
|---|---|---|---|---|---|
| 148 | 250 | 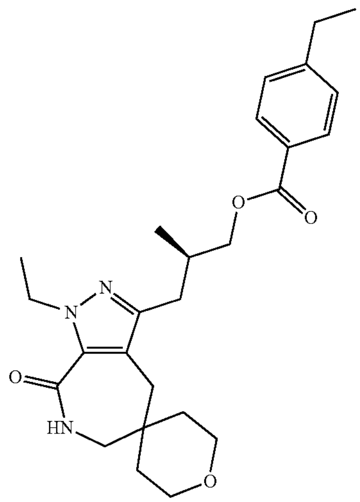 [SMILES: CCc1ccc(C(=O)OC[C@H](C)Cc2nn(CC)c3c2CC2(CCOCC2)CNC3=O)cc1] | [(2R)-3-(1-ethyl-8-oxo-spiro[6,7-dihydro-4H-pyrazolo[3,4-c]azepine-5,4'-tetrahydropyran]-3-yl)-2-methyl-propyl] 4-ethylbenzoate | 2.45 | *** |
| 149 | 251 | 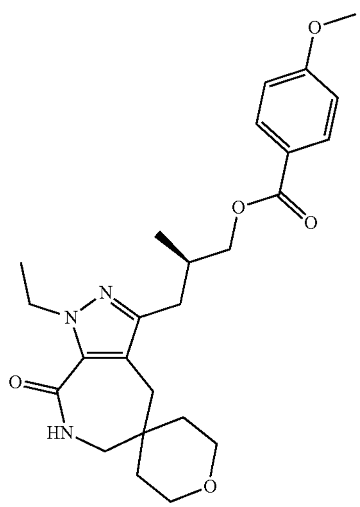 [SMILES: CCn1nc(C[C@@H](C)COC(=O)c2ccc(OC)cc2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 4-methoxybenzoate | 2.26 | *** |
| 150 | 252 | 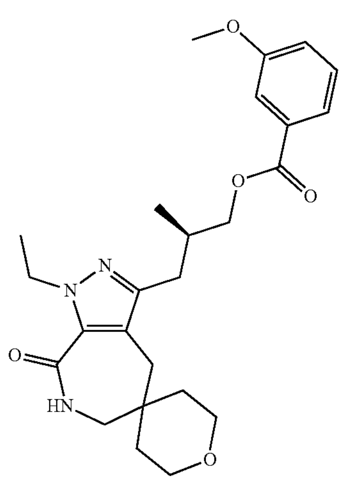 [SMILES: CCn1nc(C[C@@H](C)COC(=O)c2cccc(OC)c2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 3-methoxybenzoate | 2.28 | *** |

| Ex. | Cpd | Structure | IUPAC Name | HPLC Rt (min) | PDE4 IC$_{50}$ range |
|---|---|---|---|---|---|
| 151 | 253 | 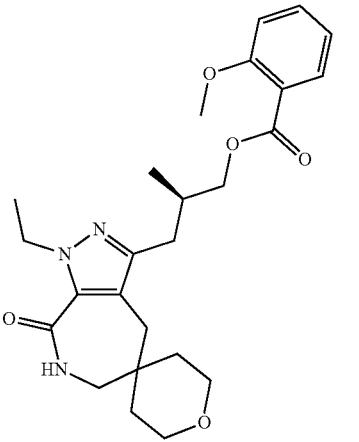 [SMILES: CCn1nc(C[C@@H](C)COC(=O)c2ccccc2OC)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 2-methoxybenzoate | 2.17 | *** |
| 152 | 254 | 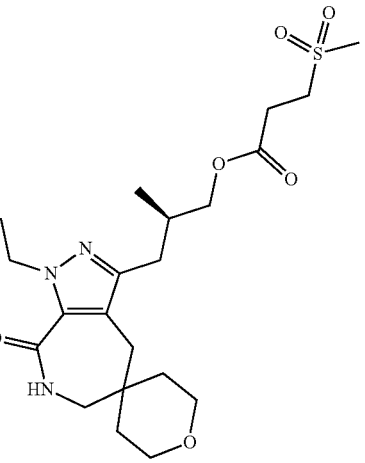 | [(2R)-3-(1-ethyl-8-oxo-spiro[6,7-dihydro-4H-pyrazolo[3,4-c]azepine-5,4'-tetrahydropyran]-3-yl)-2-methyl-propyl] 3-methylsulfonylpropanoate | 1.86 | *** |
| 153 | 255 | 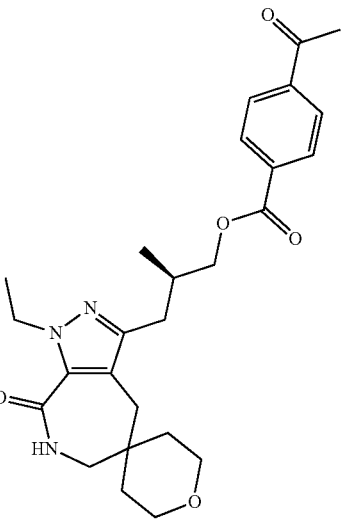 | [(2R)-3-(1-ethyl-8-oxo-spiro[6,7-dihydro-4H-pyrazolo[3,4-c]azepine-5,4'-tetrahydropyran]-3-yl)-2-methyl-propyl] 4-acetylbenzoate | 2.19 | *** |

| Ex. | Cpd | Structure | IUPAC Name | HPLC Rt (min) | PDE4 IC$_{50}$ range |
|---|---|---|---|---|---|
| 154 | 256 | 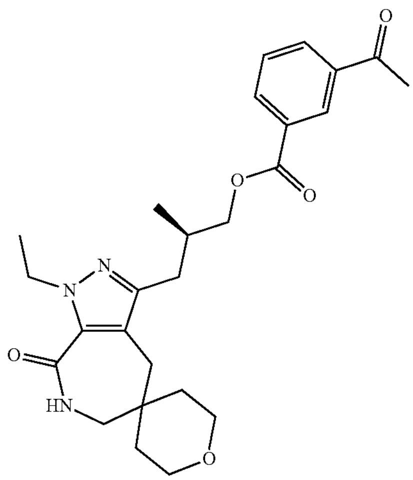 [SMILES: CCn1nc(C[C@@H](C)COC(=O)c2cccc(C(C)=O)c2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 3-acetylbenzoate | 2.18 | *** |
| 155 | 257 | 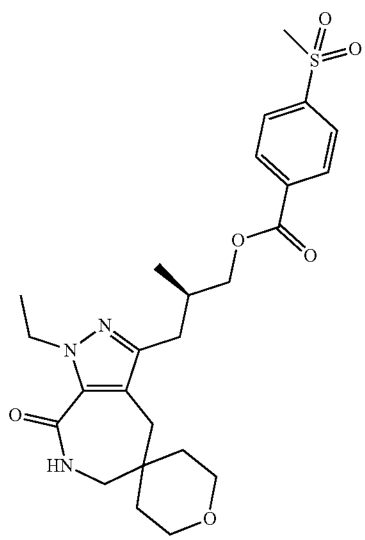 [SMILES: CCn1nc(C[C@@H](C)COC(=O)c2ccc(S(C)(=O)=O)cc2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 4-methylsulfonylbenzoate | 2.08 | *** |
| 156 | 258 | 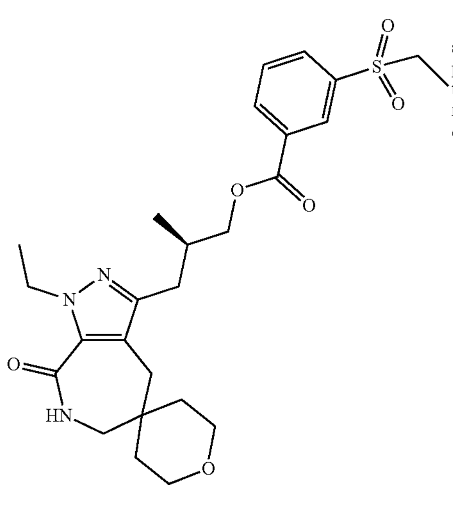 [SMILES: CCn1nc(C[C@@H](C)COC(=O)c2cccc(S(=O)(=O)CC)c2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 3-ethylsulfonylbenzoate | 2.13 | *** |

-continued

| Ex. | Cpd | Structure | IUPAC Name | HPLC Rt (min) | PDE4 IC$_{50}$ range |
|---|---|---|---|---|---|
| 157 | 259 | 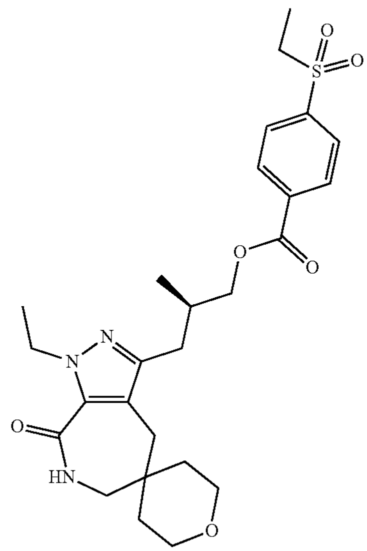 [SMILES: CCn1nc(C[C@@H](C)COC(=O)c2ccc(S(=O)(=O)CC)cc2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 4-ethylsulfonylbenzoate | 2.14 | *** |
| 158 | 260 | 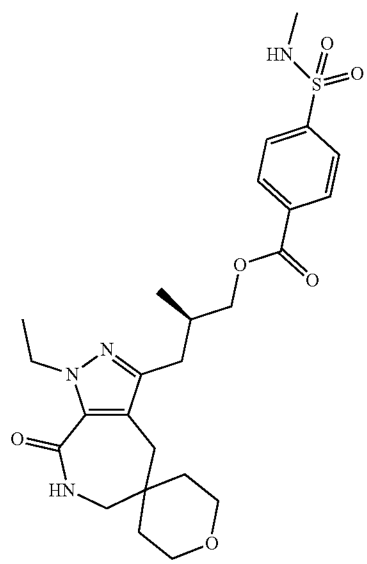 [SMILES: CCn1nc(C[C@@H](C)COC(=O)c2ccc(S(=O)(=O)NC)cc2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 4-(methylsulfamoyl)benzoate | 2.1 | *** |
| 159 | 261 | 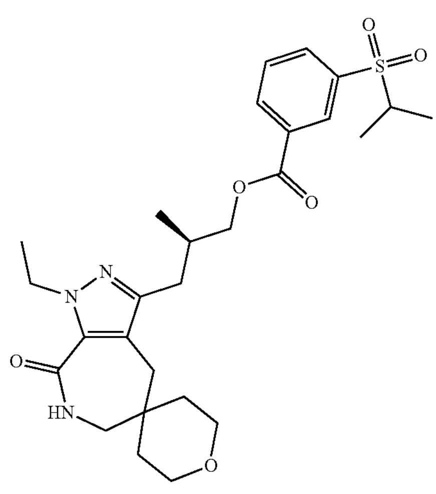 [SMILES: CCn1nc(C[C@@H](C)COC(=O)c2cccc(S(=O)(=O)C(C)C)c2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 3-isopropylsulfonylbenzoate | 2.19 | *** |

-continued

| Ex. | Cpd | Structure | IUPAC Name | HPLC Rt (min) | PDE4 IC$_{50}$ range |
|---|---|---|---|---|---|
| 160 | 262 | 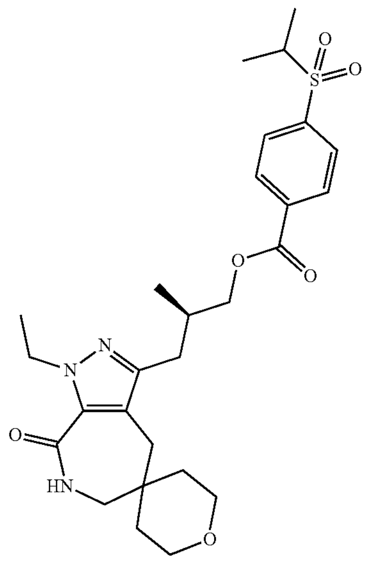 [SMILES: CCn1nc(C[C@@H](C)COC(=O)c2ccc(S(=O)(=O)C(C)C)cc2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 4-isopropylsulfonylbenzoate | 2.21 | *** |
| 161 | 263 | 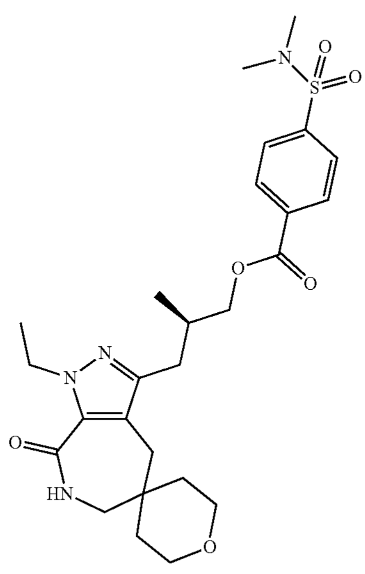 [SMILES: CCn1nc(C[C@@H](C)COC(=O)c2ccc(S(=O)(=O)N(C)C)cc2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 4-(di-methylsulfamoyl)benzoate | 2.22 | *** |

| Ex. | Cpd | Structure | IUPAC Name | HPLC Rt (min) | PDE4 IC$_{50}$ range |
|---|---|---|---|---|---|
| 162 | 264 | 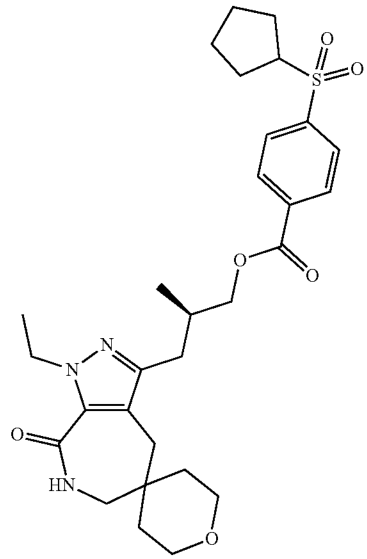 [SMILES: CCn1nc(C[C@@H](C)COC(=O)c2ccc(S(=O)(=O)C3CCCC3)cc2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 4-cyclopentylsulfonylbenzoate | 2.31 | *** |
| 163 | 265 | 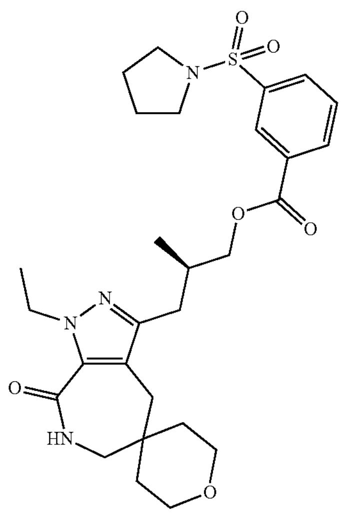 [SMILES: CCn1nc(C[C@@H](C)COC(=O)c2cccc(S(=O)(=O)N3CCCC3)c2)c2c1C(=O)NCC1(CCOCC1)C2] | [(2R)-3-(1-ethyl-8-oxo-spiro[6,7-dihydro-4H-pyrazolo[6,7-c]azepine-5,4'-tetrahydropyran]-3-yl)-2-methyl-propyl] 3-pyrrolidin-1-ylsulfonylbenzoate | 2.27 | *** |
| 164 | 266 | 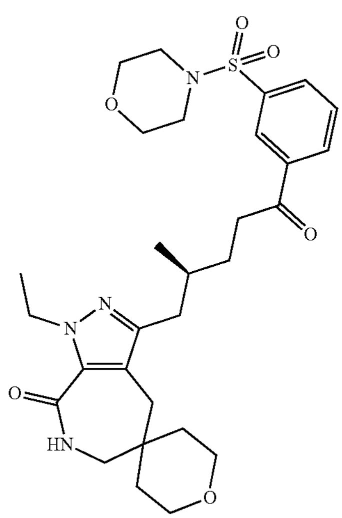 [SMILES: CCn1nc(C[C@@H](C)CCC(=O)c2cccc(S(=O)(=O)N3CCOCC3)c2)c2c1C(=O)NCC1(CCOCC1)C2] | [(2R)-3-(1-ethyl-8-oxo-spiro[6,7-dihydro-4H-pyrazolo[6,7-c]azepine-5,4'-tetrahydropyran]-3-yl)-2-methyl-propyl] 3-morpholinosulfonylbenzoate | 2.18 | *** |

-continued
| Ex. | Cpd | Structure | IUPAC Name | HPLC Rt (min) | PDE4 IC$_{50}$ range |
|---|---|---|---|---|---|
| 165 | 267 | 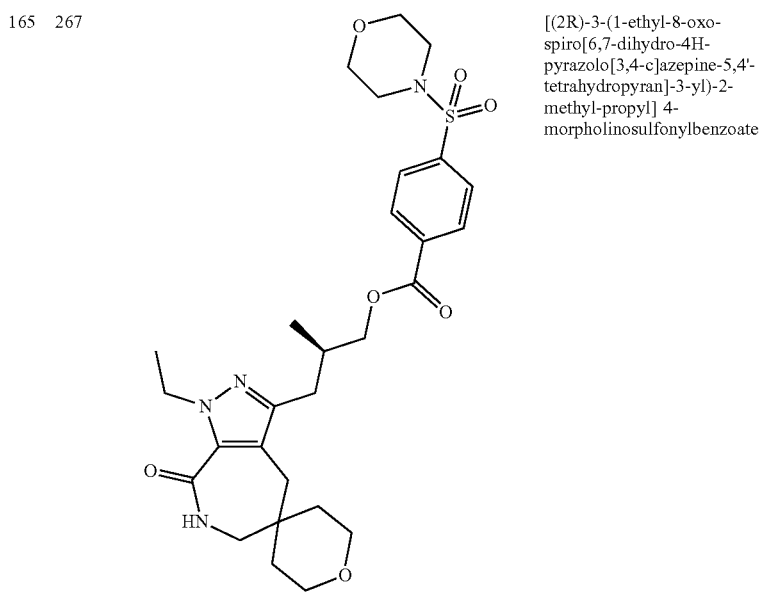 | [(2R)-3-(1-ethyl-8-oxo-spiro[6,7-dihydro-4H-pyrazolo[3,4-c]azepine-5,4'-tetrahydropyran]-3-yl)-2-methyl-propyl] 4-morpholinosulfonylbenzoate | 2.2 | *** |
| 166 | 268 | 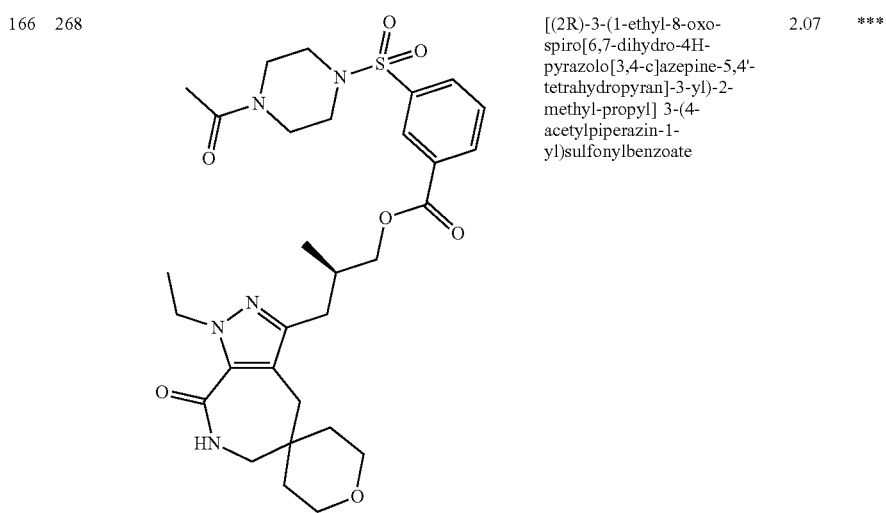 | [(2R)-3-(1-ethyl-8-oxo-spiro[6,7-dihydro-4H-pyrazolo[3,4-c]azepine-5,4'-tetrahydropyran]-3-yl)-2-methyl-propyl] 3-(4-acetylpiperazin-1-yl)sulfonylbenzoate | 2.07 | *** |

| Ex. | Cpd | Structure | IUPAC Name | HPLC Rt (min) | PDE4 IC$_{50}$ range |
|---|---|---|---|---|---|
| 167 | 269 | 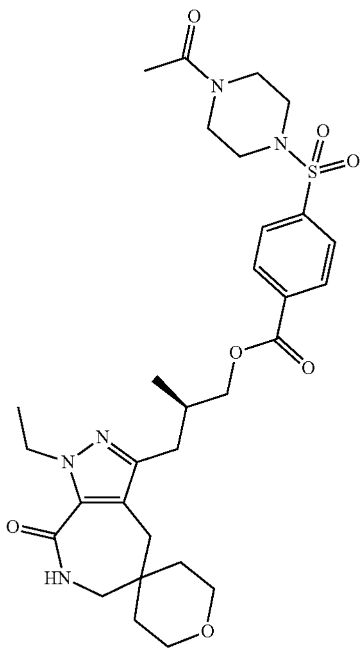 [SMILES: CCn1nc(C[C@@H](C)COC(=O)c2ccc(S(=O)(=O)N3CCN(C(C)=O)CC3)cc2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 4-(4-acetylpiperazin-1-yl)sulfonylbenzoate | 2.09 | *** |

Example 168 (Compound 270)

4-[(2R)-3-(1-Ethyl-8-oxo-spiro[6,7-dihydro-4H-pyrazolo[3,4-c]azepine-5,4'-tetrahydropyran]-3-yl)-2-methyl-propoxy]carbonylbenzoic acid

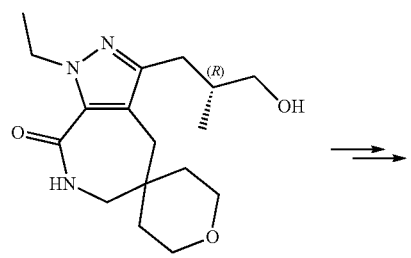

4-[(2R)-3-(1-Ethyl-8-oxo-spiro[6,7-dihydro-4H-pyrazolo[3,4-c]azepine-5,4'-tetrahydropyran]-3-yl)-2-methyl-propoxy]carbonylbenzoic acid was prepared in a manner similar to that described for 4-[3-(1-ethyl-8-oxo-spiro[6,7-dihydro-4H-pyrazolo[3,4-c]azepine-5,4'-tetrahydropyran]-3-yl)propoxycarbonyl]benzoic acid with 1-ethyl-3-(3-hydroxypropyl)spiro[6,7-dihydro-4H-pyrazolo[3,4-c]azepine-5,4'-tetrahydropyran]-8-one being replaced by 1-ethyl-3-[(2R)-3-hydroxy-2-methyl-propyl]spiro[6,7-dihydro-4H-pyrazolo[3,4-c]azepine-5,4'-tetrahydropyran]-8-one.

$^{1}$H NMR (DMSO-d$_6$) δ: 8.01 (t, J=5.8 Hz, 1H), 7.93 (d, J=8.3 Hz, 2H), 7.85 (d, J=8.3 Hz, 2H), 4.30 (q, J=7.1 Hz, 2H), 4.15 (dd, J=6.0, 2.6 Hz, 2H), 3.60-3.47 (m, 4H), 2.87 (d, J=5.8 Hz, 2H), 2.74-2.62 (m, 2H), 2.47-2.42 (m, 2H), 2.31-2.19 (m, 1H), 1.41-1.30 (m, 4H), 1.26 (t, J=7.1 Hz, 3H), 1.01 (d, J=6.7 Hz, 3H).

Retention time (XE Metode 7 CM): 2.04 minutes.

Detected "M+1"-mass: 470.23.

The Examples 169-176 Table 8 were prepared by reacting Compound 270 as described in General Procedure 2 with the appropriate amine:

| Ex. | Cpd | Structure | IUPAC Name | HPLC Rt (min) | PDE4 IC50 range |
|---|---|---|---|---|---|
| 169 | 271 | 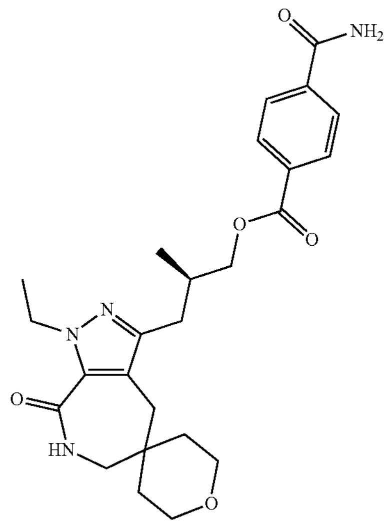 [SMILES: CCn1nc(C[C@@H](C)COC(=O)c2ccc(C(N)=O)cc2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 4-carbamoylbenzoate | 1.92 | *** |
| 170 | 272 | 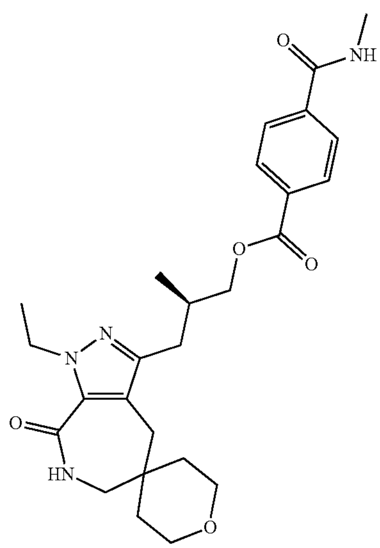 [SMILES: CCn1nc(C[C@@H](C)COC(=O)c2ccc(C(=O)NC)cc2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 4-(methylcarbamoyl)benzoate | 1.97 | *** |
| 171 | 273 | 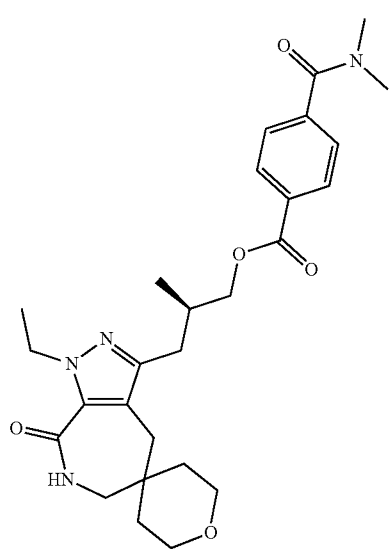 [SMILES: CCn1nc(C[C@@H](C)COC(=O)c2ccc(C(=O)N(C)C)cc2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 4-(di-methylcarbamoyl)benzoate | 2.01 | *** |

-continued

| Ex. | Cpd | Structure | IUPAC Name | HPLC Rt (min) | PDE4 IC50 range |
|---|---|---|---|---|---|
| 172 | 274 | 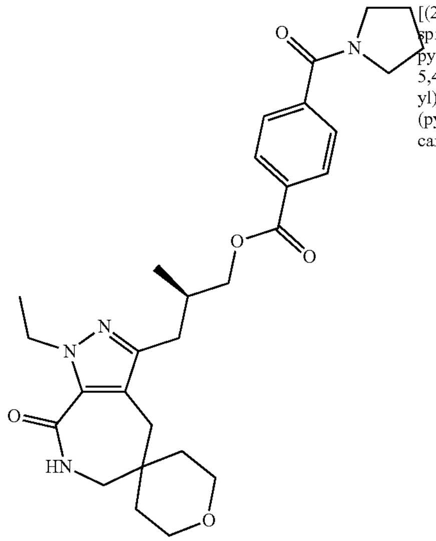 | [(2R)-3-(1-ethyl-8-oxo-spiro[6,7-dihydro-4H-pyrazolo[3,4-c]azepine-5,4'-tetrahydropyran]-3-yl)-2-methyl-propyl] 4-(pyrrolidine-1-carbonyl)benzoate | 2.09 | *** |
| 173 | 275 | 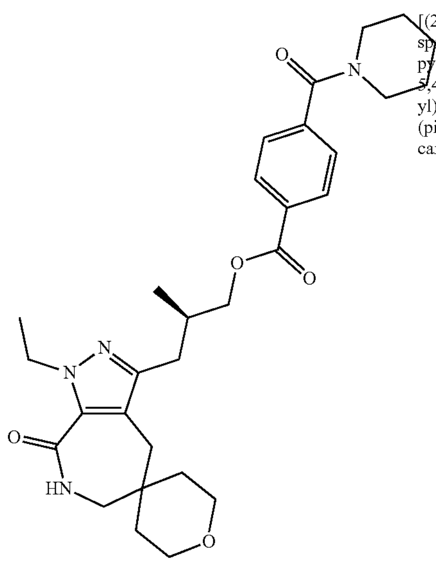 [SMILES: CCn1nc(C[C@@H](C)COC(=O)c2ccc(C(=O)N3CCCCC3)cc2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 4-(piperidine-1-carbonyl)benzoate | 2.20 | *** |

-continued

| Ex. | Cpd | Structure | IUPAC Name | HPLC Rt (min) | PDE4 IC50 range |
|---|---|---|---|---|---|
| 174 | 276 | 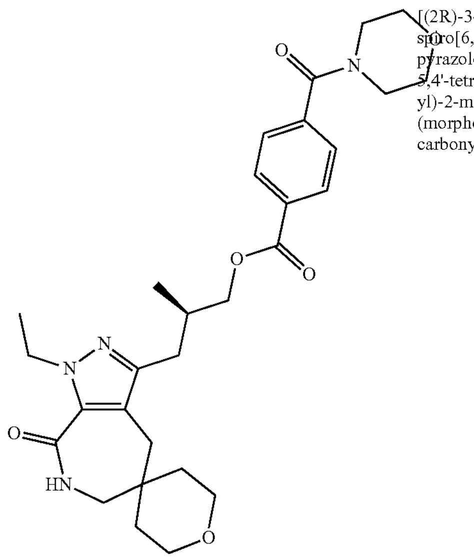 | [(2R)-3-(1-ethyl-8-oxo-spiro[6,7-dihydro-4H-pyrazolo[3,4-c]azepine-5,4'-tetrahydropyran]-3-yl)-2-methyl-propyl] 4-(morpholine-4-carbonyl)benzoate | 2.01 | *** |
| 175 | 277 | 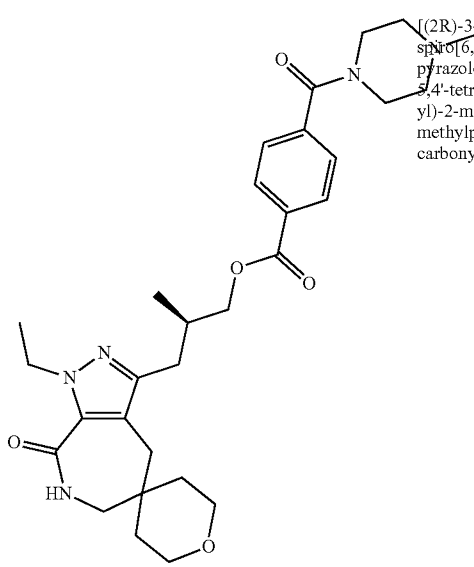 | [(2R)-3-(1-ethyl-8-oxo-spiro[6,7-dihydro-4H-pyrazolo[3,4-c]azepine-5,4'-tetrahydropyran]-3-yl)-2-methyl-propyl] 4-(4-methylpiperazine-1-carbonyl)benzoate | 1.78 | *** |

| Ex. | Cpd | Structure | IUPAC Name | HPLC Rt (min) | PDE4 IC50 range |
|---|---|---|---|---|---|
| 176 | 278 | 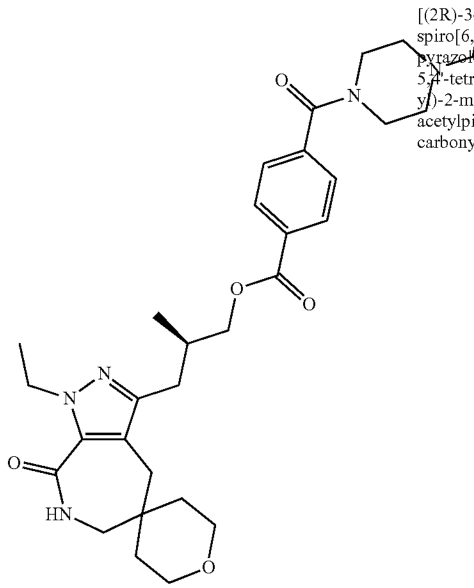 | [(2R)-3-(1-ethyl-8-oxo-spiro[6,7-dihydro-4H-pyrazolo[3,4-c]azepine-5,4'-tetrahydropyran]-3-yl)-2-methyl-propyl] 4-(4-acetylpiperazine-1-carbonyl)benzoate | 1.93 | *** |

Example 177 (Compound 279)

3-[(2R)-3-(1-Ethyl-8-oxo-spiro[6,7-dihydro-4H-pyrazolo[3,4-c]azepine-5,4'-tetrahydropyran]-3-yl)-2-methyl-propoxy]carbonylbenzoic acid

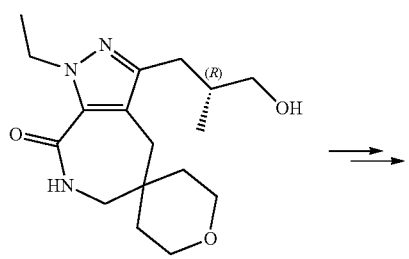

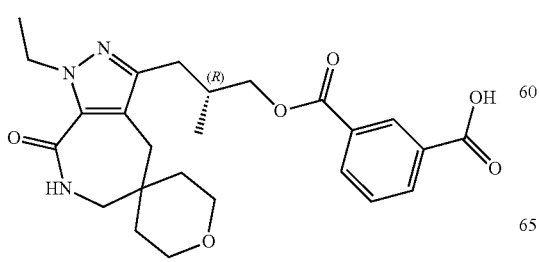

3-[(2R)-3-(1-Ethyl-8-oxo-spiro[6,7-dihydro-4H-pyrazolo[3,4-c]azepine-5,4'-tetrahydropyran]-3-yl)-2-methyl-propoxy]carbonylbenzoic acid was prepared in a manner similar to that described for 3-[3-(1-ethyl-8-oxo-spiro[6,7-dihydro-4H-pyrazolo[3,4-c]azepine-5,4'-tetrahydropyran]-3-yl)propoxycarbonyl]benzoic acid with 1-ethyl-3-(3-hydroxypropyl)spiro[6,7-dihydro-4H-pyrazolo[3,4-c]azepine-5,4'-tetrahydropyran]-8-one being replaced by 1-ethyl-3-[(2R)-3-hydroxy-2-methyl-propyl]spiro[6,7-dihydro-4H-pyrazolo[3,4-c]azepine-5,4'-tetrahydropyran]-8-one.

$^1$H NMR (DMSO-$d_6$) δ: 8.47 (t, J=1.7 Hz, 1H), 8.09 (dt, J=7.6, 1.5 Hz, 1H), 8.01 (t, J=5.7 Hz, 1H), 7.89 (dt, J=7.8, 1.6 Hz, 1H), 7.43 (t, J=7.6 Hz, 1H), 4.30 (q, J=7.1 Hz, 2H), 4.24-4.09 (m, 2H), 3.58-3.50 (m, 4H), 2.87 (d, J=5.8 Hz, 2H), 2.75-2.60 (m, 2H), 2.44 (s, 2H), 2.33-2.17 (m, 1H), 1.35 (q, J=5.6 Hz, 4H), 1.26 (t, J=7.1 Hz, 3H), 1.01 (d, J=6.6 Hz, 3H).

Retention time (XE Metode 7 CM): 2.04 minutes.

Detected "M+1"-mass: 470.23.

The Examples 178-185 Table 9 were prepared by reacting Compound 279 as described in General Procedure 2 with the appropriate amine:

| Ex. | Cpd | Structure | IUPAC Name | HPLC Rt (min) | PDE4 IC$_{50}$ range |
|---|---|---|---|---|---|
| 178 | 280 | 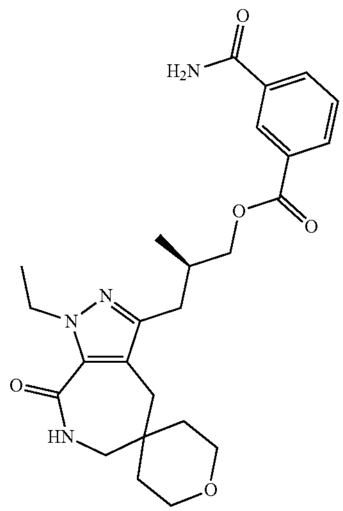 [SMILES: CCn1nc(C[C@@H](C)COC(=O)c2cccc(C(N)=O)c2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 3-carbamoylbenzoate | 1.92 | *** |
| 179 | 281 | 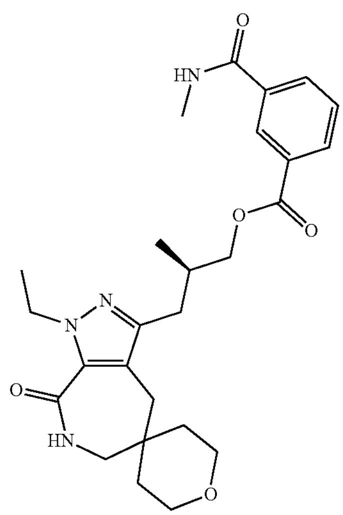 [SMILES: CCn1nc(C[C@@H](C)COC(=O)c2cccc(C(=O)NC)c2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 3-(methylcarbamoyl)benzoate | 1.97 | *** |
| 180 | 282 | 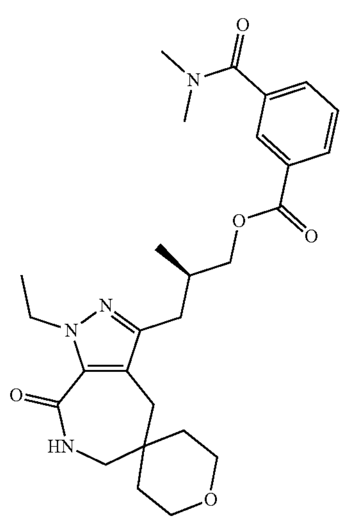 [SMILES: CCn1nc(C[C@@H](C)COC(=O)c2cccc(C(=O)N(C)C)c2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 3-(dimethylcarbamoyl)benzoate | 2.01 | *** |

-continued

| Ex. | Cpd | Structure | IUPAC Name | HPLC Rt (min) | PDE4 IC$_{50}$ range |
|---|---|---|---|---|---|
| 181 | 283 | 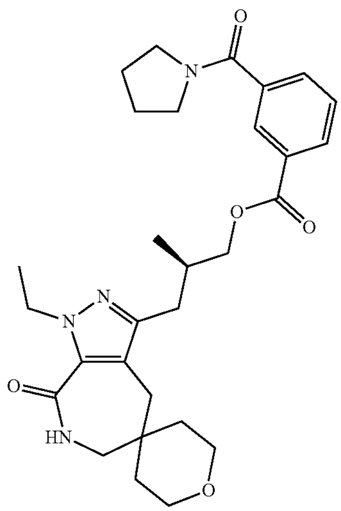 [SMILES: CCn1nc(C[C@@H](C)COC(=O)c2cccc(C(=O)N3CCCC3)c2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 3-(pyrrolidine-1-carbonyl)benzoate | 2.09 | *** |
| 182 | 284 | 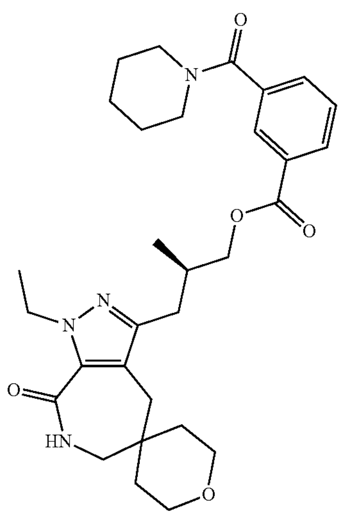 [SMILES: CCn1nc(C[C@@H](C)COC(=O)c2cccc(C(=O)N3CCCCC3)c2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 3-(piperidine-1-carbonyl)benzoate | 2.20 | *** |
| 183 | 285 | 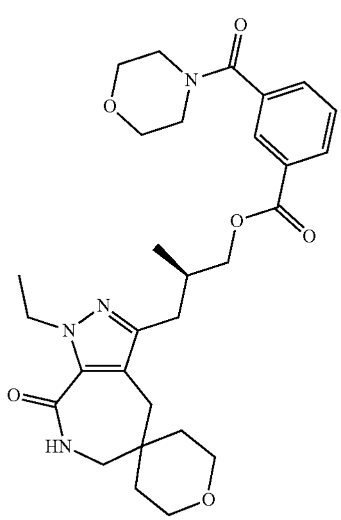 [SMILES: CCn1nc(C[C@@H](C)COC(=O)c2cccc(C(=O)N3CCOCC3)c2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 3-(morpholine-4-carbonyl)benzoate | 2.00 | *** |

| Ex. | Cpd | Structure | IUPAC Name | HPLC Rt (min) | PDE4 IC$_{50}$ range |
|---|---|---|---|---|---|
| 184 | 286 | 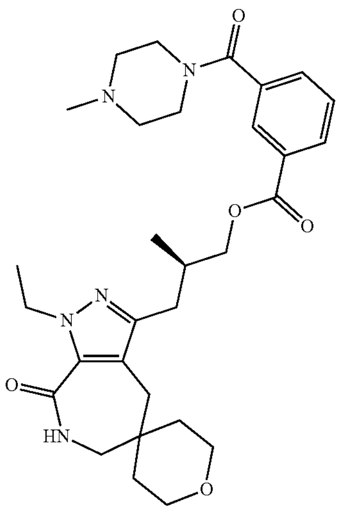 [SMILES: CCn1nc(C[C@@H](C)COC(=O)c2cccc(C(=O)N3CCN(C)CC3)c2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 3-(4-methylpiperazine-1-carbonyl)benzoate | 1.78 | *** |
| 185 | 287 | 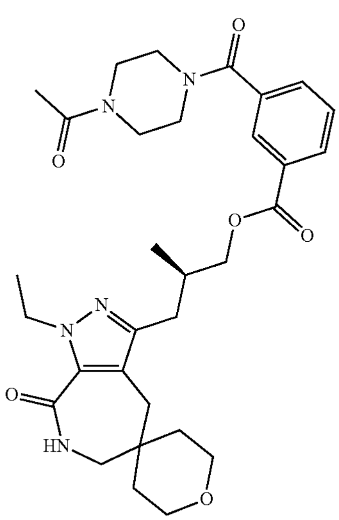 [SMILES: CCn1nc(C[C@@H](C)COC(=O)c2cccc(C(=O)N3CCN(C(C)=O)CC3)c2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 3-(4-acetylpiperazine-1-carbonyl)benzoate | 1.92 | *** |

The Examples 186-216 shown in Table 10 were prepared by reacting Compound 040 as described in General Procedure 1 with the appropriate acid:

| Ex. | Cpd | Structure | IUPAC Name | HPLC Rt (min) | PDE4 IC$_{50}$ range |
|---|---|---|---|---|---|
| 186 | 288 | 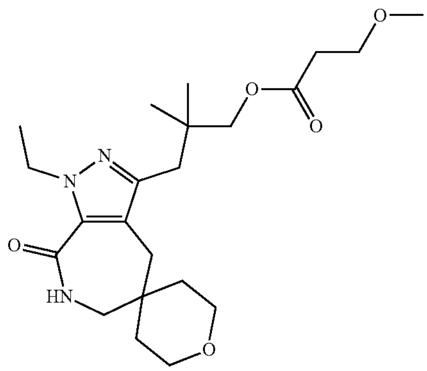 [SMILES: CCn1nc(CC(C)(C)COC(=O)CCOC)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 3-methoxypropanoate | 2.07 | *** |
| 187 | 289 | 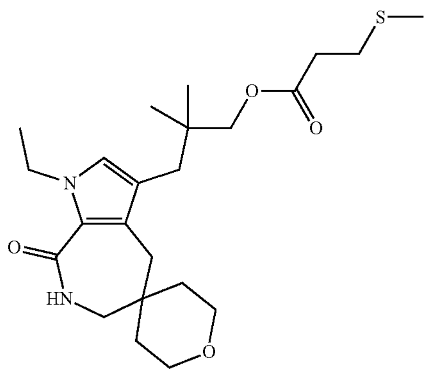 [SMILES: CCn1cc(CC(C)(C)COC(=O)CCSC)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 3-methylsulfanylpropanoate | 2.23 | *** |
| 188 | 290 | 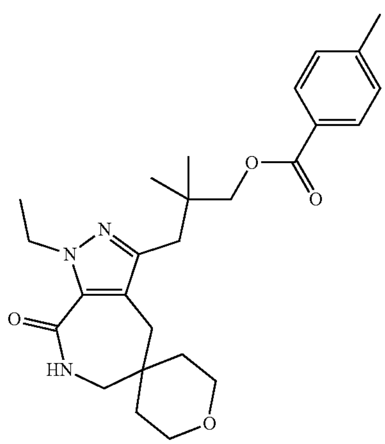 [SMILES: CCn1nc(CC(C)(C)COC(=O)c2ccc(C)cc2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 4-methylbenzoate | 2.46 | *** |
| 189 | 291 | 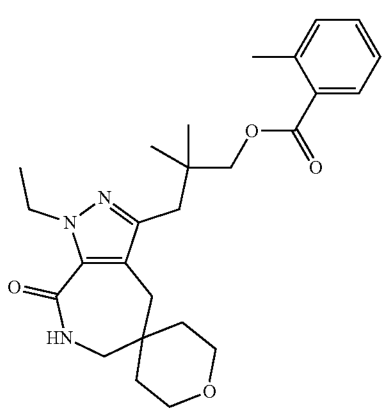 [SMILES: CCn1nc(CC(C)(C)COC(=O)c2ccccc2C)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 2-methylbenzoate | 2.47 | *** |

| Ex. | Cpd | Structure | IUPAC Name | HPLC Rt (min) | PDE4 IC$_{50}$ range |
|---|---|---|---|---|---|
| 190 | 292 | 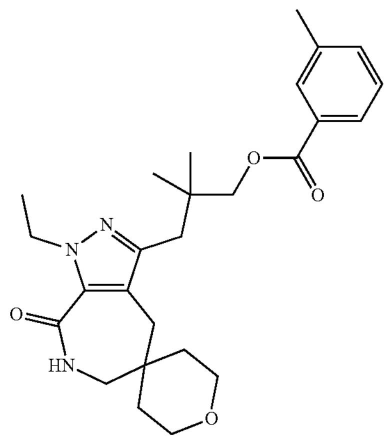 [SMILES: CCn1nc(CC(C)(C)COC(=O)c2cccc(C)c2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 3-methylbenzoate | 2.46 | *** |
| 191 | 293 | 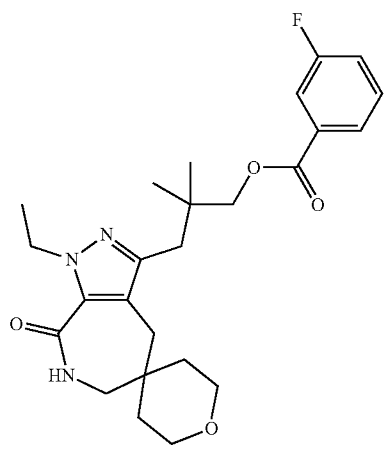 [SMILES: CCn1nc(CC(C)(C)COC(=O)c2cccc(F)c2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 3-fluorobenzoate | 2.41 | *** |
| 192 | 294 | 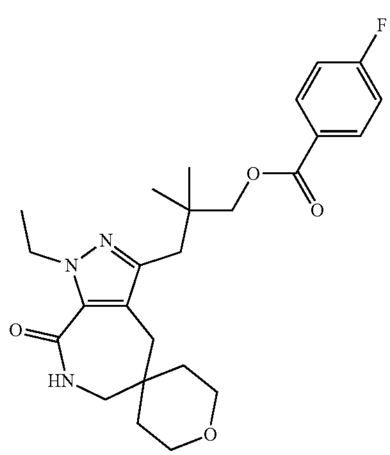 [SMILES: CCn1nc(CC(C)(C)COC(=O)c2ccc(F)cc2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 4-fluorobenzoate | 2.39 | *** |

-continued

| Ex. | Cpd | Structure | IUPAC Name | HPLC Rt (min) | PDE4 IC$_{50}$ range |
|---|---|---|---|---|---|
| 193 | 295 | 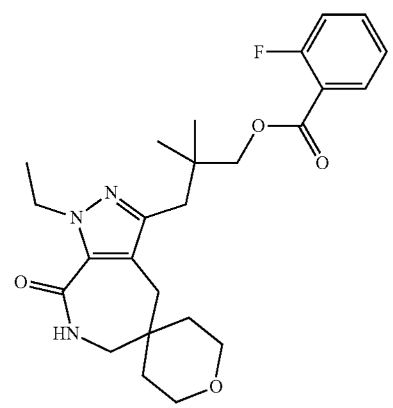 [SMILES: CCn1nc(CC(C)(C)COC(=O)c2ccccc2F)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 2-fluorobenzoate | 2.35 | *** |
| 194 | 296 | 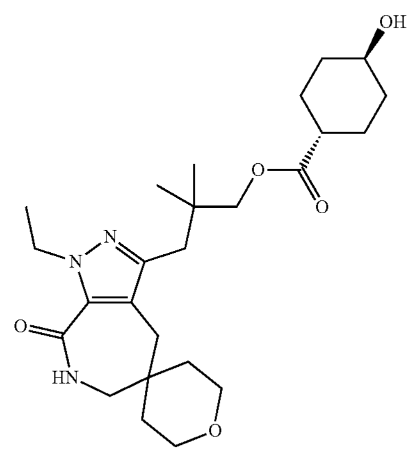 [SMILES: CCn1nc(CC(C)(C)COC(=O)[C@H]2CC[C@H](O)CC2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 4-hydroxycyclohexane-carboxylate | 1.98 | *** |
| 195 | 297 | 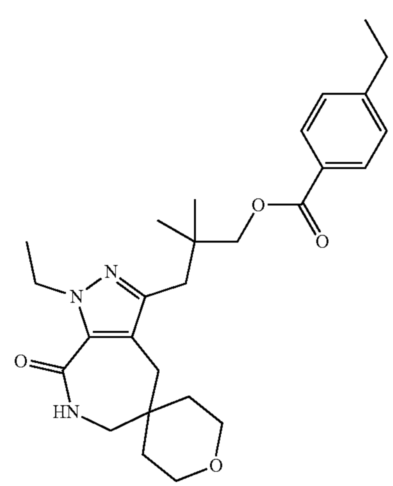 [SMILES: CCc1ccc(C(=O)OCC(C)(C)Cc2nn(CC)c3c2CC2(CCOCC2)CNC3=O)cc1] | [3-(1-ethyl-8-oxo-spiro[6,7-dihydro-4H-pyrazolo[3,4-c]azepine-5,4'-tetrahydropyran]-3-yl)-2,2-dimethyl-propyl] 4-ethylbenzoate | 2.56 | *** |

| Ex. | Cpd | Structure | IUPAC Name | HPLC Rt (min) | PDE4 IC$_{50}$ range |
|---|---|---|---|---|---|
| 196 | 298 | 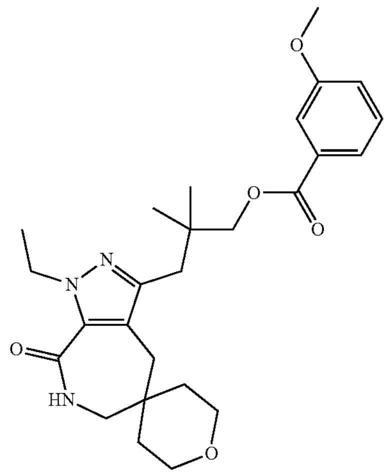 [SMILES: CCn1nc(CC(C)(C)COC(=O)c2cccc(OC)c2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 3-methoxybenzoate | 2.38 | *** |
| 197 | 299 | 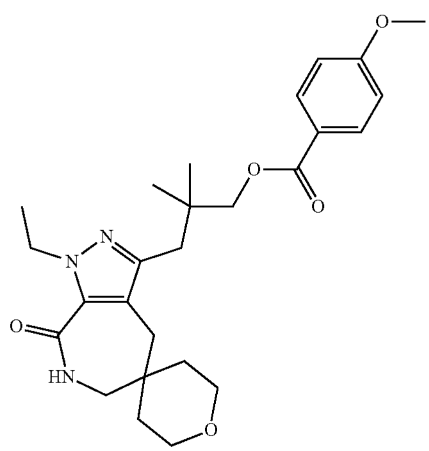 [SMILES: CCn1nc(CC(C)(C)COC(=O)c2ccc(OC)cc2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 4-methoxybenzoate | 2.35 | *** |
| 198 | 300 | 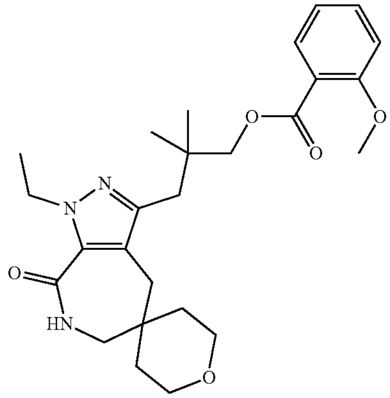 [SMILES: CCn1nc(CC(C)(C)COC(=O)c2ccccc2OC)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 2-methoxybenzoate | 2.27 | *** |

-continued

| Ex. | Cpd | Structure | IUPAC Name | HPLC Rt (min) | PDE4 IC$_{50}$ range |
|---|---|---|---|---|---|
| 199 | 301 | 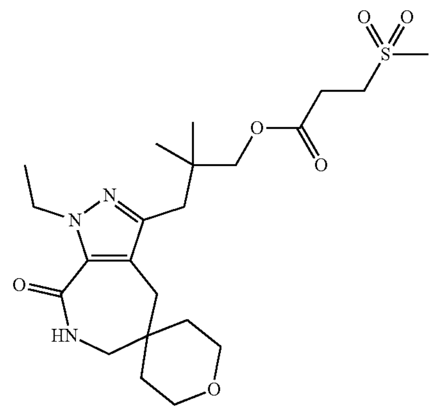 [SMILES: CCn1nc(CC(C)(C)COC(=O)CCS(C)(=O)=O)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 3-methylsulfonylpropanoate | 1.94 | *** |
| 200 | 302 | 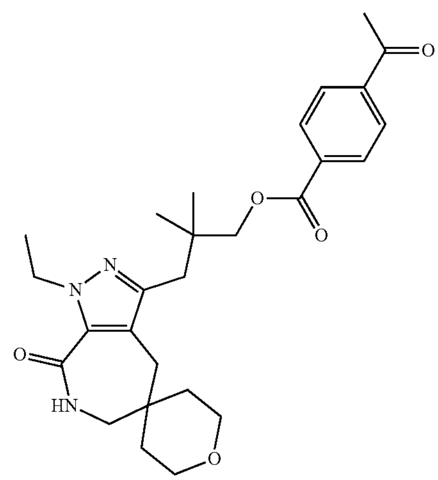 [SMILES: CCn1nc(CC(C)(C)COC(=O)c2ccc(C(C)=O)cc2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 4-acetylbenzoate | 2.29 | *** |
| 201 | 303 | 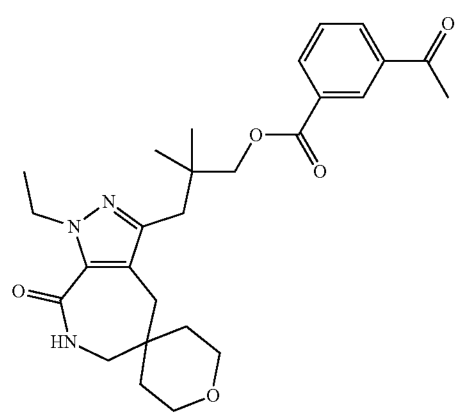 [SMILES: CCn1nc(CC(C)(C)COC(=O)c2cccc(C(C)=O)c2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 3-acetylbenzoate | 2.28 | *** |

-continued

| Ex. | Cpd | Structure | IUPAC Name | HPLC Rt (min) | PDE4 IC$_{50}$ range |
|---|---|---|---|---|---|
| 202 | 304 | 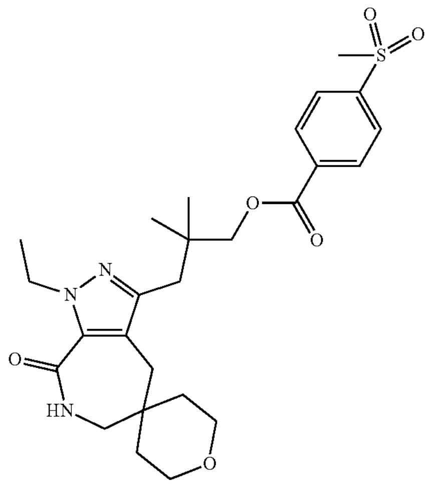 [SMILES: CCn1nc(CC(C)(C)COC(=O)c2ccc(S(C)(=O)=O)cc2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 4-methylsulfonylbenzoate | 2.17 | *** |
| 203 | 305 | 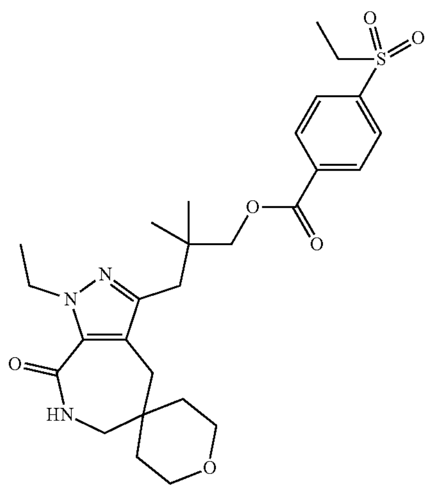 [SMILES: CCn1nc(CC(C)(C)COC(=O)c2ccc(S(=O)(=O)CC)cc2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 4-ethylsulfonylbenzoate | 2.23 | *** |
| 204 | 306 | 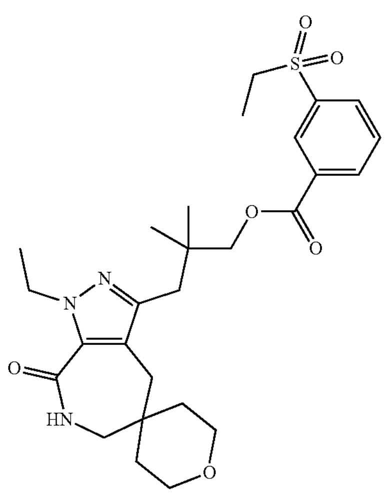 [SMILES: CCn1nc(CC(C)(C)COC(=O)c2cccc(S(=O)(=O)CC)c2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 3-ethylsulfonylbenzoate | 2.21 | *** |

-continued

| Ex. | Cpd | Structure | IUPAC Name | HPLC Rt (min) | PDE4 IC$_{50}$ range |
|---|---|---|---|---|---|
| 205 | 307 | 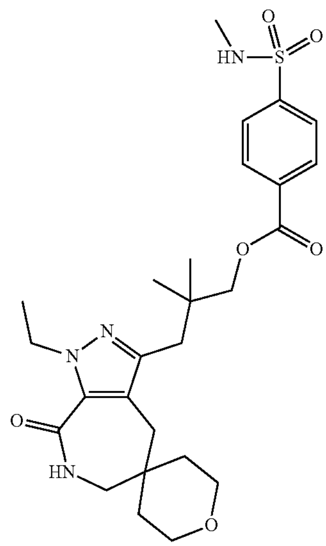 [SMILES: CCn1nc(CC(C)(C)COC(=O)c2ccc(S(=O)(=O)NC)cc2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 4-(methylsulfamoyl)benzoate | 2.18 | *** |
| 206 | 308 | 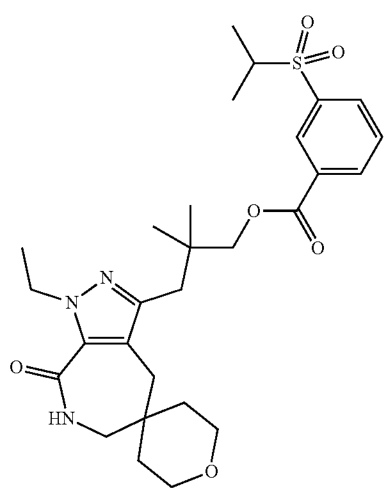 [SMILES: CCn1nc(CC(C)(C)COC(=O)c2cccc(S(=O)(=O)C(C)C)c2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 3-isopropylsulfonylbenzoate | 2.28 | *** |
| 207 | 309 | 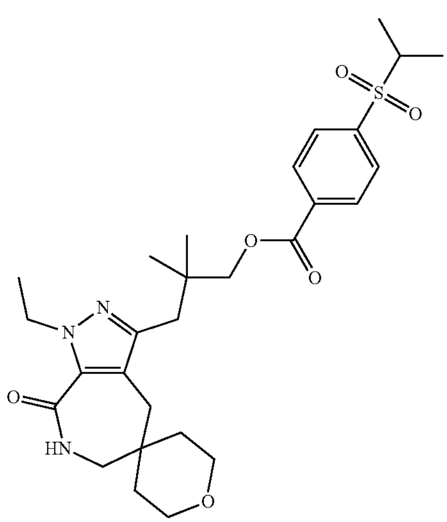 [SMILES: CCn1nc(CC(C)(C)COC(=O)c2ccc(S(=O)(=O)C(C)C)cc2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 4-isopropylsulfonylbenzoate | 2.30 | *** |

| Ex. | Cpd | Structure | IUPAC Name | HPLC Rt (min) | PDE4 IC$_{50}$ range |
|---|---|---|---|---|---|
| 208 | 310 | 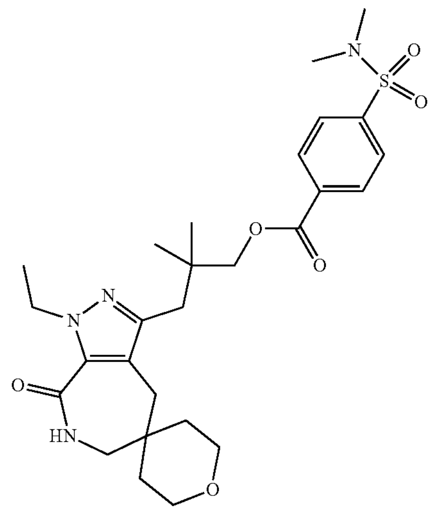 [SMILES: CCn1nc(CC(C)(C)COC(=O)c2ccc(S(=O)(=O)N(C)C)cc2)c2c1C(=O)NCC1(CCOCC1)C2] | [3-(1-ethyl-8-oxo-spiro-[6,7-dihydro-4H-pyrazolo-[3,4-c]azepine-5,4'-tetra-hydropyran]-3-yl)-2,2-dimethyl-propyl] 4-(di-methylsulfamoyl)benzoate | 2.31 | *** |
| 209 | 311 | 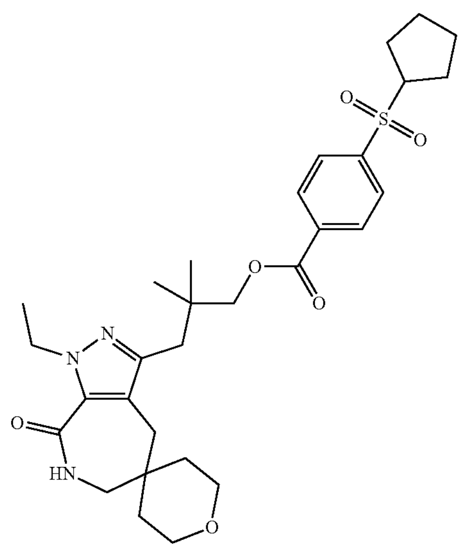 [SMILES: CCn1nc(CC(C)(C)COC(=O)c2ccc(S(=O)(=O)C3CCCC3)cc2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 4-cyclopentylsulfonylbenzoate | 2.40 | *** |
| 210 | 312 | 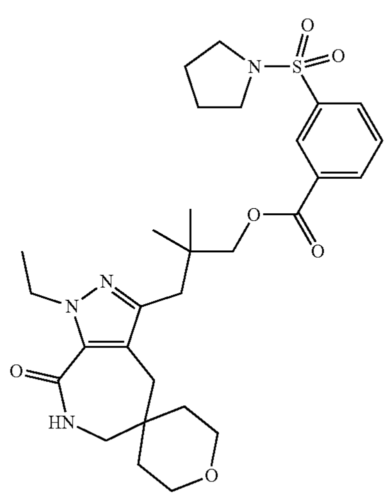 [SMILES: CCn1nc(CC(C)(C)COC(=O)c2cccc(S(=O)(=O)N3CCCC3)c2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 3-pyrrolidin-1-ylsulfonylbenzoate | 2.36 | *** |

-continued

| Ex. | Cpd | Structure | IUPAC Name | HPLC Rt (min) | PDE4 IC$_{50}$ range |
|---|---|---|---|---|---|
| 211 | 313 | 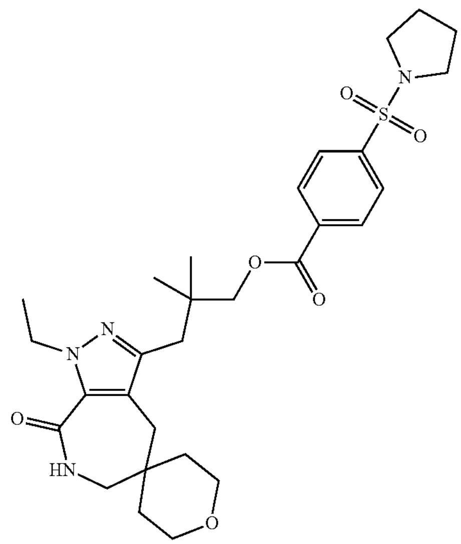 | [3-(1-ethyl-8-oxo-spiro[6,7-dihydro-4H-pyrazolo[3,4-c]azepine-5,4'-tetrahydropyran]-3-yl)-2,2-dimethyl-propyl] 4-pyrrolidin-1-ylsulfonylbenzoate | 2.38 | *** |
| 212 | 314 | 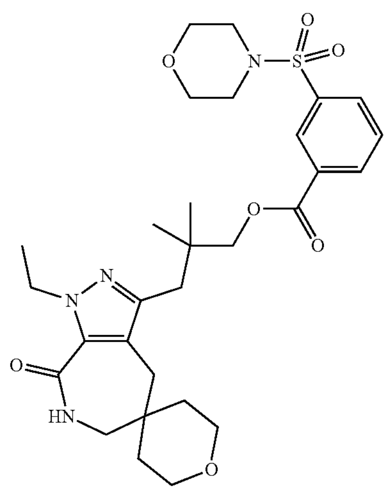 [SMILES: CCn1nc(CC(C)(C)COC(=O)c2cccc(S(=O)(=O)N3CCOCC3)c2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 3-morpholinosulfonylbenzoate | 2.27 | *** |
| 213 | 315 | 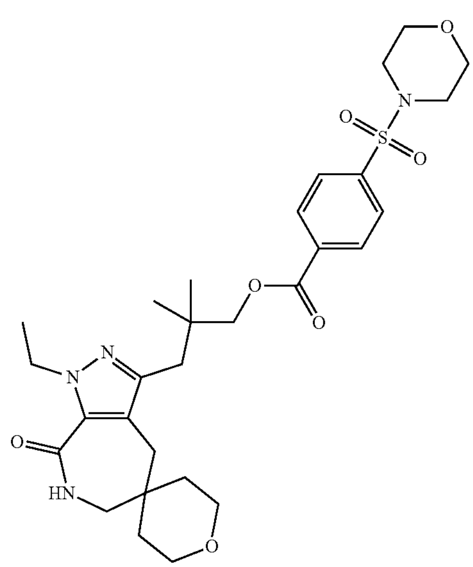 [SMILES: CCn1nc(CC(C)(C)COC(=O)c2ccc(S(=O)(=O)N3CCOCC3)cc2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 4-morpholinosulfonylbenzoate | 2.29 | *** |

| Ex. | Cpd | Structure | IUPAC Name | HPLC Rt (min) | PDE4 IC$_{50}$ range |
|---|---|---|---|---|---|
| 214 | 316 | 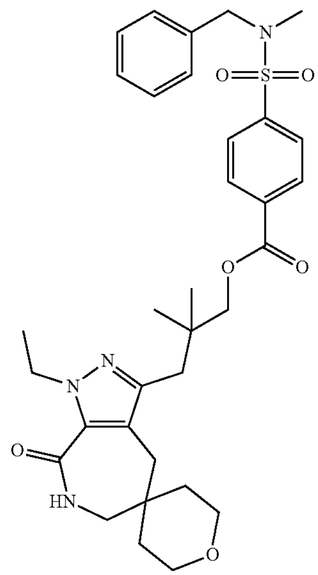 [SMILES: CCn1nc(CC(C)(C)COC(=O)c2ccc(S(=O)(=O)N(C)Cc3ccccc3)cc2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 4-[benzyl(methyl)sulfamoyl]benzoate | 2.57 | *** |
| 215 | 317 | 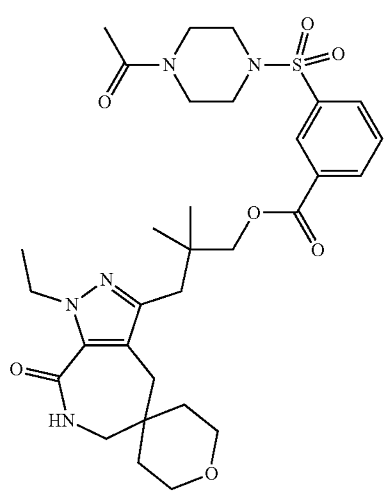 [SMILES: CCn1nc(CC(C)(C)COC(=O)c2cccc(S(=O)(=O)N3CCN(C(C)=O)CC3)c2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 3-(4-acetylpiperazin-1-yl)sulfonylbenzoate | 2.15 | *** |

| Ex. | Cpd | Structure | IUPAC Name | HPLC Rt (min) | PDE4 IC$_{50}$ range |
|---|---|---|---|---|---|
| 216 | 318 | 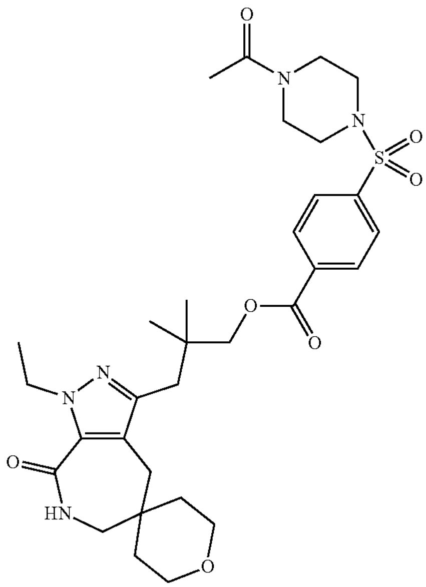 [SMILES: CCn1nc(CC(C)(C)COC(=O)c2ccc(S(=O)(=O)N3CCN(C(C)=O)CC3)cc2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 4-(4-acetylpiperazin-1-yl)sulfonylbenzoate | 2.17 | *** |

Example 217 (Compound 319)

4-[3-(1-Ethyl-8-oxo-spiro[6,7-dihydro-4H-pyrazolo[3,4-c]azepine-5,4'-tetrahydropyran]-3-yl)-2,2-dimethyl-propoxy]carbonylbenzoic acid

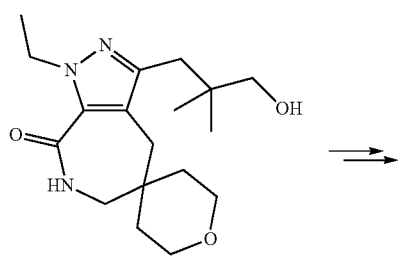

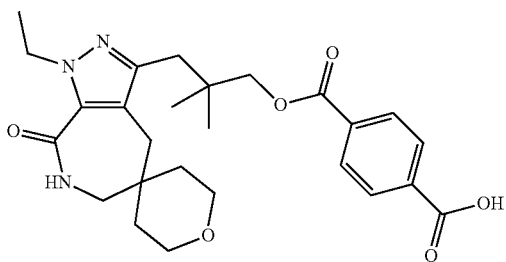

4-[3-(1-Ethyl-8-oxo-spiro[6,7-dihydro-4H-pyrazolo[3,4-c]azepine-5,4'-tetrahydropyran]-3-yl)-2,2-dimethyl-propoxy]carbonylbenzoic acid was prepared in a manner similar to that described for 4-[3-(1-ethyl-8-oxo-spiro[6,7-dihydro-4H-pyrazolo[3,4-c]azepine-5,4'-tetrahydropyran]-3-yl)propoxycarbonyl]benzoic acid with 1-ethyl-3-(3-hydroxypropyl)spiro[6,7-dihydro-4H-pyrazolo[3,4-c]azepine-5,4'-tetrahydropyran]-8-one being replaced by 1-ethyl-3-(3-hydroxy-2,2-dimethyl-propyl)spiro[6,7-dihydro-4H-pyrazolo[3,4-c]azepine-5,4'-tetrahydropyran]-8-one.

$^1$H NMR (DMSO-d$_6$) δ: 8.04 (t, J=5.9 Hz, 1H), 7.97 (d, J=8.3 Hz, 2H), 7.92 (d, J=8.3 Hz, 2H), 4.30 (q, J=7.1 Hz, 2H), 4.03 (s, 2H), 3.54-3.49 (m, 4H), 2.85 (d, J=5.9 Hz, 2H), 2.58 (s, 2H), 2.43 (s, 2H), 1.35-1.30 (m, 4H), 1.27 (t, J=7.1 Hz, 3H), 1.03 (s, 6H).

Retention time (XE Metode 7 CM): 2.12 minutes.

Detected "M+1"-mass: 484.24.

The Examples 218-225 in Table 11 were prepared by reacting Compound 319 as described in General Procedure 2 with the appropriate amine:

| Ex. | Cpd | Structure | IUPAC Name | HPLC Rt (min) | PDE4 IC$_{50}$ range |
|---|---|---|---|---|---|
| 218 | 320 | 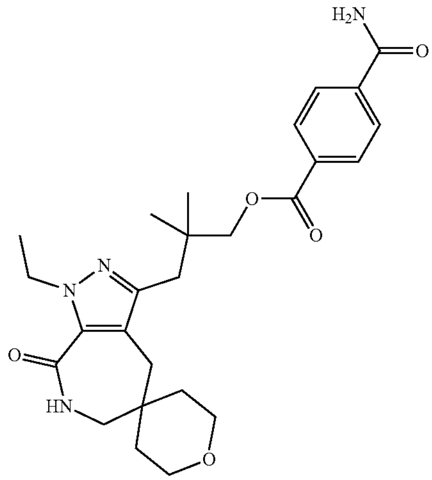 [SMILES: CCn1nc(CC(C)(C)COC(=O)c2ccc(C(N)=O)cc2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 4-carbamoylbenzoate | 1.99 | *** |
| 219 | 321 | 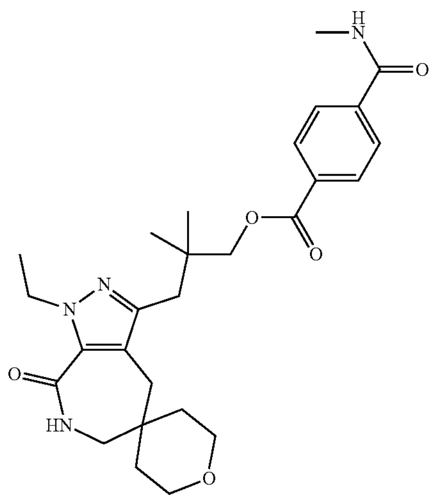 [SMILES: CCn1nc(CC(C)(C)COC(=O)c2ccc(C(=O)NC)cc2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 4-(methylcarbamoyl)benzoate | 2.05 | *** |
| 220 | 322 | 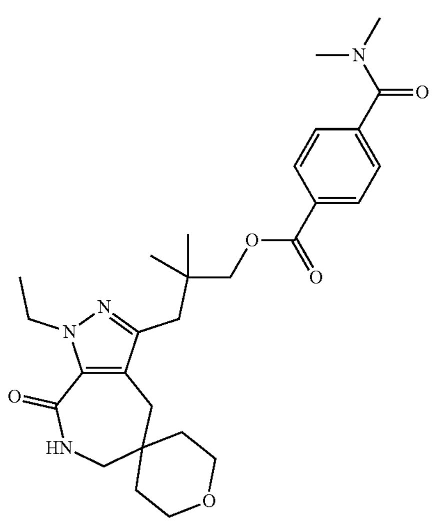 [SMILES: CCn1nc(CC(C)(C)COC(=O)c2ccc(C(=O)N(C)C)cc2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 4-(dimethylcarbamoyl)benzoate | 2.10 | *** |

-continued

| Ex. | Cpd | Structure | IUPAC Name | HPLC Rt (min) | PDE4 IC$_{50}$ range |
|---|---|---|---|---|---|
| 221 | 323 | 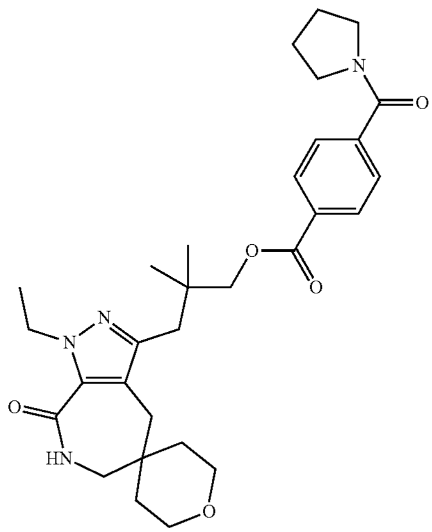 [SMILES: CCn1nc(CC(C)(C)COC(=O)c2ccc(C(=O)N3CCCC3)cc2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 4-(pyrrolidine-1-carbonyl)benzoate | 2.18 | *** |
| 222 | 324 | 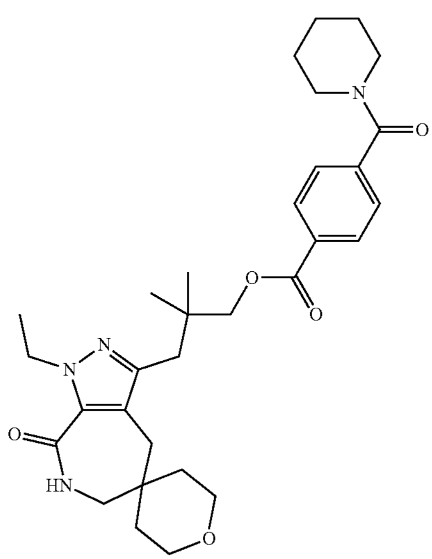 [SMILES: CCn1nc(CC(C)(C)COC(=O)c2ccc(C(=O)N3CCCCC3)cc2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 4-(piperidine-1-carbonyl)benzoate | 2.29 | *** |

-continued

| Ex. | Cpd | Structure | IUPAC Name | HPLC Rt (min) | PDE4 IC$_{50}$ range |
|---|---|---|---|---|---|
| 223 | 325 | 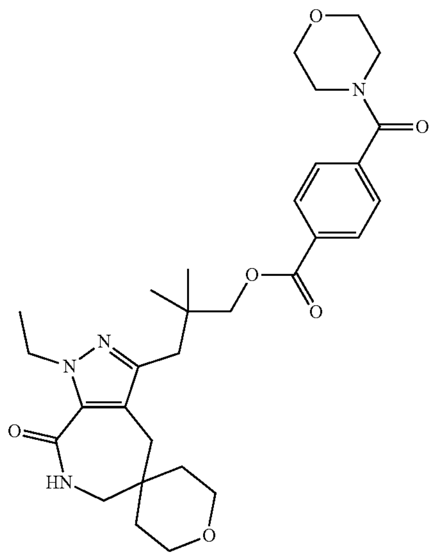 [SMILES: CCn1nc(CC(C)(C)COC(=O)c2ccc(C(=O)N3CCOCC3)cc2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 4-(morpholine-4-carbonyl)benzoate | 2.09 | *** |
| 224 | 326 | 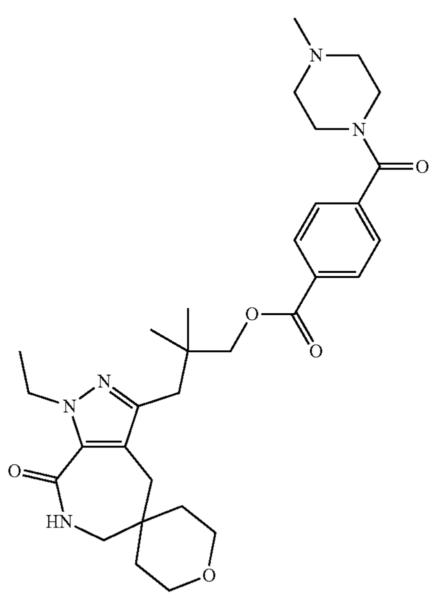 [SMILES: CCn1nc(CC(C)(C)COC(=O)c2ccc(C(=O)N3CCN(C)CC3)cc2)c2c1C(=O)NCC1(CCOCC1)C2] | [3-(1-ethyl-8-oxo-spiro[6,7-dihydro-4H-pyrazolo[3,4-c]azepine-5,4'-tetrahydro-pyran]-3-yl)-2,2-dimethyl-propyl] 4-(4-methyl-piperazine-1-carbonyl)-benzoate | 1.83 | *** |

| Ex. | Cpd | Structure | IUPAC Name | HPLC Rt (min) | PDE4 IC$_{50}$ range |
|---|---|---|---|---|---|
| 225 | 327 | 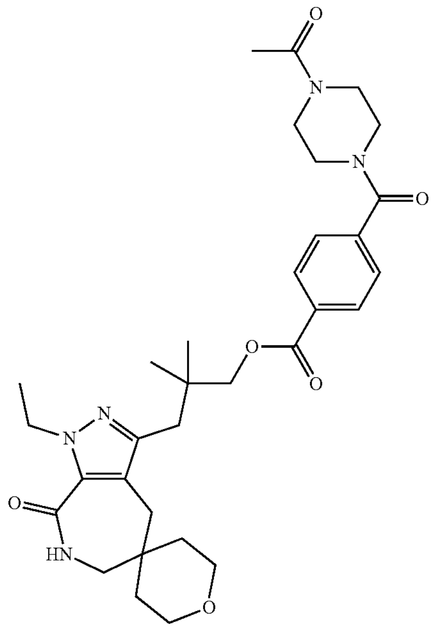 [SMILES: CCn1nc(CC(C)(C)COC(=O)c2ccc(C(=O)N3CCN(C(C)=O)CC3)cc2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 4-(4-acetylpiperazine-1-carbonyl)benzoate | 1.99 | *** |

Example 226 (Compound 328)

3-[3-(1-Ethyl-8-oxo-spiro[6,7-dihydro-4H-pyrazolo[3,4-c]azepine-5,4'-tetrahydropyran]-3-yl)-2,2-dimethyl-propoxy]carbonylbenzoic acid

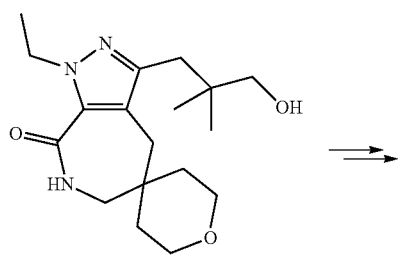

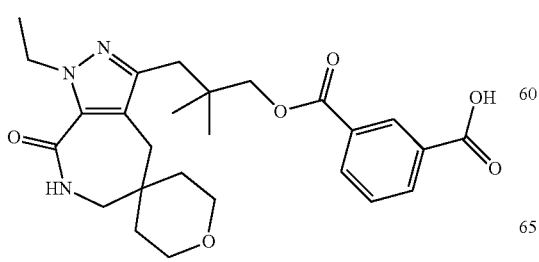

3-[3-(1-Ethyl-8-oxo-spiro[6,7-dihydro-4H-pyrazolo[3,4-c]azepine-5,4'-tetrahydropyran]-3-yl)-2,2-dimethyl-propoxy]carbonylbenzoic acid was prepared in a manner similar to that described for 3-[3-(1-ethyl-8-oxo-spiro[6,7-dihydro-4H-pyrazolo[3,4-c]azepine-5,4'-tetrahydropyran]-3-yl)propoxycarbonyl]benzoic acid with 1-ethyl-3-(3-hydroxypropyl)spiro[6,7-dihydro-4H-pyrazolo[3,4-c]azepine-5,4'-tetrahydropyran]-8-one being replaced by 1-ethyl-3-(3-hydroxy-2,2-dimethyl-propyl)spiro[6,7-dihydro-4H-pyrazolo[3,4-c]azepine-5,4'-tetrahydropyran]-8-one.

$^1$H NMR (DMSO-d$_6$) δ: 8.51 (t, J=1.7 Hz, 1H), 8.13 (dt, J=7.6, 1.5 Hz, 1H), 8.03 (t, J=5.9 Hz, 1H), 8.00 (dt, J=7.8, 1.5 Hz, 1H), 7.52 (t, J=7.7 Hz, 1H), 4.30 (q, J=7.2 Hz, 2H), 4.04 (s, 2H), 3.52-3.47 (m, 4H), 2.85 (d, J=5.9 Hz, 2H), 2.58 (s, 2H), 2.43 (s, 2H), 1.35-1.30 (m, 4H), 1.26 (t, J=7.1 Hz, 3H), 1.03 (s, 6H).

Retention time (XE Metode 7 CM): 2.13 minutes.

Detected "M+1"-mass: 484.24.

The Examples 227-234 in Table 12 were prepared by reacting Compound 328 as described in General Procedure 2 with the appropriate amine:

| Ex. | Cpd | Structure | IUPAC Name | HPLC Rt (min) | PDE4 IC$_{50}$ range |
|---|---|---|---|---|---|
| 227 | 329 | 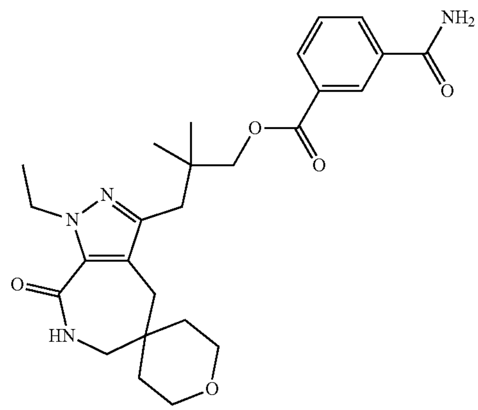 [SMILES: CCn1nc(CC(C)(C)COC(=O)c2cccc(C(N)=O)c2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 3-carbamoylbenzoate | 1.99 | *** |
| 228 | 330 | 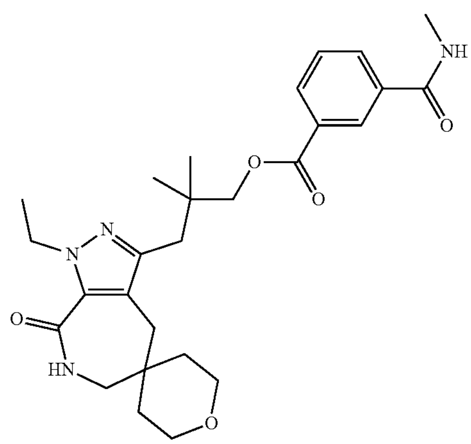 [SMILES: CCn1nc(CC(C)(C)COC(=O)c2cccc(C(=O)NC)c2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 3-(methylcarbamoyl)benzoate | 2.05 | *** |
| 229 | 331 | 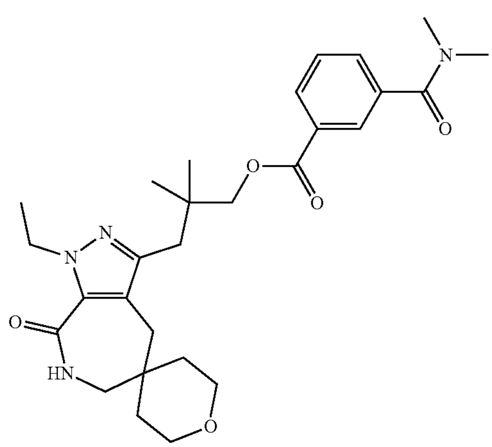 [SMILES: CCn1nc(CC(C)(C)COC(=O)c2cccc(C(=O)N(C)C)c2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 3-(dimethylcarbamoyl)benzoate | 2.09 | *** |

| Ex. | Cpd | Structure | IUPAC Name | HPLC Rt (min) | PDE4 IC$_{50}$ range |
|---|---|---|---|---|---|
| 230 | 332 | 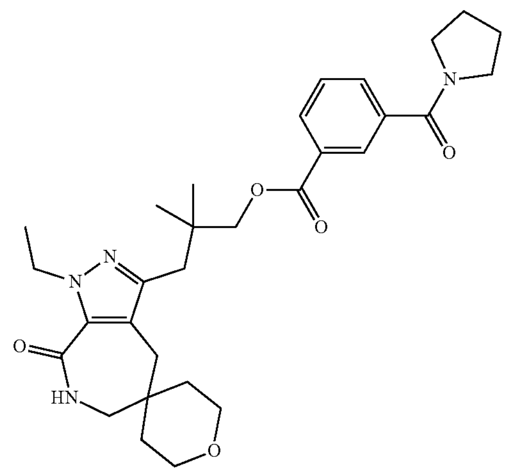 [SMILES: CCn1nc(CC(C)(C)COC(=O)c2cccc(C(=O)N3CCCC3)c2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 3-(pyrrolidine-1-carbonyl)benzoate | 2.17 | *** |
| 231 | 333 | 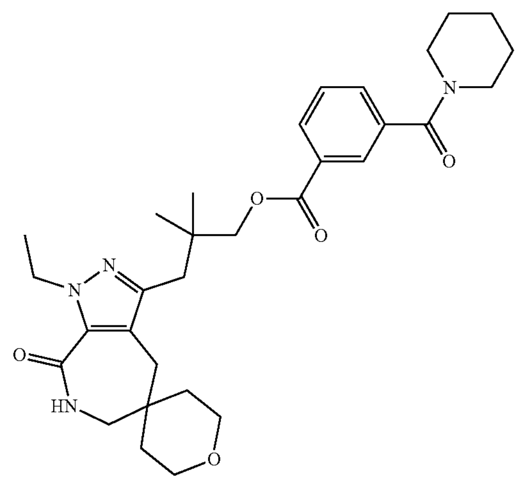 [SMILES: CCn1nc(CC(C)(C)COC(=O)c2cccc(C(=O)N3CCCCC3)c2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 3-(piperidine-1-carbonyl)benzoate | 2.29 | *** |
| 232 | 334 | 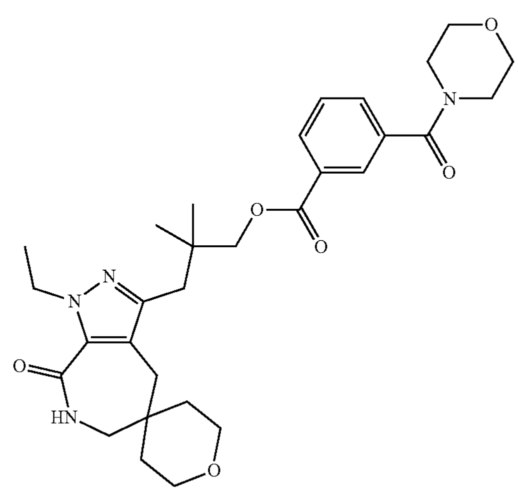 [SMILES: CCn1nc(CC(C)(C)COC(=O)c2cccc(C(=O)N3CCOCC3)c2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 3-(morpholine-4-carbonyl)benzoate | 2.08 | *** |

-continued

| Ex. | Cpd | Structure | IUPAC Name | HPLC Rt (min) | PDE4 IC$_{50}$ range |
|---|---|---|---|---|---|
| 233 | 335 | 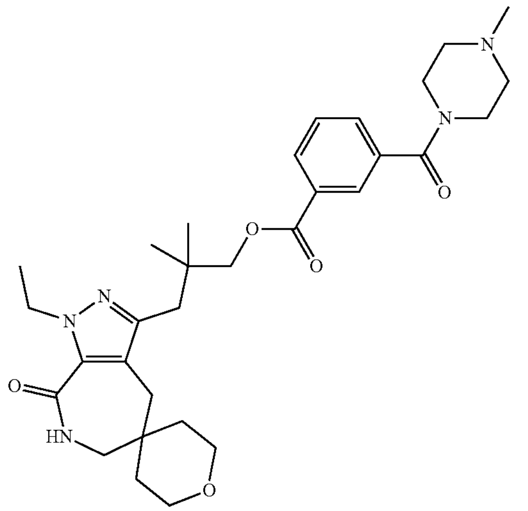 [SMILES: CCn1nc(CC(C)(C)COC(=O)c2cccc(C(=O)N3CCN(C)CC3)c2)c2c1C(=O)NCC1(CCOCC1)C2] | [3-(1-ethyl-8-oxo-spiro[6,7-dihydro-4H-pyrazolo[3,4-c]azepine-5,4'-tetrahydro-pyran]-3-yl)-2,2-dimethyl-propyl] 3-(4-methyl-piperazine-1-carbonyl)-benzoate | 1.83 | *** |
| 234 | 336 | 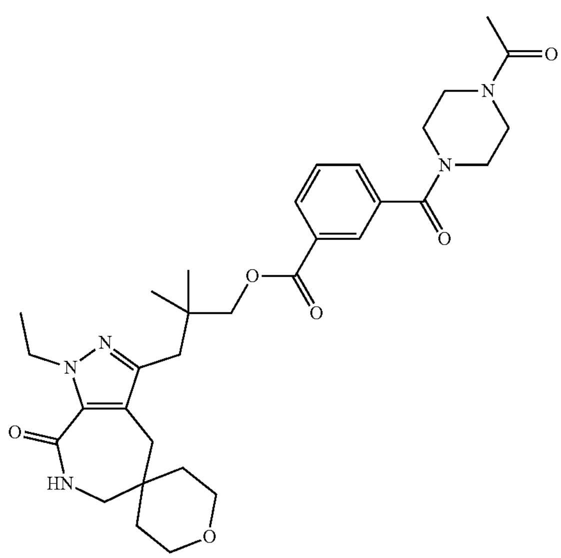 [SMILES: CCn1nc(CC(C)(C)COC(=O)c2cccc(C(=O)N3CCN(C(C)=O)CC3)c2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 3-(4-acetylpiperazine-1-carbonyl)benzoate | 1.99 | *** |

The Examples 235-264 shown in Table 13 were prepared by reacting Compound 008 as described in General Procedure 1 with the appropriate acid:

| Ex. | Cpd | Structure | IUPAC Name | HPLC Rt (min) | PDE4 IC$_{50}$ range |
|---|---|---|---|---|---|
| 235 | 337 | 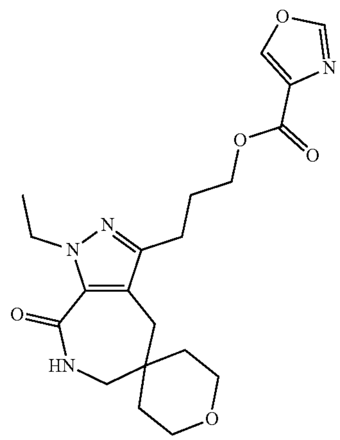 [SMILES: CCn1nc(CCCOC(=O)c2cocn2)c2c1C(=O)NCC1(CCOCC1)C2] | 3-(1-ethyl-8-oxo-spiro[6,7-dihydro-4H-pyrazolo[3,4-c]azepine-5,4'-tetrahydro-pyran]-3-yl)propyl oxazole-4-carboxylate | 1.83 | *** |
| 236 | 338 | 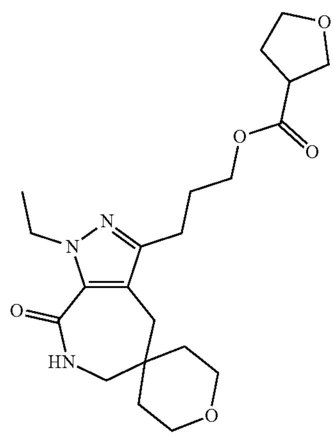 [SMILES: CCn1nc(CCCOC(=O)C2CCOC2)c2c1C(=O)NCC1(CCOCC1)C2] | 3-(1-ethyl-8-oxo-spiro[6,7-dihydro-4H-pyrazolo[3,4-c]azepine-5,4'-tetrahydro-pyran]-3-yl)propyl tetrahydrofuran-3-carboxylate | 1.89 | *** |
| 237 | 339 | 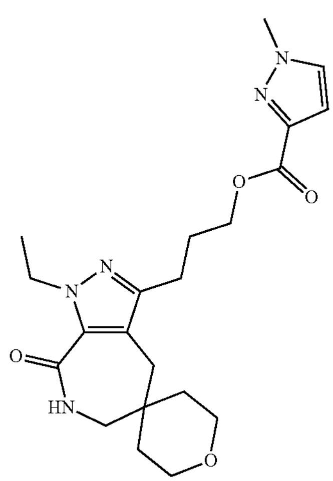 [SMILES: CCn1nc(CCCOC(=O)c2ccn(C)n2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 1-methylpyrazole-3-carboxylate | 1.85 | *** |

-continued

| Ex. | Cpd | Structure | IUPAC Name | HPLC Rt (min) | PDE4 IC$_{50}$ range |
|---|---|---|---|---|---|
| 238 | 340 | 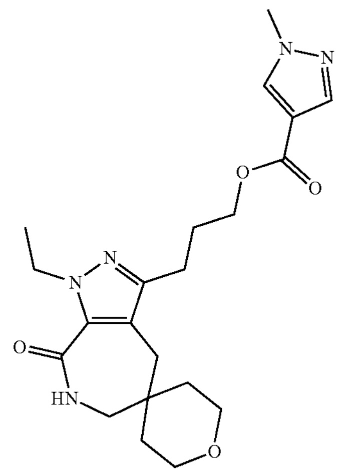 [SMILES: CCn1nc(CCCOC(=O)c2cnn(C)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 1-methylpyrazole-4-carboxylate | 1.85 | *** |
| 239 | 341 | 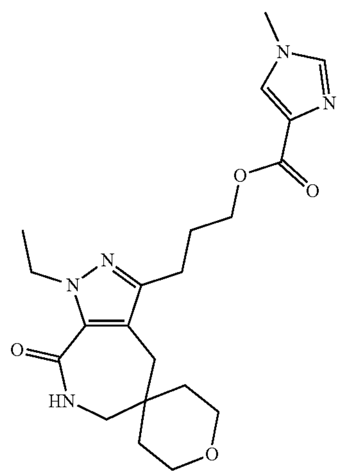 [SMILES: CCn1nc(CCCOC(=O)c2cn(C)cn2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 1-methylimidazole-4-carboxylate | 1.73 | *** |
| 240 | 342 | 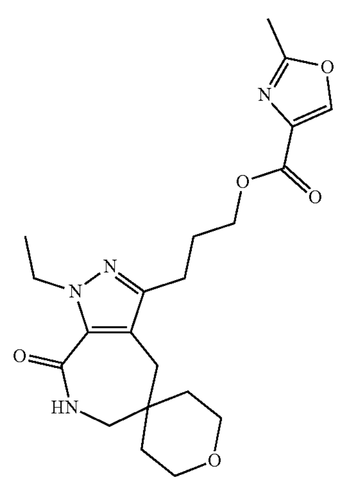 [SMILES: CCn1nc(CCCOC(=O)c2coc(C)n2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 2-methyloxazole-4-carboxylate | 1.87 | *** |

-continued

| Ex. | Cpd | Structure | IUPAC Name | HPLC Rt (min) | PDE4 IC$_{50}$ range |
|---|---|---|---|---|---|
| 241 | 343 | 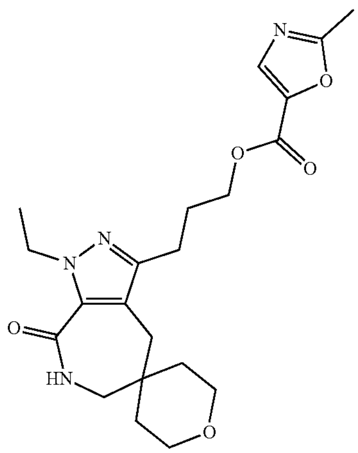 [SMILES: CCn1nc(CCCOC(=O)c2cnc(C)o2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 2-methyloxazole-5-carboxylate | 1.89 | *** |
| 242 | 344 | 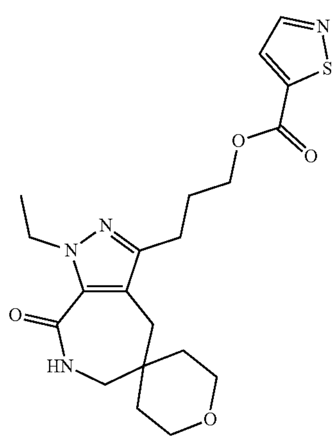 [SMILES: CCn1nc(CCCOC(=O)c2ccns2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl isothiazole-5-carboxylate | 2.03 | *** |
| 243 | 345 | 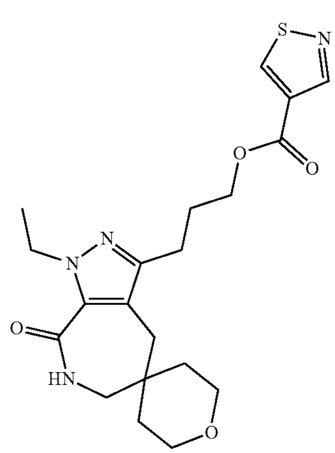 [SMILES: CCn1nc(CCCOC(=O)c2cnsc2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl isothiazole-4-carboxylate | 1.98 | *** |

-continued

| Ex. | Cpd | Structure | IUPAC Name | HPLC Rt (min) | PDE4 IC$_{50}$ range |
|---|---|---|---|---|---|
| 244 | 346 | 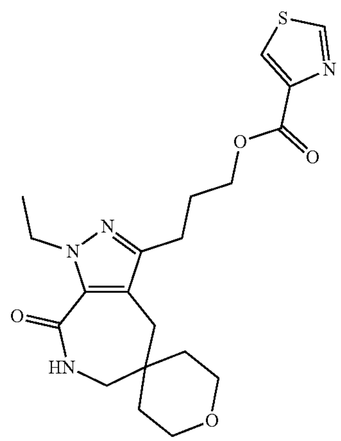 [SMILES: CCn1nc(CCCOC(=O)c2cscn2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl thiazole-4-carboxylate | 1.85 | *** |
| 245 | 347 | 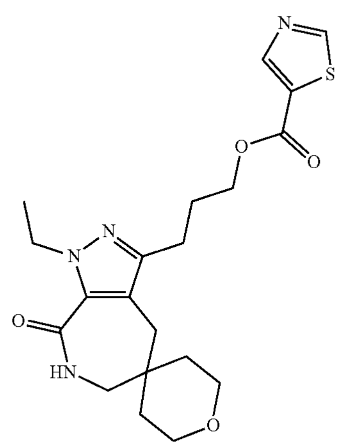 [SMILES: CCn1nc(CCCOC(=O)c2cncs2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl thiazole-5-carboxylate | 1.92 | *** |
| 246 | 348 | 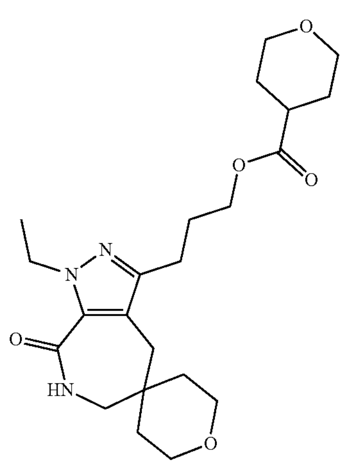 | 3-(1-ethyl-8-oxo-spiro[6,7-dihydro-4H-pyrazolo[3,4-c]azepine-5,4'-tetrahydropyran]-3-yl)propyl tetrahydropyran-4-carboxylate | 1.92 | *** |

-continued

| Ex. | Cpd | Structure | IUPAC Name | HPLC Rt (min) | PDE4 IC$_{50}$ range |
|---|---|---|---|---|---|
| 247 | 349 | 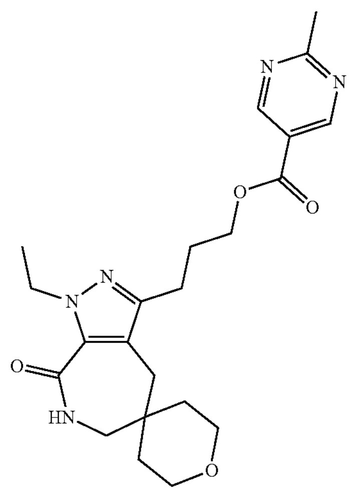 [SMILES: CCn1nc(CCCOC(=O)c2cnc(C)nc2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 2-methylpyrimidine-5-carboxylate | 1.87 | *** |
| 248 | 350 | 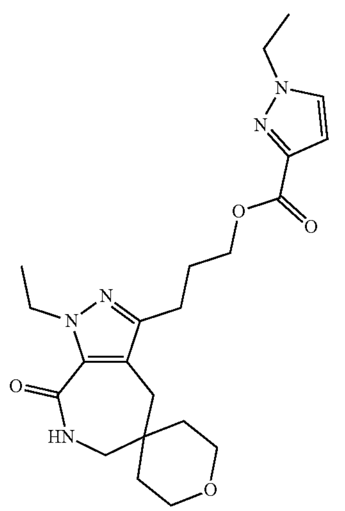 [SMILES: CCn1ccc(C(=O)OCCCc2nn(CC)c3c2CC2(CCOCC2)CNC3=O)n1] | 3-(1-ethyl-8-oxo-spiro[6,7-dihydro-4H-pyrazolo[3,4-c]azepine-5,4'-tetrahydropyran]-3-yl)propyl 1-ethylpyrazole-3-carboxylate | 1.92 | *** |
| 249 | 351 | 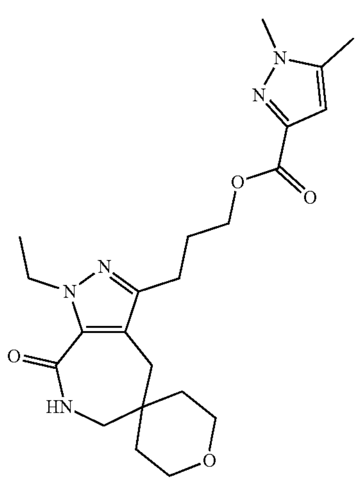 [SMILES: CCn1nc(CCCOC(=O)c2cc(C)n(C)n2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 1,5-dimethylpyrazole-3-carboxylate | 1.89 | *** |

-continued

| Ex. | Cpd | Structure | IUPAC Name | HPLC Rt (min) | PDE4 IC$_{50}$ range |
|---|---|---|---|---|---|
| 250 | 352 | 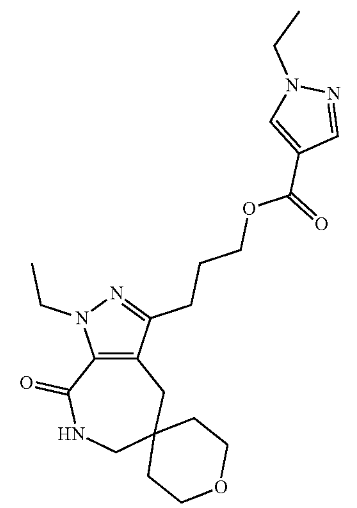 [SMILES: CCn1cc(C(=O)OCCCc2nn(CC)c3c2CC2(CCOCC2)CNC3=O)cn1] | 3-(1-ethyl-8-oxo-spiro[6,7-dihydro-4H-pyrazolo[3,4-c]azepine-5,4'-tetrahydropyran]-3-yl)propyl 1-ethylpyrazole-4-carboxylate | 1.92 | *** |
| 251 | 353 | 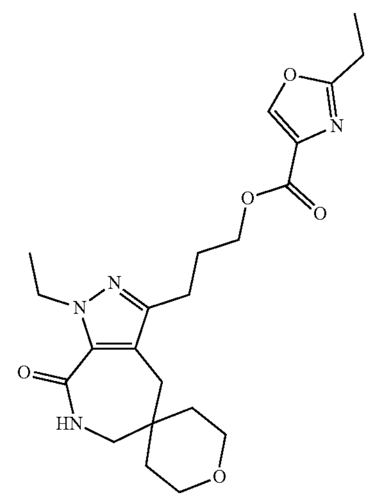 [SMILES: CCc1nc(C(=O)OCCCc2nn(CC)c3c2CC2(CCOCC2)CNC3=O)co1] | 3-(1-ethyl-8-oxo-spiro[6,7-dihydro-4H-pyrazolo[3,4-c]azepine-5,4'-tetrahydropyran]-3-yl)propyl 2-ethyloxazole-4-carboxylate | 1.96 | *** |
| 252 | 354 | 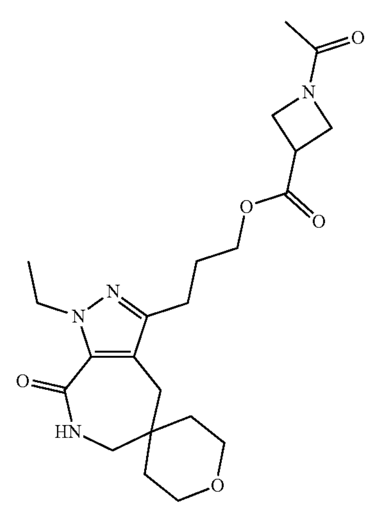 [SMILES: CCn1nc(CCCOC(=O)C2CN(C(C)=O)C2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 1-acetylazetidine-3-carboxylate | 1.76 | ** |

-continued

| Ex. | Cpd | Structure | IUPAC Name | HPLC Rt (min) | PDE4 IC$_{50}$ range |
|---|---|---|---|---|---|
| 253 | 355 | 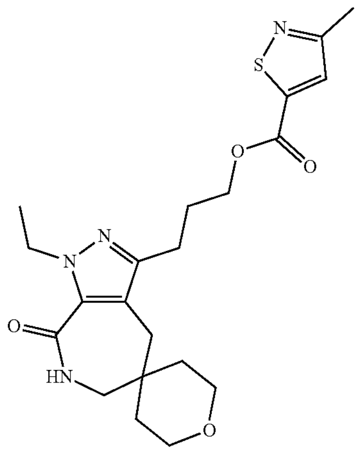 [SMILES: CCn1nc(CCCOC(=O)c2cc(C)ns2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 3-methylisothiazole-5-carboxylate | 2.1 | *** |
| 254 | 356 | 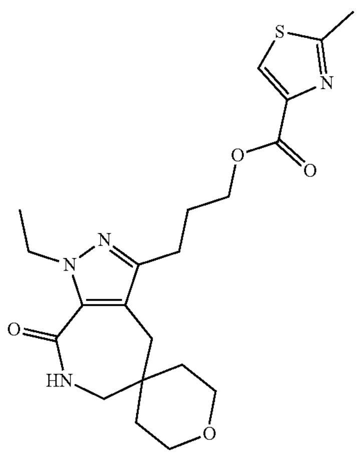 [SMILES: CCn1nc(CCCOC(=O)c2csc(C)n2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 2-methylthiazole-4-carboxylate | 1.91 | *** |
| 255 | 357 | 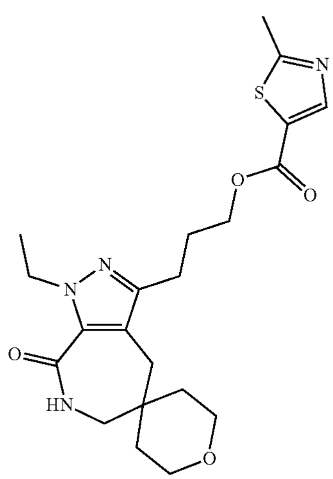 [SMILES: CCn1nc(CCCOC(=O)c2cnc(C)s2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 2-methylthiazole-5-carboxylate | 1.97 | *** |

-continued

| Ex. | Cpd | Structure | IUPAC Name | HPLC Rt (min) | PDE4 IC$_{50}$ range |
|---|---|---|---|---|---|
| 256 | 358 | 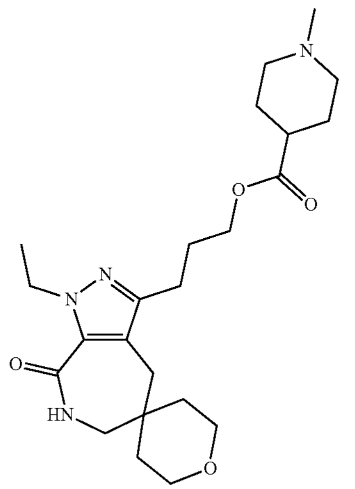 [SMILES: CCn1nc(CCCOC(=O)C2CCN(C)CC2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 1-methylpiperidine-4-carboxylate | 1.64 | ** |
| 257 | 359 | 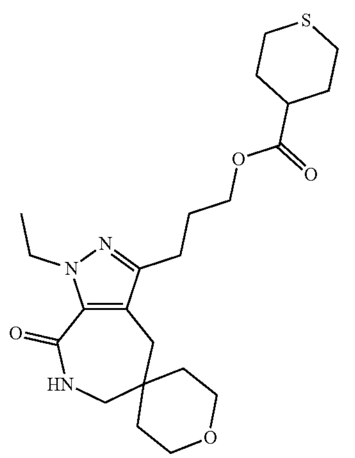 [SMILES: CCn1nc(CCCOC(=O)C2CCSCC2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl tetrahydrothiopyran-4-carboxylate | 2.14 | *** |
| 258 | 360 | 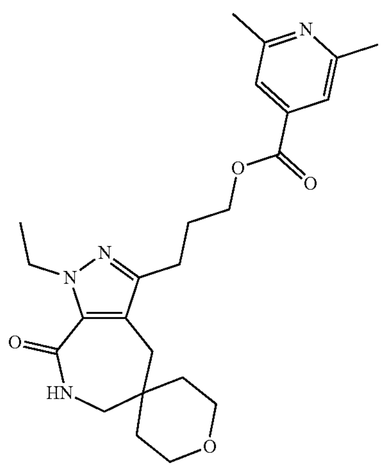 [SMILES: CCn1nc(CCCOC(=O)c2cc(C)nc(C)c2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 2,6-dimethylpyridine-4-carboxylate | 1.88 | *** |

-continued

| Ex. | Cpd | Structure | IUPAC Name | HPLC Rt (min) | PDE4 IC$_{50}$ range |
|---|---|---|---|---|---|
| 259 | 361 | 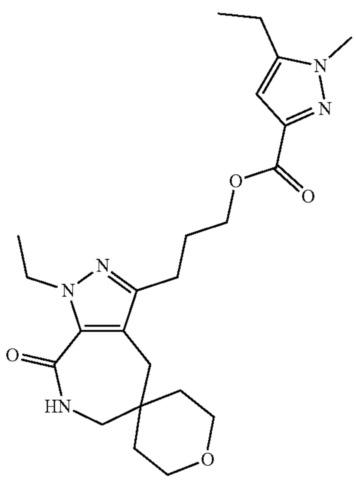 [SMILES: CCc1cc(C(=O)OCCCc2nn(CC)c3c2CC2(CCOCC2)CNC3=O)nn1C] | 3-(1-ethyl-8-oxo-spiro[6,7-dihydro-4H-pyrazolo[3,4-c]azepine-5,4'-tetrahydropyran]-3-yl)propyl 5-ethyl-1-methyl-pyrazole-3-carboxylate | 1.98 | *** |
| 260 | 362 | 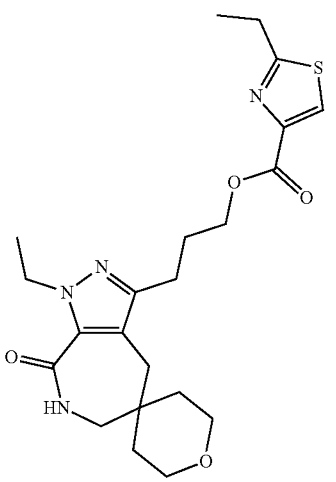 [SMILES: CCc1nc(C(=O)OCCCc2nn(CC)c3c2CC2(CCOCC2)CNC3=O)cs1] | 3-(1-ethyl-8-oxo-spiro[6,7-dihydro-4H-pyrazolo[3,4-c]azepine-5,4'-tetrahydropyran]-3-yl)propyl 2-ethylthiazole-4-carboxylate | 2.01 | *** |
| 261 | 363 | 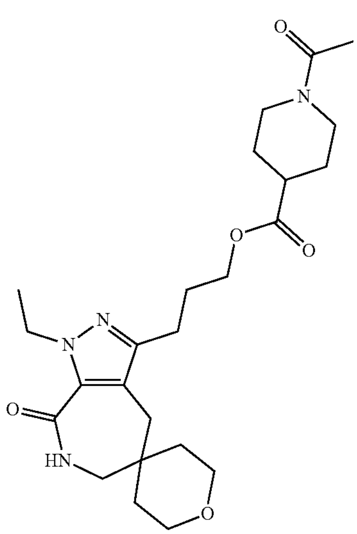 [SMILES: CCn1nc(CCCOC(=O)C2CCN(C(C)=O)CC2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 1-acetylpiperidine-4-carboxylate | 1.84 | *** |

-continued

| Ex. | Cpd | Structure | IUPAC Name | HPLC Rt (min) | PDE4 IC$_{50}$ range |
|---|---|---|---|---|---|
| 262 | 364 | 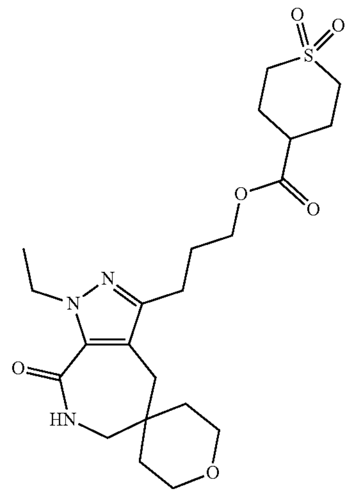 [SMILES: CCn1nc(CCCOC(=O)C2CCS(=O)(=O)CC2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 1,1-dioxothiane-4-carboxylate | 1.84 | *** |
| 263 | 365 | 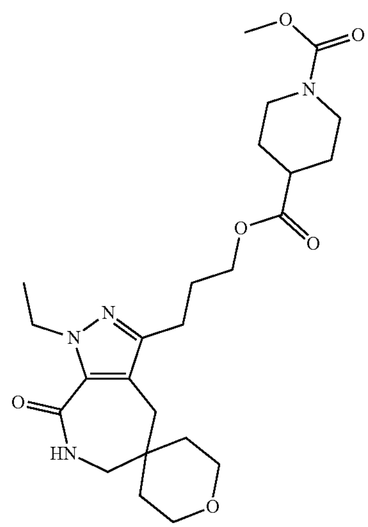 [SMILES: CCn1nc(CCCOC(=O)C2CCN(C(=O)OC)CC2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)propyl] 1-methoxycarbonylpiperidine-4-carboxylate | 1.99 | *** |
| 264 | 366 | 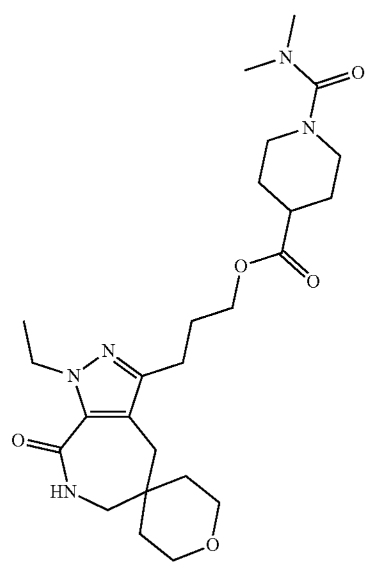 [SMILES: CCn1nc(CCCOC(=O)C2CCN(C(=O)N(C)C)CC2)c2c1C(=O)NCC1(CCOCC1)C2] | 3-(1-ethyl-8-oxo-spiro[6,7-dihydro-4H-pyrazolo[3,4-c]azepine-5,4'-tetrahydropyran]-3-yl)propyl 1-(dimethylcarbamoyl)piperidine-4-carboxylate | 1.92 | *** |

The Examples 265-274 shown in Table 14 were prepared by reacting Compound 012 as described in General Procedure 1 with the appropriate acid:

| Ex. | Cpd | Structure | IUPAC Name | HPLC Rt (min) | PDE4 IC$_{50}$ range |
|---|---|---|---|---|---|
| 265 | 367 | 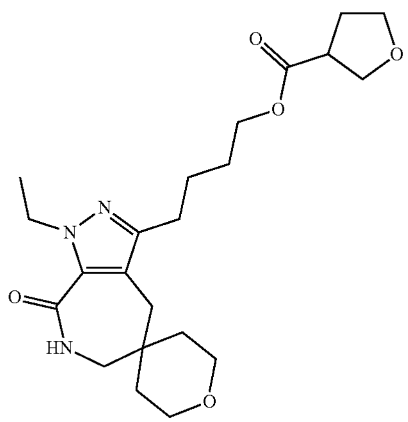 [SMILES: CCn1nc(CCCCOC(=O)C2CCOC2)c2c1C(=O)NCC1(CCOCC1)C2] | 4-(1-ethyl-8-oxo-spiro[6,7-dihydro-4H-pyrazolo[3,4-c]azepine-5,4'-tetrahydropyran]-3-yl)butyl tetrahydrofuran-3-carboxylate | 1.95 | *** |
| 266 | 368 | 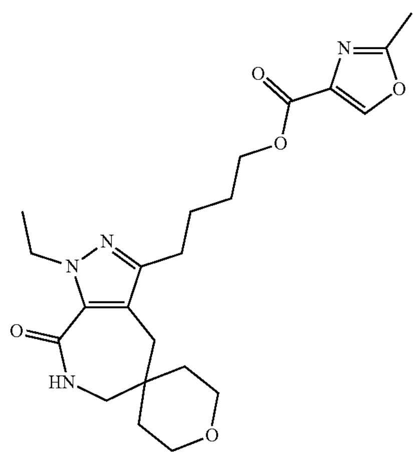 [SMILES: CCn1nc(CCCCOC(=O)c2coc(C)n2)c2c1C(=O)NCC1(CCOCC1)C2] | 4-(1-ethyl-8-oxo-spiro[6,7-dihydro-4H-pyrazolo[3,4-c]azepine-5,4'-tetrahydropyran]-3-yl)butyl 2-methyloxazole-4-carboxylate | 1.93 | *** |
| 267 | 369 | 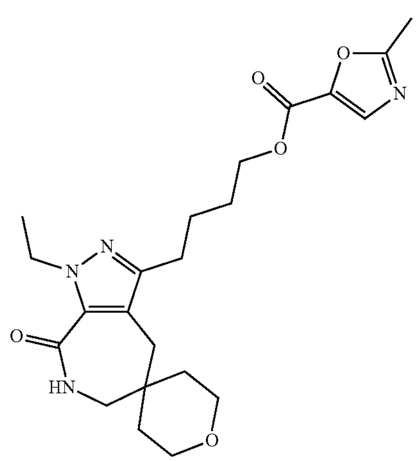 [SMILES: CCn1nc(CCCCOC(=O)c2cnc(C)o2)c2c1C(=O)NCC1(CCOCC1)C2] | 4-(1-ethyl-8-oxo-spiro[6,7-dihydro-4H-pyrazolo[3,4-c]azepine-5,4'-tetrahydropyran]-3-yl)butyl 2-methyloxazole-5-carboxylate | 1.96 | *** |

| Ex. | Cpd | Structure | IUPAC Name | HPLC Rt (min) | PDE4 IC$_{50}$ range |
|---|---|---|---|---|---|
| 268 | 370 | 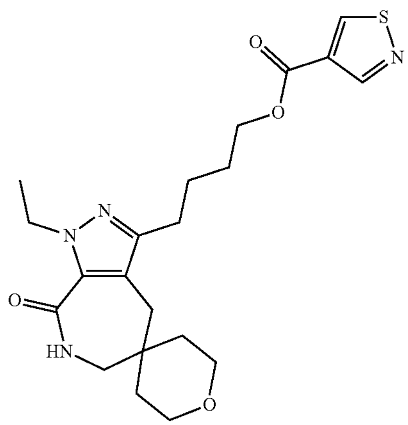 [SMILES: CCn1nc(CCCCOC(=O)c2cnsc2)c2c1C(=O)NCC1(CCOCC1)C2] | 4-(1-ethyl-8-oxo-spiro[6,7-dihydro-4H-pyrazolo[3,4-c]azepine-5,4'-tetrahydropyran]-3-yl)butyl isothiazole-4-carboxylate | 2.05 | *** |
| 269 | 371 | 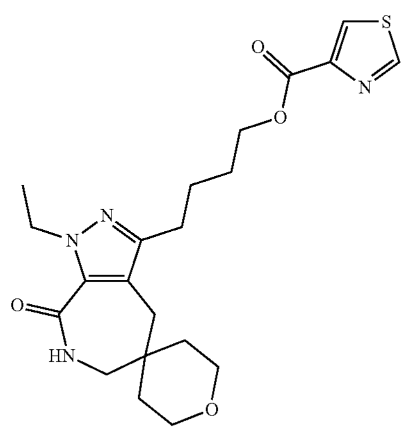 [SMILES: CCn1nc(CCCCOC(=O)c2cscn2)c2c1C(=O)NCC1(CCOCC1)C2] | 4-(1-ethyl-8-oxo-spiro[6,7-dihydro-4H-pyrazolo[3,4-c]azepine-5,4'-tetrahydropyran]-3-yl)butyl thiazole-4-carboxylate | 1.91 | *** |
| 270 | 372 | 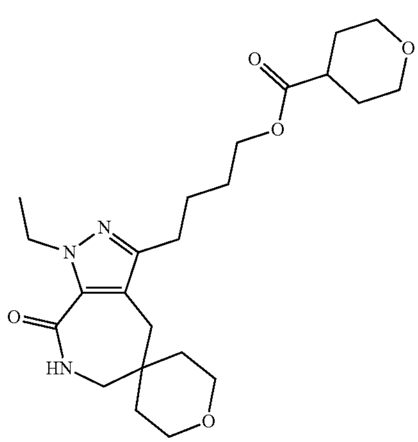 [SMILES: CCn1nc(CCCCOC(=O)C2CCOCC2)c2c1C(=O)NCC1(CCOCC1)C2] | 4-(1-ethyl-8-oxo-spiro[6,7-dihydro-4H-pyrazolo[3,4-c]azepine-5,4'-tetrahydropyran]-3-yl)butyl tetrahydropyran-4-carboxylate | 1.99 | *** |

| Ex. | Cpd | Structure | IUPAC Name | HPLC Rt (min) | PDE4 IC$_{50}$ range |
|---|---|---|---|---|---|
| 271 | 373 | 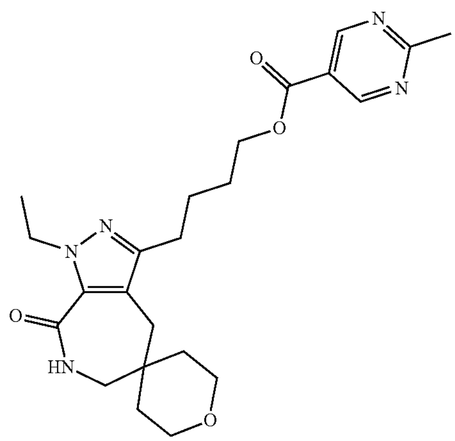 [SMILES: CCn1nc(CCCCOC(=O)c2cnc(C)nc2)c2c1C(=O)NCC1(CCOCC1)C2] | 4-(1-ethyl-8-oxo-spiro[6,7-dihydro-4H-pyrazolo[3,4-c]azepine-5,4'-tetrahydropyran]-3-yl)butyl 2-methylpyrimidine-5-carboxylate | 1.94 | *** |
| 272 | 374 | 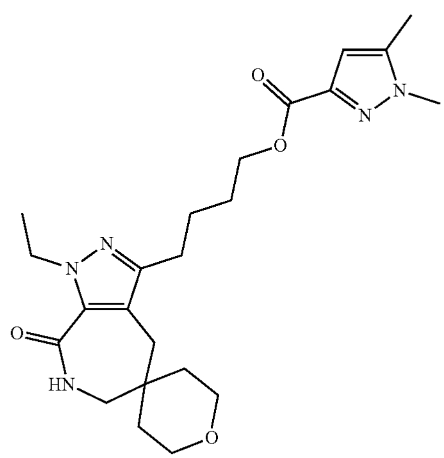 [SMILES: CCn1nc(CCCCOC(=O)c2cc(C)n(C)n2)c2c1C(=O)NCC1(CCOCC1)C2] | 4-(1-ethyl-8-oxo-spiro[6,7-dihydro-4H-pyrazolo[3,4-c]azepine-5,4'-tetrahydro-pyran]-3-yl)butyl 1,5-dimethylpyrazole-3-carboxylate | 1.95 | *** |
| 273 | 375 | 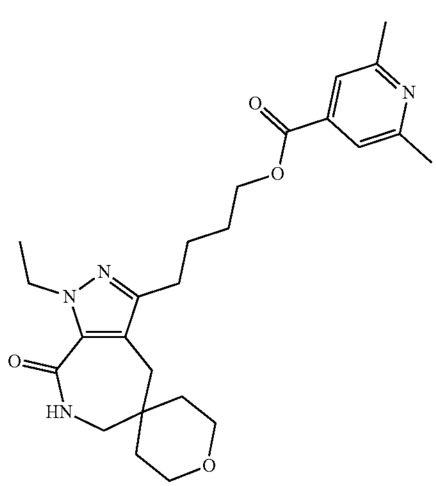 [SMILES: CCn1nc(CCCCOC(=O)c2cc(C)nc(C)c2)c2c1C(=O)NCC1(CCOCC1)C2] | 4-(1-ethyl-8-oxo-spiro[6,7-dihydro-4H-pyrazolo[3,4-c]azepine-5,4'-tetrahydro-pyran]-3-yl)butyl 2,6-dimethylpyridine-4-carboxylate | 1.95 | *** |

| Ex. | Cpd | Structure | IUPAC Name | HPLC Rt (min) | PDE4 IC$_{50}$ range |
|---|---|---|---|---|---|
| 274 | 376 | 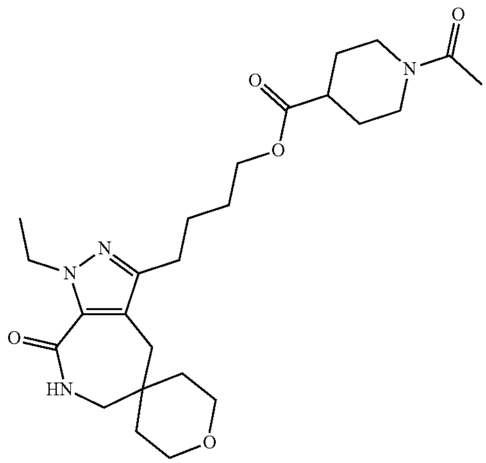 [SMILES: CCn1nc(CCCCOC(=O)C2CCN(C(C)=O)CC2)c2c1C(=O)NCC1(CCOCC1)C2] | 4-(1-ethyl-8-oxo-spiro[6,7-dihydro-4H-pyrazolo[3,4-c]azepine-5,4'-tetrahydropyran]-3-yl)butyl 1-acetylpiperidine-4-carboxylate | 1.89 | *** |

The Examples 275 and 276 shown in Table 15 were prepared by reacting Compound 016 as described in General Procedure 1 with the appropriate acid:

The Examples 277-296 shown in Table 16 were prepared by reacting Compound 028 as described in General Procedure 1 with the appropriate acid:

| Ex. | Cpd | Structure | IUPAC Name | HPLC Rt (min) | PDE4 IC$_{50}$ range |
|---|---|---|---|---|---|
| 275 | 377 | 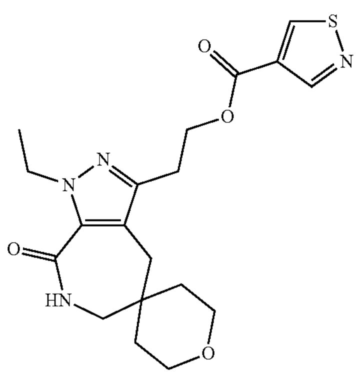 [SMILES: CCn1nc(CCOC(=O)c2cnsc2)c2c1C(=O)NCC1(CCOCC1)C2] | 2-(1-ethyl-8-oxo-spiro[6,7-dihydro-4H-pyrazolo[3,4-c]azepine-5,4'-tetrahydropyran]-3-yl)ethyl isothiazole-4-carboxylate | 1.93 | *** |
| 276 | 378 | 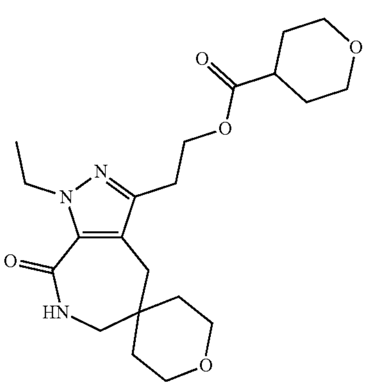 [SMILES: CCn1nc(CCOC(=O)C2CCOCC2)c2c1C(=O)NCC1(CCOCC1)C2] | 2-(1-ethyl-8-oxo-spiro[6,7-dihydro-4H-pyrazolo[3,4-c]azepine-5,4'-tetrahydropyran]-3-yl)ethyl tetrahydropyran-4-carboxylate | 1.86 | ** |

| Ex. | Cpd | Structure | IUPAC Name | HPLC Rt (min) | PDE4 IC$_{50}$ range |
|---|---|---|---|---|---|
| 277 | 379 | 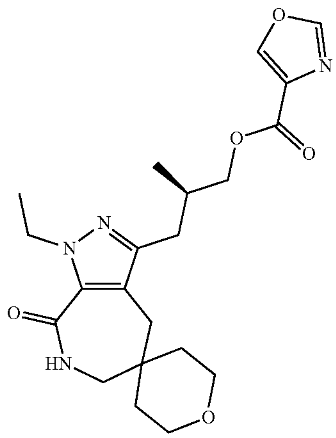 [SMILES: CCn1nc(C[C@@H](C)COC(=O)c2cocn2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] oxazole-4-carboxylate | 1.90 | *** |
| 278 | 380 | 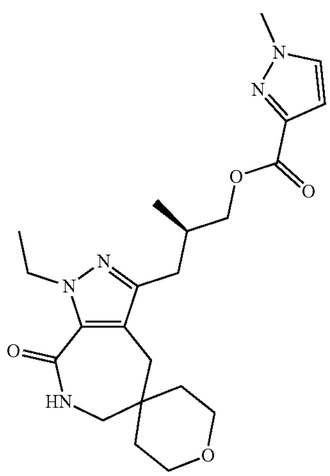 [SMILES: CCn1nc(C[C@@H](C)COC(=O)c2ccn(C)n2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 1-methylpyrazole-3-carboxylate | 1.91 | *** |
| 279 | 381 | 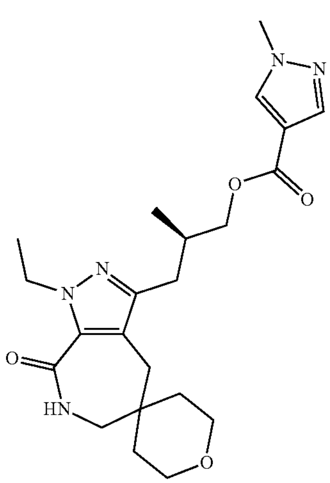 [SMILES: CCn1nc(C[C@@H](C)COC(=O)c2cnn(C)c2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 1-methylpyrazole-4-carboxylate | 1.92 | *** |

| Ex. | Cpd | Structure | IUPAC Name | HPLC Rt (min) | PDE4 IC$_{50}$ range |
|---|---|---|---|---|---|
| 280 | 382 | 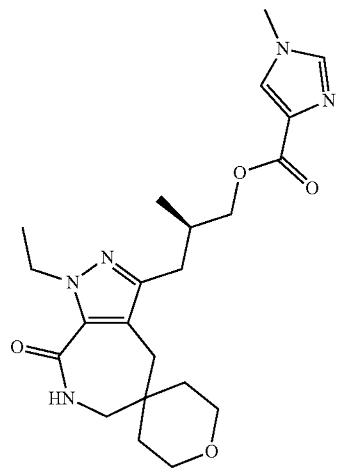 [SMILES: CCn1nc(C[C@@H](C)COC(=O)c2cn(C)cn2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 1-methylimidazole-4-carboxylate | 1.79 | *** |
| 281 | 383 | 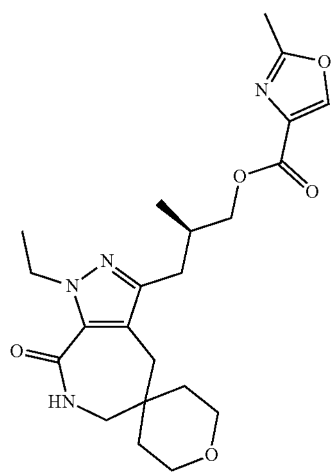 | [(2R)-3-(1-ethyl-8-oxo-spiro[6,7-dihydro-4H-pyrazolo[3,4-c]azepine-5,4'-tetrahydropyran]-3-yl)-2-methyl-propyl] 2-methyloxazole-4-carboxylate | 1.94 | *** |
| 282 | 384 | 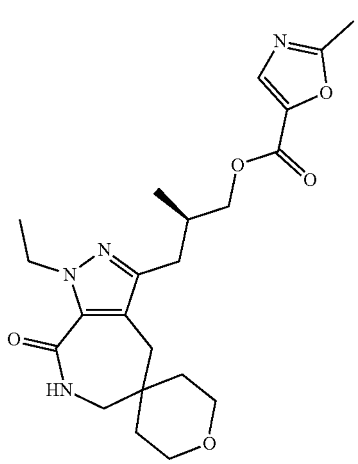 [SMILES: CCn1nc(C[C@@H](C)COC(=O)c2cnc(C)o2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 2-methyloxazole-5-carboxylate | 1.97 | *** |

-continued

| Ex. | Cpd | Structure | IUPAC Name | HPLC Rt (min) | PDE4 IC$_{50}$ range |
|---|---|---|---|---|---|
| 283 | 385 | 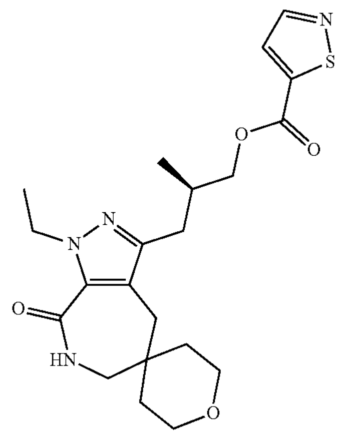 [SMILES: CCn1nc(C[C@@H](C)COC(=O)c2ccns2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] isothiazole-5-carboxylate | 2.12 | *** |
| 284 | 386 | 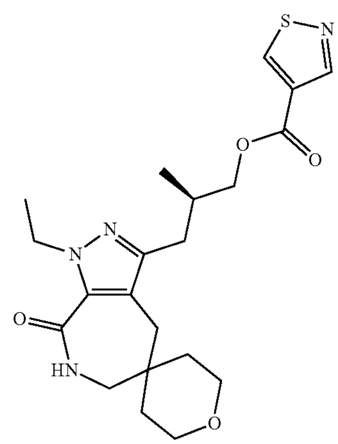 [SMILES: CCn1nc(C[C@@H](C)COC(=O)c2cnsc2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] isothiazole-4-carboxylate | 2.06 | *** |
| 285 | 387 | 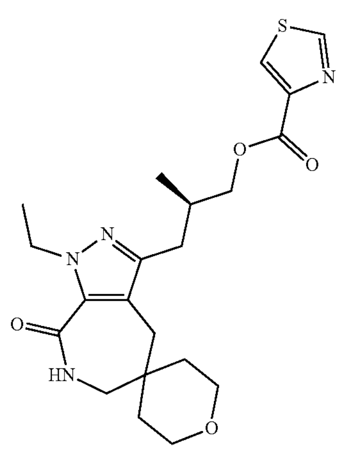 [SMILES: CCn1nc(C[C@@H](C)COC(=O)c2cscn2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] thiazole-4-carboxylate | 1.92 | *** |

| Ex. | Cpd | Structure | IUPAC Name | HPLC Rt (min) | PDE4 IC$_{50}$ range |
|---|---|---|---|---|---|
| 286 | 388 | 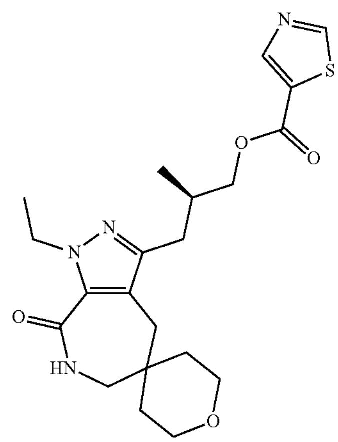 [SMILES: CCn1nc(C[C@@H](C)COC(=O)c2cncs2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] thiazole-5-carboxylate | 2.00 | *** |
| 287 | 389 | 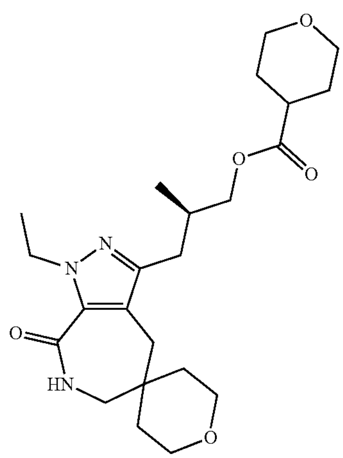 [SMILES: CCn1nc(C[C@@H](C)COC(=O)C2CCOCC2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] tetrahydropyran-4-carboxylate | 2.00 | *** |
| 288 | 390 | 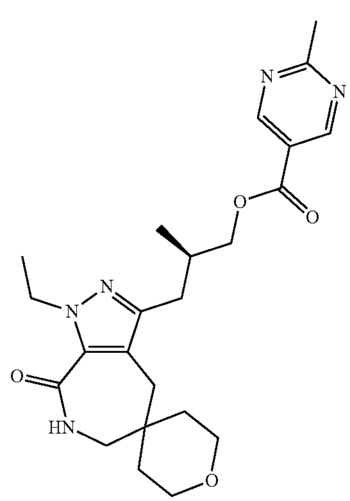 [SMILES: CCn1nc(C[C@@H](C)COC(=O)c2cnc(C)nc2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 2-methylpyrimidine-5-carboxylate | 1.94 | *** |

-continued

| Ex. | Cpd | Structure | IUPAC Name | HPLC Rt (min) | PDE4 IC$_{50}$ range |
|---|---|---|---|---|---|
| 289 | 391 | 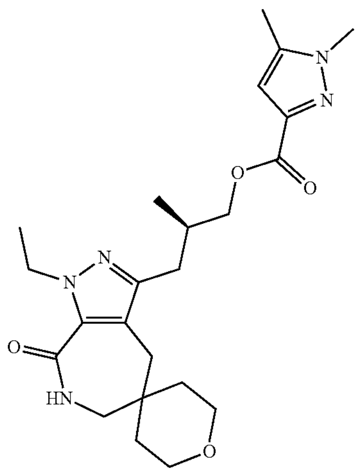 [SMILES: CCn1nc(C[C@@H](C)COC(=O)c2cc(C)n(C)n2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 1,5-dimethylpyrazole-3-carboxylate | 1.96 | *** |
| 290 | 392 | 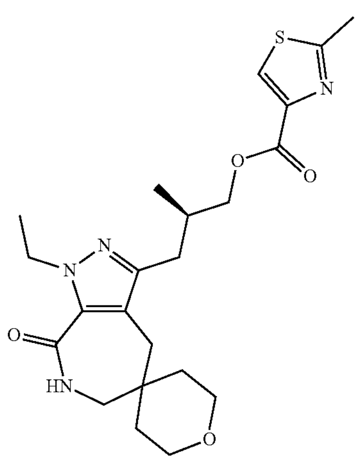 [SMILES: CCn1nc(C[C@@H](C)COC(=O)c2csc(C)n2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 2-methylthiazole-4-carboxylate | 1.98 | *** |
| 291 | 393 | 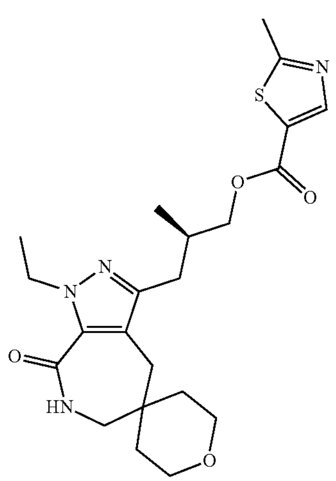 [SMILES: CCn1nc(C[C@@H](C)COC(=O)c2cnc(C)s2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 2-methylthiazole-5-carboxylate | 2.05 | *** |

| Ex. | Cpd | Structure | IUPAC Name | HPLC Rt (min) | PDE4 IC$_{50}$ range |
|---|---|---|---|---|---|
| 292 | 394 | 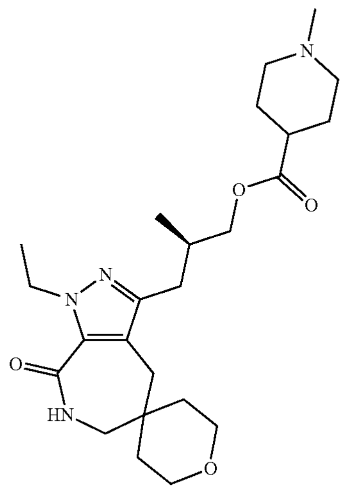 [SMILES: CCn1nc(C[C@@H](C)COC(=O)C2CCN(C)CC2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 1-methylpiperidine-4-carboxylate | 1.69 | ** |
| 293 | 395 | 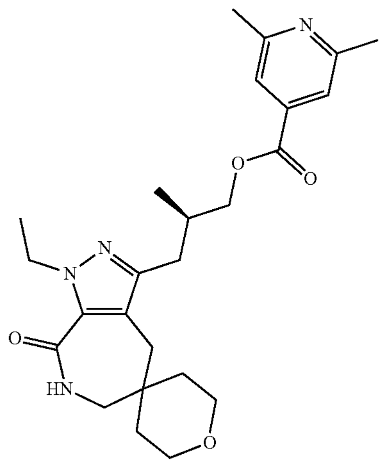 [SMILES: CCn1nc(C[C@@H](C)COC(=O)c2cc(C)nc(C)c2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 2,6-dimethylpyridine-4-carboxylate | 1.97 | *** |
| 294 | 396 | 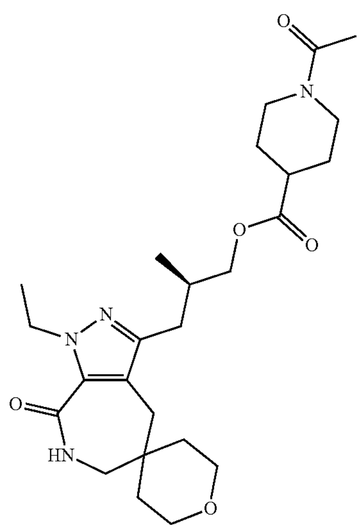 [SMILES: CCn1nc(C[C@@H](C)COC(=O)C2CCN(C(C)=O)CC2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 1-acetylpiperidine-4-carboxylate | 1.90 | *** |

| Ex. | Cpd | Structure | IUPAC Name | HPLC Rt (min) | PDE4 IC$_{50}$ range |
|---|---|---|---|---|---|
| 295 | 397 | 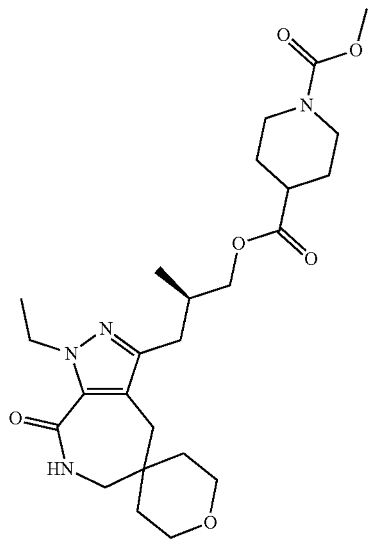 [SMILES: CCn1nc(C[C@@H](C)COC(=O)C2CCN(C(=O)OC)CC2)c2c1C(=O)NCC1(CCOCC1)C2] | [(2R)-3-(1-ethyl-8-oxo-spiro[6,7-dihydro-4H-pyrazolo-[3,4-c]azepine-5,4'-tetrahydropyran]-3-yl)-2-methyl-propyl] 1-methoxycarbonylpiperidine-4-carboxylate | 2.06 | *** |
| 296 | 398 | 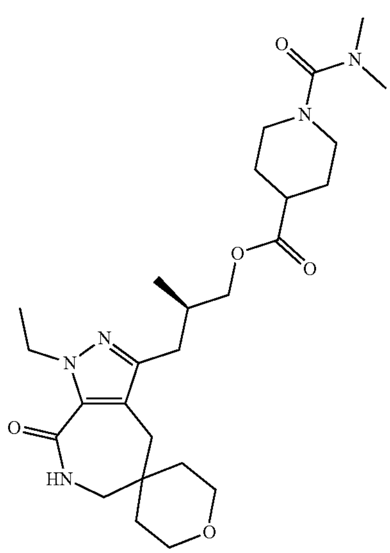 [SMILES: CCn1nc(C[C@@H](C)COC(=O)C2CCN(C(=O)N(C)C)CC2)c2c1C(=O)NCC1(CCOCC1)C2] | [(2R)-3-(1-ethyl-8-oxo-spiro[6,7-dihydro-4H-pyrazolo[3,4-c]azepine-5,4'-tetrahydropyran]-3-yl)-2-methyl-propyl] 1-(dimethylcarbamoyl)piperidine-4-carboxylate | 1.99 | *** |

The Examples 297-316 shown in Table 17 were prepared by reacting Compound 040 as described in General Procedure 1 with the appropriate acid:

| Ex. | Cpd | Structure | IUPAC Name | HPLC Rt (min) | PDE4 IC$_{50}$ range |
|---|---|---|---|---|---|
| 297 | 399 | 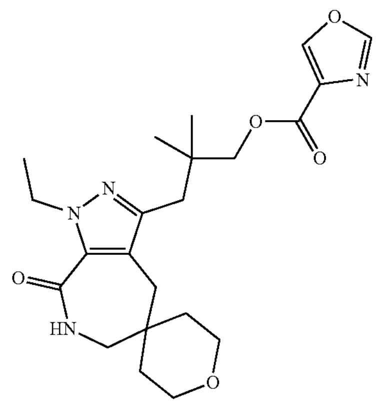 [SMILES: CCn1nc(CC(C)(C)COC(=O)c2cocn2)c2c1C(=O)NCC1(CCOCC1)C2] | [3-(1-ethyl-8-oxo-spiro[6,7-dihydro-4H-pyrazolo[3,4-c]azepine-5,4'-tetrahydro-pyran]-3-yl)-2,2-dimethyl-propyl] oxazole-4-carboxylate | 1.98 | *** |
| 298 | 400 | 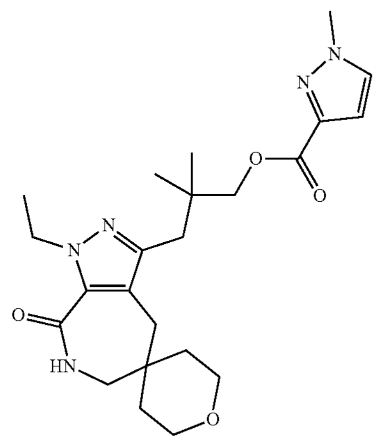 [SMILES: CCn1nc(CC(C)(C)COC(=O)c2ccn(C)n2)c2c1C(=O)NCC1(CCOCC1)C2] | [3-(1-ethyl-8-oxo-spiro[6,7-dihydro-4H-pyrazolo[3,4-c]azepine-5,4'-tetrahydro-pyran]-3-yl)-2,2-dimethyl-propyl] 1-methylpyrazole-3-carboxylate | 2.00 | *** |
| 299 | 401 | 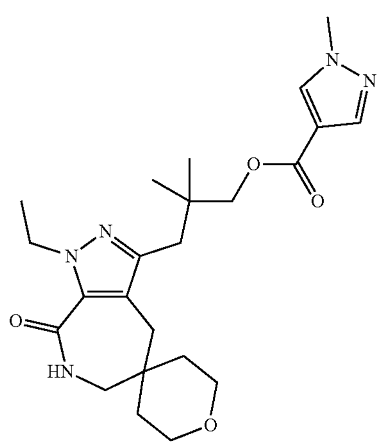 [SMILES: CCn1nc(CC(C)(C)COC(=O)c2cnn(C)c2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 1-methylpyrazole-4-carboxylate | 2.00 | *** |

-continued

| Ex. | Cpd | Structure | IUPAC Name | HPLC Rt (min) | PDE4 IC$_{50}$ range |
|---|---|---|---|---|---|
| 300 | 402 | 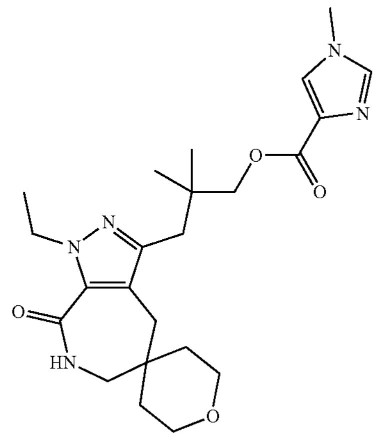 [SMILES: CCn1nc(CC(C)(C)COC(=O)c2cn(C)cn2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 1-methylimidazole-4-carboxylate | 1.85 | *** |
| 301 | 403 | 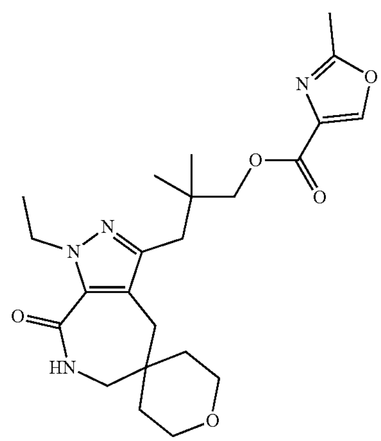 [SMILES: CCn1nc(CC(C)(C)COC(=O)c2coc(C)n2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 2-methyloxazole-4-carboxylate | 2.03 | *** |
| 302 | 404 | 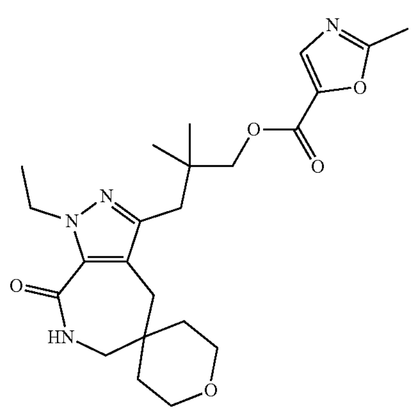 [SMILES: CCn1nc(CC(C)(C)COC(=O)c2cnc(C)o2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 2-methyloxazole-5-carboxylate | 2.06 | *** |

| Ex. | Cpd | Structure | IUPAC Name | HPLC Rt (min) | PDE4 IC$_{50}$ range |
|---|---|---|---|---|---|
| 303 | 405 | 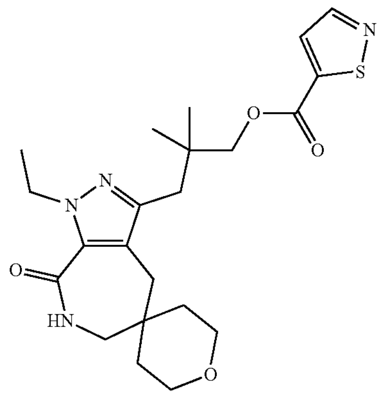 [SMILES: CCn1nc(CC(C)(C)COC(=O)c2ccns2)c2c1C(=O)NCC1(CCOCC1)C2] | [3-(1-ethyl-8-oxo-spiro[6,7-dihydro-4H-pyrazolo[3,4-c]azepine-5,4'-tetrahydro-pyran]-3-yl)-2,2-dimethyl-propyl] isothiazole-5-carboxylate | 2.23 | *** |
| 304 | 406 | 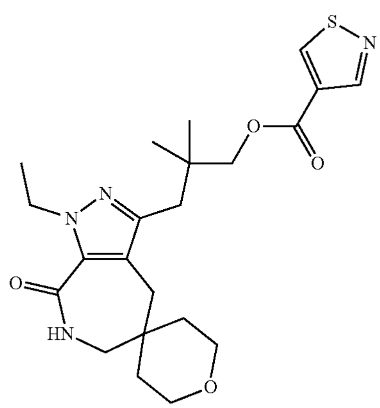 [SMILES: CCn1nc(CC(C)(C)COC(=O)c2cnsc2)c2c1C(=O)NCC1(CCOCC1)C2] | [3-(1-ethyl-8-oxo-spiro[6,7-dihydro-4H-pyrazolo[3,4-c]azepine-5,4'-tetrahydro-pyran]-3-yl)-2,2-dimethyl-propyl] isothiazole-4-carboxylate | 2.16 | *** |
| 305 | 407 | 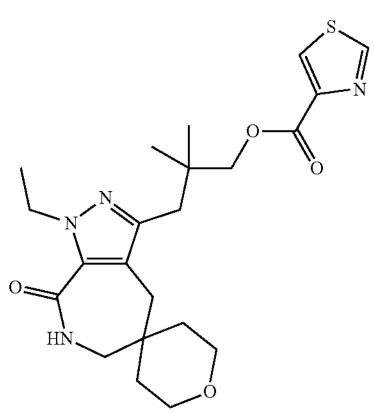 [SMILES: CCn1nc(CC(C)(C)COC(=O)c2cscn2)c2c1C(=O)NCC1(CCOCC1)C2] | [3-(1-ethyl-8-oxo-spiro[6,7-dihydro-4H-pyrazolo[3,4-c]azepine-5,4'-tetrahydro-pyran]-3-yl)-2,2-dimethyl-propyl] thiazole-4-carboxylate | 2.01 | *** |

| Ex. | Cpd | Structure | IUPAC Name | HPLC Rt (min) | PDE4 IC$_{50}$ range |
|---|---|---|---|---|---|
| 306 | 408 | 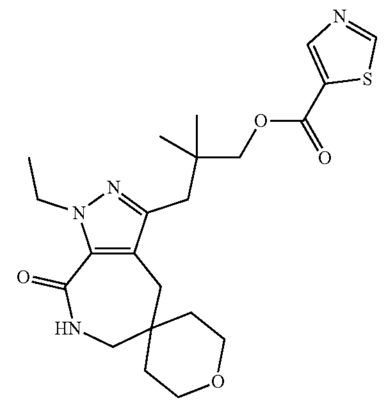 [SMILES: CCn1nc(CC(C)(C)COC(=O)c2cncs2)c2c1C(=O)NCC1(CCOCC1)C2] | [3-(1-ethyl-8-oxo-spiro[6,7-dihydro-4H-pyrazolo[3,4-c]azepine-5,4'-tetrahydro-pyran]-3-yl)-2,2-dimethyl-propyl] thiazole-5-carboxylate | 2.09 | *** |
| 307 | 409 | 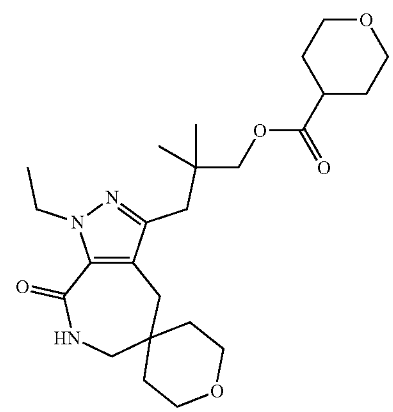 [SMILES: CCn1nc(CC(C)(C)COC(=O)C2CCOCC2)c2c1C(=O)NCC1(CCOCC1)C2] | [3-(1-ethyl-8-oxo-spiro[6,7-dihydro-4H-pyrazolo[3,4-c]azepine-5,4'-tetrahydro-pyran]-3-yl)-2,2-dimethyl-propyl] tetrahydropyran-4-carboxylate | 2.10 | *** |
| 308 | 410 | 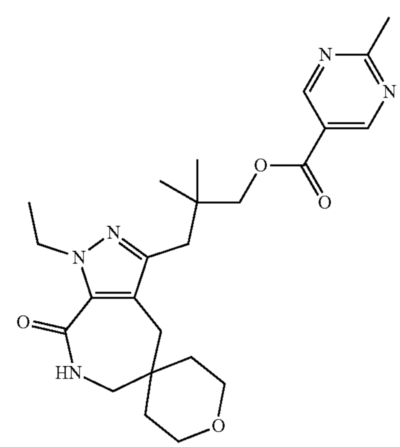 [SMILES: CCn1nc(CC(C)(C)COC(=O)c2cnc(C)nc2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 2-methylpyrimidine-5-carboxylate | 2.04 | *** |

-continued

| Ex. | Cpd | Structure | IUPAC Name | HPLC Rt (min) | PDE4 IC$_{50}$ range |
|---|---|---|---|---|---|
| 309 | 411 | 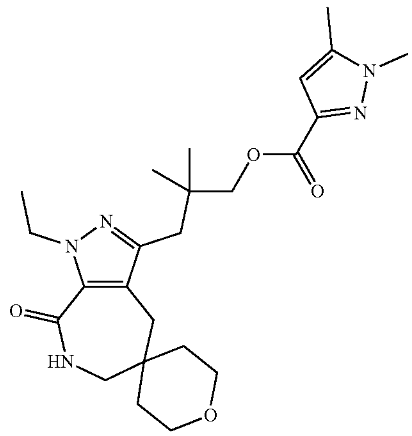 [SMILES: CCn1nc(CC(C)(C)COC(=O)c2cc(C)n(C)n2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 1,5-dimethylpyrazole-3-carboxylate | 2.05 | *** |
| 310 | 412 | 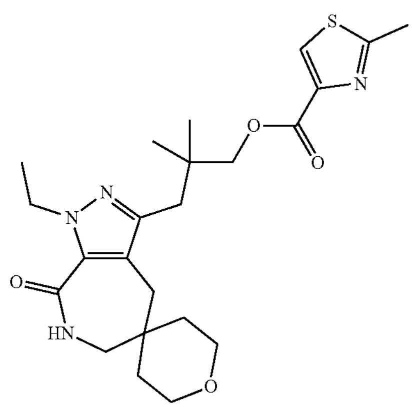 [SMILES: CCn1nc(CC(C)(C)COC(=O)c2csc(C)n2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 2-methylthiazole-4-carboxylate | 2.08 | *** |
| 311 | 413 | 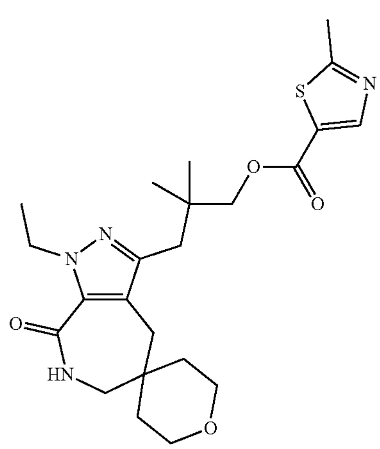 [SMILES: CCn1nc(CC(C)(C)COC(=O)c2cnc(C)s2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 2-methylthiazole-5-carboxylate | 2.15 | *** |

| Ex. | Cpd | Structure | IUPAC Name | HPLC Rt (min) | PDE4 IC$_{50}$ range |
|---|---|---|---|---|---|
| 312 | 414 | 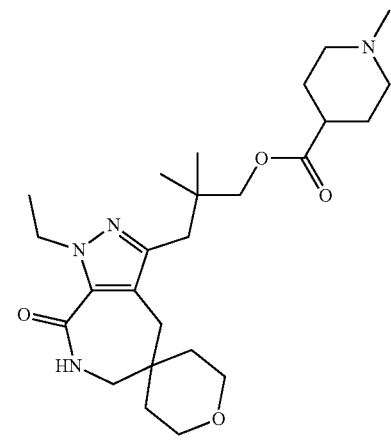 [SMILES: CCn1nc(CC(C)(C)COC(=O)C2CCN(C)CC2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 1-methylpiperidine-4-carboxylate | 1.74 | ** |
| 313 | 415 | 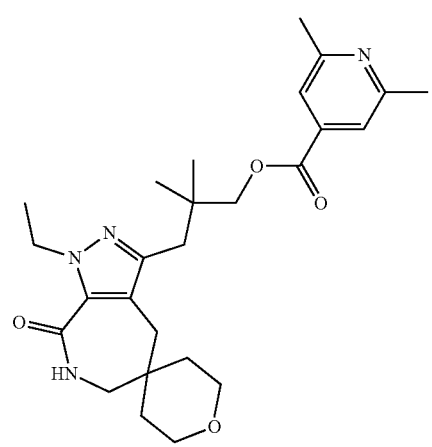 [SMILES: CCn1nc(CC(C)(C)COC(=O)c2cc(C)nc(C)c2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 2,6-dimethylpyridine-4-carboxylate | 2.08 | *** |
| 314 | 416 | 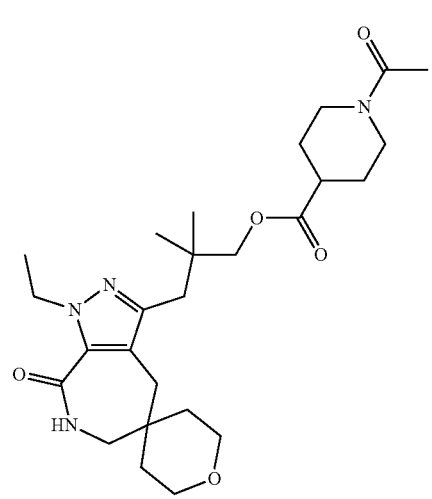 [SMILES: CCn1nc(CC(C)(C)COC(=O)C2CCN(C(C)=O)CC2)c2c1C(=O)NCC1(CCOCC1)C2] | [3-(1-ethyl-8-oxo-spiro[6,7-dihydro-4H-pyrazolo[3,4-c]azepine-5,4'-tetrahydropyran]-3-yl)-2,2-dimethyl-propyl] 1-acetylpiperidine-4-carboxylate | 1.97 | *** |

-continued

| Ex. | Cpd | Structure | IUPAC Name | HPLC Rt (min) | PDE4 IC$_{50}$ range |
|---|---|---|---|---|---|
| 315 | 417 | 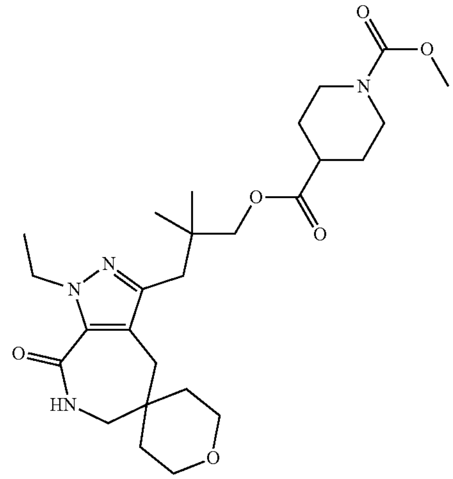 [SMILES: CCn1nc(CC(C)(C)COC(=O)C2CCN(C(=O)OC)CC2)c2c1C(=O)NCC1(CCOCC1)C2] | [3-(1-ethyl-8-oxo-spiro[6,7-dihydro-4H-pyrazolo[3,4-c]azepine-5,4'-tetrahydro-pyran]-3-yl)-2,2-dimethyl-propyl] 1-methoxycarbonyl-peridine-4-carboxylate | 2.15 | *** |
| 316 | 418 | 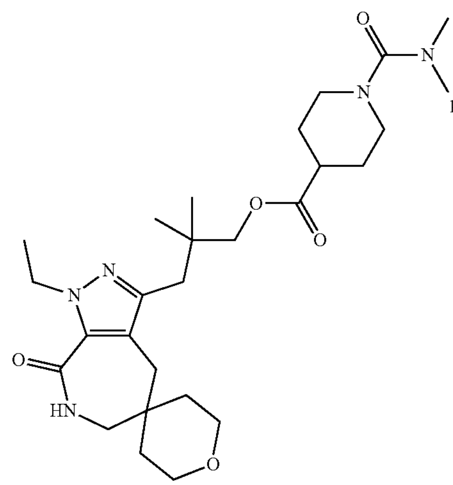 | [3-(1-ethyl-8-oxo-spiro[6,7-dihydro-4H-pyrazolo[3,4-c]azepine-5,4'-tetrahydro-pyran]-3-yl)-2,2-dimethyl-propyl] 1-(dimethylcarbamoyl)-piperidine-4-carboxylate | 2.07 | *** |

CLAUSES

In view of the description the present inventors have in particular provided:

Clause 1. A Compound of general formula (I)

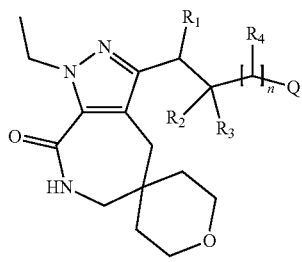

(I)

wherein $R_1$ and $R_4$ are independently selected from the group consisting of hydrogen and $(C_1-C_4)$alkyl;

$R_2$ and $R_3$ are independently selected from the group consisting of hydrogen and $(C_1-C_4)$alkyl; or $R_2$ and $R_3$ may together with the carbon atom to which they are attached form a cyclopropyl, cyclobutyl, cyclopentyl, oxetanyl, tetrahydrofuranyl or tetrahydropyranyl ring;

n=0, 1 or 2;

Q is selected from the group consisting of —O—C(O)—$R_5$;

$R_5$ is selected from the group consisting of $(C_1-C_6)$alkyl, $(C_3-C_7)$cycloalkyl, (4-7)-membered heterocycloalkyl, heteroaryl and aryl, wherein said heteroaryl and aryl are optionally substituted with one or more substituents selected from $R_6$, and wherein said $(C_1-C_6)$alkyl, $(C_3-C_7)$cycloalkyl and (4-7)-membered heterocycloalkyl are optionally substituted with one or more substituents selected from $R_7$;

$R_6$ consists of halogen, cyano, hydroxyl, $(C_1-C_4)$alkyl, halo$(C_1-C_4)$alkyl, —S(O)$_2R_x$, —S(O)$_2NR_aR_b$, C(O)NR$_aR_b$, —C(O)OR$_a$, —C(O)R$_x$ and —OR$_x$;

$R_7$ consists of halogen, hydroxyl, $(C_1-C_4)$alkyl, cyano, oxo, —C(O)NR$_aR_b$, —C(O)OR$_a$, —C(O)R$_x$, S(O)$_2R_x$, —OR$_x$, —SR$_x$, aryl and heteroaryl;

$R_x$ consist of $(C_1-C_6)$alkyl, $(C_3-C_6)$cycloalkyl;

$R_a$ and $R_b$ are independently selected from the group consisting of hydrogen, $(C_1$-$C_4)$alkyl, halo$(C_1$-$C_4)$alkyl and phenyl$(C_1$-$C_4)$alkyl, or $R_a$ and $R_b$ may together with the nitrogen atom to which they are attached form a 4-6 membered heterocycloalkyl, wherein said heterocycloalkyl is optionally substituted with one or more $(C_1$-$C_4)$alkyl or $C(O)R_x$; or a pharmaceutically acceptable salt, hydrate or solvate thereof.

Clause 2. A compound according to clause 1 wherein $R_1$ and $R_4$ are independently selected from the group consisting of hydrogen and $(C_1$-$C_4)$alkyl;

$R_2$ and $R_3$ are independently selected from the group consisting of hydrogen and $(C_1$-$C_4)$alkyl;

n=0, 1 or 2;

Q is selected from the group consisting of —O—C(O)—$R_5$;

$R_5$ is selected from the group consisting of $(C_1$-$C_6)$alkyl, $(C_3$-$C_7)$cycloalkyl, (4-7)-membered heterocycloalkyl, heteroaryl and aryl, wherein said heteroaryl and aryl are optionally substituted with one or more substituents selected from $R_6$, and wherein said $(C_1$-$C_6)$alkyl, $(C_3$-$C_7)$cycloalkyl and (4-7)-membered heterocycloalkyl are optionally substituted with one or more substituents selected from $R_7$;

$R_6$ consists of halogen, cyano, hydroxyl, $(C_1$-$C_4)$alkyl, halo$(C_1$-$C_4)$alkyl, —S(O)$_2$R$_x$, —S(O)$_2$NR$_a$R$_b$, C(O)NR$_a$R$_b$, —C(O)OR$_a$, —C(O)R$_x$ and —OR$_x$;

$R_7$ consists of halogen, hydroxyl, $(C_1$-$C_4)$alkyl, cyano, oxo, —C(O)NR$_a$R$_b$, —C(O)OR$_a$, —C(O)R$_x$, —S(O)$_2$R$_x$, —OR$_x$, —SR$_x$, aryl and heteroaryl;

$R_x$ consist of $(C_1$-$C_6)$alkyl, $(C_3$-$C_6)$cycloalkyl;

$R_a$ and $R_b$ are independently selected from the group consisting of hydrogen, $(C_1$-$C_4)$alkyl, halo$(C_1$-$C_4)$alkyl and phenyl$(C_1$-$C_4)$alkyl, or $R_a$ and $R_b$ may together with the nitrogen atom to which they are attached form a 4-6 membered heterocycloalkyl, wherein said heterocycloalkyl is optionally substituted with one or more $(C_1$-$C_4)$alkyl or —C(O)R$_x$; or a pharmaceutically acceptable salt, hydrate or solvate thereof.

Clause 3. A Compound according to clause 1 or 2 wherein $R_1$ and $R_4$ are independently selected from the group consisting of hydrogen and $(C_1$-$C_4)$alkyl;

$R_2$ and $R_3$ are independently selected from the group consisting of hydrogen and $(C_1$-$C_4)$alkyl;

n=0, 1 or 2;

Q is selected from the group consisting of —O—C(O)—$R_5$;

$R_5$ is selected from the group consisting of $(C_1$-$C_6)$alkyl, $(C_3$-$C_7)$cycloalkyl, a (4-6)-membered heterocycloalkyl, a (5-6)-membered heteroaryl and phenyl, wherein said (5-6)-membered heteroaryl and phenyl are optionally substituted with one or more substituents selected from $R_6$, and wherein said $(C_1$-$C_6)$alkyl, $(C_3$-$C_7)$cycloalkyl and (4-6)-membered heterocycloalkyl are optionally substituted with one or more substituents selected from $R_7$;

$R_6$ consists of halogen, cyano, hydroxyl, $(C_1$-$C_4)$alkyl, halo$(C_1$-$C_4)$alkyl, —S(O)$_2$R$_x$, —S(O)$_2$NR$_a$R$_b$, C(O)NR$_a$R$_b$, —C(O)R$_x$ and —OR$_x$;

$R_7$ consists of halogen, hydroxyl, $(C_1$-$C_4)$alkyl, cyano, oxo, —C(O)NR$_a$R$_b$, —C(O)OR$_a$, —C(O)R$_x$, —S(O)$_2$R$_x$, —OR$_x$, and —SR$_x$;

$R_x$ consist of $(C_1$-$C_6)$alkyl, $(C_3$-$C_6)$cycloalkyl;

$R_a$ and $R_b$ are independently selected from the group consisting of hydrogen, $(C_1$-$C_4)$alkyl, halo$(C_1$-$C_4)$alkyl and phenyl$(C_1$-$C_4)$alkyl, or $R_a$ and $R_b$ may together with the nitrogen atom to which they are attached form a 4-6 membered heterocycloalkyl, wherein said heterocycloalkyl is optionally substituted with one or more $(C_1$-$C_4)$alkyl or —C(O)R$_x$; and a pharmaceutically acceptable salt, hydrate or solvate thereof.

Clause 4. A Compound according to clause 1 wherein $R_1$ and $R_4$ are independently selected from the group consisting of hydrogen and $(C_1$-$C_4)$alkyl;

$R_2$ and $R_3$ are independently selected from the group consisting of hydrogen and $(C_1$-$C_4)$alkyl; or $R_2$ and $R_3$ may together with the carbon atom to which they are attached form a cyclopropyl, cyclobutyl, cyclopentyl, oxetanyl, tetrahydrofuranyl or tetrahydropyranyl ring;

n=0, 1 or 2;

Q is selected from the group consisting of —O—C(O)—$R_5$;

$R_5$ is selected from the group consisting of $(C_1$-$C_6)$alkyl, $(C_3$-$C_7)$cycloalkyl, (4-7)-membered heterocycloalkyl and aryl, wherein said aryl is optionally substituted with one or more substituents selected from $R_6$, and wherein said $(C_1$-$C_6)$alkyl, $(C_3$-$C_7)$cycloalkyl and (4-7)-membered heterocycloalkyl are optionally substituted with one or more substituents selected from $R_7$;

$R_5$ consists of halogen, cyano, hydroxyl, $(C_1$-$C_4)$alkyl, halo$(C_1$-$C_4)$alkyl, —S(O)$_2$R$_x$, —S(O)$_2$NR$_a$R$_b$, and —OR$_x$;

$R_7$ consists of halogen, hydroxyl, cyano, —C(O)NR$_a$R$_b$, —C(O)OR$_a$, aryl and heteroaryl;

$R_x$ is $(C_1$-$C_6)$alkyl;

$R_a$ and $R_b$ are independently selected from the group consisting of hydrogen, $(C_1$-$C_4)$alkyl, halo$(C_1$-$C_4)$alkyl and phenyl$(C_1$-$C_4)$alkyl, or $R_a$ and $R_b$ may together with the nitrogen atom to which they are attached form a 4-6 membered heterocycloalkyl, wherein said heterocycloalkyl is optionally substituted with one or more $(C_1$-$C_4)$alkyl; or pharmaceutically acceptable salts, hydrates or solvates thereof.

Clause 5. A Compound according to any one of the preceding clauses wherein $R_1$ and $R_4$ are both hydrogen.

Clause 6. A Compound according to any one of the preceding clauses wherein one of $R_2$ and $R_3$ is hydrogen and the other one of $R_2$ and $R_3$ is $(C_1$-$C_4)$alkyl.

Clause 7. A Compound according to any one of the clauses 1-5 wherein $R_2$ and $R_3$ are both hydrogen.

Clause 8. A Compound according to any one of the clauses 1-5 wherein $R_2$ and $R_3$ are both $(C_1$-$C_4)$alkyl.

Clause 9. A Compound according to clause 8 wherein $R_2$ and $R_3$ are both methyl.

Clause 10. A Compound according to any one of the clauses 1-5 wherein $R_2$ and $R_3$ together with the carbon atom to which they are attached form a cyclopropyl, cyclobutyl, cyclopentyl, oxetanyl, tetrahydrofuranyl or tetrahydropyranyl ring.

Clause 11. A Compound according to any one of the preceding clauses wherein n is 1.

Clause 12. A Compound according to any one of the clauses 1-10 wherein n is 2.

Clause 13. A Compound according to any one of the clauses 1-10 wherein n is 0.

Clause 14. A Compound according to any one of the preceding clauses wherein $R_5$ is $(C_1$-$C_6)$alkyl.

Clause 15. A Compound according to any one of the clauses 1-13 wherein $R_5$ is $(C_3$-$C_6)$cycloalkyl.

Clause 16. A Compound according to clause 15 wherein $R_5$ is cyclopentyl.

Clause 17. A Compound according to any one of the clauses 1-13 wherein $R_5$ is (4-7)-membered heterocycloalkyl, optionally substituted with one or more substituents independently selected from $R_6$.

Clause 18. A Compound according to clause 17 wherein $R_5$ is (4-6)-membered heterocycloalkyl, optionally substituted with one or more substituents independently selected from $R_6$.

Clause 19. A Compound according to clause 18 wherein $R_5$ is selected from the group consisting of piperidinyl, tetrahydrofuranyl, azetidinyl, tetrahydropyranyl, tetrahydrothiopyranyl, and dioxothianyl, all of which are optionally substituted with one or more substituents independently selected from $R_6$.

Clause 20. A Compound according to clause 19 wherein $R_5$ is tetrahydrofuranyl.

Clause 21. A Compound according to clause 19 wherein $R_5$ is tetrahydropyranyl.

Clause 22. A Compound according to any one of the clauses 1-13 wherein $R_5$ is heteroaryl, optionally substituted with one or more substituents independently selected from $R_6$.

Clause 23. A Compound according to clause 22 wherein $R_5$ is a (5-6) membered heteroaryl optionally substituted with one or more substituents independently selected from $R_6$.

Clause 24. A Compound according to clause 23 wherein $R_5$ is selected from the group consisting of imidazolyl, pyrazolyl, oxazolyl, pyrimidinyl, pyridyl, isothiazolyl, and thiazolyl, all of which are optionally substituted with one or more substituents independently selected from $R_6$.

Clause 25. A Compound according to any one of the clauses 1-13 wherein $R_5$ is aryl, optionally substituted with one or more substituents independently selected from $R_6$.

Clause 26. A Compound according to clause 25 wherein $R_5$ is phenyl, optionally substituted with one or more substituents independently selected from $R_6$.

Clause 27. A Compound according to clause 26 wherein $R_5$ is phenyl substituted with one substituent selected from $R_6$.

Clause 28. A Compound according to clause 26 wherein $R_5$ is phenyl substituted with two substituents independently selected from $R_6$.

Clause 29. A Compound according to clause 26 wherein $R_5$ is phenyl.

Clause 30. A Compound according to any one of the preceding clauses wherein $R_6$ consists of halogen, cyano, hydroxyl, $(C_1$-$C_4)$alkyl, halo$(C_1$-$C_4)$alkyl and $(C_1$-$C_4)$alkyloxy.

Clause 31. A Compound according to any one of the clauses 1-29 wherein $R_6$ consists of $(C_1$-$C_4)$alkyl, —C(O)$NR_aR_b$, and —C(O)$OR_a$, wherein all of $R_a$, $R_b$ are independently selected from hydrogen and $(C_1$-$C_4)$alkyl.

Clause 32. A Compound according to any one of the clauses 1-29 wherein $R_6$ is —S(O)$_2R_x$.

Clause 33. A Compound according to any one of the clauses 1-29, wherein $R_6$ is —C(O)$R_x$.

Clause 34. A Compound according to any one of the clauses 1-29, wherein $R_6$ is C(O)$NR_aR_b$.

Clause 35. A Compound according to any one of the clauses 1-29, wherein $R_6$ is —S(O)$_2NR_aR_b$.

Clause 36. A Compound according to any one of the preceding clauses wherein $R_7$ consists of halogen, hydroxyl, $(C_1$-$C_4)$alkyl, cyano, oxo, —C(O)$NR_aR_b$, —C(O)$OR_a$, —C(O)$R_x$, —S(O)$_2R_x$, —$OR_x$, and —$SR_x$.

Clause 37. A Compound according to any one of the preceding clauses, wherein $R_x$ is $(C_1$-$C_4)$alkyl.

Clause 38. A Compound according to clause 37, wherein $R_x$ is methyl.

Clause 39. A Compound according to any one of the clauses 1-36, wherein $R_x$ is $(C_3$-$C_6)$cycloalkyl.

Clause 40. A Compound according to any one of the preceding clauses, wherein $R_a$ and $R_b$ are independently selected from the group consisting of hydrogen and $(C_1$-$C_4)$ alkyl.

Clause 41. A Compound according to clause 40, wherein $R_a$ and $R_b$ are independently selected from the group consisting of hydrogen and methyl.

Clause 42. A Compound according to clause 40, wherein $R_a$ and $R_b$ are both $(C_1$-$C_4)$alkyl.

Clause 43. A Compound according to clause 42, wherein $R_a$ and $R_b$ are both methyl.

Clause 44. A Compound according to any one of the clauses 1-3 wherein all of $R_1$, $R_2$, $R_3$, $R_4$ are hydrogen, n is 1, $R_5$ is selected from the group consisting of $(C_1$-$C_6)$alkyl, $(C_3$-$C_7)$cycloalkyl, and aryl, wherein said aryl is optionally substituted with one or more substituents selected from $R_6$; $R_6$ consists of halogen, cyano, $(C_1$-$C_4)$alkyl, halo$(C_1$-$C_4)$ alkyl, —S(O)$_2R_x$, —S(O)$_2NR_aR_b$, —C(O)$R_x$ and —$OR_x$; $R_x$ consist of $(C_1$-$C_6)$alkyl, $(C_3$-$C_6)$cycloalkyl; $R_a$ and $R_b$ are independently selected from the group consisting of hydrogen, and $(C_1$-$C_4)$alkyl, or $R_a$ and $R_b$ may together with the nitrogen atom to which they are attached form a 4-6 membered heterocycloalkyl, wherein said heterocycloalkyl is optionally substituted with one or more $(C_1$-$C_4)$alkyl or —C(O)$R_x$.

Clause 45. A Compound according to clause 44 wherein all of $R_1$, $R_2$, $R_3$, $R_4$ are hydrogen, n is 1, $R_5$ is phenyl, optionally substituted with one or more substituents selected from $R_6$; $R_6$ consists of halogen, cyano, $(C_1$-$C_4)$alkyl, halo $(C_1$-$C_4)$alkyl, —S(O)$_2R_x$, —S(O)$_2NR_aR_b$, —C(O)$R_x$, and —$OR_x$; $R_x$ consist of $(C_1$-$C_6)$alkyl, $(C_3$-$C_6)$cycloalkyl; $R_a$ and $R_b$ are independently selected from the group consisting of hydrogen, and $(C_1$-$C_4)$alkyl, or $R_a$ and $R_b$ may together with the nitrogen atom to which they are attached form a 4-6 membered heterocycloalkyl, wherein said heterocycloalkyl is optionally substituted with one or more $(C_1$-$C_4)$alkyl or —C(O)$R_x$.

Clause 46. A Compound according to any one of the clauses 1-5 wherein all of $R_1$, $R_2$, $R_3$, $R_4$ are hydrogen, n is 1, $R_5$ is phenyl, optionally substituted with one or two of $R_6$ which is selected from the group consisting of halogen, cyano, hydroxyl, $(C_1$-$C_4)$alkyl, halo$(C_1$-$C_4)$alkyl and $(C_1$-$C_4)$alkyloxy.

Clause 47. A Compound according to clause 46 wherein all of $R_1$, $R_2$, $R_3$, $R_4$ are hydrogen, n is 1, $R_5$ is phenyl, $R_6$ is —S(O)$_2R_x$, and $R_x$ is $(C_1$-$C_4)$alkyl.

Clause 48. A Compound according to clause 46 wherein all of $R_1$, $R_2$, $R_3$, $R_4$ are hydrogen, n is 1, $R_5$ is phenyl, $R_6$ is —S(O)$_2NR_aR_b$, and $R_a$ and $R_b$ are independently selected from the group consisting of hydrogen and $(C_1$-$C_4)$alkyl.

Clause 49. A Compound according to any one of the clauses 1-3 wherein all of $R_1$, $R_2$, $R_3$, $R_4$ are hydrogen, n is 1, $R_5$ is phenyl substituted with C(O)$NR_aR_b$; $R_x$ and $R_b$ are independently selected from the group consisting of hydrogen and $(C_1$-$C_4)$alkyl, or $R_a$ and $R_b$ may together with the nitrogen atom to which they are attached form a 4-6 membered heterocycloalkyl, wherein said heterocycloalkyl is optionally substituted with one or more $(C_1$-$C_4)$alkyl or —C(O)$R_x$; $R_x$ is $(C_1$-$C_6)$alkyl.

Clause 50. A Compound according to any one of the clauses 1-3 wherein all of $R_1$, $R_2$, $R_3$, $R_4$ are hydrogen, n is 2, $R_5$ is selected from the group consisting of $(C_1$-$C_6)$alkyl, $(C_3$-$C_7)$cycloalkyl, and aryl, wherein said aryl is optionally substituted with one or more substituents selected from $R_6$; $R_6$ consists of halogen, $(C_1$-$C_4)$alkyl, —S(O)$_2R_x$, —S(O)$_2$NR$_a$R$_b$, C(O)NR$_a$R$_b$, —C(O)R$_x$ and —OR$_x$; R$_x$ consist is (C$_1$-C$_6$)alkyl; R$_x$ and R$_b$ are independently selected from the group consisting of hydrogen, (C$_1$-C$_4$)alkyl, or R$_a$ and R$_b$ may together with the nitrogen atom to which they are attached form a 4-6 membered heterocycloalkyl.

Clause 51. A Compound according to any one of the clauses 1-3 wherein R$_1$, R$_2$, R$_3$ hydrogen, n is 0, R$_5$ is selected from the group consisting of (C$_3$-C$_7$)cycloalkyl, and phenyl, wherein said phenyl is optionally substituted with one or more substituents selected from R$_6$; R$_6$ consists of (C$_1$-C$_4$)alkyl, —S(O)$_2$R$_x$; R$_x$ is (C$_1$-C$_6$)alkyl.

Clause 52. A Compound according to any one of the clauses 1-3 wherein R$_1$ and R$_4$ are both hydrogen, one of R$_2$ and R$_3$ is hydrogen and the other one of R$_2$ and R$_3$ is (C$_1$-C$_4$)alkyl, n is 1; R$_5$ is selected from the group consisting of (C$_1$-C$_6$)alkyl, (C$_3$-C$_7$)cycloalkyl, and aryl, wherein said aryl is optionally substituted with one or more substituents selected from R$_6$, and wherein said (C$_1$-C$_6$)alkyl, and (C$_3$-C$_7$) are optionally substituted with one or more substituents selected from R$_7$; R$_6$ consists of halogen, (C$_1$-C$_4$)alkyl, —S(O)$_2$R$_x$, —S(O)$_2$NR$_a$R$_b$, —C(O)R$_x$ and —OR$_x$; R$_7$ consists of hydroxyl, —OR$_x$, —SR$_x$, —S(O)$_2$R$_x$; R$_x$ consist of (C$_1$-C$_6$)alkyl, (C$_3$-C$_6$)cyclo-alkyl; R$_x$ and R$_b$ are independently selected from the group consisting of hydrogen, (C$_1$-C$_4$)alkyl, or R$_a$ and R$_b$ may together with the nitrogen atom to which they are attached form a 4-6 membered heterocycloalkyl, wherein said heterocycloalkyl is optionally substituted with one or more (C$_1$-C$_4$)alkyl or —C(O)R$_x$.

Clause 53. A Compound according to clause 52 wherein R$_1$ and R$_4$ are both hydrogen, one of R$_2$ and R$_3$ is hydrogen and the other one of R$_2$ and R$_3$ is (C$_1$-C$_4$)alkyl, n is 1; R$_5$ is phenyl which is optionally substituted with one or more substituents selected from halogen, (C$_1$-C$_4$)alkyl, —S(O)$_2$R$_x$, —S(O)$_2$NR$_a$R$_b$, —C(O)R$_x$ and —OR$_x$; R$_x$ consist of (C$_1$-C$_6$)alkyl, (C$_3$-C$_6$)cycloalkyl; R$_a$ and R$_b$ are independently selected from the group consisting of hydrogen, (C$_1$-C$_4$)alkyl, or R$_a$ and R$_b$ may together with the nitrogen atom to which they are attached form a 4-6 membered heterocycloalkyl, wherein said heterocycloalkyl is optionally substituted with one or more (C$_1$-C$_4$)alkyl or —C(O)R$_x$.

Clause 54. A Compound according to any one of the clauses 1-3 wherein R$_1$ and R$_4$ are both hydrogen, one of R$_2$ and R$_3$ is hydrogen and the other one of R$_2$ and R$_3$ is (C$_1$-C$_4$)alkyl, n is 1; R$_5$ is phenyl substituted with C(O)NR$_a$R$_b$; R$_a$ and R$_b$ are independently selected from the group consisting of hydrogen and (C$_1$-C$_4$)alkyl, or R$_a$ and R$_b$ may together with the nitrogen atom to which they are attached form a 4-6 membered heterocycloalkyl, wherein said heterocycloalkyl is optionally substituted with one or more (C$_1$-C$_4$)alkyl or —C(O)R$_x$; R$_x$ is (C$_1$-C$_6$)alkyl.

Clause 55. A Compound according to any one of the clauses 1-3 wherein R$_1$ and R$_4$ are both hydrogen, R$_2$ and R$_3$ are both (C$_1$-C$_4$)alkyl, n is 1; R$_5$ is selected from the group consisting of (C$_1$-C$_6$)alkyl, (C$_3$-C$_7$)cycloalkyl, and aryl, wherein said aryl is optionally substituted with one or more substituents selected from R$_6$, and wherein said (C$_1$-C$_6$)alkyl, and (C$_3$-C$_7$) are optionally substituted with one or more substituents selected from R$_7$; R$_6$ consists of halogen, (C$_1$-C$_4$)alkyl, —S(O)$_2$R$_x$, —S(O)$_2$NR$_a$R$_b$, —C(O)R$_x$ and —OR$_x$; R$_7$ consists of hydroxyl, —OR$_x$, —S(O)$_2$R$_x$; R$_x$ consist of (C$_1$-C$_6$)alkyl, (C$_3$-C$_6$)cycloalkyl; R$_a$ and R$_b$ are independently selected from the group consisting of hydrogen, (C$_1$-C$_4$)alkyl and phenyl(C$_1$-C$_4$)alkyl, or R$_a$ and R$_b$ may together with the nitrogen atom to which they are attached form a 4-6 membered heterocycloalkyl, wherein said heterocycloalkyl is optionally substituted with one or more (C$_1$-C$_4$)alkyl or —C(O)R$_x$.

Clause 56. A Compound according to clause 55 wherein R$_1$ and R$_4$ are both hydrogen, R$_2$ and R$_3$ are both (C$_1$-C$_4$)alkyl, n is 1; R$_5$ is phenyl which is optionally substituted with one or more of halogen, (C$_1$-C$_4$)alkyl, —S(O)$_2$R$_x$, —S(O)$_2$NR$_a$R$_b$, —C(O)R$_x$ and —OR$_x$; R$_7$ consists of hydroxyl, —OR$_x$, —SR$_x$, —S(O)$_2$R$_x$; R$_x$ consist of (C$_1$-C$_6$)alkyl, (C$_3$-C$_6$)cyclo-alkyl; R$_a$ and R$_b$ are independently selected from the group consisting of hydrogen, (C$_1$-C$_4$)alkyl and phenyl(C$_1$-C$_4$)alkyl, or R$_a$ and R$_b$ may together with the nitrogen atom to which they are attached form a 4-6 membered heterocycloalkyl, wherein said heterocycloalkyl is optionally substituted with one or more (C$_1$-C$_4$)alkyl or —C(O)R$_x$.

Clause 57. A Compound according to any one of the clauses 1-3 wherein R$_1$ and R$_4$ are both hydrogen, R$_2$ and R$_3$ are both (C$_1$-C$_4$)alkyl, n is 1; R$_5$ is phenyl substituted with C(O)NR$_a$R$_b$; R$_a$ and R$_b$ are independently selected from the group consisting of hydrogen and (C$_1$-C$_4$)alkyl, or R$_a$ and R$_b$ may together with the nitrogen atom to which they are attached form a 4-6 membered heterocycloalkyl, wherein said heterocycloalkyl is optionally substituted with one or more (C$_1$-C$_4$)alkyl or —C(O)R$_x$; R$_x$ is (C$_1$-C$_6$)alkyl.

Clause 58. A compound according to any one of the clauses 1-3 wherein all of R$_1$, R$_2$, R$_3$, R$_4$ are hydrogen, n is 1, Q is —O—C(O)—R$_5$; wherein R$_5$ is selected from the group consisting of a (5-6) membered heteroaryl, and a (4-6) membered heterocycloalkyl, wherein said heteroaryl is optionally substituted with one or more substituents independently selected from R$_6$, and wherein said heterocycloalkyl is optionally substituted with one or more substituents independently selected from R$_7$; R$_6$ consists of cyano, (C$_1$-C$_4$)alkyl, —C(O)NR$_a$R$_b$, —C(O)OR$_a$, —C(O)R$_x$; R$_7$ consists of (C$_1$-C$_4$)alkyl, —C(O)NR$_a$R$_b$, —C(O)OR$_a$, —C(O)R$_x$; R$_a$, R$_b$ are independently selected from hydrogen and (C$_1$-C$_4$)alkyl.

Clause 59. A compound according to any one of the clauses 1-3 wherein all of R$_1$, R$_2$, R$_3$, R$_4$ are hydrogen, n is 2, Q is —O—C(O)—R$_5$; wherein R$_5$ is selected from the group consisting of a (5-6) membered heteroaryl, and a (4-6) membered heterocycloalkyl, wherein said heteroaryl is optionally substituted with one or more substituents independently selected from R$_6$, and wherein said heterocycloalkyl is optionally substituted with one or more substituents independently selected from R$_7$; R$_6$ consists of (C$_1$-C$_4$)alkyl, —C(O)R$_a$, R$_7$ consists of (C$_1$-C$_4$)alkyl, —C(O)R$_a$; R$_a$ is (C$_1$-C$_4$)alkyl.

Clause 60. A compound according to any one of the clauses 1-3 wherein all of R$_1$, R$_2$, R$_3$ are hydrogen, n is 0, Q is selected from the group consisting of —O—C(O)—R$_5$, wherein R$_5$ is selected from the group consisting of a (5-6) membered heteroaryl and a (4-6) membered heterocycloalkyl.

Clause 61. A compound according to any one of the clauses 1-3 wherein R$_1$ and R$_4$ are both hydrogen, one of R$_2$ and R$_3$ is hydrogen and the other one of R$_2$ and R$_3$ is (C$_1$-C$_4$)alkyl; n is 1, Q is —O—C(O)—R$_5$, wherein R$_5$ is selected from the group consisting of a (5-6) membered heteroaryl and a (4-6) membered heterocycloalkyl, wherein said heteroaryl is optionally substituted with one or more substituents independently selected from R$_6$, and wherein said heterocycloalkyl is optionally substituted with one or more substituents independently selected from R$_7$; R$_6$ consists of (C$_1$-C$_4$)alkyl, —C(O)NR$_a$R$_b$, —C(O)OR$_a$, —C(O)

$R_x$; $R_7$ consists of $(C_1-C_4)$alkyl, —C(O)NR$_a$R$_b$, —C(O)R$_a$, —C(O)R$_x$, R$_a$, R$_b$ are independently selected from hydrogen and $(C_1-C_4)$alkyl.

Clause 62. A compound according to any one of the clauses 1-3 wherein $R_1$ and $R_4$ are both hydrogen, $R_2$ and $R_3$ are both $(C_1-C_4)$alkyl; n is 1, Q is —O—C(O)—R$_6$, wherein $R_5$ is selected from the group consisting of a (5-6) membered heteroaryl and a (4-6) membered heterocycloalkyl, wherein said heteroaryl is optionally substituted with one or more substituents independently selected from $R_6$, and wherein said heterocycloalkyl is optionally substituted with one or more substituents independently selected from $R_7$; $R_6$ consists of $(C_1-C_4)$alkyl, —C(O)NR$_a$R$_b$, —C(O)OR$_a$, —C(O)R$_x$; $R_7$ consists of $(C_1-C_4)$alkyl, —C(O)NR$_a$R$_b$, —C(O)OR$_a$, —C(O)R$_x$; R$_a$, R$_b$ are independently selected from hydrogen and $(C_1-C_4)$alkyl.

Clause 63. A Compound according to any one of the clauses 1-62 selected from the group consisting of 3-(1-Ethyl-8-oxo-spiro[6,7-dihydro-4H-pyrazolo[3,4-c]azepine-5,4'-tetrahydropyran]-3-yl)propyl 4-(methylsulfamoyl)benzoate (Compound 101), 3-(1-Ethyl-8-oxo-spiro[6,7-dihydro-4H-pyrazolo[3,4-c]azepine-5,4'-tetrahydropyran]-3-yl)propyl 4-(dimethylsulfamoyl)benzoate (Compound 102), 3-(1-Ethyl-8-oxo-spiro[6,7-dihydro-4H-pyrazolo[3,4-c]azepine-5,4'-tetrahydropyran]-3-yl)propyl 4-methylsulfonylbenzoate (Compound 103); or pharmaceutically acceptable salts, hydrates or solvates thereof.

Clause 64. A Compound which is 3-(1-Ethyl-8-oxo-spiro[6,7-dihydro-4H-pyrazolo[3,4-c]azepine-5,4'-tetrahydropyran]-3-yl)propyl 4-(methylsulfamoyl)benzoate (Compound 101), or a pharmaceutically acceptable salt, hydrate or solvate thereof.

Clause 65. A Compound which is 3-(1-Ethyl-8-oxo-spiro[6,7-dihydro-4H-pyrazolo[3,4-c]azepine-5,4'-tetrahydropyran]-3-yl)propyl 4-(dimethylsulfamoyl)benzoate (Compound 102), or a pharmaceutically acceptable salt, hydrate or solvate thereof.

Clause 66. A Compound which is 3-(1-Ethyl-8-oxo-spiro[6,7-dihydro-4H-pyrazolo[3,4-c]azepine-5,4'-tetrahydropyran]-3-yl)propyl 4-methylsulfonylbenzoate (Compound 103); or a pharmaceutically acceptable salt, hydrate or solvate thereof.

Clause 67. A Compound according to any one of the clauses 1-62 selected from the group consisting of 3-(1-ethyl-8-oxo-spiro[6,7-dihydro-4H-pyrazolo[3,4-c]azepine-5,4'-tetrahydropyran]-3-yl)propyl 2-methylpropanoate 3-(1-ethyl-8-oxo-spiro[6,7-dihydro-4H-pyrazolo[3,4-c]azepine-5,4'-tetrahydropyran]-3-yl)propyl cyclopentanecarboxylate 3-(1-ethyl-8-oxo-spiro[6,7-dihydro-4H-pyrazolo[3,4-c]azepine-5,4'-tetrahydropyran]-3-yl)propyl 2-ethylbutanoate 3-(1-ethyl-8-oxo-spiro[6,7-dihydro-4H-pyrazolo[3,4-c]azepine-5,4'-tetrahydropyran]-3-yl)propyl benzoate 3-(1-ethyl-8-oxo-spiro[6,7-dihydro-4H-pyrazolo[3,4-c]azepine-5,4'-tetrahydropyran]-3-yl)propyl 4-methylbenzoate 3-(1-ethyl-8-oxo-spiro[6,7-dihydro-4H-pyrazolo[3,4-c]azepine-5,4'-tetrahydropyran]-3-yl)propyl 3-fluorobenzoate 3-(1-ethyl-8-oxo-spiro[6,7-dihydro-4H-pyrazolo[3,4-c]azepine-5,4'-tetrahydropyran]-3-yl)propyl 4-fluorobenzoate 3-(1-ethyl-8-oxo-spiro[6,7-dihydro-4H-pyrazolo[3,4-c]azepine-5,4'-tetrahydropyran]-3-yl)propyl 3-cyanobenzoate 3-(1-ethyl-8-oxo-spiro[6,7-dihydro-4H-pyrazolo[3,4-c]azepine-5,4'-tetrahydropyran]-3-yl)propyl 4-cyanobenzoate 3-(1-ethyl-8-oxo-spiro[6,7-dihydro-4H-pyrazolo[3,4-c]azepine-5,4'-tetrahydropyran]-3-yl)propyl 3,4-dimethylbenzoate 3-(1-ethyl-8-oxo-spiro[6,7-dihydro-4H-pyrazolo[3,4-c]azepine-5,4'-tetrahydropyran]-3-yl)propyl 2,4-dimethylbenzoate 3-(1-ethyl-8-oxo-spiro[6,7-dihydro-4H-pyrazolo[3,4-c]azepine-5,4'-tetrahydropyran]-3-yl)propyl 4-ethylbenzoate 3-(1-ethyl-8-oxo-spiro[6,7-dihydro-4H-pyrazolo[3,4-c]azepine-5,4'-tetrahydropyran]-3-yl)propyl 4-methoxybenzoate 3-(1-ethyl-8-oxo-spiro[6,7-dihydro-4H-pyrazolo[3,4-c]azepine-5,4'-tetrahydropyran]-3-yl)propyl 3-methoxybenzoate 3-(1-ethyl-8-oxo-spiro[6,7-dihydro-4H-pyrazolo[3,4-c]azepine-5,4'-tetrahydropyran]-3-yl)propyl 2-fluoro-4-methyl-benzoate 3-(1-ethyl-8-oxo-spiro[6,7-dihydro-4H-pyrazolo[3,4-c]azepine-5,4'-tetrahydropyran]-3-yl)propyl 4-fluoro-2-methyl-benzoate 3-(1-ethyl-8-oxo-spiro[6,7-dihydro-4H-pyrazolo[3,4-c]azepine-5,4'-tetrahydropyran]-3-yl)propyl 5-fluoro-2-methyl-benzoate 3-(1-ethyl-8-oxo-spiro[6,7-dihydro-4H-pyrazolo[3,4-c]azepine-5,4'-tetrahydropyran]-3-yl)propyl 3-fluoro-2-methyl-benzoate 3-(1-ethyl-8-oxo-spiro[6,7-dihydro-4H-pyrazolo[3,4-c]azepine-5,4'-tetrahydropyran]-3-yl)propyl 4-chlorobenzoate 3-(1-ethyl-8-oxo-spiro[6,7-dihydro-4H-pyrazolo[3,4-c]azepine-5,4'-tetrahydropyran]-3-yl)propyl 3,4-difluorobenzoate 3-(1-ethyl-8-oxo-spiro[6,7-dihydro-4H-pyrazolo[3,4-c]azepine-5,4'-tetrahydropyran]-3-yl)propyl 2,3-difluorobenzoate 3-(1-ethyl-8-oxo-spiro[6,7-dihydro-4H-pyrazolo[3,4-c]azepine-5,4'-tetrahydropyran]-3-yl)propyl 2,5-difluorobenzoate 3-(1-ethyl-8-oxo-spiro[6,7-dihydro-4H-pyrazolo[3,4-c]azepine-5,4'-tetrahydropyran]-3-yl)propyl 2,6-difluorobenzoate 3-(1-ethyl-8-oxo-spiro[6,7-dihydro-4H-pyrazolo[3,4-c]azepine-5,4'-tetrahydropyran]-3-yl)propyl 4-acetylbenzoate 3-(1-ethyl-8-oxo-spiro[6,7-dihydro-4H-pyrazolo[3,4-c]azepine-5,4'-tetrahydropyran]-3-yl)propyl 3-acetylbenzoate 3-(1-ethyl-8-oxo-spiro[6,7-dihydro-4H-pyrazolo[3,4-c]azepine-5,4'-tetrahydropyran]-3-yl)propyl 3-cyano-5-fluoro-benzoate 3-(1-ethyl-8-oxo-spiro[6,7-dihydro-4H-pyrazolo[3,4-c]azepine-5,4'-tetrahydropyran]-3-yl)propyl 3-cyano-4-fluoro-benzoate 3-(1-ethyl-8-oxo-spiro[6,7-dihydro-4H-pyrazolo[3,4-c]azepine-5,4'-tetrahydropyran]-3-yl)propyl 5-cyano-2-fluoro-benzoate 3-(1-ethyl-8-oxo-spiro[6,7-dihydro-4H-pyrazolo[3,4-c]azepine-5,4'-tetrahydropyran]-3-yl)propyl 4-cyano-3-fluoro-benzoate 3-(1-ethyl-8-oxo-spiro[6,7-dihydro-4H-pyrazolo[3,4-c]azepine-5,4'-tetrahydropyran]-3-yl)propyl 4-methoxy-3-methyl-benzoate 3-(1-ethyl-8-oxo-spiro[6,7-dihydro-4H-pyrazolo[3,4-c]azepine-5,4'-tetrahydropyran]-3-yl)propyl 2-methoxy-4-methyl-benzoate 3-(1-ethyl-8-oxo-spiro[6,7-dihydro-4H-pyrazolo[3,4-c]azepine-5,4'-tetrahydropyran]-3-yl)propyl 3-fluoro-4-methoxy-benzoate 3-(1-ethyl-8-oxo-spiro[6,7-dihydro-4H-pyrazolo[3,4-c]azepine-5,4'-tetrahydropyran]-3-yl)propyl 4-fluoro-3-methoxy-benzoate 3-(1-ethyl-8-oxo-spiro[6,7-dihydro-4H-pyrazolo[3,4-c]azepine-5,4'-tetrahydropyran]-3-yl)propyl 2-fluoro-5-methoxy-benzoate 3-(1-ethyl-8-oxo-spiro[6,7-dihydro-4H-pyrazolo[3,4-c]azepine-5,4'-tetrahydropyran]-3-yl)propyl 2-fluoro-4-methoxy-benzoate 3-(1-ethyl-8-oxo-spiro[6,7-dihydro-4H-pyrazolo[3,4-c]azepine-5,4'-tetrahydropyran]-3-yl)propyl 2-fluoro-3-methoxy-benzoate 3-(1-ethyl-8-oxo-spiro[6,7-dihydro-4H-pyrazolo[3,4-c]azepine-5,4'-tetrahydropyran]-3-yl)propyl 4-fluoro-2-methoxy-benzoate 3-(1-ethyl-8-oxo-spiro[6,7-dihydro-4H-pyrazolo[3,4-c]azepine-5,4'-tetrahydropyran]-3-yl)propyl 2-fluoro-6-methoxy-benzoate 3-(1-ethyl-8-oxo-spiro[6,7-dihydro-4H-pyrazolo[3,4-c]azepine-5,4'-tetrahydropyran]-3-yl)propyl 2-chloro-4-methyl-benzoate 3-(1-ethyl-8-oxo-spiro[6,7-dihydro-4H-pyrazolo[3,4-c]azepine-5,4'-tetrahydropyran]-3-yl)propyl 4-chloro-2-methyl-benzoate 3-(1-ethyl-8-oxo-spiro[6,7-dihydro-4H-pyrazolo[3,4-c]azepine-5,4'-tetrahydropyran]-3-yl)propyl 5-chloro-2-methyl-benzoate 3-(1-ethyl-8-oxo-spiro[6,7-dihydro-4H-pyrazolo[3,4-c]azepine-5,4'-tetrahydropyran]-3-yl)propyl 4-(difluoromethyl)benzoate 3-(1-ethyl-8-oxo-spiro[6,7-dihydro-4H-pyrazolo[3,4-c]azepine-5,4'-tetrahydropyran]-3-yl)propyl 2-chloro-5-fluoro-benzoate 3-(1-ethyl-8-oxo-spiro[6,7-dihydro-4H-pyrazolo[3,4-c]azepine-5,4'-tetrahydropyran]-3-yl)propyl 3-chloro-5-fluoro-benzoate 3-(1-ethyl-8-oxo-spiro[6,7-dihydro-4H-pyrazolo[3,4-c]azepine-5,4'-tetrahydropyran]-3-yl)propyl 4-chloro-3-fluoro-benzoate 3-(1-ethyl-8-oxo-spiro[6,7-dihydro-4H-pyrazolo[3,4-c]azepine-5,4'-tetrahydropyran]-3-yl)propyl 2-chloro-3-fluoro-benzoate 3-(1-ethyl-8-oxo-spiro[6,7-dihydro-4H-pyrazolo[3,4-c]azepine-5,4'-tetrahydropyran]-3-yl)propyl 3-chloro-2-fluoro-benzoate 3-(1-ethyl-8-oxo-spiro[6,7-dihydro-4H-pyrazolo[3,4-c]azepine-5,4'-tetrahydropyran]-3-yl)propyl 5-chloro-2-fluoro-benzoate 3-(1-ethyl-8-oxo-spiro[6,7-dihydro-4H-pyrazolo[3,4-c]azepine-5,4'-tetrahydropyran]-3-yl)propyl 2-chloro-6-fluoro-benzoate 3-(1-ethyl-8-oxo-spiro[6,7-dihydro-4H-pyrazolo[3,4-c]azepine-5,4'-tetrahydropyran]-3-yl)propyl 4-chloro-2-fluoro-benzoate 3-(1-ethyl-8-oxo-spiro[6,7-dihydro-4H-pyrazolo[3,4-c]azepine-5,4'-tetrahydropyran]-3-yl)propyl 3-chloro-4-fluoro-benzoate 3-(1-ethyl-8-oxo-spiro[6,7-dihydro-4H-pyrazolo[3,4-c]azepine-5,4'-tetrahydropyran]-3-yl)propyl 4-chloro-3-methoxy-benzoate 3-(1-ethyl-8-oxo-spiro[6,7-dihydro-4H-pyrazolo[3,4-c]azepine-5,4'-tetrahydropyran]-3-yl)propyl 2-chloro-5-methoxy-benzoate 3-(1-ethyl-8-oxo-spiro[6,7-dihydro-4H-pyrazolo[3,4-c]azepine-5,4'-tetrahydropyran]-3-yl)propyl 2-chloro-3-methoxy-benzoate 3-(1-ethyl-8-oxo-spiro[6,7-dihydro-4H-pyrazolo[3,4-c]azepine-5,4'-tetrahydropyran]-3-yl)propyl 3-chloro-4-methoxy-benzoate 3-(1-ethyl-8-oxo-spiro[6,7-dihydro-4H-pyrazolo[3,4-c]azepine-5,4'-tetrahydropyran]-3-yl)propyl 3-chloro-2-methoxy-benzoate 3-(1-ethyl-8-oxo-spiro[6,7-dihydro-4H-pyrazolo[3,4-c]azepine-5,4'-tetrahydropyran]-3-yl)propyl 5-chloro-2-methoxy-benzoate 3-(1-ethyl-8-oxo-spiro[6,7-dihydro-4H-pyrazolo[3,4-c]azepine-5,4'-tetrahydropyran]-3-yl)propyl 4-chloro-2-methoxy-benzoate 3-(1-ethyl-8-oxo-spiro[6,7-dihydro-4H-pyrazolo[3,4-c]azepine-5,4'-tetrahydropyran]-3-yl)propyl 4-(trifluoromethyl)benzoate 3-(1-ethyl-8-oxo-spiro[6,7-dihydro-4H-pyrazolo[3,4-c]azepine-5,4'-tetrahydropyran]-3-yl)propyl 3-methylsulfonylbenzoate 3-(1-ethyl-8-oxo-spiro[6,7-dihydro-4H-pyrazolo[3,4-c]azepine-5,4'-tetrahydropyran]-3-yl)propyl 2-methylsulfonylbenzoate 3-(1-ethyl-8-oxo-spiro[6,7-dihydro-4H-pyrazolo[3,4-c]azepine-5,4'-tetrahydropyran]-3-yl)propyl 4-sulfamoyl-benzoate 3-(1-ethyl-8-oxo-spiro[6,7-dihydro-4H-pyrazolo[3,4-c]azepine-5,4'-tetrahydropyran]-3-yl)propyl 3-sulfamoyl-benzoate 3-(1-ethyl-8-oxo-spiro[6,7-dihydro-4H-pyrazolo[3,4-c]azepine-5,4'-tetrahydropyran]-3-yl)propyl 2-methyl-5-(trifluoromethyl)benzoate 3-(1-ethyl-8-oxo-spiro[6,7-dihydro-4H-pyrazolo[3,4-c]azepine-5,4'-tetrahydropyran]-3-yl)propyl 2-methyl-3-(trifluoromethyl)benzoate 3-(1-ethyl-8-oxo-spiro[6,7-dihydro-4H-pyrazolo[3,4-c]azepine-5,4'-tetrahydropyran]-3-yl)propyl 4-fluoro-3-(trifluoromethyl)benzoate 3-(1-ethyl-8-oxo-spiro[6,7-dihydro-4H-pyrazolo[3,4-c]azepine-5,4'-tetrahydropyran]-3-yl)propyl 2-fluoro-4-(trifluoromethyl)benzoate 3-(1-ethyl-8-oxo-spiro[6,7-dihydro-4H-pyrazolo[3,4-c]azepine-5,4'-tetrahydropyran]-3-yl)propyl 4-fluoro-2-(trifluoromethyl)benzoate 3-(1-ethyl-8-oxo-spiro[6,7-dihydro-4H-pyrazolo[3,4-c]azepine-5,4'-tetrahydropyran]-3-yl)propyl 3-fluoro-5-(trifluoromethyl)benzoate 3-(1-ethyl-8-oxo-spiro[6,7-dihydro-4H-pyrazolo[3,4-c]azepine-5,4'-tetrahydropyran]-3-yl)propyl 2-fluoro-5-(trifluoromethyl)benzoate 3-(1-ethyl-8-oxo-spiro[6,7-dihydro-4H-pyrazolo[3,4-c]azepine-5,4'-tetrahydropyran]-3-yl)propyl 5-fluoro-2-(trifluoromethyl)benzoate 3-(1-ethyl-8-oxo-spiro[6,7-dihydro-4H-pyrazolo[3,4-c]azepine-5,4'-tetrahydropyran]-3-yl)propyl 3-fluoro-4-(trifluoromethyl)benzoate 3-(1-ethyl-8-oxo-spiro[6,7-dihydro-4H-pyrazolo[3,4-c]
   azepine-5,4'-tetrahydropyran]-3-yl)propyl 3-ethylsulfonylbenzoate
3-(1-ethyl-8-oxo-spiro[6,7-dihydro-4H-pyrazolo[3,4-c]
   azepine-5,4'-tetrahydropyran]-3-yl)propyl 4-ethylsulfonylbenzoate
3-(1-ethyl-8-oxo-spiro[6,7-dihydro-4H-pyrazolo[3,4-c]
   azepine-5,4'-tetrahydropyran]-3-yl)propyl 3-(methylsulfamoyl)benzoate
3-(1-ethyl-8-oxo-spiro[6,7-dihydro-4H-pyrazolo[3,4-c]
   azepine-5,4'-tetrahydropyran]-3-yl)propyl 4-methoxy-3-(trifluoromethyl)benzoate
3-(1-ethyl-8-oxo-spiro[6,7-dihydro-4H-pyrazolo[3,4-c]
   azepine-5,4'-tetrahydropyran]-3-yl)propyl 5-methoxy-2-(trifluoromethyl)benzoate
3-(1-ethyl-8-oxo-spiro[6,7-dihydro-4H-pyrazolo[3,4-c]
   azepine-5,4'-tetrahydropyran]-3-yl)propyl 4-methoxy-2-(trifluoromethyl)benzoate
3-(1-ethyl-8-oxo-spiro[6,7-dihydro-4H-pyrazolo[3,4-c]
   azepine-5,4'-tetrahydropyran]-3-yl)propyl 3-methoxy-5-(trifluoromethyl)benzoate
3-(1-ethyl-8-oxo-spiro[6,7-dihydro-4H-pyrazolo[3,4-c]
   azepine-5,4'-tetrahydropyran]-3-yl)propyl 3-methoxy-4-(trifluoromethyl)benzoate
3-(1-ethyl-8-oxo-spiro[6,7-dihydro-4H-pyrazolo[3,4-c]
   azepine-5,4'-tetrahydropyran]-3-yl)propyl 4-chloro-2-(trifluoromethyl)benzoate
3-(1-ethyl-8-oxo-spiro[6,7-dihydro-4H-pyrazolo[3,4-c]
   azepine-5,4'-tetrahydropyran]-3-yl)propyl 2-chloro-3-(trifluoromethyl)benzoate
3-(1-ethyl-8-oxo-spiro[6,7-dihydro-4H-pyrazolo[3,4-c]
   azepine-5,4'-tetrahydropyran]-3-yl)propyl 3-chloro-4-(trifluoromethyl)benzoate
3-(1-ethyl-8-oxo-spiro[6,7-dihydro-4H-pyrazolo[3,4-c]
   azepine-5,4'-tetrahydropyran]-3-yl)propyl 5-chloro-2-(trifluoromethyl)benzoate
3-(1-ethyl-8-oxo-spiro[6,7-dihydro-4H-pyrazolo[3,4-c]
   azepine-5,4'-tetrahydropyran]-3-yl)propyl 2-chloro-4-(trifluoromethyl)benzoate
3-(1-ethyl-8-oxo-spiro[6,7-dihydro-4H-pyrazolo[3,4-c]
   azepine-5,4'-tetrahydropyran]-3-yl)propyl 4-chloro-3-(trifluoromethyl)benzoate
3-(1-ethyl-8-oxo-spiro[6,7-dihydro-4H-pyrazolo[3,4-c]
   azepine-5,4'-tetrahydropyran]-3-yl)propyl 3-chloro-5-(trifluoromethyl)benzoate
3-(1-ethyl-8-oxo-spiro[6,7-dihydro-4H-pyrazolo[3,4-c]
   azepine-5,4'-tetrahydropyran]-3-yl)propyl 2-chloro-5-(trifluoromethyl)benzoate
3-(1-ethyl-8-oxo-spiro[6,7-dihydro-4H-pyrazolo[3,4-c]
   azepine-5,4'-tetrahydropyran]-3-yl)propyl 3-isopropylsulfonylbenzoate
3-(1-ethyl-8-oxo-spiro[6,7-dihydro-4H-pyrazolo[3,4-c]
   azepine-5,4'-tetrahydropyran]-3-yl)propyl 4-isopropylsulfonylbenzoate
3-(1-ethyl-8-oxo-spiro[6,7-dihydro-4H-pyrazolo[3,4-c]
   azepine-5,4'-tetrahydropyran]-3-yl)propyl 4-cyclopentylsulfonylbenzoate
3-(1-ethyl-8-oxo-spiro[6,7-dihydro-4H-pyrazolo[3,4-c]
   azepine-5,4'-tetrahydropyran]-3-yl)propyl 3-pyrrolidin-1-ylsulfonylbenzoate
3-(1-ethyl-8-oxo-spiro[6,7-dihydro-4H-pyrazolo[3,4-c]
   azepine-5,4'-tetrahydropyran]-3-yl)propyl 4-pyrrolidin-1-ylsulfonylbenzoate
3-(1-ethyl-8-oxo-spiro[6,7-dihydro-4H-pyrazolo[3,4-c]
   azepine-5,4'-tetrahydropyran]-3-yl)propyl 2,4-bis(trifluoromethyl)benzoate
3-(1-ethyl-8-oxo-spiro[6,7-dihydro-4H-pyrazolo[3,4-c]
   azepine-5,4'-tetrahydropyran]-3-yl)propyl 3,4-bis(trifluoromethyl)benzoate
3-(1-ethyl-8-oxo-spiro[6,7-dihydro-4H-pyrazolo[3,4-c]
   azepine-5,4'-tetrahydropyran]-3-yl)propyl 3-morpholinosulfonylbenzoate
3-(1-ethyl-8-oxo-spiro[6,7-dihydro-4H-pyrazolo[3,4-c]
   azepine-5,4'-tetrahydropyran]-3-yl)propyl 4-morpholinosulfonylbenzoate
3-(1-ethyl-8-oxo-spiro[6,7-dihydro-4H-pyrazolo[3,4-c]
   azepine-5,4'-tetrahydropyran]-3-yl)propyl 3-(4-acetylpiperazin-1-yl)sulfonylbenzoate
3-(1-ethyl-8-oxo-spiro[6,7-dihydro-4H-pyrazolo[3,4-c]
   azepine-5,4'-tetrahydropyran]-3-yl)propyl 4-(4-acetylpiperazin-1-yl)sulfonylbenzoate, or
a pharmaceutically acceptable salt, hydrate or solvate thereof.

Clause 68. A Compound according to any one of the clauses 1-62 selected from the group consisting of
3-(1-ethyl-8-oxo-spiro[6,7-dihydro-4H-pyrazolo[3,4-c]
   azepine-5,4'-tetrahydropyran]-3-yl)propyl 4-carbamoylbenzoate
3-(1-ethyl-8-oxo-spiro[6,7-dihydro-4H-pyrazolo[3,4-c]
   azepine-5,4'-tetrahydropyran]-3-yl)propyl 4-(methylcarbamoyl)benzoate
3-(1-ethyl-8-oxo-spiro[6,7-dihydro-4H-pyrazolo[3,4-c]
   azepine-5,4'-tetrahydropyran]-3-yl)propyl 4-(dimethylcarbamoyl)benzoate
3-(1-ethyl-8-oxo-spiro[6,7-dihydro-4H-pyrazolo[3,4-c]
   azepine-5,4'-tetrahydropyran]-3-yl)propyl 4-(pyrrolidine-1-carbonyl)benzoate
3-(1-ethyl-8-oxo-spiro[6,7-dihydro-4H-pyrazolo[3,4-c]
   azepine-5,4'-tetrahydropyran]-3-yl)propyl 4-(piperidine-1-carbonyl)benzoate
3-(1-ethyl-8-oxo-spiro[6,7-dihydro-4H-pyrazolo[3,4-c]
   azepine-5,4'-tetrahydropyran]-3-yl)propyl 4-(morpholine-4-carbonyl)benzoate
3-(1-ethyl-8-oxo-spiro[6,7-dihydro-4H-pyrazolo[3,4-c]
   azepine-5,4'-tetrahydropyran]-3-yl)propyl 4-(4-methylpiperazine-1-carbonyl)benzoate
3-(1-ethyl-8-oxo-spiro[6,7-dihydro-4H-pyrazolo[3,4-c]
   azepine-5,4'-tetrahydropyran]-3-yl)propyl 4-(4-acetylpiperazine-1-carbonyl)benzoate, or
a pharmaceutically acceptable salt, hydrate or solvate thereof.

Clause 69. A Compound according to any one of the clauses 1-62 selected from the group consisting of
3-(1-ethyl-8-oxo-spiro[6,7-dihydro-4H-pyrazolo[3,4-c]
   azepine-5,4'-tetrahydropyran]-3-yl)propyl 3-carbamoylbenzoate
3-(1-ethyl-8-oxo-spiro[6,7-dihydro-4H-pyrazolo[3,4-c]
   azepine-5,4'-tetrahydropyran]-3-yl)propyl 3-(methylcarbamoyl)benzoate
3-(1-ethyl-8-oxo-spiro[6,7-dihydro-4H-pyrazolo[3,4-c]
   azepine-5,4'-tetrahydropyran]-3-yl)propyl 3-(dimethylcarbamoyl)benzoate
3-(1-ethyl-8-oxo-spiro[6,7-dihydro-4H-pyrazolo[3,4-c]
   azepine-5,4'-tetrahydropyran]-3-yl)propyl 3-(pyrrolidine-1-carbonyl)benzoate
3-(1-ethyl-8-oxo-spiro[6,7-dihydro-4H-pyrazolo[3,4-c]
   azepine-5,4'-tetrahydropyran]-3-yl)propyl 3-(piperidine-1-carbonyl)benzoate
3-(1-ethyl-8-oxo-spiro[6,7-dihydro-4H-pyrazolo[3,4-c]
   azepine-5,4'-tetrahydropyran]-3-yl)propyl 3-(morpholine-4-carbonyl)benzoate 3-(1-ethyl-8-oxo-spiro[6,7-dihydro-4H-pyrazolo[3,4-c]
azepine-5,4'-tetrahydropyran]-3-yl)propyl 3-(4-methyl-piperazine-1-carbonyl)benzoate
3-(1-ethyl-8-oxo-spiro[6,7-dihydro-4H-pyrazolo[3,4-c]
azepine-5,4'-tetrahydropyran]-3-yl)propyl 3-(4-acetylpiperazine-1-carbonyl)benzoate, or
a pharmaceutically acceptable salt, hydrate or solvate thereof.

Clause 70. A Compound according to any one of the clauses 1-62 selected from the group consisting of
4-(1-ethyl-8-oxo-spiro[6,7-dihydro-4H-pyrazolo[3,4-c]
azepine-5,4'-tetrahydropyran]-3-yl)butyl 2-methylpropanoate
4-(1-ethyl-8-oxo-spiro[6,7-dihydro-4H-pyrazolo[3,4-c]
azepine-5,4'-tetrahydropyran]-3-yl)butyl cyclopentanecarboxylate
4-(1-ethyl-8-oxo-spiro[6,7-dihydro-4H-pyrazolo[3,4-c]
azepine-5,4'-tetrahydropyran]-3-yl)butyl 4-methylbenzoate
4-(1-ethyl-8-oxo-spiro[6,7-dihydro-4H-pyrazolo[3,4-c]
azepine-5,4'-tetrahydropyran]-3-yl)butyl 4-fluorobenzoate
4-(1-ethyl-8-oxo-spiro[6,7-dihydro-4H-pyrazolo[3,4-c]
azepine-5,4'-tetrahydropyran]-3-yl)butyl 4-methoxybenzoate
4-(1-ethyl-8-oxo-spiro[6,7-dihydro-4H-pyrazolo[3,4-c]
azepine-5,4'-tetrahydropyran]-3-yl)butyl 4-acetylbenzoate
4-(1-ethyl-8-oxo-spiro[6,7-dihydro-4H-pyrazolo[3,4-c]
azepine-5,4'-tetrahydropyran]-3-yl)butyl 4-carbamoylbenzoate
4-(1-ethyl-8-oxo-spiro[6,7-dihydro-4H-pyrazolo[3,4-c]
azepine-5,4'-tetrahydropyran]-3-yl)butyl 4-(methylcarbamoyl)benzoate
4-(1-ethyl-8-oxo-spiro[6,7-dihydro-4H-pyrazolo[3,4-c]
azepine-5,4'-tetrahydropyran]-3-yl)butyl 4-(dimethylcarbamoyl)benzoate
4-(1-ethyl-8-oxo-spiro[6,7-dihydro-4H-pyrazolo[3,4-c]
azepine-5,4'-tetrahydropyran]-3-yl)butyl 4-methylsulfonylbenzoate
4-(1-ethyl-8-oxo-spiro[6,7-dihydro-4H-pyrazolo[3,4-c]
azepine-5,4'-tetrahydropyran]-3-yl)butyl 4-(methylsulfamoyl)benzoate
4-(1-ethyl-8-oxo-spiro[6,7-dihydro-4H-pyrazolo[3,4-c]
azepine-5,4'-tetrahydropyran]-3-yl)butyl 4-(dimethylsulfamoyl)benzoate
4-(1-ethyl-8-oxo-spiro[6,7-dihydro-4H-pyrazolo[3,4-c]
azepine-5,4'-tetrahydropyran]-3-yl)butyl 4-(morpholine-4-carbonyl)benzoate, or
a pharmaceutically acceptable salt, hydrate or solvate thereof.

Clause 71. A Compound according to any one of the clauses 1-62 selected from the group consisting of
2-(1-ethyl-8-oxo-spiro[6,7-dihydro-4H-pyrazolo[3,4-c]
azepine-5,4'-tetrahydropyran]-3-yl)ethyl cyclopentanecarboxylate
2-(1-ethyl-8-oxo-spiro[6,7-dihydro-4H-pyrazolo[3,4-c]
azepine-5,4'-tetrahydropyran]-3-yl)ethyl 4-methylbenzoate
2-(1-ethyl-8-oxo-spiro[6,7-dihydro-4H-pyrazolo[3,4-c]
azepine-5,4'-tetrahydropyran]-3-yl)ethyl 4-methylsulfonylbenzoate, or
a pharmaceutically acceptable salt, hydrate or solvate thereof.

Clause 72. A Compound according to any one of the clauses 1-62 selected from the group consisting of

[(2R)-3-(1-ethyl-8-oxo-spiro[6,7-dihydro-4H-pyrazolo[3,4-c]azepine-5,4'-tetrahydropyran]-3-yl)-2-methyl-propyl]3-methoxypropanoate
[(2R)-3-(1-ethyl-8-oxo-spiro[6,7-dihydro-4H-pyrazolo[3,4-c]azepine-5,4'-tetrahydropyran]-3-yl)-2-methyl-propyl]3-hydroxycyclobutanecarboxylate
[(2R)-3-(1-ethyl-8-oxo-spiro[6,7-dihydro-4H-pyrazolo[3,4-c]azepine-5,4'-tetrahydropyran]-3-yl)-2-methyl-propyl]3-methylsulfanylpropanoate
[(2R)-3-(1-ethyl-8-oxo-spiro[6,7-dihydro-4H-pyrazolo[3,4-c]azepine-5,4'-tetrahydropyran]-3-yl)-2-methyl-propyl]4-methylbenzoate
[(2R)-3-(1-ethyl-8-oxo-spiro[6,7-dihydro-4H-pyrazolo[3,4-c]azepine-5,4'-tetrahydropyran]-3-yl)-2-methyl-propyl]2-methylbenzoate
[(2R)-3-(1-ethyl-8-oxo-spiro[6,7-dihydro-4H-pyrazolo[3,4-c]azepine-5,4'-tetrahydropyran]-3-yl)-2-methyl-propyl]3-methylbenzoate
[(2R)-3-(1-ethyl-8-oxo-spiro[6,7-dihydro-4H-pyrazolo[3,4-c]azepine-5,4'-tetrahydropyran]-3-yl)-2-methyl-propyl]3-fluorobenzoate
[(2R)-3-(1-ethyl-8-oxo-spiro[6,7-dihydro-4H-pyrazolo[3,4-c]azepine-5,4'-tetrahydropyran]-3-yl)-2-methyl-propyl]2-fluorobenzoate
[(2R)-3-(1-ethyl-8-oxo-spiro[6,7-dihydro-4H-pyrazolo[3,4-c]azepine-5,4'-tetrahydropyran]-3-yl)-2-methyl-propyl]4-fluorobenzoate
[(2R)-3-(1-ethyl-8-oxo-spiro[6,7-dihydro-4H-pyrazolo[3,4-c]azepine-5,4'-tetrahydropyran]-3-yl)-2-methyl-propyl]4-hydroxycyclohexanecarboxylate
[(2R)-3-(1-ethyl-8-oxo-spiro[6,7-dihydro-4H-pyrazolo[3,4-c]azepine-5,4'-tetrahydropyran]-3-yl)-2-methyl-propyl]4-hydroxycyclohexanecarboxylate
[(2R)-3-(1-ethyl-8-oxo-spiro[6,7-dihydro-4H-pyrazolo[3,4-c]azepine-5,4'-tetrahydropyran]-3-yl)-2-methyl-propyl]4-ethylbenzoate
[(2R)-3-(1-ethyl-8-oxo-spiro[6,7-dihydro-4H-pyrazolo[3,4-c]azepine-5,4'-tetrahydropyran]-3-yl)-2-methyl-propyl]4-methoxybenzoate
[(2R)-3-(1-ethyl-8-oxo-spiro[6,7-dihydro-4H-pyrazolo[3,4-c]azepine-5,4'-tetrahydropyran]-3-yl)-2-methyl-propyl]3-methoxybenzoate
[(2R)-3-(1-ethyl-8-oxo-spiro[6,7-dihydro-4H-pyrazolo[3,4-c]azepine-5,4'-tetrahydropyran]-3-yl)-2-methyl-propyl]2-methoxybenzoate
[(2R)-3-(1-ethyl-8-oxo-spiro[6,7-dihydro-4H-pyrazolo[3,4-c]azepine-5,4'-tetrahydropyran]-3-yl)-2-methyl-propyl]3-methylsulfonylpropanoate
[(2R)-3-(1-ethyl-8-oxo-spiro[6,7-dihydro-4H-pyrazolo[3,4-c]azepine-5,4'-tetrahydropyran]-3-yl)-2-methyl-propyl]4-acetylbenzoate
[(2R)-3-(1-ethyl-8-oxo-spiro[6,7-dihydro-4H-pyrazolo[3,4-c]azepine-5,4'-tetrahydropyran]-3-yl)-2-methyl-propyl]3-acetylbenzoate
[(2R)-3-(1-ethyl-8-oxo-spiro[6,7-dihydro-4H-pyrazolo[3,4-c]azepine-5,4'-tetrahydropyran]-3-yl)-2-methyl-propyl]4-methylsulfonylbenzoate
[(2R)-3-(1-ethyl-8-oxo-spiro[6,7-dihydro-4H-pyrazolo[3,4-c]azepine-5,4'-tetrahydropyran]-3-yl)-2-methyl-propyl]3-ethylsulfonylbenzoate
[(2R)-3-(1-ethyl-8-oxo-spiro[6,7-dihydro-4H-pyrazolo[3,4-c]azepine-5,4'-tetrahydropyran]-3-yl)-2-methyl-propyl]4-ethylsulfonylbenzoate
[(2R)-3-(1-ethyl-8-oxo-spiro[6,7-dihydro-4H-pyrazolo[3,4-c]azepine-5,4'-tetrahydropyran]-3-yl)-2-methyl-propyl]4-(methylsulfamoyl)benzoate

[(2R)-3-(1-ethyl-8-oxo-spiro[6,7-dihydro-4H-pyrazolo[3,4-c]azepine-5,4'-tetrahydropyran]-3-yl)-2-methyl-propyl]3-isopropylsulfonylbenzoate

[(2R)-3-(1-ethyl-8-oxo-spiro[6,7-dihydro-4H-pyrazolo[3,4-c]azepine-5,4'-tetrahydropyran]-3-yl)-2-methyl-propyl]4-isopropylsulfonylbenzoate

[(2R)-3-(1-ethyl-8-oxo-spiro[6,7-dihydro-4H-pyrazolo[3,4-c]azepine-5,4'-tetrahydropyran]-3-yl)-2-methyl-propyl]4-(dimethylsulfamoyl)benzoate

[(2R)-3-(1-ethyl-8-oxo-spiro[6,7-dihydro-4H-pyrazolo[3,4-c]azepine-5,4'-tetrahydropyran]-3-yl)-2-methyl-propyl]4-cyclopentylsulfonylbenzoate

[(2R)-3-(1-ethyl-8-oxo-spiro[6,7-dihydro-4H-pyrazolo[3,4-c]azepine-5,4'-tetrahydropyran]-3-yl)-2-methyl-propyl]3-pyrrolidin-1-ylsulfonylbenzoate

[(2R)-3-(1-ethyl-8-oxo-spiro[6,7-dihydro-4H-pyrazolo[3,4-c]azepine-5,4'-tetrahydropyran]-3-yl)-2-methyl-propyl]3-morpholinosulfonylbenzoate

[(2R)-3-(1-ethyl-8-oxo-spiro[6,7-dihydro-4H-pyrazolo[3,4-c]azepine-5,4'-tetrahydropyran]-3-yl)-2-methyl-propyl]4-morpholinosulfonylbenzoate

[(2R)-3-(1-ethyl-8-oxo-spiro[6,7-dihydro-4H-pyrazolo[3,4-c]azepine-5,4'-tetrahydropyran]-3-yl)-2-methyl-propyl]3-(4-acetylpiperazin-1-yl)sulfonylbenzoate

[(2R)-3-(1-ethyl-8-oxo-spiro[6,7-dihydro-4H-pyrazolo[3,4-c]azepine-5,4'-tetrahydropyran]-3-yl)-2-methyl-propyl]4-(4-acetylpiperazin-1-yl)sulfonylbenzoate, or a pharmaceutically acceptable salt, hydrate or solvate thereof.

Clause 73. A Compound according to any one of the clauses 1-62 selected from the group consisting of

[(2R)-3-(1-ethyl-8-oxo-spiro[6,7-dihydro-4H-pyrazolo[3,4-c]azepine-5,4'-tetrahydropyran]-3-yl)-2-methyl-propyl]4-carbamoylbenzoate

[(2R)-3-(1-ethyl-8-oxo-spiro[6,7-dihydro-4H-pyrazolo[3,4-c]azepine-5,4'-tetrahydropyran]-3-yl)-2-methyl-propyl]4-(methylcarbamoyl)benzoate

[(2R)-3-(1-ethyl-8-oxo-spiro[6,7-dihydro-4H-pyrazolo[3,4-c]azepine-5,4'-tetrahydropyran]-3-yl)-2-methyl-propyl]4-(dimethylcarbamoyl)benzoate

[(2R)-3-(1-ethyl-8-oxo-spiro[6,7-dihydro-4H-pyrazolo[3,4-c]azepine-5,4'-tetrahydropyran]-3-yl)-2-methyl-propyl]4-(pyrrolidine-1-carbonyl)benzoate

[(2R)-3-(1-ethyl-8-oxo-spiro[6,7-dihydro-4H-pyrazolo[3,4-c]azepine-5,4'-tetrahydropyran]-3-yl)-2-methyl-propyl]4-(piperidine-1-carbonyl)benzoate

[(2R)-3-(1-ethyl-8-oxo-spiro[6,7-dihydro-4H-pyrazolo[3,4-c]azepine-5,4'-tetrahydropyran]-3-yl)-2-methyl-propyl]4-(morpholine-4-carbonyl)benzoate

[(2R)-3-(1-ethyl-8-oxo-spiro[6,7-dihydro-4H-pyrazolo[3,4-c]azepine-5,4'-tetrahydropyran]-3-yl)-2-methyl-propyl]4-(4-methylpiperazine-1-carbonyl)benzoate

[(2R)-3-(1-ethyl-8-oxo-spiro[6,7-dihydro-4H-pyrazolo[3,4-c]azepine-5,4'-tetrahydropyran]-3-yl)-2-methyl-propyl]4-(4-acetylpiperazine-1-carbonyl)benzoate, or a pharmaceutically acceptable salt, hydrate or solvate thereof.

Clause 74. A Compound according to any one of the clauses 1-62 selected from the group consisting of

[(2R)-3-(1-ethyl-8-oxo-spiro[6,7-dihydro-4H-pyrazolo[3,4-c]azepine-5,4'-tetrahydropyran]-3-yl)-2-methyl-propyl]3-carbamoylbenzoate

[(2R)-3-(1-ethyl-8-oxo-spiro[6,7-dihydro-4H-pyrazolo[3,4-c]azepine-5,4'-tetrahydropyran]-3-yl)-2-methyl-propyl]3-(methylcarbamoyl)benzoate

[(2R)-3-(1-ethyl-8-oxo-spiro[6,7-dihydro-4H-pyrazolo[3,4-c]azepine-5,4'-tetrahydropyran]-3-yl)-2-methyl-propyl]3-(dimethylcarbamoyl)benzoate

[(2R)-3-(1-ethyl-8-oxo-spiro[6,7-dihydro-4H-pyrazolo[3,4-c]azepine-5,4'-tetrahydropyran]-3-yl)-2-methyl-propyl]3-(pyrrolidine-1-carbonyl)benzoate

[(2R)-3-(1-ethyl-8-oxo-spiro[6,7-dihydro-4H-pyrazolo[3,4-c]azepine-5,4'-tetrahydropyran]-3-yl)-2-methyl-propyl]3-(piperidine-1-carbonyl)benzoate [(2R)-3-(1-ethyl-8-oxo-spiro[6,7-dihydro-4H-pyrazolo[3,4-c]azepine-5,4'-tetrahydropyran]-3-yl)-2-methyl-propyl]3-(morpholine-4-carbonyl)benzoate

[(2R)-3-(1-ethyl-8-oxo-spiro[6,7-dihydro-4H-pyrazolo[3,4-c]azepine-5,4'-tetrahydropyran]-3-yl)-2-methyl-propyl]3-(4-methylpiperazine-1-carbonyl)benzoate

[(2R)-3-(1-ethyl-8-oxo-spiro[6,7-dihydro-4H-pyrazolo[3,4-c]azepine-5,4'-tetrahydropyran]-3-yl)-2-methyl-propyl]3-(4-acetylpiperazine-1-carbonyl)benzoate, or a pharmaceutically acceptable salt, hydrate or solvate thereof.

Clause 75. A Compound according to any one of the clauses 1-62 selected from the group consisting of

[3-(1-ethyl-8-oxo-spiro[6,7-dihydro-4H-pyrazolo[3,4-c]azepine-5,4'-tetrahydropyran]-3-yl)-2,2-dimethyl-propyl] 3-methoxypropanoate

[3-(1-ethyl-8-oxo-spiro[6,7-dihydro-4H-pyrazolo[3,4-c]azepine-5,4'-tetrahydropyran]-3-yl)-2,2-dimethyl-propyl] 3-methylsulfanylpropanoate

[3-(1-ethyl-8-oxo-spiro[6,7-dihydro-4H-pyrazolo[3,4-c]azepine-5,4'-tetrahydropyran]-3-yl)-2,2-dimethyl-propyl] 4-methylbenzoate

[3-(1-ethyl-8-oxo-spiro[6,7-dihydro-4H-pyrazolo[3,4-c]azepine-5,4'-tetrahydropyran]-3-yl)-2,2-dimethyl-propyl] 2-methylbenzoate

[3-(1-ethyl-8-oxo-spiro[6,7-dihydro-4H-pyrazolo[3,4-c]azepine-5,4'-tetrahydropyran]-3-yl)-2,2-dimethyl-propyl] 3-methylbenzoate

[3-(1-ethyl-8-oxo-spiro[6,7-dihydro-4H-pyrazolo[3,4-c]azepine-5,4'-tetrahydropyran]-3-yl)-2,2-dimethyl-propyl] 3-fluorobenzoate

[3-(1-ethyl-8-oxo-spiro[6,7-dihydro-4H-pyrazolo[3,4-c]azepine-5,4'-tetrahydropyran]-3-yl)-2,2-dimethyl-propyl] 4-fluorobenzoate

[3-(1-ethyl-8-oxo-spiro[6,7-dihydro-4H-pyrazolo[3,4-c]azepine-5,4'-tetrahydropyran]-3-yl)-2,2-dimethyl-propyl] 2-fluorobenzoate

[3-(1-ethyl-8-oxo-spiro[6,7-dihydro-4H-pyrazolo[3,4-c]azepine-5,4'-tetrahydropyran]-3-yl)-2,2-dimethyl-propyl] 4-hydroxycyclohexanecarboxylate

[3-(1-ethyl-8-oxo-spiro[6,7-dihydro-4H-pyrazolo[3,4-c]azepine-5,4'-tetrahydropyran]-3-yl)-2,2-dimethyl-propyl] 4-ethylbenzoate

[3-(1-ethyl-8-oxo-spiro[6,7-dihydro-4H-pyrazolo[3,4-c]azepine-5,4'-tetrahydropyran]-3-yl)-2,2-dimethyl-propyl] 3-methoxybenzoate

[3-(1-ethyl-8-oxo-spiro[6,7-dihydro-4H-pyrazolo[3,4-c]azepine-5,4'-tetrahydropyran]-3-yl)-2,2-dimethyl-propyl] 4-methoxybenzoate

[3-(1-ethyl-8-oxo-spiro[6,7-dihydro-4H-pyrazolo[3,4-c]azepine-5,4'-tetrahydropyran]-3-yl)-2,2-dimethyl-propyl] 2-methoxybenzoate

[3-(1-ethyl-8-oxo-spiro[6,7-dihydro-4H-pyrazolo[3,4-c]azepine-5,4'-tetrahydropyran]-3-yl)-2,2-dimethyl-propyl] 3-methylsulfonylpropanoate

[3-(1-ethyl-8-oxo-spiro[6,7-dihydro-4H-pyrazolo[3,4-c]azepine-5,4'-tetrahydropyran]-3-yl)-2,2-dimethyl-propyl] 4-acetylbenzoate

[3-(1-ethyl-8-oxo-spiro[6,7-dihydro-4H-pyrazolo[3,4-c] azepine-5,4'-tetrahydropyran]-3-yl)-2,2-dimethyl-propyl] 3-acetylbenzoate
[3-(1-ethyl-8-oxo-spiro[6,7-dihydro-4H-pyrazolo[3,4-c] azepine-5,4'-tetrahydropyran]-3-yl)-2,2-dimethyl-propyl] 4-methylsulfonylbenzoate
[3-(1-ethyl-8-oxo-spiro[6,7-dihydro-4H-pyrazolo[3,4-c] azepine-5,4'-tetrahydropyran]-3-yl)-2,2-dimethyl-propyl] 4-ethylsulfonylbenzoate
[3-(1-ethyl-8-oxo-spiro[6,7-dihydro-4H-pyrazolo[3,4-c] azepine-5,4'-tetrahydropyran]-3-yl)-2,2-dimethyl-propyl] 3-ethylsulfonylbenzoate
[3-(1-ethyl-8-oxo-spiro[6,7-dihydro-4H-pyrazolo[3,4-c] azepine-5,4'-tetrahydropyran]-3-yl)-2,2-dimethyl-propyl] 4-(methylsulfamoyl)benzoate
[3-(1-ethyl-8-oxo-spiro[6,7-dihydro-4H-pyrazolo[3,4-c] azepine-5,4'-tetrahydropyran]-3-yl)-2,2-dimethyl-propyl] 3-isopropylsulfonylbenzoate
[3-(1-ethyl-8-oxo-spiro[6,7-dihydro-4H-pyrazolo[3,4-c] azepine-5,4'-tetrahydropyran]-3-yl)-2,2-dimethyl-propyl] 4-isopropylsulfonylbenzoate
[3-(1-ethyl-8-oxo-spiro[6,7-dihydro-4H-pyrazolo[3,4-c] azepine-5,4'-tetrahydropyran]-3-yl)-2,2-dimethyl-propyl] 4-(dimethylsulfamoyl)benzoate
[3-(1-ethyl-8-oxo-spiro[6,7-dihydro-4H-pyrazolo[3,4-c] azepine-5,4'-tetrahydropyran]-3-yl)-2,2-dimethyl-propyl] 4-cyclopentylsulfonylbenzoate
[3-(1-ethyl-8-oxo-spiro[6,7-dihydro-4H-pyrazolo[3,4-c] azepine-5,4'-tetrahydropyran]-3-yl)-2,2-dimethyl-propyl] 3-pyrrolidin-1-ylsulfonylbenzoate
[3-(1-ethyl-8-oxo-spiro[6,7-dihydro-4H-pyrazolo[3,4-c] azepine-5,4'-tetrahydropyran]-3-yl)-2,2-dimethyl-propyl] 4-pyrrolidin-1-ylsulfonylbenzoate
[3-(1-ethyl-8-oxo-spiro[6,7-dihydro-4H-pyrazolo[3,4-c] azepine-5,4'-tetrahydropyran]-3-yl)-2,2-dimethyl-propyl] 3-morpholinosulfonylbenzoate
[3-(1-ethyl-8-oxo-spiro[6,7-dihydro-4H-pyrazolo[3,4-c] azepine-5,4'-tetrahydropyran]-3-yl)-2,2-dimethyl-propyl] 4-morpholinosulfonylbenzoate
[3-(1-ethyl-8-oxo-spiro[6,7-dihydro-4H-pyrazolo[3,4-c] azepine-5,4'-tetrahydropyran]-3-yl)-2,2-dimethyl-propyl] 4-[benzyl(methyl)sulfamoyl]benzoate
[3-(1-ethyl-8-oxo-spiro[6,7-dihydro-4H-pyrazolo[3,4-c] azepine-5,4'-tetrahydropyran]-3-yl)-2,2-dimethyl-propyl] 3-(4-acetylpiperazin-1-yl)sulfonylbenzoate
[3-(1-ethyl-8-oxo-spiro[6,7-dihydro-4H-pyrazolo[3,4-c] azepine-5,4'-tetrahydropyran]-3-yl)-2,2-dimethyl-propyl] 4-(4-acetylpiperazin-1-yl)sulfonylbenzoate, or
a pharmaceutically acceptable salt, hydrate or solvate thereof.

Clause 76. A Compound according to any one of the preceding clauses 1-62 selected from the group consisting of
[3-(1-ethyl-8-oxo-spiro[6,7-dihydro-4H-pyrazolo[3,4-c] azepine-5,4'-tetrahydropyran]-3-yl)-2,2-dimethyl-propyl] 4-carbamoylbenzoate
[3-(1-ethyl-8-oxo-spiro[6,7-dihydro-4H-pyrazolo[3,4-c] azepine-5,4'-tetrahydropyran]-3-yl)-2,2-dimethyl-propyl] 4-(methylcarbamoyl)benzoate
[3-(1-ethyl-8-oxo-spiro[6,7-dihydro-4H-pyrazolo[3,4-c] azepine-5,4'-tetrahydropyran]-3-yl)-2,2-dimethyl-propyl] 4-(dimethylcarbamoyl)benzoate
[3-(1-ethyl-8-oxo-spiro[6,7-dihydro-4H-pyrazolo[3,4-c] azepine-5,4'-tetrahydropyran]-3-yl)-2,2-dimethyl-propyl] 4-(pyrrolidine-1-carbonyl)benzoate
[3-(1-ethyl-8-oxo-spiro[6,7-dihydro-4H-pyrazolo[3,4-c] azepine-5,4'-tetrahydropyran]-3-yl)-2,2-dimethyl-propyl] 4-(piperidine-1-carbonyl)benzoate
[3-(1-ethyl-8-oxo-spiro[6,7-dihydro-4H-pyrazolo[3,4-c] azepine-5,4'-tetrahydropyran]-3-yl)-2,2-dimethyl-propyl] 4-(morpholine-4-carbonyl)benzoate
[3-(1-ethyl-8-oxo-spiro[6,7-dihydro-4H-pyrazolo[3,4-c] azepine-5,4'-tetrahydropyran]-3-yl)-2,2-dimethyl-propyl] 4-(4-methylpiperazine-1-carbonyl)benzoate
[3-(1-ethyl-8-oxo-spiro[6,7-dihydro-4H-pyrazolo[3,4-c] azepine-5,4'-tetrahydropyran]-3-yl)-2,2-dimethyl-propyl] 4-(4-acetylpiperazine-1-carbonyl)benzoate, or
a pharmaceutically acceptable salt, hydrate or solvate thereof.

Clause 77. A Compound according to any one of the clauses 1-62 selected from the group consisting of
[3-(1-ethyl-8-oxo-spiro[6,7-dihydro-4H-pyrazolo[3,4-c] azepine-5,4'-tetrahydropyran]-3-yl)-2,2-dimethyl-propyl] 3-carbamoylbenzoate
[3-(1-ethyl-8-oxo-spiro[6,7-dihydro-4H-pyrazolo[3,4-c] azepine-5,4'-tetrahydropyran]-3-yl)-2,2-dimethyl-propyl] 3-(methylcarbamoyl)benzoate
[3-(1-ethyl-8-oxo-spiro[6,7-dihydro-4H-pyrazolo[3,4-c] azepine-5,4'-tetrahydropyran]-3-yl)-2,2-dimethyl-propyl] 3-(dimethylcarbamoyl)benzoate
[3-(1-ethyl-8-oxo-spiro[6,7-dihydro-4H-pyrazolo[3,4-c] azepine-5,4'-tetrahydropyran]-3-yl)-2,2-dimethyl-propyl] 3-(pyrrolidine-1-carbonyl)benzoate
[3-(1-ethyl-8-oxo-spiro[6,7-dihydro-4H-pyrazolo[3,4-c] azepine-5,4'-tetrahydropyran]-3-yl)-2,2-dimethyl-propyl] 3-(piperidine-1-carbonyl)benzoate
[3-(1-ethyl-8-oxo-spiro[6,7-dihydro-4H-pyrazolo[3,4-c] azepine-5,4'-tetrahydropyran]-3-yl)-2,2-dimethyl-propyl] 3-(morpholine-4-carbonyl)benzoate
[3-(1-ethyl-8-oxo-spiro[6,7-dihydro-4H-pyrazolo[3,4-c] azepine-5,4'-tetrahydropyran]-3-yl)-2,2-dimethyl-propyl] 3-(4-methylpiperazine-1-carbonyl)benzoate
[3-(1-ethyl-8-oxo-spiro[6,7-dihydro-4H-pyrazolo[3,4-c] azepine-5,4'-tetrahydropyran]-3-yl)-2,2-dimethyl-propyl] 3-(4-acetylpiperazine-1-carbonyl)benzoate, or
a pharmaceutically acceptable salt, hydrate or solvate thereof.

Clause 78. A compound according to any one of the clauses 1-62 selected from the group consisting of
3-(1-ethyl-8-oxo-spiro[6,7-dihydro-4H-pyrazolo[3,4-c] azepine-5,4'-tetrahydropyran]-3-yl)propyl oxazole-4-carboxylate
3-(1-ethyl-8-oxo-spiro[6,7-dihydro-4H-pyrazolo[3,4-c] azepine-5,4'-tetrahydropyran]-3-yl)propyl tetrahydrofuran-3-carboxylate
3-(1-ethyl-8-oxo-spiro[6,7-dihydro-4H-pyrazolo[3,4-c] azepine-5,4'-tetrahydropyran]-3-yl)propyl 1-methylpyrazole-3-carboxylate
3-(1-ethyl-8-oxo-spiro[6,7-dihydro-4H-pyrazolo[3,4-c] azepine-5,4'-tetrahydropyran]-3-yl)propyl 1-methylpyrazole-4-carboxylate
3-(1-ethyl-8-oxo-spiro[6,7-dihydro-4H-pyrazolo[3,4-c] azepine-5,4'-tetrahydropyran]-3-yl)propyl 1-methylimidazole-4-carboxylate
3-(1-ethyl-8-oxo-spiro[6,7-dihydro-4H-pyrazolo[3,4-c] azepine-5,4'-tetrahydropyran]-3-yl)propyl 2-methyloxazole-4-carboxylate
3-(1-ethyl-8-oxo-spiro[6,7-dihydro-4H-pyrazolo[3,4-c] azepine-5,4'-tetrahydropyran]-3-yl)propyl 2-methyloxazole-5-carboxylate
3-(1-ethyl-8-oxo-spiro[6,7-dihydro-4H-pyrazolo[3,4-c] azepine-5,4'-tetrahydropyran]-3-yl)propyl isothiazole-5-carboxylate 3-(1-ethyl-8-oxo-spiro[6,7-dihydro-4H-pyrazolo[3,4-c]azepine-5,4'-tetrahydropyran]-3-yl)propyl isothiazole-4-carboxylate 3-(1-ethyl-8-oxo-spiro[6,7-dihydro-4H-pyrazolo[3,4-c]azepine-5,4'-tetrahydropyran]-3-yl)propyl thiazole-4-carboxylate 3-(1-ethyl-8-oxo-spiro[6,7-dihydro-4H-pyrazolo[3,4-c]azepine-5,4'-tetrahydropyran]-3-yl)propyl thiazole-5-carboxylate 3-(1-ethyl-8-oxo-spiro[6,7-dihydro-4H-pyrazolo[3,4-c]azepine-5,4'-tetrahydropyran]-3-yl)propyl tetrahydropyran-4-carboxylate 3-(1-ethyl-8-oxo-spiro[6,7-dihydro-4H-pyrazolo[3,4-c]azepine-5,4'-tetrahydropyran]-3-yl)propyl 2-methylpyrimidine-5-carboxylate 3-(1-ethyl-8-oxo-spiro[6,7-dihydro-4H-pyrazolo[3,4-c]azepine-5,4'-tetrahydropyran]-3-yl)propyl 1-ethylpyrazole-3-carboxylate 3-(1-ethyl-8-oxo-spiro[6,7-dihydro-4H-pyrazolo[3,4-c]azepine-5,4'-tetrahydropyran]-3-yl)propyl 1,5-dimethylpyrazole-3-carboxylate 3-(1-ethyl-8-oxo-spiro[6,7-dihydro-4H-pyrazolo[3,4-c]azepine-5,4'-tetrahydropyran]-3-yl)propyl 1-ethyl pyrazole-4-carboxylate 3-(1-ethyl-8-oxo-spiro[6,7-dihydro-4H-pyrazolo[3,4-c]azepine-5,4'-tetrahydropyran]-3-yl)propyl 2-ethyloxazole-4-carboxylate 3-(1-ethyl-8-oxo-spiro[6,7-dihydro-4H-pyrazolo[3,4-c]azepine-5,4'-tetrahydropyran]-3-yl)propyl 1-acetylazetidine-3-carboxylate 3-(1-ethyl-8-oxo-spiro[6,7-dihydro-4H-pyrazolo[3,4-c]azepine-5,4'-tetrahydropyran]-3-yl)propyl 3-methylisothiazole-5-carboxylate 3-(1-ethyl-8-oxo-spiro[6,7-dihydro-4H-pyrazolo[3,4-c]azepine-5,4'-tetrahydropyran]-3-yl)propyl 2-methylthiazole-4-carboxylate 3-(1-ethyl-8-oxo-spiro[6,7-dihydro-4H-pyrazolo[3,4-c]azepine-5,4'-tetrahydropyran]-3-yl)propyl 2-methylthiazole-5-carboxylate 3-(1-ethyl-8-oxo-spiro[6,7-dihydro-4H-pyrazolo[3,4-c]azepine-5,4'-tetrahydropyran]-3-yl)propyl 1-methylpiperidine-4-carboxylate 3-(1-ethyl-8-oxo-spiro[6,7-dihydro-4H-pyrazolo[3,4-c]azepine-5,4'-tetrahydropyran]-3-yl)propyl tetrahydrothiopyran-4-carboxylate 3-(1-ethyl-8-oxo-spiro[6,7-dihydro-4H-pyrazolo[3,4-c]azepine-5,4'-tetrahydropyran]-3-yl)propyl 2,6-dimethylpyridine-4-carboxylate 3-(1-ethyl-8-oxo-spiro[6,7-dihydro-4H-pyrazolo[3,4-c]azepine-5,4'-tetrahydropyran]-3-yl)propyl 5-ethyl-1-methyl-pyrazole-3-carboxylate 3-(1-ethyl-8-oxo-spiro[6,7-dihydro-4H-pyrazolo[3,4-c]azepine-5,4'-tetrahydropyran]-3-yl)propyl 2-ethylthiazole-4-carboxylate 3-(1-ethyl-8-oxo-spiro[6,7-dihydro-4H-pyrazolo[3,4-c]azepine-5,4'-tetrahydropyran]-3-yl)propyl 1-acetylpiperidine-4-carboxylate 3-(1-ethyl-8-oxo-spiro[6,7-dihydro-4H-pyrazolo[3,4-c]azepine-5,4'-tetrahydropyran]-3-yl)propyl 1,1-dioxothiane-4-carboxylate

[3-(1-ethyl-8-oxo-spiro[6,7-dihydro-4H-pyrazolo[3,4-c]azepine-5,4'-tetrahydropyran]-3-yl)propyl] 1-methoxycarbonyl piperidine-4-carboxylate 3-(1-ethyl-8-oxo-spiro[6,7-dihydro-4H-pyrazolo[3,4-c]azepine-5,4'-tetrahydropyran]-3-yl)propyl 1-(dimethylcarbamoyl)piperidine-4-carboxylate, or a pharmaceutically acceptable salt, hydrate or solvate thereof.

Clause 79. A compound according to any one of the clauses 1-62 selected from the group consisting of 4-(1-ethyl-8-oxo-spiro[6,7-dihydro-4H-pyrazolo[3,4-c]azepine-5,4'-tetrahydropyran]-3-yl)butyl tetrahydrofuran-3-carboxylate 4-(1-ethyl-8-oxo-spiro[6,7-dihydro-4H-pyrazolo[3,4-c]azepine-5,4'-tetrahydropyran]-3-yl)butyl 2-methyloxazole-4-carboxylate 4-(1-ethyl-8-oxo-spiro[6,7-dihydro-4H-pyrazolo[3,4-c]azepine-5,4-tetrahydropyran]-3-yl)butyl 2-methyloxazole-5-carboxylate 4-(1-ethyl-8-oxo-spiro[6,7-dihydro-4H-pyrazolo[3,4-c]azepine-5,4'-tetrahydropyran]-3-yl)butyl isothiazole-4-carboxylate 4-(1-ethyl-8-oxo-spiro[6,7-dihydro-4H-pyrazolo[3,4-c]azepine-5,4'-tetrahydropyran]-3-yl)butyl thiazole-4-carboxylate 4-(1-ethyl-8-oxo-spiro[6,7-dihydro-4H-pyrazolo[3,4-c]azepine-5,4'-tetrahydropyran]-3-yl)butyl tetrahydropyran-4-carboxylate 4-(1-ethyl-8-oxo-spiro[6,7-dihydro-4H-pyrazolo[3,4-c]azepine-5,4'-tetrahydropyran]-3-yl)butyl 2-methylpyrimidine-5-carboxylate 4-(1-ethyl-8-oxo-spiro[6,7-dihydro-4H-pyrazolo[3,4-c]azepine-5,4'-tetrahydropyran]-3-yl)butyl 1,5-dimethylpyrazole-3-carboxylate 4-(1-ethyl-8-oxo-spiro[6,7-dihydro-4H-pyrazolo[3,4-c]azepine-5,4'-tetrahydropyran]-3-yl)butyl 2,6-dimethylpyridine-4-carboxylate 4-(1-ethyl-8-oxo-spiro[6,7-dihydro-4H-pyrazolo[3,4-c]azepine-5,4'-tetrahydropyran]-3-yl)butyl 1-acetylpiperidine-4-carboxylate, or a pharmaceutically acceptable salt, hydrate or solvate thereof.

Clause 80. A compound according to any one of the clauses 1-62 selected from the group consisting of 2-(1-ethyl-8-oxo-spiro[6,7-dihydro-4H-pyrazolo[3,4-c]azepine-5,4'-tetrahydropyran]-3-yl)ethyl isothiazole-4-carboxylate 2-(1-ethyl-8-oxo-spiro[6,7-dihydro-4H-pyrazolo[3,4-c]azepine-5,4'-tetrahydropyran]-3-yl)ethyl tetrahydropyran-4-carboxylate, or a pharmaceutically acceptable salt, hydrate or solvate thereof.

Clause 81. A compound according to any one of the clauses 1-62 selected from the group consisting of

[(2R)-3-(1-ethyl-8-oxo-spiro[6,7-dihydro-4H-pyrazolo[3,4-c]azepine-5,4'-tetrahydropyran]-3-yl)-2-methyl-propyl] oxazole-4-carboxylate

[(2R)-3-(1-ethyl-8-oxo-spiro[6,7-dihydro-4H-pyrazolo[3,4-c]azepine-5,4'-tetrahydropyran]-3-yl)-2-methyl-propyl] 1-methylpyrazole-3-carboxylate

[(2R)-3-(1-ethyl-8-oxo-spiro[6,7-dihydro-4H-pyrazolo[3,4-c]azepine-5,4'-tetrahydropyran]-3-yl)-2-methyl-propyl] 1-methylpyrazole-4-carboxylate

[(2R)-3-(1-ethyl-8-oxo-spiro[6,7-dihydro-4H-pyrazolo[3,4-c]azepine-5,4'-tetrahydropyran]-3-yl)-2-methyl-propyl] 1-methylimidazole-4-carboxylate

[(2R)-3-(1-ethyl-8-oxo-spiro[6,7-dihydro-4H-pyrazolo[3,4-c]azepine-5,4'-tetrahydropyran]-3-yl)-2-methyl-propyl]2-methyloxazole-4-carboxylate

[(2R)-3-(1-ethyl-8-oxo-spiro[6,7-dihydro-4H-pyrazolo[3,4-c]azepine-5,4'-tetrahydropyran]-3-yl)-2-methyl-propyl]2-methyloxazole-5-carboxylate

[(2R)-3-(1-ethyl-8-oxo-spiro[6,7-dihydro-4H-pyrazolo[3,4-c]azepine-5,4'-tetrahydropyran]-3-yl)-2-methyl-propyl] isothiazole-5-carboxylate
[(2R)-3-(1-ethyl-8-oxo-spiro[6,7-dihydro-4H-pyrazolo[3,4-c]azepine-5,4'-tetrahydropyran]-3-yl)-2-methyl-propyl] isothiazole-4-carboxylate
[(2R)-3-(1-ethyl-8-oxo-spiro[6,7-dihydro-4H-pyrazolo[3,4-c]azepine-5,4'-tetrahydropyran]-3-yl)-2-methyl-propyl] thiazole-4-carboxylate
[(2R)-3-(1-ethyl-8-oxo-spiro[6,7-dihydro-4H-pyrazolo[3,4-c]azepine-5,4'-tetrahydropyran]-3-yl)-2-methyl-propyl] thiazole-5-carboxylate
[(2R)-3-(1-ethyl-8-oxo-spiro[6,7-dihydro-4H-pyrazolo[3,4-c]azepine-5,4'-tetrahydropyran]-3-yl)-2-methyl-propyl] tetrahydropyran-4-carboxylate
[(2R)-3-(1-ethyl-8-oxo-spiro[6,7-dihydro-4H-pyrazolo[3,4-c]azepine-5,4'-tetrahydropyran]-3-yl)-2-methyl-propyl]2-methylpyrimidine-5-carboxylate
[(2R)-3-(1-ethyl-8-oxo-spiro[6,7-dihydro-4H-pyrazolo[3,4-c]azepine-5,4'-tetrahydropyran]-3-yl)-2-methyl-propyl]1,5-dimethylpyrazole-3-carboxylate
[(2R)-3-(1-ethyl-8-oxo-spiro[6,7-dihydro-4H-pyrazolo[3,4-c]azepine-5,4'-tetrahydropyran]-3-yl)-2-methyl-propyl]2-methylthiazole-4-carboxylate
[(2R)-3-(1-ethyl-8-oxo-spiro[6,7-dihydro-4H-pyrazolo[3,4-c]azepine-5,4'-tetrahydropyran]-3-yl)-2-methyl-propyl]2-methylthiazole-5-carboxylate
[(2R)-3-(1-ethyl-8-oxo-spiro[6,7-dihydro-4H-pyrazolo[3,4-c]azepine-5,4'-tetrahydropyran]-3-yl)-2-methyl-propyl] 1-methylpiperidine-4-carboxylate
[(2R)-3-(1-ethyl-8-oxo-spiro[6,7-dihydro-4H-pyrazolo[3,4-c]azepine-5,4'-tetrahydropyran]-3-yl)-2-methyl-propyl]2,6-dimethylpyridine-4-carboxylate
[(2R)-3-(1-ethyl-8-oxo-spiro[6,7-dihydro-4H-pyrazolo[3,4-c]azepine-5,4'-tetrahydropyran]-3-yl)-2-methyl-propyl] 1-acetylpiperidine-4-carboxylate
[(2R)-3-(1-ethyl-8-oxo-spiro[6,7-dihydro-4H-pyrazolo[3,4-c]azepine-5,4'-tetra-hydropyran]-3-yl)-2-methyl-propyl] 1-metoxycarbonylpiperidine-4-carboxylate
[(2R)-3-(1-ethyl-8-oxo-spiro[6,7-dihydro-4H-pyrazolo[3,4-c]azepine-5,4'-tetrahydropyran]-3-yl)-2-methyl-propyl] 1-(dimethylcarbamoyl)piperidine-4-carboxylate, or
a pharmaceutically acceptable salt, hydrate or solvate thereof.

Clause 82. A compound according to any one of the clauses 1-62 selected from the group consisting of
[3-(1-ethyl-8-oxo-spiro[6,7-dihydro-4H-pyrazolo[3,4-c]azepine-5,4'-tetrahydropyran]-3-yl)-2,2-dimethyl-propyl] oxazole-4-carboxylate
[3-(1-ethyl-8-oxo-spiro[6,7-dihydro-4H-pyrazolo[3,4-c]azepine-5,4'-tetrahydropyran]-3-yl)-2,2-dimethyl-propyl] 1-methylpyrazole-3-carboxylate
[3-(1-ethyl-8-oxo-spiro[6,7-dihydro-4H-pyrazolo[3,4-c]azepine-5,4'-tetrahydropyran]-3-yl)-2,2-dimethyl-propyl] 1-methylpyrazole-4-carboxylate
[3-(1-ethyl-8-oxo-spiro[6,7-dihydro-4H-pyrazolo[3,4-c]azepine-5,4'-tetrahydropyran]-3-yl)-2,2-dimethyl-propyl] 1-methylimidazole-4-carboxylate
[3-(1-ethyl-8-oxo-spiro[6,7-dihydro-4H-pyrazolo[3,4-c]azepine-5,4'-tetrahydropyran]-3-yl)-2,2-dimethyl-propyl] 2-methyloxazole-4-carboxylate
[3-(1-ethyl-8-oxo-spiro[6,7-dihydro-4H-pyrazolo[3,4-c]azepine-5,4'-tetrahydropyran]-3-yl)-2,2-dimethyl-propyl] 2-methyloxazole-5-carboxylate
[3-(1-ethyl-8-oxo-spiro[6,7-dihydro-4H-pyrazolo[3,4-c]azepine-5,4'-tetrahydropyran]-3-yl)-2,2-dimethyl-propyl] isothiazole-5-carboxylate
[3-(1-ethyl-8-oxo-spiro[6,7-dihydro-4H-pyrazolo[3,4-c]azepine-5,4'-tetrahydropyran]-3-yl)-2,2-dimethyl-propyl] isothiazole-4-carboxylate
[3-(1-ethyl-8-oxo-spiro[6,7-dihydro-4H-pyrazolo[3,4-c]azepine-5,4'-tetrahydropyran]-3-yl)-2,2-dimethyl-propyl] thiazole-4-carboxylate
[3-(1-ethyl-8-oxo-spiro[6,7-dihydro-4H-pyrazolo[3,4-c]azepine-5,4'-tetrahydropyran]-3-yl)-2,2-dimethyl-propyl] thiazole-5-carboxylate
[3-(1-ethyl-8-oxo-spiro[6,7-dihydro-4H-pyrazolo[3,4-c]azepine-5,4'-tetrahydropyran]-3-yl)-2,2-dimethyl-propyl] tetrahydropyran-4-carboxylate
[3-(1-ethyl-8-oxo-spiro[6,7-dihydro-4H-pyrazolo[3,4-c]azepine-5,4'-tetrahydropyran]-3-yl)-2,2-dimethyl-propyl] 2-methylpyrimidine-5-carboxylate
[3-(1-ethyl-8-oxo-spiro[6,7-dihydro-4H-pyrazolo[3,4-c]azepine-5,4'-tetrahydropyran]-3-yl)-2,2-dimethyl-propyl] 1,5-dimethylpyrazole-3-carboxylate
[3-(1-ethyl-8-oxo-spiro[6,7-dihydro-4H-pyrazolo[3,4-c]azepine-5,4'-tetrahydropyran]-3-yl)-2,2-dimethyl-propyl] 2-methylthiazole-4-carboxylate
[3-(1-ethyl-8-oxo-spiro[6,7-dihydro-4H-pyrazolo[3,4-c]azepine-5,4'-tetrahydropyran]-3-yl)-2,2-dimethyl-propyl] 2-methylthiazole-5-carboxylate
[3-(1-ethyl-8-oxo-spiro[6,7-dihydro-4H-pyrazolo[3,4-c]azepine-5,4'-tetrahydropyran]-3-yl)-2,2-dimethyl-propyl] 1-methylpiperidine-4-carboxylate
[3-(1-ethyl-8-oxo-spiro[6,7-dihydro-4H-pyrazolo[3,4-c]azepine-5,4'-tetrahydropyran]-3-yl)-2,2-dimethyl-propyl] 2,6-dimethylpyridine-4-carboxylate
[3-(1-ethyl-8-oxo-spiro[6,7-dihydro-4H-pyrazolo[3,4-c]azepine-5,4'-tetrahydropyran]-3-yl)-2,2-dimethyl-propyl] 1-acetylpiperidine-4-carboxylate
[3-(1-ethyl-8-oxo-spiro[6,7-dihydro-4H-pyrazolo[3,4-c]azepine-5,4'-tetrahydropyran]-3-yl)-2,2-dimethyl-propyl] 1-methoxycarbonylpiperidine-4-carboxylate
[3-(1-ethyl-8-oxo-spiro[6,7-dihydro-4H-pyrazolo[3,4-c]azepine-5,4'-tetrahydropyran]-3-yl)-2,2-dimethyl-propyl] 1-(dimethylcarbamoyl)piperidine-4-carboxylate, or
a pharmaceutically acceptable salt, hydrate or solvate thereof.

Clause 83. A pharmaceutical composition comprising a Compound according to any one of clauses 1-82 together with a pharmaceutically acceptable vehicle or excipient or pharmaceutically acceptable carrier(s).

Clause 84. The pharmaceutical composition according to clause 83 further comprising one or more other therapeutically active Compound(s).

Clause 85. A use of the Compound according to any of the clauses 1-82, for the manufacture of a pharmaceutical composition.

Clause 86. The use of a Compound according to clause 85 in the manufacture of a pharmaceutical composition for the treatment or amelioration of a disease, disorder or condition responsive to PDE4 inhibitory activity.

Clause 87. The use according to clause 86, wherein the disease, disorder or condition is dermal diseases or conditions.

Clause 88. The use according to clause 87, wherein the disease, disorder or condition is proliferative and inflammatory skin disorders, dermatitis, atopic dermatitis, seborrheic dermatitis, contact dermatitis, psoriasis, cancer, epidermal inflammation, alopecia, alopecia areata, skin atrophy, steroid induced skin atrophy, skin ageing, photo skin ageing, acne, urticaria, pruritis, and eczema.

Clause 89. The Compound according to any of the clauses 1-82, for use as a medicament.

Clause 90. The Compound according to clause 89 for use in the treatment or amelioration of a disease, disorder or condition responsive to PDE4 inhibitory activity.

Clause 91. The Compound according to clause 89 for use in the treatment or amelioration of dermal diseases or conditions.

Clause 92. The Compound according to clause 89 for use in the treatment of proliferative and inflammatory skin disorders, dermatitis, atopic dermatitis, seborrheic dermatitis, contact dermatitis, psoriasis, cancer, epidermal inflammation, alopecia, alopecia areata, skin atrophy, steroid induced skin atrophy, skin ageing, photo skin ageing, acne, urticaria, pruritis, and eczema.

Clause 93. A method for treatment or alleviation of a disease or a disorder or a condition responsive to PDE4 inhibitory activity, which method comprises the step of administering to a living animal body a therapeutically effective amount of a Compound according to any of the clauses 1-82.

Clause 94. A method of treating or ameliorating dermal diseases or conditions, the method comprising administering to a person suffering from at least one of said diseases an effective amount of one or more Compounds according to according to any one of clauses 1-82, optionally together with a pharmaceutically acceptable carrier or one or more excipients, optionally in combination with other therapeutically active Compounds.

Clause 95. The method according to clause 94, wherein the dermal disease or condition is selected from the group consisting of proliferative and inflammatory skin disorders, dermatitis, atopic dermatitis, seborrheic dermatitis, contact dermatitis, psoriasis, cancer, epidermal inflammation, alopecia, alopecia areata, skin atrophy, steroid induced skin atrophy, skin ageing, photo skin ageing, acne, urticaria, pruritis, and eczema.

The invention claimed is:

1. A Compound of general formula (I)

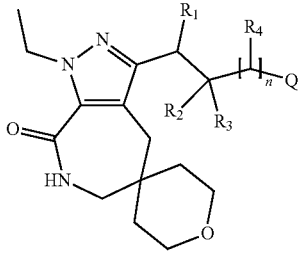

(I)

wherein $R_1$ and $R_4$ are independently selected from the group consisting of hydrogen and $(C_1-C_4)$alkyl;

$R_2$ and $R_3$ are independently selected from the group consisting of hydrogen and $(C_1-C_4)$alkyl; or $R_2$ and $R_3$ may together with the carbon atom to which they are attached form a cyclopropyl, cyclobutyl, cyclopentyl, oxetanyl, tetrahydrofuranyl or tetrahydropyranyl ring;

n=0, 1 or 2;

Q is selected from the group consisting of —O—C(O)—$R_5$;

$R_5$ is selected from the group consisting of $(C_1-C_6)$alkyl, $(C_3-C_7)$cycloalkyl, (4-7)-membered heterocycloalkyl heteroaryl and aryl, wherein said heteroaryl and aryl are optionally substituted with one or more substituents selected from $R_6$, and wherein said $(C_1-C_6)$alkyl, $(C_3-C_7)$cycloalkyl and (4-7)-membered heterocycloalkyl are optionally substituted with one or more substituents selected from $R_7$;

$R_6$ consists of halogen, cyano, hydroxyl, $(C_1-C_4)$alkyl, halo$(C_1-C_4)$alkyl, —S(O)$_2$R$_x$, —S(O)$_2$NR$_a$R$_b$, C(O)N-R$_a$R$_b$, —C(O)OR$_a$, —C(O)R$_x$ and —OR$_x$;

$R_7$ consists of halogen, hydroxyl, $(C_1-C_4)$alkyl, cyano, oxo, —C(O)NR$_a$R$_b$, —C(O)OR$_a$, —C(O)R$_x$, S(O)$_2$R$_x$, —OR$_x$, —SR$_x$, aryl and heteroaryl;

$R_x$ consist of $(C_1-C_6)$alkyl, $(C_3-C_6)$cycloalkyl;

$R_a$ and $R_b$ are independently selected from the group consisting of hydrogen, $(C_1-C_4)$alkyl, halo$(C_1-C_4)$alkyl and phenyl$(C_1-C_4)$alkyl, or $R_a$ and $R_b$ may together with the nitrogen atom to which they are attached form a 4-6 membered heterocycloalkyl, wherein said heterocycloalkyl is optionally substituted with one or more $(C_1-C_4)$alkyl or —C(O)R$_x$;

or a pharmaceutically acceptable salt, hydrate or solvate thereof.

2. A Compound of general formula (I) according to claim 1 wherein $R_1$ and $R_4$ are independently selected from the group consisting of hydrogen and $(C_1-C_4)$alkyl;

$R_2$ and $R_3$ are independently selected from the group consisting of hydrogen and $(C_1-C_4)$alkyl;

n=0, 1 or 2;

Q is selected from the group consisting of —O—C(O)—$R_5$;

$R_5$ is selected from the group consisting of $(C_1-C_6)$alkyl, $(C_3-C_7)$cycloalkyl, a (4-6)-membered heterocycloalkyl, a (5-6)-membered heteroaryl and phenyl, wherein said (5-6)-membered heteroaryl and phenyl are optionally substituted with one or more substituents selected from $R_6$, and wherein said $(C_1-C_6)$alkyl, $(C_3-C_7)$cycloalkyl and (4-6)-membered heterocycloalkyl are optionally substituted with one or more substituents selected from $R_7$;

$R_6$ consists of halogen, cyano, hydroxyl, $(C_1-C_4)$alkyl, halo$(C_1-C_4)$alkyl, —S(O)$_2$R$_x$, —S(O)$_2$NR$_a$R$_b$, C(O)N-R$_a$R$_b$, —C(O)R$_x$ and —OR$_x$;

$R_7$ consists of halogen, hydroxyl, $(C_1-C_4)$alkyl, cyano, oxo, —C(O)NR$_a$R$_b$, —C(O)OR$_a$, —C(O)R$_x$, —S(O)$_2$R$_x$, —OR$_x$, —SR$_x$, aryl and heteroaryl;

$R_x$ consist of $(C_1-C_6)$alkyl, $(C_3-C_6)$cycloalkyl;

$R_a$ and $R_b$ are independently selected from the group consisting of hydrogen, $(C_1-C_4)$alkyl, halo$(C_1-C_4)$alkyl and phenyl$(C_1-C_4)$alkyl, or $R_a$ and $R_b$ may together with the nitrogen atom to which they are attached form a 4-6 membered heterocycloalkyl, wherein said heterocycloalkyl is optionally substituted with one or more $(C_1-C_4)$alkyl or —C(O)R$_x$;

or a pharmaceutically acceptable salt, hydrate or solvate thereof.

3. A Compound of general formula (I)

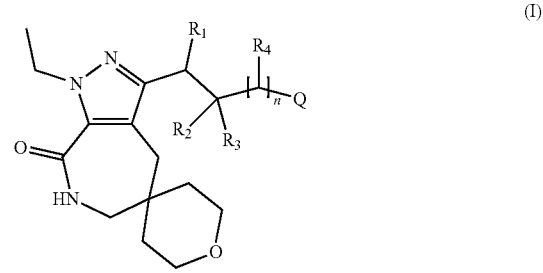

(I)

wherein $R_1$ and $R_4$ are independently selected from the group consisting of hydrogen and $(C_1-C_4)$alkyl;

R$_2$ and R$_3$ are independently selected from the group consisting of hydrogen and (C$_1$-C$_4$)alkyl; or R$_2$ and R$_3$ may together with the carbon atom to which they are attached form a cyclopropyl, cyclobutyl, cyclopentyl, oxetanyl, tetrahydrofuranyl or tetrahydropyranyl ring; n=0, 1 or 2;

Q is selected from the group consisting of —O—C(O)—R$_5$;

R$_5$ is selected from the group consisting of (C$_1$-C$_6$)alkyl, (C$_3$-C$_7$)cycloalkyl, (4-7)-membered heterocycloalkyl and aryl, wherein said aryl is optionally substituted with one or more substituents selected from R$_6$, and wherein said (C$_1$-C$_6$)alkyl, (C$_3$-C$_7$)cycloalkyl and (4-7)-membered heterocycloalkyl are optionally substituted with one or more substituents selected from R$_7$;

R$_6$ consists of halogen, cyano, hydroxyl, (C$_1$-C$_4$)alkyl, halo(C$_1$-C$_4$)alkyl, —S(O)$_2$R$_x$, —S(O)$_2$NR$_a$R$_b$, and —OR$_x$;

R$_7$ consists of halogen, hydroxyl, cyano, —C(O)NR$_a$R$_b$, —C(O)OR$_a$, aryl and heteroaryl;

R$_x$ is (C$_1$-C$_6$)alkyl;

R$_a$ and R$_b$ are independently selected from the group consisting of hydrogen, (C$_1$-C$_4$)alkyl, halo(C$_1$-C$_4$)alkyl and phenyl(C$_1$-C$_4$)alkyl, or R$_a$ and R$_b$ may together with the nitrogen atom to which they are attached form a 4-6 membered heterocycloalkyl, wherein said heterocycloalkyl is optionally substituted with one or more (C$_1$-C$_4$)alkyl; or a pharmaceutically acceptable salt, hydrate or solvate thereof.

4. A Compound according to claim 1 wherein all of R$_1$, R$_2$, R$_3$, R$_4$ are hydrogen, n is 1, and R$_5$ is phenyl optionally substituted with one or two of R$_6$.

5. A Compound according to claim 1 selected from the group consisting of
(i) 3-(1-Ethyl-8-oxo-spiro[6,7-dihydro-4H-pyrazolo[3,4-c]azepine-5,4'-tetrahydropyran]-3-yl)propyl 4-(methylsulfamoyl)benzoate (Compound 101),
(ii) 3-(1-Ethyl-8-oxo-spiro[6,7-dihydro-4H-pyrazolo[3,4-c]azepine-5,4'-tetrahydropyran]-3-yl)propyl 4-(dimethylsulfamoyl)benzoate (Compound 102),
(iii) 3-(1-Ethyl-8-oxo-spiro[6,7-dihydro-4H-pyrazolo[3,4-c]azepine-5,4'-tetrahydropyran]-3-yl)propyl 4-methylsulfonylbenzoate (Compound 103);
or a pharmaceutically acceptable salt, hydrate or solvate thereof.

6. A Compound according to claim 1 selected from the group consisting of:
(i) 3-(1-ethyl-8-oxo-spiro[6,7-dihydro-4H-pyrazolo[3,4-c]azepine-5,4'-tetrahydropyran]-3-yl)propyl 2-methylpropanoate
(ii) 3-(1-ethyl-8-oxo-spiro[6,7-dihydro-4H-pyrazolo[3,4-c]azepine-5,4'-tetrahydropyran]-3-yl)propyl cyclopentanecarboxylate
(iii) 3-(1-ethyl-8-oxo-spiro[6,7-dihydro-4H-pyrazolo[3,4-c]azepine-5,4'-tetrahydropyran]-3-yl)propyl 2-ethylbutanoate
(iv) 3-(1-ethyl-8-oxo-spiro[6,7-dihydro-4H-pyrazolo[3,4-c]azepine-5,4'-tetrahydropyran]-3-yl)propyl benzoate
(v) 3-(1-ethyl-8-oxo-spiro[6,7-dihydro-4H-pyrazolo[3,4-c]azepine-5,4'-tetrahydropyran]-3-yl)propyl 4-methylbenzoate
(vi) 3-(1-ethyl-8-oxo-spiro[6,7-dihydro-4H-pyrazolo[3,4-c]azepine-5,4'-tetrahydropyran]-3-yl)propyl 3-fluorobenzoate
(vii) 3-(1-ethyl-8-oxo-spiro[6,7-dihydro-4H-pyrazolo[3,4-c]azepine-5,4'-tetrahydropyran]-3-yl)propyl 4-fluorobenzoate
(viii) 3-(1-ethyl-8-oxo-spiro[6,7-dihydro-4H-pyrazolo[3,4-c]azepine-5,4'-tetrahydropyran]-3-yl)propyl 3-cyanobenzoate
(ix) 3-(1-ethyl-8-oxo-spiro[6,7-dihydro-4H-pyrazolo[3,4-c]azepine-5,4'-tetrahydropyran]-3-yl)propyl 4-cyanobenzoate
(x) 3-(1-ethyl-8-oxo-spiro[6,7-dihydro-4H-pyrazolo[3,4-c]azepine-5,4'-tetrahydropyran]-3-yl)propyl 3,4-dimethylbenzoate
(xi) 3-(1-ethyl-8-oxo-spiro[6,7-dihydro-4H-pyrazolo[3,4-c]azepine-5,4'-tetrahydropyran]-3-yl)propyl 2,4-dimethylbenzoate
(xii) 3-(1-ethyl-8-oxo-spiro[6,7-dihydro-4H-pyrazolo[3,4-c]azepine-5,4'-tetrahydropyran]-3-yl)propyl 4-ethylbenzoate
(xiii) 3-(1-ethyl-8-oxo-spiro[6,7-dihydro-4H-pyrazolo[3,4-c]azepine-5,4'-tetrahydropyran]-3-yl)propyl 4-methoxybenzoate
(xiv) 3-(1-ethyl-8-oxo-spiro[6,7-dihydro-4H-pyrazolo[3,4-c]azepine-5,4'-tetrahydropyran]-3-yl)propyl 3-methoxybenzoate
(xv) 3-(1-ethyl-8-oxo-spiro[6,7-dihydro-4H-pyrazolo[3,4-c]azepine-5,4'-tetrahydropyran]-3-yl)propyl 2-fluoro-4-methyl-benzoate
(xvi) 3-(1-ethyl-8-oxo-spiro[6,7-dihydro-4H-pyrazolo[3,4-c]azepine-5,4'-tetrahydropyran]-3-yl)propyl 4-fluoro-2-methyl-benzoate
(xvii) 3-(1-ethyl-8-oxo-spiro[6,7-dihydro-4H-pyrazolo[3,4-c]azepine-5,4'-tetrahydropyran]-3-yl)propyl 5-fluoro-2-methyl-benzoate
(xviii) 3-(1-ethyl-8-oxo-spiro[6,7-dihydro-4H-pyrazolo[3,4-c]azepine-5,4'-tetrahydropyran]-3-yl)propyl 3-fluoro-2-methyl-benzoate
(xix) 3-(1-ethyl-8-oxo-spiro[6,7-dihydro-4H-pyrazolo[3,4-c]azepine-5,4'-tetrahydropyran]-3-yl)propyl 4-chlorobenzoate
(xx) (3-(1-ethyl-8-oxo-spiro[6,7-dihydro-4H-pyrazolo[3,4-c]azepine-5,4'-tetrahydropyran]-3-yl)propyl 3,4-difluorobenzoate
(xxi) 3-(1-ethyl-8-oxo-spiro[6,7-dihydro-4H-pyrazolo[3,4-c]azepine-5,4'-tetrahydropyran]-3-yl)propyl 2,3-difluorobenzoate
(xxii) 3-(1-ethyl-8-oxo-spiro[6,7-dihydro-4H-pyrazolo[3,4-c]azepine-5,4'-tetrahydropyran]-3-yl)propyl 2,5-difluorobenzoate
(xxiii) 3-(1-ethyl-8-oxo-spiro[6,7-dihydro-4H-pyrazolo[3,4-c]azepine-5,4'-tetrahydropyran]-3-yl)propyl 2,6-difluorobenzoate
(xxiv) 3-(1-ethyl-8-oxo-spiro[6,7-dihydro-4H-pyrazolo[3,4-c]azepine-5,4'-tetrahydropyran]-3-yl)propyl 4-acetyl benzoate
(xxv) 3-(1-ethyl-8-oxo-spiro[6,7-dihydro-4H-pyrazolo[3,4-c]azepine-5,4'-tetrahydropyran]-3-yl)propyl 3-acetyl benzoate
(xxvi) 3-(1-ethyl-8-oxo-spiro[6,7-dihydro-4H-pyrazolo[3,4-c]azepine-5,4'-tetrahydropyran]-3-yl)propyl 3-cyano-5-fluoro-benzoate
(xxvii) 3-(1-ethyl-8-oxo-spiro[6,7-dihydro-4H-pyrazolo[3,4-c]azepine-5,4'-tetrahydropyran]-3-yl)propyl 3-cyano-4-fluoro-benzoate
(xxviii) 3-(1-ethyl-8-oxo-spiro[6,7-dihydro-4H-pyrazolo[3,4-c]azepine-5,4'-tetrahydropyran]-3-yl)propyl 5-cyano-2-fluoro-benzoate (xxix) 3-(1-ethyl-8-oxo-spiro[6,7-dihydro-4H-pyrazolo[3,4-c]azepine-5,4'-tetrahydropyran]-3-yl)propyl 4-cyano-3-fluoro-benzoate (xxx) 3-(1-ethyl-8-oxo-spiro[6,7-dihydro-4H-pyrazolo[3,4-c]azepine-5,4'-tetrahydropyran]-3-yl)propyl 4-methoxy-3-methyl-benzoate (xxxi) 3-(1-ethyl-8-oxo-spiro[6,7-dihydro-4H-pyrazolo[3,4-c]azepine-5,4'-tetrahydropyran]-3-yl)propyl 2-methoxy-4-methyl-benzoate (xxxii) 3-(1-ethyl-8-oxo-spiro[6,7-dihydro-4H-pyrazolo[3,4-c]azepine-5,4'-tetrahydropyran]-3-yl)propyl 3-fluoro-4-methoxy-benzoate (xxxiii) 3-(1-ethyl-8-oxo-spiro[6,7-dihydro-4H-pyrazolo[3,4-c]azepine-5,4'-tetrahydropyran]-3-yl)propyl 4-fluoro-3-methoxy-benzoate (xxxiv) 3-(1-ethyl-8-oxo-spiro[6,7-dihydro-4H-pyrazolo[3,4-c]azepine-5,4'-tetrahydropyran]-3-yl)propyl 2-fluoro-5-methoxy-benzoate (xxxv) 3-(1-ethyl-8-oxo-spiro[6,7-dihydro-4H-pyrazolo[3,4-c]azepine-5,4'-tetrahydropyran]-3-yl)propyl 2-fluoro-4-methoxy-benzoate (xxxvi) 3-(1-ethyl-8-oxo-spiro[6,7-dihydro-4H-pyrazolo[3,4-c]azepine-5,4'-tetrahydropyran]-3-yl)propyl 2-fluoro-3-methoxy-benzoate (xxxvii) 3-(1-ethyl-8-oxo-spiro[6,7-dihydro-4H-pyrazolo[3,4-c]azepine-5,4'-tetrahydropyran]-3-yl)propyl 4-fluoro-2-methoxy-benzoate (xxxviii) 3-(1-ethyl-8-oxo-spiro[6,7-dihydro-4H-pyrazolo[3,4-c]azepine-5,4'-tetrahydropyran]-3-yl)propyl 2-fluoro-6-methoxy-benzoate (xxxix) 3-(1-ethyl-8-oxo-spiro[6,7-dihydro-4H-pyrazolo[3,4-c]azepine-5,4'-tetrahydropyran]-3-yl)propyl 2-chloro-4-methyl-benzoate (xl) 3-(1-ethyl-8-oxo-spiro[6,7-dihydro-4H-pyrazolo[3,4-c]azepine-5,4'-tetrahydropyran]-3-yl)propyl 4-chloro-2-methyl-benzoate (xli) 3-(1-ethyl-8-oxo-spiro[6,7-dihydro-4H-pyrazolo[3,4-c]azepine-5,4'-tetrahydropyran]-3-yl)propyl 5-chloro-2-methyl-benzoate (xlii) 3-(1-ethyl-8-oxo-spiro[6,7-dihydro-4H-pyrazolo[3,4-c]azepine-5,4'-tetrahydropyran]-3-yl)propyl 4-(difluoromethyl)benzoate (xliii) 3-(1-ethyl-8-oxo-spiro[6,7-dihydro-4H-pyrazolo[3,4-c]azepine-5,4'-tetrahydropyran]-3-yl)propyl 2-chloro-5-fluoro-benzoate (xliv) 3-(1-ethyl-8-oxo-spiro[6,7-dihydro-4H-pyrazolo[3,4-c]azepine-5,4'-tetrahydropyran]-3-yl)propyl 3-chloro-5-fluoro-benzoate (xlv) 3-(1-ethyl-8-oxo-spiro[6,7-dihydro-4H-pyrazolo[3,4-c]azepine-5,4'-tetrahydropyran]-3-yl)propyl 4-chloro-3-fluoro-benzoate (xlvi) 3-(1-ethyl-8-oxo-spiro[6,7-dihydro-4H-pyrazolo[3,4-c]azepine-5,4'-tetrahydropyran]-3-yl)propyl 2-chloro-3-fluoro-benzoate (xlvii) 3-(1-ethyl-8-oxo-spiro[6,7-dihydro-4H-pyrazolo[3,4-c]azepine-5,4'-tetrahydropyran]-3-yl)propyl 3-chloro-2-fluoro-benzoate (xlviii) 3-(1-ethyl-8-oxo-spiro[6,7-dihydro-4H-pyrazolo[3,4-c]azepine-5,4'-tetrahydropyran]-3-yl)propyl 5-chloro-2-fluoro-benzoate (xlix) 3-(1-ethyl-8-oxo-spiro[6,7-dihydro-4H-pyrazolo[3,4-c]azepine-5,4'-tetrahydropyran]-3-yl)propyl 2-chloro-6-fluoro-benzoate (l) 3-(1-ethyl-8-oxo-spiro[6,7-dihydro-4H-pyrazolo[3,4-c]azepine-5,4'-tetrahydropyran]-3-yl)propyl 4-chloro-2-fluoro-benzoate (li) 3-(1-ethyl-8-oxo-spiro[6,7-dihydro-4H-pyrazolo[3,4-c]azepine-5,4'-tetrahydropyran]-3-yl)propyl 3-chloro-4-fluoro-benzoate (lii) 3-(1-ethyl-8-oxo-spiro[6,7-dihydro-4H-pyrazolo[3,4-c]azepine-5,4'-tetrahydropyran]-3-yl)propyl 4-chloro-3-methoxy-benzoate (liii) 3-(1-ethyl-8-oxo-spiro[6,7-dihydro-4H-pyrazolo[3,4-c]azepine-5,4'-tetrahydropyran]-3-yl)propyl 2-chloro-5-methoxy-benzoate (liv) 3-(1-ethyl-8-oxo-spiro[6,7-dihydro-4H-pyrazolo[3,4-c]azepine-5,4'-tetrahydropyran]-3-yl)propyl 2-chloro-3-methoxy-benzoate (lv) 3-(1-ethyl-8-oxo-spiro[6,7-dihydro-4H-pyrazolo[3,4-c]azepine-5,4'-tetrahydropyran]-3-yl)propyl 3-chloro-4-methoxy-benzoate (lvi) 3-(1-ethyl-8-oxo-spiro[6,7-dihydro-4H-pyrazolo[3,4-c]azepine-5,4'-tetrahydropyran]-3-yl)propyl 3-chloro-2-methoxy-benzoate (lvii) 3-(1-ethyl-8-oxo-spiro[6,7-dihydro-4H-pyrazolo[3,4-c]azepine-5,4'-tetrahydropyran]-3-yl)propyl 5-chloro-2-methoxy-benzoate (lviii) 3-(1-ethyl-8-oxo-spiro[6,7-dihydro-4H-pyrazolo[3,4-c]azepine-5,4'-tetrahydropyran]-3-yl)propyl 4-chloro-2-methoxy-benzoate (lix) (3-(1-ethyl-8-oxo-spiro[6,7-dihydro-4H-pyrazolo[3,4-c]azepine-5,4'-tetrahydropyran]-3-yl)propyl 4-(trifluoromethyl)benzoate (lx) 3-(1-ethyl-8-oxo-spiro[6,7-dihydro-4H-pyrazolo[3,4-c]azepine-5,4'-tetrahydropyran]-3-yl)propyl 3-methylsulfonylbenzoate (lxi) 3-(1-ethyl-8-oxo-spiro[6,7-dihydro-4H-pyrazolo[3,4-c]azepine-5,4'-tetrahydropyran]-3-yl)propyl 2-methylsulfonylbenzoate (lxii) 3-(1-ethyl-8-oxo-spiro[6,7-dihydro-4H-pyrazolo[3,4-c]azepine-5,4'-tetrahydropyran]-3-yl)propyl 4-sulfamoylbenzoate (lxiii) 3-(1-ethyl-8-oxo-spiro[6,7-dihydro-4H-pyrazolo[3,4-c]azepine-5,4'-tetrahydropyran]-3-yl)propyl 3-sulfamoylbenzoate (lxiv) 3-(1-ethyl-8-oxo-spiro[6,7-dihydro-4H-pyrazolo[3,4-c]azepine-5,4'-tetrahydropyran]-3-yl)propyl 2-methyl-5-(trifluoromethyl)benzoate (lxv) 3-(1-ethyl-8-oxo-spiro[6,7-dihydro-4H-pyrazolo[3,4-c]azepine-5,4'-tetrahydropyran]-3-yl)propyl 2-methyl-3-(trifluoromethyl)benzoate (lxvi) 3-(1-ethyl-8-oxo-spiro[6,7-dihydro-4H-pyrazolo[3,4-c]azepine-5,4'-tetrahydropyran]-3-yl)propyl 4-fluoro-3-(trifluoromethyl)benzoate (lxvii) 3-(1-ethyl-8-oxo-spiro[6,7-dihydro-4H-pyrazolo[3,4-c]azepine-5,4'-tetrahydropyran]-3-yl)propyl 2-fluoro-4-(trifluoromethyl)benzoate (lxviii) 3-(1-ethyl-8-oxo-spiro[6,7-dihydro-4H-pyrazolo[3,4-c]azepine-5,4'-tetrahydropyran]-3-yl)propyl 4-fluoro-2-(trifluoromethyl)benzoate (lxix) 3-(1-ethyl-8-oxo-spiro[6,7-dihydro-4H-pyrazolo[3,4-c]azepine-5,4'-tetrahydropyran]-3-yl)propyl 3-fluoro-5-(trifluoromethyl)benzoate (lxx) 3-(1-ethyl-8-oxo-spiro[6,7-dihydro-4H-pyrazolo[3,4-c]azepine-5,4'-tetrahydropyran]-3-yl)propyl 2-fluoro-5-(trifluoromethyl)benzoate (lxxi) 3-(1-ethyl-8-oxo-spiro[6,7-dihydro-4H-pyrazolo[3,4-c]azepine-5,4'-tetrahydropyran]-3-yl)propyl 5-fluoro-2-(trifluoromethyl)benzoate (lxxii) 3-(1-ethyl-8-oxo-spiro[6,7-dihydro-4H-pyrazolo[3,4-c]azepine-5,4'-tetrahydropyran]-3-yl)propyl 3-fluoro-4-(trifluoromethyl)benzoate (lxxiii) 3-(1-ethyl-8-oxo-spiro[6,7-dihydro-4H-pyrazolo[3,4-c]azepine-5,4'-tetrahydropyran]-3-yl)propyl 3-ethylsulfonylbenzoate (lxxiv) 3-(1-ethyl-8-oxo-spiro[6,7-dihydro-4H-pyrazolo[3,4-c]azepine-5,4'-tetrahydropyran]-3-yl)propyl 4-ethylsulfonylbenzoate (lxxv) 3-(1-ethyl-8-oxo-spiro[6,7-dihydro-4H-pyrazolo[3,4-c]azepine-5,4'-tetrahydropyran]-3-yl)propyl 3-(methylsulfamoyl)benzoate (lxxvi) 3-(1-ethyl-8-oxo-spiro[6,7-dihydro-4H-pyrazolo[3,4-c]azepine-5,4'-tetrahydropyran]-3-yl)propyl 4-methoxy-3-(trifluoromethyl)benzoate (lxxvii) 3-(1-ethyl-8-oxo-spiro[6,7-dihydro-4H-pyrazolo[3,4-c]azepine-5,4'-tetrahydropyran]-3-yl)propyl 5-methoxy-2-(trifluoromethyl)benzoate (lxxviii) 3-(1-ethyl-8-oxo-spiro[6,7-dihydro-4H-pyrazolo[3,4-c]azepine-5,4'-tetrahydropyran]-3-yl)propyl 4-methoxy-2-(trifluoromethyl)benzoate (lxxix) 3-(1-ethyl-8-oxo-spiro[6,7-dihydro-4H-pyrazolo[3,4-c]azepine-5,4'-tetrahydropyran]-3-yl)propyl 3-methoxy-5-(trifluoromethyl)benzoate (lxxx) 3-(1-ethyl-8-oxo-spiro[6,7-dihydro-4H-pyrazolo[3,4-c]azepine-5,4'-tetrahydropyran]-3-yl)propyl 3-methoxy-4-(trifluoromethyl)benzoate (lxxxi) 3-(1-ethyl-8-oxo-spiro[6,7-dihydro-4H-pyrazolo[3,4-c]azepine-5,4'-tetrahydropyran]-3-yl)propyl 4-chloro-2-(trifluoromethyl)benzoate (lxxxii) 3-(1-ethyl-8-oxo-spiro[6,7-dihydro-4H-pyrazolo[3,4-c]azepine-5,4'-tetrahydropyran]-3-yl)propyl 2-chloro-3-(trifluoromethyl)benzoate (lxxxiii) 3-(1-ethyl-8-oxo-spiro[6,7-dihydro-4H-pyrazolo[3,4-c]azepine-5,4'-tetrahydropyran]-3-yl)propyl 3-chloro-4-(trifluoromethyl)benzoate (lxxxiv) 3-(1-ethyl-8-oxo-spiro[6,7-dihydro-4H-pyrazolo[3,4-c]azepine-5,4'-tetrahydropyran]-3-yl)propyl 5-chloro-2-(trifluoromethyl)benzoate (lxxxv) 3-(1-ethyl-8-oxo-spiro[6,7-dihydro-4H-pyrazolo[3,4-c]azepine-5,4'-tetrahydropyran]-3-yl)propyl 2-chloro-4-(trifluoromethyl)benzoate (lxxxvi) 3-(1-ethyl-8-oxo-spiro[6,7-dihydro-4H-pyrazolo[3,4-c]azepine-5,4'-tetrahydropyran]-3-yl)propyl 4-chloro-3-(trifluoromethyl)benzoate (lxxxvii) 3-(1-ethyl-8-oxo-spiro[6,7-dihydro-4H-pyrazolo[3,4-c]azepine-5,4'-tetrahydropyran]-3-yl)propyl 3-chloro-5-(trifluoromethyl)benzoate (lxxxviii) 3-(1-ethyl-8-oxo-spiro[6,7-dihydro-4H-pyrazolo[3,4-c]azepine-5,4'-tetrahydropyran]-3-yl)propyl 2-chloro-5-(trifluoromethyl)benzoate (lxxxix) 3-(1-ethyl-8-oxo-spiro[6,7-dihydro-4H-pyrazolo[3,4-c]azepine-5,4'-tetrahydropyran]-3-yl)propyl 3-isopropylsulfonylbenzoate (xc) 3-(1-ethyl-8-oxo-spiro[6,7-dihydro-4H-pyrazolo[3,4-c]azepine-5,4'-tetrahydropyran]-3-yl)propyl 4-isopropylsulfonylbenzoate (xci) 3-(1-ethyl-8-oxo-spiro[6,7-dihydro-4H-pyrazolo[3,4-c]azepine-5,4'-tetrahydropyran]-3-yl)propyl 4-cyclopentylsulfonylbenzoate (xcii) 3-(1-ethyl-8-oxo-spiro[6,7-dihydro-4H-pyrazolo[3,4-c]azepine-5,4'-tetrahydropyran]-3-yl)propyl 3-pyrrolidin-1-ylsulfonylbenzoate (xciii) 3-(1-ethyl-8-oxo-spiro[6,7-dihydro-4H-pyrazolo[3,4-c]azepine-5,4'-tetrahydropyran]-3-yl)propyl 4-pyrrolidin-1-ylsulfonylbenzoate (xciv) 3-(1-ethyl-8-oxo-spiro[6,7-dihydro-4H-pyrazolo[3,4-c]azepine-5,4'-tetrahydropyran]-3-yl)propyl 2,4-bis(trifluoromethyl)benzoate (xcv) 3-(1-ethyl-8-oxo-spiro[6,7-dihydro-4H-pyrazolo[3,4-c]azepine-5,4'-tetrahydropyran]-3-yl)propyl 3,4-bis(trifluoromethyl)benzoate (xcvi) 3-(1-ethyl-8-oxo-spiro[6,7-dihydro-4H-pyrazolo[3,4-c]azepine-5,4'-tetrahydropyran]-3-yl)propyl 3-morpholinosulfonylbenzoate (xcvii) 3-(1-ethyl-8-oxo-spiro[6,7-dihydro-4H-pyrazolo[3,4-c]azepine-5,4'-tetrahydropyran]-3-yl)propyl 4-morpholinosulfonylbenzoate (xcviii) 3-(1-ethyl-8-oxo-spiro[6,7-dihydro-4H-pyrazolo[3,4-c]azepine-5,4'-tetrahydropyran]-3-yl)propyl 3-(4-acetylpiperazin-1-yl)sulfonylbenzoate (xcix) 3-(1-ethyl-8-oxo-spiro[6,7-dihydro-4H-pyrazolo[3,4-c]azepine-5,4'-tetrahydropyran]-3-yl)propyl 4-(4-acetylpiperazin-1-yl)sulfonylbenzoate (c) 3-(1-ethyl-8-oxo-spiro[6,7-dihydro-4H-pyrazolo[3,4-c]azepine-5,4'-tetrahydropyran]-3-yl)propyl 4-carbamoylbenzoate (ci) 3-(1-ethyl-8-oxo-spiro[6,7-dihydro-4H-pyrazolo[3,4-c]azepine-5,4'-tetrahydropyran]-3-yl)propyl 4-(methylcarbamoyl)benzoate (cii) 3-(1-ethyl-8-oxo-spiro[6,7-dihydro-4H-pyrazolo[3,4-c]azepine-5,4'-tetrahydropyran]-3-yl)propyl 4-(dimethylcarbamoyl)benzoate (ciii) 3-(1-ethyl-8-oxo-spiro[6,7-dihydro-4H-pyrazolo[3,4-c]azepine-5,4'-tetrahydropyran]-3-yl)propyl 4-(pyrrolidine-1-carbonyl)benzoate (civ) 3-(1-ethyl-8-oxo-spiro[6,7-dihydro-4H-pyrazolo[3,4-c]azepine-5,4'-tetrahydropyran]-3-yl)propyl 4-(piperidine-1-carbonyl)benzoate (cv) 3-(1-ethyl-8-oxo-spiro[6,7-dihydro-4H-pyrazolo[3,4-c]azepine-5,4'-tetrahydropyran]-3-yl)propyl 4-(morpholine-4-carbonyl)benzoate (cvi) 3-(1-ethyl-8-oxo-spiro[6,7-dihydro-4H-pyrazolo[3,4-c]azepine-5,4'-tetrahydropyran]-3-yl)propyl 4-(4-methylpiperazine-1-carbonyl)benzoate (cvii) 3-(1-ethyl-8-oxo-spiro[6,7-dihydro-4H-pyrazolo[3,4-c]azepine-5,4'-tetrahydropyran]-3-yl)propyl 4-(4-acetylpiperazine-1-carbonyl)benzoate (cviii) 3-(1-ethyl-8-oxo-spiro[6,7-dihydro-4H-pyrazolo[3,4-c]azepine-5,4'-tetrahydropyran]-3-yl)propyl 3-carbamoylbenzoate (cix) 3-(1-ethyl-8-oxo-spiro[6,7-dihydro-4H-pyrazolo[3,4-c]azepine-5,4'-tetrahydropyran]-3-yl)propyl 3-(methylcarbamoyl)benzoate (cx) 3-(1-ethyl-8-oxo-spiro[6,7-dihydro-4H-pyrazolo[3,4-c]azepine-5,4'-tetrahydropyran]-3-yl)propyl 3-(dimethylcarbamoyl)benzoate (cxi) 3-(1-ethyl-8-oxo-spiro[6,7-dihydro-4H-pyrazolo[3,4-c]azepine-5,4'-tetrahydropyran]-3-yl)propyl 3-(pyrrolidine-1-carbonyl)benzoate (cxii) 3-(1-ethyl-8-oxo-spiro[6,7-dihydro-4H-pyrazolo[3,4-c]azepine-5,4'-tetrahydropyran]-3-yl)propyl 3-(piperidine-1-carbonyl)benzoate (cxiii) 3-(1-ethyl-8-oxo-spiro[6,7-dihydro-4H-pyrazolo[3,4-c]azepine-5,4'-tetrahydropyran]-3-yl)propyl 3-(morpholine-4-carbonyl)benzoate (cxiv) 3-(1-ethyl-8-oxo-spiro[6,7-dihydro-4H-pyrazolo[3,4-c]azepine-5,4'-tetrahydropyran]-3-yl)propyl 3-(4-methylpiperazine-1-carbonyl)benzoate (cxv) 3-(1-ethyl-8-oxo-spiro[6,7-dihydro-4H-pyrazolo[3,4-c]azepine-5,4'-tetrahydropyran]-3-yl)propyl 3-(4-acetylpiperazine-1-carbonyl)benzoate (cxvi) 4-(1-ethyl-8-oxo-spiro[6,7-dihydro-4H-pyrazolo[3,4-c]azepine-5,4'-tetrahydropyran]-3-yl)butyl 2-methyl propanoate (cxvii) 4-(1-ethyl-8-oxo-spiro[6,7-dihydro-4H-pyrazolo[3,4-c]azepine-5,4'-tetrahydropyran]-3-yl)butyl cyclopentanecarboxylate
(cxviii) 4-(1-ethyl-8-oxo-spiro[6,7-dihydro-4H-pyrazolo[3,4-c]azepine-5,4'-tetrahydropyran]-3-yl)butyl 4-methylbenzoate
(cxix) 4-(1-ethyl-8-oxo-spiro[6,7-dihydro-4H-pyrazolo[3,4-c]azepine-5,4'-tetrahydropyran]-3-yl)butyl 4-fluorobenzoate
(cxx) 4-(1-ethyl-8-oxo-spiro[6,7-dihydro-4H-pyrazolo[3,4-c]azepine-5,4'-tetrahydropyran]-3-yl)butyl 4-methoxybenzoate
(cxxi) 4-(1-ethyl-8-oxo-spiro[6,7-dihydro-4H-pyrazolo[3,4-c]azepine-5,4'-tetrahydropyran]-3-yl)butyl 4-acetylbenzoate
(cxxii) 4-(1-ethyl-8-oxo-spiro[6,7-dihydro-4H-pyrazolo[3,4-c]azepine-5,4'-tetrahydropyran]-3-yl)butyl 4-carbamoylbenzoate
(cxxiii) 4-(1-ethyl-8-oxo-spiro[6,7-dihydro-4H-pyrazolo[3,4-c]azepine-5,4'-tetrahydropyran]-3-yl)butyl 4-(methylcarbamoyl)benzoate
(cxxiv) 4-(1-ethyl-8-oxo-spiro[6,7-dihydro-4H-pyrazolo[3,4-c]azepine-5,4'-tetrahydropyran]-3-yl)butyl 4-(dimethylcarbamoyl)benzoate
(cxxv) 4-(1-ethyl-8-oxo-spiro[6,7-dihydro-4H-pyrazolo[3,4-c]azepine-5,4'-tetrahydropyran]-3-yl)butyl 4-methylsulfonylbenzoate
(cxxvi) 4-(1-ethyl-8-oxo-spiro[6,7-dihydro-4H-pyrazolo[3,4-c]azepine-5,4'-tetrahydropyran]-3-yl)butyl 4-(methylsulfamoyl)benzoate
(cxxvii) 4-(1-ethyl-8-oxo-spiro[6,7-dihydro-4H-pyrazolo[3,4-c]azepine-5,4'-tetrahydropyran]-3-yl)butyl 4-(dimethylsulfamoyl)benzoate
(cxxviii) 4-(1-ethyl-8-oxo-spiro[6,7-dihydro-4H-pyrazolo[3,4-c]azepine-5,4'-tetrahydropyran]-3-yl)butyl 4-(morpholine-4-carbonyl)benzoate
(cxxix) 2-(1-ethyl-8-oxo-spiro[6,7-dihydro-4H-pyrazolo[3,4-c]azepine-5,4'-tetrahydropyran]-3-yl)ethyl cyclopentanecarboxylate
(cxxx) 2-(1-ethyl-8-oxo-spiro[6,7-dihydro-4H-pyrazolo[3,4-c]azepine-5,4'-tetrahydropyran]-3-yl)ethyl 4-methylbenzoate
(cxxxi) 2-(1-ethyl-8-oxo-spiro[6,7-dihydro-4H-pyrazolo[3,4-c]azepine-5,4'-tetrahydropyran]-3-yl)ethyl 4-methylsulfonylbenzoate
(cxxxii) [(2R)-3-(1-ethyl-8-oxo-spiro[6,7-dihydro-4H-pyrazolo[3,4-c]azepine-5,4'-tetrahydropyran]-3-yl)-2-methyl-propyl]3-methoxypropanoate
(cxxxiii) [(2R)-3-(1-ethyl-8-oxo-spiro[6,7-dihydro-4H-pyrazolo[3,4-c]azepine-5,4'-tetrahydropyran]-3-yl)-2-methyl-propyl]3-hydroxycyclobutanecarboxylate
(cxxxiv) [(2R)-3-(1-ethyl-8-oxo-spiro[6,7-dihydro-4H-pyrazolo[3,4-c]azepine-5,4'-tetrahydropyran]-3-yl)-2-methyl-propyl]3-methylsulfanylpropanoate
(cxxxv) [(2R)-3-(1-ethyl-8-oxo-spiro[6,7-dihydro-4H-pyrazolo[3,4-c]azepine-5,4'-tetrahydropyran]-3-yl)-2-methyl-propyl]4-methylbenzoate
(cxxxvi) [(2R)-3-(1-ethyl-8-oxo-spiro[6,7-dihydro-4H-pyrazolo[3,4-c]azepine-5,4'-tetrahydropyran]-3-yl)-2-methyl-propyl]2-methylbenzoate
(cxxxvii) [(2R)-3-(1-ethyl-8-oxo-spiro[6,7-dihydro-4H-pyrazolo[3,4-c]azepine-5,4'-tetrahydropyran]-3-yl)-2-methyl-propyl]3-methylbenzoate
(cxxxviii) [(2R)-3-(1-ethyl-8-oxo-spiro[6,7-dihydro-4H-pyrazolo[3,4-c]azepine-5,4'-tetrahydropyran]-3-yl)-2-methyl-propyl]3-fluorobenzoate
(cxxxix) [(2R)-3-(1-ethyl-8-oxo-spiro[6,7-dihydro-4H-pyrazolo[3,4-c]azepine-5,4'-tetrahydropyran]-3-yl)-2-methyl-propyl]2-fluorobenzoate
(cxl) [(2R)-3-(1-ethyl-8-oxo-spiro[6,7-dihydro-4H-pyrazolo[3,4-c]azepine-5,4'-tetrahydropyran]-3-yl)-2-methyl-propyl]4-fluorobenzoate
(cxli) [(2R)-3-(1-ethyl-8-oxo-spiro[6,7-dihydro-4H-pyrazolo[3,4-c]azepine-5,4'-tetrahydropyran]-3-yl)-2-methyl-propyl]4-hydroxycyclohexanecarboxylate
(cxlii) [(2R)-3-(1-ethyl-8-oxo-spiro[6,7-dihydro-4H-pyrazolo[3,4-c]azepine-5,4'-tetrahydropyran]-3-yl)-2-methyl-propyl]4-hydroxycyclohexanecarboxylate
(cxliii) [(2R)-3-(1-ethyl-8-oxo-spiro[6,7-dihydro-4H-pyrazolo[3,4-c]azepine-5,4'-tetrahydropyran]-3-yl)-2-methyl-propyl]4-ethylbenzoate
(cxliv) [(2R)-3-(1-ethyl-8-oxo-spiro[6,7-dihydro-4H-pyrazolo[3,4-c]azepine-5,4'-tetrahydropyran]-3-yl)-2-methyl-propyl]4-methoxybenzoate
(cxlv) [(2R)-3-(1-ethyl-8-oxo-spiro[6,7-dihydro-4H-pyrazolo[3,4-c]azepine-5,4'-tetrahydropyran]-3-yl)-2-methyl-propyl]3-methoxybenzoate
(cxlvi) [(2R)-3-(1-ethyl-8-oxo-spiro[6,7-dihydro-4H-pyrazolo[3,4-c]azepine-5,4'-tetrahydropyran]-3-yl)-2-methyl-propyl]2-methoxybenzoate
(cxlvii) [(2R)-3-(1-ethyl-8-oxo-spiro[6,7-dihydro-4H-pyrazolo[3,4-c]azepine-5,4'-tetrahydropyran]-3-yl)-2-methyl-propyl]3-methylsulfonylpropanoate
(cxlviii) [(2R)-3-(1-ethyl-8-oxo-spiro[6,7-dihydro-4H-pyrazolo[3,4-c]azepine-5,4'-tetrahydropyran]-3-yl)-2-methyl-propyl]4-acetylbenzoate
(cxlix) [(2R)-3-(1-ethyl-8-oxo-spiro[6,7-dihydro-4H-pyrazolo[3,4-c]azepine-5,4'-tetrahydropyran]-3-yl)-2-methyl-propyl]3-acetylbenzoate
(cl) [(2R)-3-(1-ethyl-8-oxo-spiro[6,7-dihydro-4H-pyrazolo[3,4-c]azepine-5,4'-tetrahydropyran]-3-yl)-2-methyl-propyl]4-methylsulfonylbenzoate
(cli) [(2R)-3-(1-ethyl-8-oxo-spiro[6,7-dihydro-4H-pyrazolo[3,4-c]azepine-5,4'-tetrahydropyran]-3-yl)-2-methyl-propyl]3-ethylsulfonylbenzoate
(clii) [(2R)-3-(1-ethyl-8-oxo-spiro[6,7-dihydro-4H-pyrazolo[3,4-c]azepine-5,4'-tetrahydropyran]-3-yl)-2-methyl-propyl]4-ethylsulfonylbenzoate
(cliii) [(2R)-3-(1-ethyl-8-oxo-spiro[6,7-dihydro-4H-pyrazolo[3,4-c]azepine-5,4'-tetrahydropyran]-3-yl)-2-methyl-propyl]4-(methylsulfamoyl)benzoate
(cliv) [(2R)-3-(1-ethyl-8-oxo-spiro[6,7-dihydro-4H-pyrazolo[3,4-c]azepine-5,4'-tetrahydropyran]-3-yl)-2-methyl-propyl]3-isopropylsulfonylbenzoate
(clv) [(2R)-3-(1-ethyl-8-oxo-spiro[6,7-dihydro-4H-pyrazolo[3,4-c]azepine-5,4'-tetrahydropyran]-3-yl)-2-methyl-propyl]4-isopropylsulfonylbenzoate
(clvi) [(2R)-3-(1-ethyl-8-oxo-spiro[6,7-dihydro-4H-pyrazolo[3,4-c]azepine-5,4'-tetrahydropyran]-3-yl)-2-methyl-propyl]4-(dimethylsulfamoyl)benzoate
(clvii) [(2R)-3-(1-ethyl-8-oxo-spiro[6,7-dihydro-4H-pyrazolo[3,4-c]azepine-5,4'-tetrahydropyran]-3-yl)-2-methyl-propyl]4-cyclopentylsulfonylbenzoate
(clviii) [(2R)-3-(1-ethyl-8-oxo-spiro[6,7-dihydro-4H-pyrazolo[3,4-c]azepine-5,4'-tetrahydropyran]-3-yl)-2-methyl-propyl]3-pyrrolidin-1-ylsulfonylbenzoate
(clix) [(2R)-3-(1-ethyl-8-oxo-spiro[6,7-dihydro-4H-pyrazolo[3,4-c]azepine-5,4'-tetrahydropyran]-3-yl)-2-methyl-propyl]3-morpholinosulfonylbenzoate
(clx) [(2R)-3-(1-ethyl-8-oxo-spiro[6,7-dihydro-4H-pyrazolo[3,4-c]azepine-5,4'-tetrahydropyran]-3-yl)-2-methyl-propyl]4-morpholinosulfonylbenzoate (clxi) [(2R)-3-(1-ethyl-8-oxo-spiro[6,7-dihydro-4H-pyrazolo[3,4-c]azepine-5,4'-tetrahydropyran]-3-yl)-2-methyl-propyl]3-(4-acetylpiperazin-1-yl)sulfonylbenzoate (clxii) [(2R)-3-(1-ethyl-8-oxo-spiro[6,7-dihydro-4H-pyrazolo[3,4-c]azepine-5,4'-tetrahydropyran]-3-yl)-2-methyl-propyl]4-(4-acetylpiperazin-1-yl)sulfonylbenzoate (clxiii) [(2R)-3-(1-ethyl-8-oxo-spiro[6,7-dihydro-4H-pyrazolo[3,4-c]azepine-5,4'-tetrahydropyran]-3-yl)-2-methyl-propyl]4-carbamoylbenzoate (clxiv) [(2R)-3-(1-ethyl-8-oxo-spiro[6,7-dihydro-4H-pyrazolo[3,4-c]azepine-5,4'-tetrahydropyran]-3-yl)-2-methyl-propyl]4-(methylcarbamoyl)benzoate (clxv) [(2R)-3-(1-ethyl-8-oxo-spiro[6,7-dihydro-4H-pyrazolo[3,4-c]azepine-5,4'-tetrahydropyran]-3-yl)-2-methyl-propyl]4-(dimethylcarbamoyl)benzoate (clxvi) [(2R)-3-(1-ethyl-8-oxo-spiro[6,7-dihydro-4H-pyrazolo[3,4-c]azepine-5,4'-tetrahydropyran]-3-yl)-2-methyl-propyl]4-(pyrrolidine-1-carbonyl)benzoate (clxvii) [(2R)-3-(1-ethyl-8-oxo-spiro[6,7-dihydro-4H-pyrazolo[3,4-c]azepine-5,4'-tetrahydropyran]-3-yl)-2-methyl-propyl]4-(piperidine-1-carbonyl)benzoate (clxviii) [(2R)-3-(1-ethyl-8-oxo-spiro[6,7-dihydro-4H-pyrazolo[3,4-c]azepine-5,4'-tetrahydropyran]-3-yl)-2-methyl-propyl]4-(morpholine-4-carbonyl)benzoate (clxix) [(2R)-3-(1-ethyl-8-oxo-spiro[6,7-dihydro-4H-pyrazolo[3,4-c]azepine-5,4'-tetrahydropyran]-3-yl)-2-methyl-propyl]4-(4-methylpiperazine-1-carbonyl)benzoate (clxx) [(2R)-3-(1-ethyl-8-oxo-spiro[6,7-dihydro-4H-pyrazolo[3,4-c]azepine-5,4'-tetrahydropyran]-3-yl)-2-methyl-propyl]4-(4-acetylpiperazine-1-carbonyl)benzoate (clxxi) [(2R)-3-(1-ethyl-8-oxo-spiro[6,7-dihydro-4H-pyrazolo[3,4-c]azepine-5,4'-tetrahydropyran]-3-yl)-2-methyl-propyl]3-carbamoylbenzoate (clxxii) [(2R)-3-(1-ethyl-8-oxo-spiro[6,7-dihydro-4H-pyrazolo[3,4-c]azepine-5,4'-tetrahydropyran]-3-yl)-2-methyl-propyl]3-(methylcarbamoyl)benzoate (clxxiii) [(2R)-3-(1-ethyl-8-oxo-spiro[6,7-dihydro-4H-pyrazolo[3,4-c]azepine-5,4'-tetrahydropyran]-3-yl)-2-methyl-propyl]3-(dimethylcarbamoyl)benzoate (clxxiv) [(2R)-3-(1-ethyl-8-oxo-spiro[6,7-dihydro-4H-pyrazolo[3,4-c]azepine-5,4'-tetrahydropyran]-3-yl)-2-methyl-propyl]3-(pyrrolidine-1-carbonyl)benzoate (clxxv) [(2R)-3-(1-ethyl-8-oxo-spiro[6,7-dihydro-4H-pyrazolo[3,4-c]azepine-5,4'-tetrahydropyran]-3-yl)-2-methyl-propyl]3-(piperidine-1-carbonyl)benzoate (clxxvi) [(2R)-3-(1-ethyl-8-oxo-spiro[6,7-dihydro-4H-pyrazolo[3,4-c]azepine-5,4'-tetrahydropyran]-3-yl)-2-methyl-propyl]3-(morpholine-4-carbonyl)benzoate (clxxvii) [(2R)-3-(1-ethyl-8-oxo-spiro[6,7-dihydro-4H-pyrazolo[3,4-c]azepine-5,4'-tetrahydropyran]-3-yl)-2-methyl-propyl]3-(4-methylpiperazine-1-carbonyl)benzoate (clxxviii) [(2R)-3-(1-ethyl-8-oxo-spiro[6,7-dihydro-4H-pyrazolo[3,4-c]azepine-5,4'-tetrahydropyran]-3-yl)-2-methyl-propyl]3-(4-acetylpiperazine-1-carbonyl)benzoate (clxxix) [3-(1-ethyl-8-oxo-spiro[6,7-dihydro-4H-pyrazolo[3,4-c]azepine-5,4'-tetrahydropyran]-3-yl)-2,2-dimethyl-propyl]3-methoxypropanoate (clxxx) [3-(1-ethyl-8-oxo-spiro[6,7-dihydro-4H-pyrazolo[3,4-c]azepine-5,4'-tetrahydropyran]-3-yl)-2,2-dimethyl-propyl]3-methylsulfanylpropanoate (clxxxi) [3-(1-ethyl-8-oxo-spiro[6,7-dihydro-4H-pyrazolo[3,4-c]azepine-5,4'-tetrahydropyran]-3-yl)-2,2-dimethyl-propyl]4-methylbenzoate (clxxxii) [3-(1-ethyl-8-oxo-spiro[6,7-dihydro-4H-pyrazolo[3,4-c]azepine-5,4'-tetrahydropyran]-3-yl)-2,2-dimethyl-propyl]2-methylbenzoate (clxxxiii) [3-(1-ethyl-8-oxo-spiro[6,7-dihydro-4H-pyrazolo[3,4-c]azepine-5,4'-tetrahydropyran]-3-yl)-2,2-dimethyl-propyl]3-methylbenzoate (clxxxiv) [3-(1-ethyl-8-oxo-spiro[6,7-dihydro-4H-pyrazolo[3,4-c]azepine-5,4'-tetrahydropyran]-3-yl)-2,2-dimethyl-propyl]3-fluorobenzoate (clxxxv) [3-(1-ethyl-8-oxo-spiro[6,7-dihydro-4H-pyrazolo[3,4-c]azepine-5,4'-tetrahydropyran]-3-yl)-2,2-dimethyl-propyl]4-fluorobenzoate (clxxxvi) [3-(1-ethyl-8-oxo-spiro[6,7-dihydro-4H-pyrazolo[3,4-c]azepine-5,4'-tetrahydropyran]-3-yl)-2,2-dimethyl-propyl]2-fluorobenzoate (clxxxvii) [3-(1-ethyl-8-oxo-spiro[6,7-dihydro-4H-pyrazolo[3,4-c]azepine-5,4'-tetrahydropyran]-3-yl)-2,2-dimethyl-propyl]4-hydroxycyclohexanecarboxylate (clxxxviii) [3-(1-ethyl-8-oxo-spiro[6,7-dihydro-4H-pyrazolo[3,4-c]azepine-5,4'-tetrahydropyran]-3-yl)-2,2-dimethyl-propyl]4-ethylbenzoate (clxxxix) [3-(1-ethyl-8-oxo-spiro[6,7-dihydro-4H-pyrazolo[3,4-c]azepine-5,4'-tetrahydropyran]-3-yl)-2,2-dimethyl-propyl]3-methoxybenzoate (cxc) [3-(1-ethyl-8-oxo-spiro[6,7-dihydro-4H-pyrazolo[3,4-c]azepine-5,4'-tetrahydropyran]-3-yl)-2,2-dimethyl-propyl]4-methoxybenzoate (cxci) [3-(1-ethyl-8-oxo-spiro[6,7-dihydro-4H-pyrazolo[3,4-c]azepine-5,4'-tetrahydropyran]-3-yl)-2,2-dimethyl-propyl]2-methoxybenzoate (cxcii) [3-(1-ethyl-8-oxo-spiro[6,7-dihydro-4H-pyrazolo[3,4-c]azepine-5,4'-tetrahydropyran]-3-yl)-2,2-dimethyl-propyl]3-methylsulfonylpropanoate (cxciii) [3-(1-ethyl-8-oxo-spiro[6,7-dihydro-4H-pyrazolo[3,4-c]azepine-5,4'-tetrahydropyran]-3-yl)-2,2-dimethyl-propyl]4-acetylbenzoate (cxciv) [3-(1-ethyl-8-oxo-spiro[6,7-dihydro-4H-pyrazolo[3,4-c]azepine-5,4'-tetrahydropyran]-3-yl)-2,2-dimethyl-propyl]3-acetylbenzoate (cxcv) [3-(1-ethyl-8-oxo-spiro[6,7-dihydro-4H-pyrazolo[3,4-c]azepine-5,4'-tetrahydropyran]-3-yl)-2,2-dimethyl-propyl]4-methylsulfonylbenzoate (cxcvi) [3-(1-ethyl-8-oxo-spiro[6,7-dihydro-4H-pyrazolo[3,4-c]azepine-5,4'-tetrahydropyran]-3-yl)-2,2-dimethyl-propyl]4-ethylsulfonylbenzoate (cxcvii) [3-(1-ethyl-8-oxo-spiro[6,7-dihydro-4H-pyrazolo[3,4-c]azepine-5,4'-tetrahydropyran]-3-yl)-2,2-dimethyl-propyl]3-ethylsulfonylbenzoate (cxcviii) [3-(1-ethyl-8-oxo-spiro[6,7-dihydro-4H-pyrazolo[3,4-c]azepine-5,4'-tetrahydropyran]-3-yl)-2,2-dimethyl-propyl]4-(methylsulfamoyl)benzoate (cxcix) [3-(1-ethyl-8-oxo-spiro[6,7-dihydro-4H-pyrazolo[3,4-c]azepine-5,4'-tetrahydropyran]-3-yl)-2,2-dimethyl-propyl]3-isopropylsulfonylbenzoate (cc) [3-(1-ethyl-8-oxo-spiro[6,7-dihydro-4H-pyrazolo[3,4-c]azepine-5,4'-tetrahydropyran]-3-yl)-2,2-dimethyl-propyl]4-isopropylsulfonylbenzoate (cci) [3-(1-ethyl-8-oxo-spiro[6,7-dihydro-4H-pyrazolo[3,4-c]azepine-5,4'-tetrahydropyran]-3-yl)-2,2-dimethyl-propyl]4-(dimethylsulfamoyl)benzoate (ccii) [3-(1-ethyl-8-oxo-spiro[6,7-dihydro-4H-pyrazolo[3,4-c]azepine-5,4'-tetrahydropyran]-3-yl)-2,2-dimethyl-propyl]4-cyclopentylsulfonylbenzoate (cciii) [3-(1-ethyl-8-oxo-spiro[6,7-dihydro-4H-pyrazolo[3,4-c]azepine-5,4'-tetrahydropyran]-3-yl)-2,2-dimethyl-propyl]3-pyrrolidin-1-ylsulfonylbenzoate
(cciv) [3-(1-ethyl-8-oxo-spiro[6,7-dihydro-4H-pyrazolo[3,4-c]azepine-5,4'-tetrahydropyran]-3-yl)-2,2-dimethyl-propyl]4-pyrrolidin-1-ylsulfonylbenzoate
(ccv) [3-(1-ethyl-8-oxo-spiro[6,7-dihydro-4H-pyrazolo[3,4-c]azepine-5,4'-tetrahydropyran]-3-yl)-2,2-dimethyl-propyl]3-morpholinosulfonylbenzoate
(ccvi) [3-(1-ethyl-8-oxo-spiro[6,7-dihydro-4H-pyrazolo[3,4-c]azepine-5,4'-tetrahydropyran]-3-yl)-2,2-dimethyl-propyl]4-morpholinosulfonylbenzoate
(ccvii) [3-(1-ethyl-8-oxo-spiro[6,7-dihydro-4H-pyrazolo[3,4-c]azepine-5,4'-tetrahydropyran]-3-yl)-2,2-dimethyl-propyl]4-[benzyl(methyl)sulfamoyl]benzoate
(ccviii) [3-(1-ethyl-8-oxo-spiro[6,7-dihydro-4H-pyrazolo[3,4-c]azepine-5,4'-tetrahydropyran]-3-yl)-2,2-dimethyl-propyl]3-(4-acetylpiperazin-1-yl)sulfonylbenzoate
(ccix) [3-(1-ethyl-8-oxo-spiro[6,7-dihydro-4H-pyrazolo[3,4-c]azepine-5,4'-tetrahydropyran]-3-yl)-2,2-dimethyl-propyl]4-(4-acetylpiperazin-1-yl)sulfonylbenzoate
(ccx) [3-(1-ethyl-8-oxo-spiro[6,7-dihydro-4H-pyrazolo[3,4-c]azepine-5,4'-tetrahydropyran]-3-yl)-2,2-dimethyl-propyl]4-carbamoylbenzoate
(ccxi) [3-(1-ethyl-8-oxo-spiro[6,7-dihydro-4H-pyrazolo[3,4-c]azepine-5,4'-tetrahydropyran]-3-yl)-2,2-dimethyl-propyl]4-(methylcarbamoyl)benzoate
(ccxii) [3-(1-ethyl-8-oxo-spiro[6,7-dihydro-4H-pyrazolo[3,4-c]azepine-5,4'-tetrahydropyran]-3-yl)-2,2-dimethyl-propyl]4-(dimethylcarbamoyl)benzoate
(ccxiii) [3-(1-ethyl-8-oxo-spiro[6,7-dihydro-4H-pyrazolo[3,4-c]azepine-5,4'-tetrahydropyran]-3-yl)-2,2-dimethyl-propyl]4-(pyrrolidine-1-carbonyl)benzoate
(ccxiv) [3-(1-ethyl-8-oxo-spiro[6,7-dihydro-4H-pyrazolo[3,4-c]azepine-5,4'-tetrahydropyran]-3-yl)-2,2-dimethyl-propyl]4-(piperidine-1-carbonyl)benzoate
(ccxv) [3-(1-ethyl-8-oxo-spiro[6,7-dihydro-4H-pyrazolo[3,4-c]azepine-5,4'-tetrahydropyran]-3-yl)-2,2-dimethyl-propyl]4-(morpholine-4-carbonyl)benzoate
(ccxvi) [3-(1-ethyl-8-oxo-spiro[6,7-dihydro-4H-pyrazolo[3,4-c]azepine-5,4'-tetrahydropyran]-3-yl)-2,2-dimethyl-propyl]4-(4-methylpiperazine-1-carbonyl)benzoate
(ccxvii) [3-(1-ethyl-8-oxo-spiro[6,7-dihydro-4H-pyrazolo[3,4-c]azepine-5,4'-tetrahydropyran]-3-yl)-2,2-dimethyl-propyl]4-(4-acetylpiperazine-1-carbonyl)benzoate
(ccxviii) [3-(1-ethyl-8-oxo-spiro[6,7-dihydro-4H-pyrazolo[3,4-c]azepine-5,4'-tetrahydropyran]-3-yl)-2,2-dimethyl-propyl]3-carbamoylbenzoate
(ccxix) [3-(1-ethyl-8-oxo-spiro[6,7-dihydro-4H-pyrazolo[3,4-c]azepine-5,4'-tetrahydropyran]-3-yl)-2,2-dimethyl-propyl]3-(methylcarbamoyl)benzoate
(ccxx) [3-(1-ethyl-8-oxo-spiro[6,7-dihydro-4H-pyrazolo[3,4-c]azepine-5,4'-tetrahydropyran]-3-yl)-2,2-dimethyl-propyl]3-(dimethylcarbamoyl)benzoate
(ccxxi) [3-(1-ethyl-8-oxo-spiro[6,7-dihydro-4H-pyrazolo[3,4-c]azepine-5,4'-tetrahydropyran]-3-yl)-2,2-dimethyl-propyl]3-(pyrrolidine-1-carbonyl)benzoate
(ccxxii) [3-(1-ethyl-8-oxo-spiro[6,7-dihydro-4H-pyrazolo[3,4-c]azepine-5,4'-tetrahydropyran]-3-yl)-2,2-dimethyl-propyl]3-(piperidine-1-carbonyl)benzoate
(ccxxiii) [3-(1-ethyl-8-oxo-spiro[6,7-dihydro-4H-pyrazolo[3,4-c]azepine-5,4'-tetrahydropyran]-3-yl)-2,2-dimethyl-propyl]3-(morpholine-4-carbonyl)benzoate
(ccxxiv) [3-(1-ethyl-8-oxo-spiro[6,7-dihydro-4H-pyrazolo[3,4-c]azepine-5,4'-tetrahydropyran]-3-yl)-2,2-dimethyl-propyl]3-(4-methylpiperazine-1-carbonyl)benzoate
(ccxxv) [3-(1-ethyl-8-oxo-spiro[6,7-dihydro-4H-pyrazolo[3,4-c]azepine-5,4'-tetrahydropyran]-3-yl)-2,2-dimethyl-propyl]3-(4-acetylpiperazine-1-carbonyl)benzoate, or a pharmaceutically acceptable salt, hydrate or solvate thereof.

7. A compound according to claim 1 selected from the group consisting of:
(i) 3-(1-ethyl-8-oxo-spiro[6,7-dihydro-4H-pyrazolo[3,4-c]azepine-5,4'-tetrahydropyran]-3-yl)propyl oxazole-4-carboxylate
(ii) 3-(1-ethyl-8-oxo-spiro[6,7-dihydro-4H-pyrazolo[3,4-c]azepine-5,4'-tetrahydropyran]-3-yl)propyl tetrahydrofuran-3-carboxylate
(iii) 3-(1-ethyl-8-oxo-spiro[6,7-dihydro-4H-pyrazolo[3,4-c]azepine-5,4'-tetrahydropyran]-3-yl)propyl 1-methylpyrazole-3-carboxylate
(iv) 3-(1-ethyl-8-oxo-spiro[6,7-dihydro-4H-pyrazolo[3,4-c]azepine-5,4'-tetrahydropyran]-3-yl)propyl 1-methylpyrazole-4-carboxylate
(v) 3-(1-ethyl-8-oxo-spiro[6,7-dihydro-4H-pyrazolo[3,4-c]azepine-5,4'-tetrahydropyran]-3-yl)propyl 1-methylimidazole-4-carboxylate
(vi) 3-(1-ethyl-8-oxo-spiro[6,7-dihydro-4H-pyrazolo[3,4-c]azepine-5,4'-tetrahydropyran]-3-yl)propyl 2-methyloxazole-4-carboxylate
(vii) 3-(1-ethyl-8-oxo-spiro[6,7-dihydro-4H-pyrazolo[3,4-c]azepine-5,4'-tetrahydropyran]-3-yl)propyl 2-methyloxazole-5-carboxylate
(viii) 3-(1-ethyl-8-oxo-spiro[6,7-dihydro-4H-pyrazolo[3,4-c]azepine-5,4'-tetrahydropyran]-3-yl)propyl isothiazole-5-carboxylate
(ix) 3-(1-ethyl-8-oxo-spiro[6,7-dihydro-4H-pyrazolo[3,4-c]azepine-5,4'-tetrahydropyran]-3-yl)propyl isothiazole-4-carboxylate
(x) 3-(1-ethyl-8-oxo-spiro[6,7-dihydro-4H-pyrazolo[3,4-c]azepine-5,4'-tetrahydropyran]-3-yl)propyl thiazole-4-carboxylate
(xi) 3-(1-ethyl-8-oxo-spiro[6,7-dihydro-4H-pyrazolo[3,4-c]azepine-5,4'-tetrahydropyran]-3-yl)propyl thiazole-5-carboxylate
(xii) 3-(1-ethyl-8-oxo-spiro[6,7-dihydro-4H-pyrazolo[3,4-c]azepine-5,4'-tetrahydropyran]-3-yl)propyl tetrahydropyran-4-carboxylate
(xiii) 3-(1-ethyl-8-oxo-spiro[6,7-dihydro-4H-pyrazolo[3,4-c]azepine-5,4'-tetrahydropyran]-3-yl)propyl 2-methylpyrimidine-5-carboxylate
(xiv) 3-(1-ethyl-8-oxo-spiro[6,7-dihydro-4H-pyrazolo[3,4-c]azepine-5,4'-tetrahydropyran]-3-yl)propyl 1-ethyl pyrazole-3-carboxylate
(xv) 3-(1-ethyl-8-oxo-spiro[6,7-dihydro-4H-pyrazolo[3,4-c]azepine-5,4'-tetrahydropyran]-3-yl)propyl 1,5-dimethylpyrazole-3-carboxylate
(xvi) 3-(1-ethyl-8-oxo-spiro[6,7-dihydro-4H-pyrazolo[3,4-c]azepine-5,4'-tetrahydropyran]-3-yl)propyl 1-ethyl pyrazole-4-carboxylate
(xvii) 3-(1-ethyl-8-oxo-spiro[6,7-dihydro-4H-pyrazolo[3,4-c]azepine-5,4'-tetrahydropyran]-3-yl)propyl 2-ethyloxazole-4-carboxylate
(xviii) 3-(1-ethyl-8-oxo-spiro[6,7-dihydro-4H-pyrazolo[3,4-c]azepine-5,4'-tetrahydropyran]-3-yl)propyl 1-acetylazetidine-3-carboxylate (xix) 3-(1-ethyl-8-oxo-spiro[6,7-dihydro-4H-pyrazolo[3,4-c]azepine-5,4'-tetrahydropyran]-3-yl)propyl 3-methylisothiazole-5-carboxylate (xx) 3-(1-ethyl-8-oxo-spiro[6,7-dihydro-4H-pyrazolo[3,4-c]azepine-5,4'-tetrahydropyran]-3-yl)propyl 2-methylthiazole-4-carboxylate (xxi) 3-(1-ethyl-8-oxo-spiro[6,7-dihydro-4H-pyrazolo[3,4-c]azepine-5,4'-tetrahydropyran]-3-yl)propyl 2-methylthiazole-5-carboxylate (xxii) 3-(1-ethyl-8-oxo-spiro[6,7-dihydro-4H-pyrazolo[3,4-c]azepine-5,4'-tetrahydropyran]-3-yl)propyl 1-methylpiperidine-4-carboxylate (xxiii) 3-(1-ethyl-8-oxo-spiro[6,7-dihydro-4H-pyrazolo[3,4-c]azepine-5,4'-tetrahydropyran]-3-yl)propyl tetrahydrothiopyran-4-carboxylate (xxiv) 3-(1-ethyl-8-oxo-spiro[6,7-dihydro-4H-pyrazolo[3,4-c]azepine-5,4'-tetrahydropyran]-3-yl)propyl 2,6-dimethylpyridine-4-carboxylate (xxv) 3-(1-ethyl-8-oxo-spiro[6,7-dihydro-4H-pyrazolo[3,4-c]azepine-5,4'-tetrahydropyran]-3-yl)propyl 5-ethyl-1-methyl-pyrazole-3-carboxylate (xxvi) 3-(1-ethyl-8-oxo-spiro[6,7-dihydro-4H-pyrazolo[3,4-c]azepine-5,4'-tetrahydropyran]-3-yl)propyl 2-ethylthiazole-4-carboxylate (xxvii) 3-(1-ethyl-8-oxo-spiro[6,7-dihydro-4H-pyrazolo[3,4-c]azepine-5,4'-tetrahydropyran]-3-yl)propyl 1-acetylpiperidine-4-carboxylate (xxviii) 3-(1-ethyl-8-oxo-spiro[6,7-dihydro-4H-pyrazolo[3,4-c]azepine-5,4'-tetrahydropyran]-3-yl)propyl 1,1-dioxothiane-4-carboxylate (xxix) [3-(1-ethyl-8-oxo-spiro[6,7-dihydro-4H-pyrazolo[3,4-c]azepine-5,4'-tetrahydropyran]-3-yl)propyl] 1-methoxycarbonylpiperidine-4-carboxylate (xxx) 3-(1-ethyl-8-oxo-spiro[6,7-dihydro-4H-pyrazolo[3,4-c]azepine-5,4'-tetrahydropyran]-3-yl)propyl 1-(dimethylcarbamoyl)piperidine-4-carboxylate (xxxi) 4-(1-ethyl-8-oxo-spiro[6,7-dihydro-4H-pyrazolo[3,4-c]azepine-5,4'-tetrahydropyran]-3-yl)butyl tetrahydrofuran-3-carboxylate (xxxii) 4-(1-ethyl-8-oxo-spiro[6,7-dihydro-4H-pyrazolo[3,4-c]azepine-5,4'-tetrahydropyran]-3-yl)butyl 2-methyloxazole-4-carboxylate (xxxiii) 4-(1-ethyl-8-oxo-spiro[6,7-dihydro-4H-pyrazolo[3,4-c]azepine-5,4'-tetrahydropyran]-3-yl)butyl 2-methyloxazole-5-carboxylate (xxxiv) 4-(1-ethyl-8-oxo-spiro[6,7-dihydro-4H-pyrazolo[3,4-c]azepine-5,4'-tetrahydropyran]-3-yl)butyl isothiazole-4-carboxylate (xxxv) 4-(1-ethyl-8-oxo-spiro[6,7-dihydro-4H-pyrazolo[3,4-c]azepine-5,4'-tetrahydropyran]-3-yl)butyl thiazole-4-carboxylate (xxxvi) 4-(1-ethyl-8-oxo-spiro[6,7-dihydro-4H-pyrazolo[3,4-c]azepine-5,4'-tetrahydropyran]-3-yl)butyl tetrahydropyran-4-carboxylate (xxxvii) 4-(1-ethyl-8-oxo-spiro[6,7-dihydro-4H-pyrazolo[3,4-c]azepine-5,4'-tetrahydropyran]-3-yl)butyl 2-methylpyrimidine-5-carboxylate (xxxviii) 4-(1-ethyl-8-oxo-spiro[6,7-dihydro-4H-pyrazolo[3,4-c]azepine-5,4'-tetrahydropyran]-3-yl)butyl 1,5-dimethylpyrazole-3-carboxylate (xxxix) 4-(1-ethyl-8-oxo-spiro[6,7-dihydro-4H-pyrazolo[3,4-c]azepine-5,4'-tetrahydropyran]-3-yl)butyl 2,6-dimethylpyridine-4-carboxylate (xl) 4-(1-ethyl-8-oxo-spiro[6,7-dihydro-4H-pyrazolo[3,4-c]azepine-5,4'-tetrahydropyran]-3-yl)butyl 1-acetylpiperidine-4-carboxylate (xli) 2-(1-ethyl-8-oxo-spiro[6,7-dihydro-4H-pyrazolo[3,4-c]azepine-5,4'-tetrahydropyran]-3-yl)ethyl isothiazole-4-carboxylate (xlii) 2-(1-ethyl-8-oxo-spiro[6,7-dihydro-4H-pyrazolo[3,4-c]azepine-5,4'-tetrahydropyran]-3-yl)ethyl tetrahydropyran-4-carboxylate (xliii) [(2R)-3-(1-ethyl-8-oxo-spiro[6,7-dihydro-4H-pyrazolo[3,4-c]azepine-5,4'-tetrahydropyran]-3-yl)-2-methyl-propyl] oxazole-4-carboxylate (xliv) [(2R)-3-(1-ethyl-8-oxo-spiro[6,7-dihydro-4H-pyrazolo[3,4-c]azepine-5,4'-tetrahydropyran]-3-yl)-2-methyl-propyl] 1-methylpyrazole-3-carboxylate (xlv) [(2R)-3-(1-ethyl-8-oxo-spiro[6,7-dihydro-4H-pyrazolo[3,4-c]azepine-5,4'-tetrahydropyran]-3-yl)-2-methyl-propyl] 1-methylpyrazole-4-carboxylate (xlvi) [(2R)-3-(1-ethyl-8-oxo-spiro[6,7-dihydro-4H-pyrazolo[3,4-c]azepine-5,4'-tetrahydropyran]-3-yl)-2-methyl-propyl] 1-methylimidazole-4-carboxylate (xlvii) [(2R)-3-(1-ethyl-8-oxo-spiro[6,7-dihydro-4H-pyrazolo[3,4-c]azepine-5,4'-tetrahydropyran]-3-yl)-2-methyl-propyl]2-methyloxazole-4-carboxylate (xlviii) [(2R)-3-(1-ethyl-8-oxo-spiro[6,7-dihydro-4H-pyrazolo[3,4-c]azepine-5,4'-tetrahydropyran]-3-yl)-2-methyl-propyl]2-methyloxazole-5-carboxylate (xlix) [(2R)-3-(1-ethyl-8-oxo-spiro[6,7-dihydro-4H-pyrazolo[3,4-c]azepine-5,4'-tetrahydropyran]-3-yl)-2-methyl-propyl] isothiazole-5-carboxylate (l) [(2R)-3-(1-ethyl-8-oxo-spiro[6,7-dihydro-4H-pyrazolo[3,4-c]azepine-5,4'-tetrahydropyran]-3-yl)-2-methyl-propyl] isothiazole-4-carboxylate (li) [(2R)-3-(1-ethyl-8-oxo-spiro[6,7-dihydro-4H-pyrazolo[3,4-c]azepine-5,4'-tetrahydropyran]-3-yl)-2-methyl-propyl] thiazole-4-carboxylate (lii) [(2R)-3-(1-ethyl-8-oxo-spiro[6,7-dihydro-4H-pyrazolo[3,4-c]azepine-5,4'-tetrahydropyran]-3-yl)-2-methyl-propyl] thiazole-5-carboxylate (liii) [(2R)-3-(1-ethyl-8-oxo-spiro[6,7-dihydro-4H-pyrazolo[3,4-c]azepine-5,4'-tetrahydropyran]-3-yl)-2-methyl-propyl] tetrahydropyran-4-carboxylate (liv) [(2R)-3-(1-ethyl-8-oxo-spiro[6,7-dihydro-4H-pyrazolo[3,4-c]azepine-5,4'-tetrahydropyran]-3-yl)-2-methyl-propyl]2-methylpyrimidine-5-carboxylate (lv) [(2R)-3-(1-ethyl-8-oxo-spiro[6,7-dihydro-4H-pyrazolo[3,4-c]azepine-5,4'-tetrahydropyran]-3-yl)-2-methyl-propyl]1,5-dimethylpyrazole-3-carboxylate (lvi) [(2R)-3-(1-ethyl-8-oxo-spiro[6,7-dihydro-4H-pyrazolo[3,4-c]azepine-5,4'-tetrahydropyran]-3-yl)-2-methyl-propyl]2-methylthiazole-4-carboxylate (lvii) [(2R)-3-(1-ethyl-8-oxo-spiro[6,7-dihydro-4H-pyrazolo[3,4-c]azepine-5,4'-tetrahydropyran]-3-yl)-2-methyl-propyl]2-methylthiazole-5-carboxylate (lviii) [(2R)-3-(1-ethyl-8-oxo-spiro[6,7-dihydro-4H-pyrazolo[3,4-c]azepine-5,4'-tetrahydropyran]-3-yl)-2-methyl-propyl] 1-methyl piperidine-4-carboxylate (lix) [(2R)-3-(1-ethyl-8-oxo-spiro[6,7-dihydro-4H-pyrazolo[3,4-c]azepine-5,4'-tetrahydropyran]-3-yl)-2-methyl-propyl]2,6-dimethylpyridine-4-carboxylate (lx) [(2R)-3-(1-ethyl-8-oxo-spiro[6,7-dihydro-4H-pyrazolo[3,4-c]azepine-5,4'-tetrahydropyran]-3-yl)-2-methyl-propyl] 1-acetylpiperidine-4-carboxylate (lxi) [(2R)-3-(1-ethyl-8-oxo-spiro[6,7-dihydro-4H-pyrazolo[3,4-c]azepine-5,4'-tetrahydropyran]-3-yl)-2-methyl-propyl] 1-methoxycarbonylpiperidine-4-carboxylate (lxii) [(2R)-3-(1-ethyl-8-oxo-spiro[6,7-dihydro-4H-pyrazolo[3,4-c]azepine-5,4'-tetrahydropyran]-3-yl)-2-methyl-propyl] 1-(dimethylcarbamoyl)piperidine-4-carboxylate (lxiii) [3-(1-ethyl-8-oxo-spiro[6,7-dihydro-4H-pyrazolo[3,4-c]azepine-5,4'-tetrahydropyran]-3-yl)-2,2-dimethyl-propyl] oxazole-4-carboxylate (lxiv) [3-(1-ethyl-8-oxo-spiro[6,7-dihydro-4H-pyrazolo[3,4-c]azepine-5,4'-tetrahydropyran]-3-yl)-2,2-dimethyl-propyl] 1-methylpyrazole-3-carboxylate (lxv) [3-(1-ethyl-8-oxo-spiro[6,7-dihydro-4H-pyrazolo[3,4-c]azepine-5,4'-tetrahydropyran]-3-yl)-2,2-dimethyl-propyl] 1-methylpyrazole-4-carboxylate (lxvi) [3-(1-ethyl-8-oxo-spiro[6,7-dihydro-4H-pyrazolo[3,4-c]azepine-5,4'-tetrahydropyran]-3-yl)-2,2-dimethyl-propyl] 1-methylimidazole-4-carboxylate (lxvii) [3-(1-ethyl-8-oxo-spiro[6,7-dihydro-4H-pyrazolo[3,4-c]azepine-5,4'-tetrahydropyran]-3-yl)-2,2-dimethyl-propyl]2-methyloxazole-4-carboxylate (lxviii) [3-(1-ethyl-8-oxo-spiro[6,7-dihydro-4H-pyrazolo[3,4-c]azepine-5,4'-tetrahydropyran]-3-yl)-2,2-dimethyl-propyl]2-methyloxazole-5-carboxylate (lxix) [3-(1-ethyl-8-oxo-spiro[6,7-dihydro-4H-pyrazolo[3,4-c]azepine-5,4'-tetrahydropyran]-3-yl)-2,2-dimethyl-propyl] isothiazole-5-carboxylate (lxx) [3-(1-ethyl-8-oxo-spiro[6,7-dihydro-4H-pyrazolo[3,4-c]azepine-5,4'-tetrahydropyran]-3-yl)-2,2-dimethyl-propyl] isothiazole-4-carboxylate (lxxi) [3-(1-ethyl-8-oxo-spiro[6,7-dihydro-4H-pyrazolo[3,4-c]azepine-5,4'-tetrahydropyran]-3-yl)-2,2-dimethyl-propyl] thiazole-4-carboxylate (lxxii) [3-(1-ethyl-8-oxo-spiro[6,7-dihydro-4H-pyrazolo[3,4-c]azepine-5,4'-tetrahydropyran]-3-yl)-2,2-dimethyl-propyl] thiazole-5-carboxylate (lxxiii) [3-(1-ethyl-8-oxo-spiro[6,7-dihydro-4H-pyrazolo[3,4-c]azepine-5,4'-tetrahydropyran]-3-yl)-2,2-dimethyl-propyl] tetrahydropyran-4-carboxylate (lxxiv) [3-(1-ethyl-8-oxo-spiro[6,7-dihydro-4H-pyrazolo[3,4-c]azepine-5,4'-tetrahydropyran]-3-yl)-2,2-dimethyl-propyl]2-methylpyrimidine-5-carboxylate (lxxv) [3-(1-ethyl-8-oxo-spiro[6,7-dihydro-4H-pyrazolo[3,4-c]azepine-5,4'-tetrahydropyran]-3-yl)-2,2-dimethyl-propyl]1,5-dimethylpyrazole-3-carboxylate (lxxvi) [3-(1-ethyl-8-oxo-spiro[6,7-dihydro-4H-pyrazolo[3,4-c]azepine-5,4'-tetrahydropyran]-3-yl)-2,2-dimethyl-propyl]2-methylthiazole-4-carboxylate (lxxvii) [3-(1-ethyl-8-oxo-spiro[6,7-dihydro-4H-pyrazolo[3,4-c]azepine-5,4'-tetrahydropyran]-3-yl)-2,2-dimethyl-propyl]2-methylthiazole-5-carboxylate (lxxviii) [3-(1-ethyl-8-oxo-spiro[6,7-dihydro-4H-pyrazolo[3,4-c]azepine-5,4'-tetrahydropyran]-3-yl)-2,2-dimethyl-propyl] 1-methylpiperidine-4-carboxylate (lxxix) [3-(1-ethyl-8-oxo-spiro[6,7-dihydro-4H-pyrazolo[3,4-c]azepine-5,4'-tetrahydropyran]-3-yl)-2,2-dimethyl-propyl]2,6-dimethylpyridine-4-carboxylate (lxxx) [3-(1-ethyl-8-oxo-spiro[6,7-dihydro-4H-pyrazolo[3,4-c]azepine-5,4'-tetrahydropyran]-3-yl)-2,2-dimethyl-propyl] 1-acetylpiperidine-4-carboxylate (lxxxi) [3-(1-ethyl-8-oxo-spiro[6,7-dihydro-4H-pyrazolo[3,4-c]azepine-5,4'-tetrahydropyran]-3-yl)-2,2-dimethyl-propyl] 1-methoxycarbonylpiperidine-4-carboxylate (lxxxii)[3-(1-ethyl-8-oxo-spiro[6,7-dihydro-4H-pyrazolo[3,4-c]azepine-5,4'-tetrahydropyran]-3-yl)-2,2-dimethyl-propyl]1-(dimethylcarbamoyl)piperidine-4-carboxylate, or a pharmaceutically acceptable salt, hydrate or solvate thereof.

8. A pharmaceutical composition comprising a Compound according to claim 1 together with one or more pharmaceutically acceptable vehicles or excipients or one or more pharmaceutically acceptable carriers.

9. The pharmaceutical composition according to claim 8 further comprising one or more other therapeutically active compounds.

10. A method for treatment or alleviation of a disease or a disorder or a condition responsive to PDE4 inhibitory activity, comprising administering to a subject in need thereof a therapeutically effective amount of a Compound according to claim 1.

11. A method of treating or ameliorating one or more dermal diseases or conditions, comprising administering to a person suffering from at least one of said diseases an effective amount of one or more Compounds according to according to claim 1.

12. The method according to claim 11, wherein the dermal disease or condition is selected from the group consisting of proliferative and inflammatory skin disorders, dermatitis, atopic dermatitis, seborrheic dermatitis, contact dermatitis, psoriasis, cancer, epidermal inflammation, alopecia, alopecia areata, skin atrophy, steroid induced skin atrophy, skin ageing, photo skin ageing, acne, urticaria, pruritis, and eczema.

13. A method of treating or ameliorating one or more dermal diseases or conditions, comprising administering to a person suffering from at least one of said diseases an effective amount of the pharmaceutical composition according to claim 8.

* * * * *